US010059779B2

(12) United States Patent
Nambiar et al.

(10) Patent No.: US 10,059,779 B2
(45) Date of Patent: Aug. 28, 2018

(54) ENZYMATICALLY POLYMERIZED GELLING DEXTRANS

(71) Applicant: E I DU PONT DE NEMOURS AND COMPANY, Wilmington, DE (US)

(72) Inventors: Rakesh Nambiar, West Chester, PA (US); Rong Guan, Wilmington, DE (US); Qiong Cheng, Wilmington, DE (US); Robert Dicosimo, Chadds Ford, PA (US); Jayme L Paullin, Claymont, DE (US); Yuanfeng Liang, Chadds Ford, PA (US); Charles R Powley, Wilmington, DE (US); Yefim Brun, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 174 days.

(21) Appl. No.: 14/933,128

(22) Filed: Nov. 5, 2015

(65) Prior Publication Data
US 2016/0122445 A1 May 5, 2016

Related U.S. Application Data

(60) Provisional application No. 62/075,460, filed on Nov. 5, 2014.

(51) Int. Cl.
*C08B 37/02* (2006.01)
*C12P 19/08* (2006.01)
*C11D 3/22* (2006.01)
*C08L 5/02* (2006.01)

(52) U.S. Cl.
CPC .......... *C08B 37/0021* (2013.01); *C08L 5/02* (2013.01); *C11D 3/222* (2013.01); *C12P 19/08* (2013.01)

(58) Field of Classification Search
CPC ....... C08B 37/0021; C08L 5/02; C11D 3/222; C12P 19/08
See application file for complete search history.

(56) References Cited

U.S. PATENT DOCUMENTS

| 6,977,249 | B1 | 12/2005 | Andreasen et al. |
| 7,531,073 | B2 | 5/2009 | Barron et al. |
| 7,595,182 | B2 | 9/2009 | Koga et al. |
| 8,569,033 | B2 | 10/2013 | Watanabe et al. |
| 2005/0059633 | A1 | 3/2005 | Van Geel-Schuten |
| 2006/0100171 | A1 | 5/2006 | Ekhart et al. |
| 2009/0046274 | A1 | 2/2009 | McHugh et al. |
| 2010/0003515 | A1 | 1/2010 | Tanaka et al. |
| 2014/0142294 | A1 | 5/2014 | Wieser |

FOREIGN PATENT DOCUMENTS

CN    103992978 A    8/2014

OTHER PUBLICATIONS

International Search Report, Corresponding PCT International Application No. PCT/US2015/059261, dated Feb. 29, 2016.
(Anonymous) NCBI Database, Hydrolase (*Leuconostoc pseudomesenteroides*), Accession No. WP_010278815, May 27, 2013.
(Anonymous) NCBI Database, YG Repeat-Containing Glycosyl Hydrolase Family 70 Protein (*Weissella cibaria* KACC 11862), NCBI Database, Accession No. ZP_08417432, May 11, 2011.
Kuwahara et al., Glucosyltransferase-T (*Streptococcus sobrinus*), NCBI Database, Accession No. AAX76986, Apr. 25, 2005.
Nam et al., YG Repeat-Containing Glycosyl Hydrolase Family 70 Protein (*Lactobacillus animalis* KCTC 3501), NCBI Database, Accession No. ZP_08549987, Nov. 28, 2012.
ASTM International, Designation: E1490-03, Standard Practice For Descriptive Skinfeel Analysis of Creams and Lotions, Current Edition Approved Feb. 10, 2003.
Arond et al., Molecular Weight, Molecular Weight Distribution and Molecular Size of a Native Dextran, Journal of Physical Chemistry, vol. 58 (1954), pp. 953-957.
Antonini et al., Studies on Dextran and Dextran Derivatives. I. Properties of Native Dextran in Different Solvents, Biopolymers, vol. 2 (1964), pp. 27-34.
Glycobiology, Glycosaminoglycans and polysaccharides, From Life Science Biofiles, vol. 3, No. 10, Undated, pp. 1-28.
Bozonnet et al., Molecular Characterization of DSR-E, an α-1,2 Linkage-Synthesizing Dextransucrase With Two Catalytic Domains, Journal of Bacteriology, vol. 184, No. 20 (2002), pp. 5753-5761.
Cantarel et al., The Carbohydrate-Active Enzymes Database (CAZY): An Expert Resource for Glycogenomics, Nucleic Acids Research, vol. 37 (2009), Database Issue D233-D238.
Covacevich et al., Frequency and Distribution of Branching in a Dextran: An Enzymic Method, Carbohydrate Research, vol. 54 (1977), pp. 311-315.
Elias, Ultra Centrifuge and Diffusion Measurements to Non-Newtonian Solutions Native Dextrans, About Extreme Coarse Macromolecules, Makromolecular Chemistry, vol. 33 (1959), pp. 166-180. (English Abstract).
Ioan et al., Structure Properties of Dextran, 2. Dilute Solution, Macromolecules, vol. 33 (2000), pp. 5730-5739.
Irague et al., Structure and Property Engineering of a α-D-Glucans Synthesized by Dextransucrase Mutants, Biomacromolecules, vol. 13 (2012), pp. 187-195.

(Continued)

*Primary Examiner* — Lisa J Hobbs

(57) ABSTRACT

Compositions are disclosed herein comprising dextran that comprises (i) 87-93 wt % glucose linked at positions 1 and 6; (ii) 0.1-1.2 wt % glucose linked at positions 1 and 3; (iii) 0.1-0.7 wt % glucose linked at positions 1 and 4; (iv) 7.7-8.6 wt % glucose linked at positions 1, 3 and 6; and (v) about 0.4-1.7 wt % glucose linked at (a) positions 1, 2 and 6, or (b) positions 1, 4 and 6. Aqueous forms of this composition have enhanced viscosity profiles. Further disclosed are methods of using compositions comprising dextran, such as increasing the viscosity of an aqueous composition. Enzymatic reactions for producing dextran are also disclosed.

12 Claims, 4 Drawing Sheets

Figure 1:
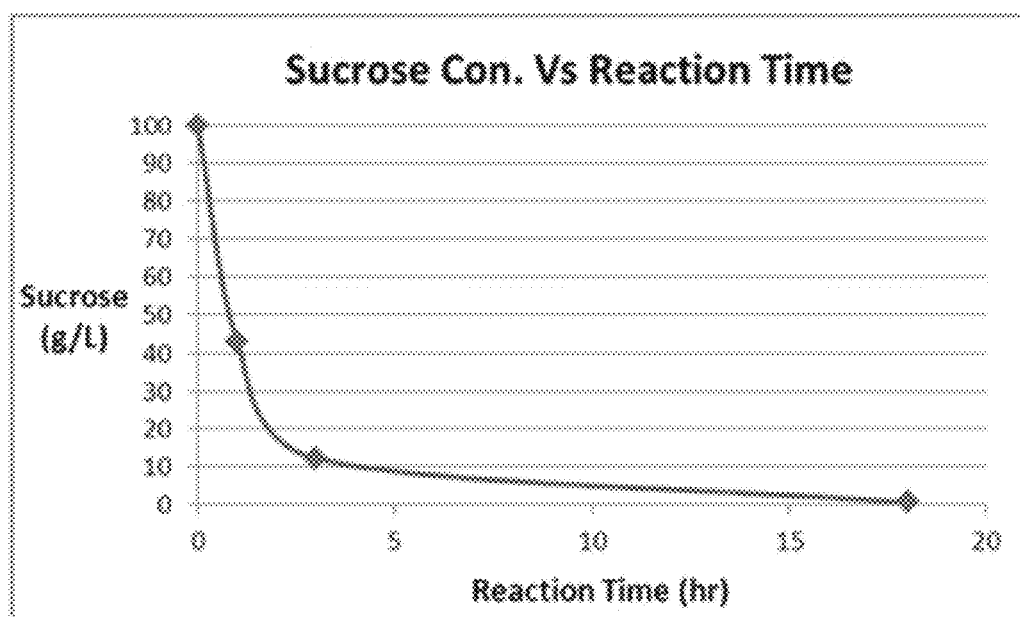

Specification includes a Sequence Listing.

(56) References Cited

OTHER PUBLICATIONS

Jeanes et al., Characterization and Classification of Dextrans From Ninety-Six Strains of Bacteria, Contribution From the Starch and Dextrose Section, Northern Utilization Research Branch (1954), pp. 5041-5052.

Kim et al., Dextran Molecular Size and Degree of Branching as a Function of Sucrose Concentration, PH, and Temperature of Reaction of Leuconostoc Mesenteroides B-512FMCM Dextransucrase, Carbohydrate Research, vol. 338 (2003), pp. 1183-1189.

Naessens et al., Review Leuconostoc Dextransucrase and Dextran: Production, Properties and Applications, Journal of Chemical Technology and Biotechnology, vol. 80 (2005), pp. 845-860.

Onilude et al., Effects of Cultural Conditions on Dextran Production by *Leuconostoc* spp., International Food Research Journal, vol. 20, No. 4 (2013), pp. 1645-1651.

Paulo et al., Production, Extraction and Characterization of Exopolysaccharides Produced by the Native Leuconostoc Pseudomesenteroides R2 Strain, Anais Da Academia Brasileira De Ciencias, vol. 84, No. 2 (2012), pp. 495-507.

Pidoux et al., Microscopic and Chemical Studies of a Gelling Polysaccharide from Lactobacillus Hilgardii, Carbohydrate Polymers, vol. 13 (1990), pp. 351-362.

Robyt et al., Production, Purification and Properties of Dextran-Sucrase From Leuconostoc Mesenteroides NRRL B-512F, Carbohydrate Research, vol. 68 (1979), pp. 95-111.

Sarwat et al., Production & Characterization of a Unique Dextran From an Indigenous Leuconostoc Mesenteroides CMB713, International Journal of Biological Sciences, vol. 4, No. 6 (2008), pp. 379-386.

Uzochukwu et al., Structural Analysis by 13C-Nuclear Magnetic Resonance Spectroscopy of Glucans Elaborated by Gum-Producing Bacteria Isolated From Palm Wine, Food Chemistry, vol. 73 (2001), pp. 225-233.

Kelly et al., Differentiation of Dextran-Producing Leuconostoc Strains From Fermented Rice Cake (PUTO) Using Pulsed-Field Gel Electrophoresis, International Journal of Food Microbiology, vol. 26 (1995), pp. 345-352.

SEQUENCE LISTING

<160> NUMBER OF SEQ ID NOS: 18

<210> SEQ ID NO 1
<211> LENGTH: 1447
<212> TYPE: PRT
<213> ORGANISM: Leuconostoc pseudomesenteroides
<220> FEATURE:
<221> NAME/KEY: MISC_FEATURE
<222> LOCATION: (1)..(1447)
<223> OTHER INFORMATION: mature 0768 gtf

<400> SEQUENCE: 1

Asp Gln Asn Val Asn Asp Pro Ser Val Ala Thr Thr Gln Asn Val
1               5                   10                  15

Val Thr Asp Gln Asp Thr Ser Ile Asp Ala Ser Val Ala Thr Thr Val
            20                  25                  30

Asn Pro Asn Leu Asp Asp Thr Gln Ala Asp Asn Thr Asn Ile Gln Thr
        35                  40                  45

Pro Thr Asp Gln Asn Asp Glu Ser Lys Asp Thr Thr Pro Lys Val Glu
    50                  55                  60

Thr Gly Asp Thr Thr Asn Ser Gln Ser Thr Glu Ala Gln Glu Thr Thr
65                  70                  75                  80

Ala Gln Thr Asn Asn Asp Val Glu Thr Pro Gln Asn Ser Asp Ala Ala
                85                  90                  95

Ile Glu Thr Gly Leu Leu Thr Thr Asn Asn Gln Ile Arg Tyr Val Asn
            100                 105                 110

Pro Asp Gly Thr Val Leu Thr Gly Ala Tyr Lys Thr Ile Asn Gly Asn
        115                 120                 125

Thr Tyr Tyr Phe Asp Asp Ser Gly Val Ala Leu Val Gly Leu His
130                 135                 140

Lys Ile Gly Asp Thr Leu Lys Gly Phe Ser Leu Asn Gly Val Gln Val
145                 150                 155                 160

Lys Gly Asp Tyr Leu Thr Ala Ala Asn Gly Asp Lys Tyr Tyr Phe Asp
                165                 170                 175

Ser Asn Gly Asn Ala Val Ser Gly Val Gln Gln Ile Asn Gly Lys Thr
            180                 185                 190

Tyr Tyr Phe Asp Ser Thr Gly Lys Leu Met Lys Gly Tyr Thr Ala Val
        195                 200                 205

Leu Asn Gly Val Val Thr Phe Phe Asn Ser Thr Thr Gly Glu Ala Asp

```
              210                 215                 220
Asn Thr Asp Ala Ser Thr Ile Lys Thr Gly Val Thr Ile Asp Asn Ser
225                 230                 235                 240
Asp Tyr Thr Val His Asn Ala Ala Tyr Asp Asn Thr Ala Ala Ser Phe
                    245                 250                 255
Asp Asn Ile Asn Gly Tyr Leu Thr Ala Glu Ser Trp Tyr Arg Pro Lys
                260                 265                 270
Glu Ile Leu Glu Asn Gly Glu Ser Trp Arg Pro Ser Thr Ala Glu Asp
            275                 280                 285
Lys Arg Pro Ile Leu Ile Thr Trp Gln Pro Asp Ile Val Thr Glu Val
        290                 295                 300
Asn Tyr Leu Asn Met Met Ala Ala Asn Gly Leu Leu Ser Ile Asn Ala
305                 310                 315                 320
Pro Phe Thr Thr Ala Ser Asp Leu Ala Ile Met Asn Asp Ala Val Arg
                    325                 330                 335
Ala Val Gln Lys Asn Ile Glu Met Arg Ile Ser Gln Glu Lys Ser Thr
                340                 345                 350
Asp Trp Leu Lys Ala Leu Met Thr Gln Phe Ile Asn Thr Gln Pro Gln
            355                 360                 365
Trp Asn Glu Val Ser Glu Ser Pro Ser Asn Asp His Leu Gln Gly Gly
        370                 375                 380
Ala Leu Thr Tyr Val Asn Ser Pro Leu Thr Pro Asp Ala Asn Ser Asn
385                 390                 395                 400
Phe Arg Leu Leu Asn Arg Thr Pro Thr Asn Gln Ser Gly Thr Thr Arg
                    405                 410                 415
Tyr Asp Thr Asp Lys Ser Lys Gly Gly Phe Glu Leu Leu Leu Ala Asn
                420                 425                 430
Asp Val Asp Asn Ser Asn Pro Val Val Gln Ala Glu Gln Leu Asn Trp
            435                 440                 445
Leu Tyr Tyr Leu Met Asn Phe Gly Ser Ile Thr Ala Asn Asp Pro Thr
        450                 455                 460
Ala Asn Phe Asp Gly Ile Arg Val Asp Ala Val Asp Asn Val Asp Ala
465                 470                 475                 480
Asp Leu Leu Gln Ile Ala Ser Asp Tyr Phe Lys Leu Ala Tyr Gly Thr
                    485                 490                 495
Ser Leu Ser Asp Thr Asn Ala Asn Gln His Leu Ser Ile Leu Glu Asp
                500                 505                 510
Trp Ser Ala Asn Asp Ala Glu Tyr Met Ser Lys Thr Gly Ser Asn Gln
            515                 520                 525
Leu Thr Met Asp Thr Tyr Thr Gln Gln Gln Leu Leu Phe Ser Leu Thr
        530                 535                 540
Lys Gln Val Gly Asn Arg Ala Asp Met Arg Arg Phe Leu Glu Tyr Phe
545                 550                 555                 560
Met Ile Asn Arg Ala Asn Asp Ser Thr Glu Asn Val Ala Thr Pro Asn
                    565                 570                 575
Tyr Ser Phe Val Arg Ala His Asp Ser Glu Val Gln Thr Val Ile Ala
                580                 585                 590
Thr Ile Ile Lys Asp Leu His Pro Asp Val Val Asn Ser Leu Ala Pro
            595                 600                 605
Thr Gln Ala Gln Leu Glu Glu Ala Phe Ala Val Tyr Asn Ala Asp Met
        610                 615                 620
Asn Arg Val Asp Lys Gln Tyr Thr Gln Tyr Asn Met Pro Ser Ala Tyr
625                 630                 635                 640
```

-continued

```
Ala Met Leu Leu Thr Asn Lys Asp Thr Ile Pro Arg Val Tyr Tyr Gly
            645                 650                 655

Asp Leu Tyr Thr Asp Asp Gly Glu Tyr Met Gly Thr Gln Thr Pro Tyr
            660                 665                 670

Tyr Asp Ala Ile Val Asn Leu Leu Gln Ser Arg Val Lys Tyr Val Ala
            675                 680                 685

Gly Gly Gln Ser Met Ala Val Asp Gln His Asp Ile Leu Thr Ser Val
            690                 695                 700

Arg Tyr Gly Lys Asn Leu Ala Asp Ala Asn Ala Thr Ser Asp Asp Leu
705                 710                 715                 720

Thr Ser Ile Asn Ser Gly Ile Gly Val Ile Val Ser Asn Asn Pro Asn
            725                 730                 735

Leu Ser Leu Ala Ser Gly Glu Thr Val Val Leu His Met Gly Ile Ala
            740                 745                 750

His Ala Asn Gln Val Tyr Arg Glu Ile Leu Glu Thr Thr Asp Asn Gly
            755                 760                 765

Ile Ala Asn Asn Thr Asp Ile Phe Lys Thr Thr Asp Ser Asn Gly Asp
            770                 775                 780

Leu Ile Phe Thr Ala Ser Glu Ile His Gly Tyr Ser Asn Val Gln Val
785                 790                 795                 800

Ser Gly Phe Leu Ser Val Trp Ala Pro Lys Asp Ala Thr Asp Asp Gln
            805                 810                 815

Asp Val Arg Thr Ala Ala Ser Glu Ser Thr Ser Asn Asp Gly Asn Thr
            820                 825                 830

Leu His Ser Asn Ala Ala Leu Asp Ser Asn Leu Ile Tyr Glu Gly Phe
            835                 840                 845

Ser Asn Phe Gln Ser Thr Pro Gln Ser Glu Ser Glu Phe Ala Asn Val
            850                 855                 860

Lys Ile Ala Ala Asn Val Asn Leu Phe Lys Ser Trp Gly Val Thr Ser
865                 870                 875                 880

Phe Gln Met Ala Pro Gln Tyr Arg Ser Ser Thr Asp Thr Ser Phe Leu
            885                 890                 895

Asp Ser Ile Ile Gln Asn Gly Tyr Ala Phe Thr Asp Arg Tyr Asp Leu
            900                 905                 910

Gly Phe Glu Thr Pro Thr Lys Tyr Gly Thr Asp Gln Gln Leu Arg Asp
            915                 920                 925

Ala Ile Lys Ala Leu His Ala Asn Gly Ile Gln Ala Met Ala Asp Phe
            930                 935                 940

Val Pro Asp Gln Ile Tyr Asn Leu Pro Gln Thr Glu Leu Val Ser Val
945                 950                 955                 960

Ser Arg Thr Asp Ser Leu Gly Asn Gln Ser Ala Asn Ser Asn Ala Ala
            965                 970                 975

Asn Val Leu Tyr Val Ser His Thr Val Gly Gly Gly Glu Tyr Gln Ser
            980                 985                 990

Lys Tyr Gly Gly Glu Phe Leu Ala Ile Ile Lys Ser Lys Tyr Pro Ser
            995                 1000                1005

Leu Phe Lys Thr Ile Gln Val Ser Thr Gly Leu Pro Ile Asp Asp
            1010                1015                1020

Ser Thr Lys Ile Lys Glu Trp Ser Ala Lys Tyr Phe Asn Gly Ser
            1025                1030                1035

Asn Ile Gln Gly Arg Gly Phe Gly Tyr Val Leu Ser Asp Gly Gly
            1040                1045                1050
```

-continued

```
Thr Gln Asn Tyr Phe Lys Val Ile Ser Asn Ser Thr Asp Asp Asp
    1055                1060                1065

Phe Leu Pro Asn Gln Leu Thr Gly Lys Pro Thr Met Thr Gly Phe
    1070                1075                1080

Glu Gln Thr Ser Lys Gly Ile Val Tyr Tyr Ser Lys Ser Gly Ile
    1085                1090                1095

Gln Ala Lys Asn Gln Phe Val Lys Asp Asp Val Ser Gly Asn Tyr
    1100                1105                1110

Tyr Tyr Phe Asn Lys Asn Gly Leu Met Thr Val Gly Ser Lys Thr
    1115                1120                1125

Ile Asn Gly Lys Asn Tyr Met Phe Leu Pro Asn Gly Val Glu Leu
    1130                1135                1140

Arg Gly Ser Phe Leu Gln Thr Ala Asp Gly Thr Val Asn Tyr Tyr
    1145                1150                1155

Ala Thr Asn Gly Ala Gln Val Gln Asp Ser Tyr Val Thr Asp Thr
    1160                1165                1170

Glu Gly Asn Ser Tyr Tyr Phe Asp Gly Asp Gly Glu Met Val Thr
    1175                1180                1185

Gly Thr Tyr Thr Val Asp Gly His Ala Gln Tyr Phe Asp Val Asn
    1190                1195                1200

Gly Val Gln Thr Lys Gly Ala Ile Ile Thr Leu Gly Gly Val Gln
    1205                1210                1215

Arg Tyr Tyr Gln Ala Gly Asn Gly Asn Leu Ala Thr Asn Gln Tyr
    1220                1225                1230

Val Ser Tyr Asn Asn Ser Trp Tyr Tyr Ala Asn Thr Lys Gly Glu
    1235                1240                1245

Leu Val Thr Gly Val Gln Ser Ile Asn Gly Asn Val Gln Tyr Phe
    1250                1255                1260

Ala Ser Asn Gly Gln Gln Ile Lys Gly Gln Ile Val Val Thr Gly
    1265                1270                1275

Asn Gln Lys Ser Tyr Tyr Asp Ala Asn Thr Gly Asn Leu Ile Lys
    1280                1285                1290

Asn Asp Phe Leu Thr Pro Asp Gln Gly Lys Thr Trp Tyr Tyr Ala
    1295                1300                1305

Asp Gln Asp Gly Asn Leu Val Val Gly Ala Gln Glu Val Asn Gly
    1310                1315                1320

His Lys Leu Tyr Phe Asp Asp Asn Gly Ile Gln Ile Lys Asp Gln
    1325                1330                1335

Ile Ile Ser Asn Asp Gly Gln Gln Tyr Tyr Gln Gly Gly Asn
    1340                1345                1350

Gly Asp Leu Val Thr Asn Arg Tyr Ile Ser Tyr Asn Asp Ser Trp
    1355                1360                1365

Tyr Tyr Ala Asp Ala Thr Gly Val Leu Val Thr Gly Gln Gln Ile
    1370                1375                1380

Ile Asn Gly Glu Thr Gln Tyr Phe Arg Thr Asp Gly Arg Gln Val
    1385                1390                1395

Lys Gly Gln Ile Ile Ala Asp Gly Asp Lys Gln His Tyr Tyr Asp
    1400                1405                1410

Ala Asp Ser Gly Asn Leu Val Lys Asn Asn Phe Val Thr Val Asp
    1415                1420                1425

Gln Gly Lys Thr Trp Tyr Tyr Ala Asp Gln Asp Gly Asn Leu Ser
    1430                1435                1440

Leu Val Asp Arg
```

1445

<210> SEQ ID NO 2
<211> LENGTH: 1457
<212> TYPE: PRT
<213> ORGANISM: Artificial sequence
<220> FEATURE:
<223> OTHER INFORMATION: 0768 gtf mature protein with start codon and
      other added sequences

<400> SEQUENCE: 2

Met Ala Ser Ala Asp Gln Asn Val Asn Asp Pro Ser Val Ala Thr Thr
1               5                   10                  15

Thr Gln Asn Val Val Thr Asp Gln Asp Thr Ser Ile Asp Ala Ser Val
                20                  25                  30

Ala Thr Thr Val Asn Pro Asn Leu Asp Asp Gln Ala Asp Asn Thr
            35                  40                  45

Asn Ile Gln Thr Pro Thr Asp Gln Asn Asp Glu Ser Lys Asp Thr Thr
    50                  55                  60

Pro Lys Val Glu Thr Gly Asp Thr Thr Asn Ser Gln Ser Thr Glu Ala
65                  70                  75                  80

Gln Glu Thr Thr Ala Gln Thr Asn Asn Asp Val Glu Thr Pro Gln Asn
                85                  90                  95

Ser Asp Ala Ala Ile Glu Thr Gly Leu Leu Thr Thr Asn Asn Gln Ile
            100                 105                 110

Arg Tyr Val Asn Pro Asp Gly Thr Val Leu Thr Gly Ala Tyr Lys Thr
        115                 120                 125

Ile Asn Gly Asn Thr Tyr Tyr Phe Asp Asp Asp Ser Gly Val Ala Leu
    130                 135                 140

Val Gly Leu His Lys Ile Gly Asp Thr Leu Lys Gly Phe Ser Leu Asn
145                 150                 155                 160

Gly Val Gln Val Lys Gly Asp Tyr Leu Thr Ala Ala Asn Gly Asp Lys
                165                 170                 175

Tyr Tyr Phe Asp Ser Asn Gly Asn Ala Val Ser Gly Val Gln Gln Ile
            180                 185                 190

Asn Gly Lys Thr Tyr Tyr Phe Asp Ser Thr Gly Lys Leu Met Lys Gly
        195                 200                 205

Tyr Thr Ala Val Leu Asn Gly Val Val Thr Phe Phe Asn Ser Thr Thr
    210                 215                 220

Gly Glu Ala Asp Asn Thr Asp Ala Ser Thr Ile Lys Thr Gly Val Thr
225                 230                 235                 240

Ile Asp Asn Ser Asp Tyr Thr Val His Asn Ala Ala Tyr Asp Asn Thr
                245                 250                 255

Ala Ala Ser Phe Asp Asn Ile Asn Gly Tyr Leu Thr Ala Glu Ser Trp
            260                 265                 270

Tyr Arg Pro Lys Glu Ile Leu Glu Asn Gly Glu Ser Trp Arg Pro Ser
        275                 280                 285

Thr Ala Glu Asp Lys Arg Pro Ile Leu Ile Thr Trp Gln Pro Asp Ile
    290                 295                 300

Val Thr Glu Val Asn Tyr Leu Asn Met Met Ala Ala Asn Gly Leu Leu
305                 310                 315                 320

Ser Ile Asn Ala Pro Phe Thr Thr Ala Ser Asp Leu Ala Ile Met Asn
                325                 330                 335

Asp Ala Val Arg Ala Val Gln Lys Asn Ile Glu Met Arg Ile Ser Gln
            340                 345                 350

-continued

Glu Lys Ser Thr Asp Trp Leu Lys Ala Leu Met Thr Gln Phe Ile Asn
        355                 360                 365

Thr Gln Pro Gln Trp Asn Glu Val Ser Glu Ser Pro Ser Asn Asp His
    370                 375                 380

Leu Gln Gly Gly Ala Leu Thr Tyr Val Asn Ser Pro Leu Thr Pro Asp
385                 390                 395                 400

Ala Asn Ser Asn Phe Arg Leu Leu Asn Arg Thr Pro Thr Asn Gln Ser
            405                 410                 415

Gly Thr Thr Arg Tyr Asp Thr Asp Lys Ser Lys Gly Gly Phe Glu Leu
            420                 425                 430

Leu Leu Ala Asn Asp Val Asp Asn Ser Asn Pro Val Val Gln Ala Glu
            435                 440                 445

Gln Leu Asn Trp Leu Tyr Tyr Leu Met Asn Phe Gly Ser Ile Thr Ala
    450                 455                 460

Asn Asp Pro Thr Ala Asn Phe Asp Gly Ile Arg Val Asp Ala Val Asp
465                 470                 475                 480

Asn Val Asp Ala Asp Leu Leu Gln Ile Ala Ser Asp Tyr Phe Lys Leu
                485                 490                 495

Ala Tyr Gly Thr Ser Leu Ser Asp Thr Asn Ala Asn Gln His Leu Ser
            500                 505                 510

Ile Leu Glu Asp Trp Ser Ala Asn Asp Ala Glu Tyr Met Ser Lys Thr
            515                 520                 525

Gly Ser Asn Gln Leu Thr Met Asp Thr Tyr Thr Gln Gln Leu Leu
    530                 535                 540

Phe Ser Leu Thr Lys Gln Val Gly Asn Arg Ala Asp Met Arg Arg Phe
545                 550                 555                 560

Leu Glu Tyr Phe Met Ile Asn Arg Ala Asn Asp Ser Thr Glu Asn Val
                565                 570                 575

Ala Thr Pro Asn Tyr Ser Phe Val Arg Ala His Asp Ser Glu Val Gln
            580                 585                 590

Thr Val Ile Ala Thr Ile Ile Lys Asp Leu His Pro Asp Val Val Asn
            595                 600                 605

Ser Leu Ala Pro Thr Gln Ala Gln Leu Glu Glu Ala Phe Ala Val Tyr
610                 615                 620

Asn Ala Asp Met Asn Arg Val Asp Lys Gln Tyr Thr Gln Tyr Asn Met
625                 630                 635                 640

Pro Ser Ala Tyr Ala Met Leu Leu Thr Asn Lys Asp Thr Ile Pro Arg
            645                 650                 655

Val Tyr Tyr Gly Asp Leu Tyr Thr Asp Asp Gly Glu Tyr Met Gly Thr
            660                 665                 670

Gln Thr Pro Tyr Tyr Asp Ala Ile Val Asn Leu Leu Gln Ser Arg Val
            675                 680                 685

Lys Tyr Val Ala Gly Gln Ser Met Ala Val Asp Gln His Asp Ile
    690                 695                 700

Leu Thr Ser Val Arg Tyr Gly Lys Asn Leu Ala Asp Ala Asn Ala Thr
705                 710                 715                 720

Ser Asp Asp Leu Thr Ser Ile Asn Ser Gly Ile Gly Val Ile Val Ser
            725                 730                 735

Asn Asn Pro Asn Leu Ser Leu Ala Ser Gly Glu Thr Val Val Leu His
            740                 745                 750

Met Gly Ile Ala His Ala Asn Gln Val Tyr Arg Glu Ile Leu Glu Thr
            755                 760                 765

Thr Asp Asn Gly Ile Ala Asn Asn Thr Asp Ile Phe Lys Thr Thr Asp

```
            770              775              780
Ser Asn Gly Asp Leu Ile Phe Thr Ala Ser Glu Ile His Gly Tyr Ser
785              790              795              800

Asn Val Gln Val Ser Gly Phe Leu Ser Val Trp Ala Pro Lys Asp Ala
            805              810              815

Thr Asp Asp Gln Asp Val Arg Thr Ala Ala Ser Glu Ser Thr Ser Asn
            820              825              830

Asp Gly Asn Thr Leu His Ser Asn Ala Ala Leu Asp Ser Asn Leu Ile
            835              840              845

Tyr Glu Gly Phe Ser Asn Phe Gln Ser Thr Pro Gln Ser Glu Ser Glu
850              855              860

Phe Ala Asn Val Lys Ile Ala Ala Asn Val Asn Leu Phe Lys Ser Trp
865              870              875              880

Gly Val Thr Ser Phe Gln Met Ala Pro Gln Tyr Arg Ser Ser Thr Asp
            885              890              895

Thr Ser Phe Leu Asp Ser Ile Ile Gln Asn Gly Tyr Ala Phe Thr Asp
            900              905              910

Arg Tyr Asp Leu Gly Phe Glu Thr Pro Thr Lys Tyr Gly Thr Asp Gln
            915              920              925

Gln Leu Arg Asp Ala Ile Lys Ala Leu His Ala Asn Gly Ile Gln Ala
            930              935              940

Met Ala Asp Phe Val Pro Asp Gln Ile Tyr Asn Leu Pro Gln Thr Glu
945              950              955              960

Leu Val Ser Val Ser Arg Thr Asp Ser Leu Gly Asn Gln Ser Ala Asn
            965              970              975

Ser Asn Ala Ala Asn Val Leu Tyr Val Ser His Thr Val Gly Gly Gly
            980              985              990

Glu Tyr Gln Ser Lys Tyr Gly Gly Glu Phe Leu Ala Ile Ile Lys Ser
            995              1000             1005

Lys Tyr Pro Ser Leu Phe Lys Thr Ile Gln Val Ser Thr Gly Leu
            1010             1015             1020

Pro Ile Asp Asp Ser Thr Lys Ile Lys Glu Trp Ser Ala Lys Tyr
            1025             1030             1035

Phe Asn Gly Ser Asn Ile Gln Gly Arg Gly Phe Gly Tyr Val Leu
            1040             1045             1050

Ser Asp Gly Gly Thr Gln Asn Tyr Phe Lys Val Ile Ser Asn Ser
            1055             1060             1065

Thr Asp Asp Phe Leu Pro Asn Gln Leu Thr Gly Lys Pro Thr
            1070             1075             1080

Met Thr Gly Phe Glu Gln Thr Ser Lys Gly Ile Val Tyr Tyr Ser
            1085             1090             1095

Lys Ser Gly Ile Gln Ala Lys Asn Gln Phe Val Lys Asp Asp Val
            1100             1105             1110

Ser Gly Asn Tyr Tyr Tyr Phe Asn Lys Asn Gly Leu Met Thr Val
            1115             1120             1125

Gly Ser Lys Thr Ile Asn Gly Lys Asn Tyr Met Phe Leu Pro Asn
            1130             1135             1140

Gly Val Glu Leu Arg Gly Ser Phe Leu Gln Thr Ala Asp Gly Thr
            1145             1150             1155

Val Asn Tyr Tyr Ala Thr Asn Gly Ala Gln Val Gln Asp Ser Tyr
            1160             1165             1170

Val Thr Asp Thr Glu Gly Asn Ser Tyr Tyr Phe Asp Gly Asp Gly
            1175             1180             1185
```

-continued

```
Glu Met Val Thr Gly Thr Tyr Thr Val Asp Gly His Ala Gln Tyr
    1190            1195                1200

Phe Asp Val Asn Gly Val Gln Thr Lys Gly Ala Ile Ile Thr Leu
    1205            1210                1215

Gly Gly Val Gln Arg Tyr Tyr Gln Ala Gly Asn Gly Asn Leu Ala
    1220            1225                1230

Thr Asn Gln Tyr Val Ser Tyr Asn Asn Ser Trp Tyr Tyr Ala Asn
    1235            1240                1245

Thr Lys Gly Glu Leu Val Thr Gly Val Gln Ser Ile Asn Gly Asn
    1250            1255                1260

Val Gln Tyr Phe Ala Ser Asn Gly Gln Gln Ile Lys Gly Gln Ile
    1265            1270                1275

Val Val Thr Gly Asn Gln Lys Ser Tyr Tyr Asp Ala Asn Thr Gly
    1280            1285                1290

Asn Leu Ile Lys Asn Asp Phe Leu Thr Pro Asp Gln Gly Lys Thr
    1295            1300                1305

Trp Tyr Tyr Ala Asp Gln Asp Gly Asn Leu Val Val Gly Ala Gln
    1310            1315                1320

Glu Val Asn Gly His Lys Leu Tyr Phe Asp Asp Asn Gly Ile Gln
    1325            1330                1335

Ile Lys Asp Gln Ile Ile Ser Asn Asp Gly Gln Gln Tyr Tyr Tyr
    1340            1345                1350

Gln Gly Gly Asn Gly Asp Leu Val Thr Asn Arg Tyr Ile Ser Tyr
    1355            1360                1365

Asn Asp Ser Trp Tyr Tyr Ala Asp Ala Thr Gly Val Leu Val Thr
    1370            1375                1380

Gly Gln Gln Ile Ile Asn Gly Glu Thr Gln Tyr Phe Arg Thr Asp
    1385            1390                1395

Gly Arg Gln Val Lys Gly Gln Ile Ile Ala Asp Gly Asp Lys Gln
    1400            1405                1410

His Tyr Tyr Asp Ala Asp Ser Gly Asn Leu Val Lys Asn Asn Phe
    1415            1420                1425

Val Thr Val Asp Gln Gly Lys Thr Trp Tyr Tyr Ala Asp Gln Asp
    1430            1435                1440

Gly Asn Leu Ser Leu Val Asp Arg His His His His His
    1445            1450                1455
```

<210> SEQ ID NO 3
<211> LENGTH: 4347
<212> TYPE: DNA
<213> ORGANISM: Weissella cibaria

<400> SEQUENCE: 3

```
atgtacaagt ccggaaagtt ttgggtagct gccggtgctt tgtttgttgg gctggcattc      60
gctggtaaca cgcaggctga tactgtatta ccaagtgaac aacgtgcaac ggagacgaca     120
cagacgacac agaccagtga agacacgtcc gccactaaga cgccggcatc ggcgtcgact     180
tcaagctcag tcaatgttga cacgagtgac ctgcctgaca gttcaagtac ggtagttgat     240
agtacaagtg caagtgcaag cgtagtgagt gatagcgtcg ctgtgccaga tactggatca     300
caatttacga gttcgtcagg gtcaatgtca tcatcatttg ttaagtcatc actagcggca     360
acaactagtg atgcttctgg cagtcagtcg gcggcggtga ctagcgcaac cgttagttcg     420
gtggccacga gtagttcagc atcttcagtg acaacagcca caagcgaatc agcagtgata     480
```

-continued

| | | | | |
|---|---|---|---|---|
| agcagcgccg | tgtcagatgg | ttaccatgat | gaaggtggtg | attgggtcta  ttatcgagct | 540 |
| ggaaaaaagt | tagtcggtcg | acaaacgatt | gatacgtttg | cggtttactt  tgacgccgat | 600 |
| ggcaaacaag | tcaagggtga | ttggcgtgaa | agtgatggta | accgtgcgta  ttatgatgga | 660 |
| caagaaggac | gagcattaac | gcaaacgcaa | gcagtcaatg | gcgttatcta  cggttttaat | 720 |
| caaagcggct | atcaaatcaa | gaatgatttc | ggccaaacag | cgaatcgaga  tacgtattat | 780 |
| ttcgacgcac | aaggtcatgt | tgtcacggga | atccaaacaa | ttgcaaacaa  ggtttatgat | 840 |
| tttgatgagc | aaggtcgaat | gctgaaaggc | attgccacgt | cagttgatga  caagatgatg | 900 |
| tattttgatg | atcaaacagg | tgttggacaa | ccggctgatc | atcctgaatt  caaccctgaa | 960 |
| acggaaccgg | ttcctgacga | caatatcaaa | cataatgcag | cacatggtac  gacaccagca | 1020 |
| gattttgatt | cgatggctgg | ctacctgacg | gctgatactt | ggtatcgccc  aaccgatatt | 1080 |
| ttggaaaatg | gtgagacgtg | gcgcgaatcg | caaccaactg | aatttcgacc  actgttagca | 1140 |
| acttggtggc | caacaaaaca | aactcaggcc | gattacgtga | actacatgaa  tcacgcatta | 1200 |
| gatatgtcaa | atgcaagtgt | gtcagctgcc | gattcagaag | ccacgctaac  tgcggcaacc | 1260 |
| gatgctattc | aagcggccgt | tgagcaccaa | attacggtgc | gccaatcaac  ggcctggtta | 1320 |
| cgtgaattaa | tggccgcgtt | tgttgtgaca | cagccacagt | ggaataaaac  cagtgaagat | 1380 |
| gttaatgatg | atcatttgca | aggtggggcg | ctaacatttg | agaataacgg  cgacacagac | 1440 |
| gctaattcgg | attatcgcct | catgaatcgc | acgccaacaa | atcagactgg  tgaacgcttg | 1500 |
| tatcacattg | atgactcgct | tggcggttac | gaattattgc | tggcaaatga  cgttgacaat | 1560 |
| tcaaatccac | aagttcaggc | agaacaattg | aattggttgt | actacttgat  gcattttggg | 1620 |
| gatattacag | ctgatgatcc | ggatgcaaat | tttgatgcca | tacggattga  tgcggtcgat | 1680 |
| aatgtcgatg | ctgatttact | tcaactagca | gctcagtatt | ccgtgatgc  ctatggcatg | 1740 |
| gccacgactg | acgcgacatc | aaataagcat | ctttcaatac | ttgaggattg  gagccataac | 1800 |
| gatccggcgt | atatgcaagc | acacggcaat | gatcaattaa | cgatggatga  ttatatgcac | 1860 |
| acacagttga | tttggtcatt | aaccaagcca | gaggcacaac | gtggcaccat  ggcacgcttt | 1920 |
| atggacttct | atctcaccaa | ccgtgctaat | gatgatacag | aaaacacggc  gcaacctagt | 1980 |
| tactcgtttg | tgcgtgccca | tgatagcgaa | gtgcaaacag | tcattgctga  aatcgtgacg | 2040 |
| aagctacatc | cagaagcagg | aaacgggtta | atgcctacgg | aagaacaaat  ggcagaagcg | 2100 |
| tttaagattt | acaatgcgga | ccaaaagaag | gccgttaaaa | cttacacgca  ctacaatatg | 2160 |
| ccatctgcat | acgccatgct | gttaacgaac | aaggatgtta | ttccacgaat  ttactatggt | 2220 |
| gacttgtaca | ctgacgatgg | gcaattcatg | gcgacaaaat | caccctattt  tgatgcgatt | 2280 |
| tcggctatgt | tacaagcgcg | cacgaagtat | gtagctggtg | gacaaacgat  ggcggttgac | 2340 |
| cagcacgacg | tcttgactag | cgttcggttt | ggtaagggtg | ccatgacggc  cagtgattta | 2400 |
| ggaaatgctg | agactcggac | tgagggtgtg | ggattaatta | ttagcaacaa  cccaaagttg | 2460 |
| caattgggac | aacaagataa | cgtggtgtta | cacatggcac | ttgcgcacgc  gaatcaagca | 2520 |
| ttccgagcag | ttgtactaac | gaccgcgacc | ggattaacca | tttataatga  cgatgatgct | 2580 |
| ccaattcgtt | ataccgataa | taagggtgat | ttaattttca | ataaccatga  cgtatatggc | 2640 |
| gtgttgaatc | cacaagtgtc | aggcttcttg | gcaatgtggg | tgccaactgg  tgcaccagcg | 2700 |
| aaccaggatg | cgcgatctac | tgcgtcaacc | aacagttcaa | cggatggatc  tgcctaccat | 2760 |
| tctaatgcgc | ctttagatag | tcaagtcatc | tttgaatcat | tttcgaattt  ccaggctatg | 2820 |
| ccaacaagcc | atgacacgta | caccaacgtt | gtgttagcca | atcatgctga  ccagttacac | 2880 |

```
gattgcggaa taacttcggt acagttagcg ccacaatacc ggtcttcaac cgacggaacc    2940 ttttttggatg cgattattca aaatggctat gccttcactg accgttatga tttagggttt    3000
ggtacgccaa ctaagtatgg ggatgatacg gatttgcgga acgtcatcaa agcattgcat    3060
gcaaatggca tgcaagtaat ggctgatttt gtgccggatc aattgtatac attaccaggt    3120
aaggaattgg tacaagtcac ccgaacaaac aatatgggtg agccagatac acactctgac    3180
atccaacata ttttatatgt gacgagcact cggggtggcg gtgagtatca gaaacagtac    3240
ggtggtgagt tccttgagcg gttacgtgcg ctctaccctg atttatttac gacacgtcaa    3300
atttcaaccg gacaaaccat tgatgattca gtaaaaatta agaatggtc agctaagtat    3360 ttgaatggta ccgcaattca aggccgtgga gctggctatg tgctacgtga taatggtaca    3420
aatgcttatt acaaggtgac ggcaaatgac ggtaatgtga acttaccaaa gcaattactc    3480
ggacaaccag tgatgaccgg attctatcac gaggcagatg gttatcattt tgaaacattg    3540
agtggtacgt cggccaaaga tgccttcatt atgggtgacg atggggcgct gtattatttt    3600
gatgatcagg gcgtcatggt aacgggtaag caacgtgtgc accaagacca gtatttcttc    3660
ctaccaaacg gtattgctct gacggatgcg tttgtacaaa gtgcggatgg tcaacgtcag    3720
tactatgata aaacaggtcg cctggtcatt aatcaatatg tgactgacca ccaagcaaat    3780
gcgttccggg ttgatgcaga cggtaacgtt gttcgtaacc aagctttgac tgttgacggc    3840
catgaacaat atttcggcac aaacggtgtc caagcgaaag cagtgctcat tcgaactgac    3900
gataatcagg cacggtacta cgaagccaat agtggtaatc tcgtgaagca acagtttatt    3960
cttgatacag atggacattg ttgtacgcc gatgctgcag gagacttggc acgcggacaa    4020
attacggttg gccaagacac gttgtattt gatgataata atcatcaggt aaaagatgat    4080
tttgtctatg atactaacgg tgtgcattat tttaatggca caacaggcgc tgaaatcaaa    4140
caagattacg cgtttcatga tggcaaatgg tactattttg atgatttggg acgaatggta    4200 accggttttgc agcgtattaa tggtgagtat cgctattttg atgctaatgg tgtgcaacta    4260
aagggtggta ccgtgaccga tccactaacg caccaaacgt acacttttga tgcgcaaact    4320
ggtgttggta cgttggtgac gttttaa                                         4347
```

<210> SEQ ID NO 4  
<211> LENGTH: 1448  
<212> TYPE: PRT  
<213> ORGANISM: Weissella cibaria

<400> SEQUENCE: 4

```
Met Tyr Lys Ser Gly Lys Phe Trp Val Ala Ala Gly Ala Leu Phe Val
1               5                   10                  15

Gly Leu Ala Phe Ala Gly Asn Thr Gln Ala Asp Thr Val Leu Pro Ser
            20                  25                  30

Glu Gln Arg Ala Thr Glu Thr Thr Gln Thr Thr Gln Thr Ser Glu Asp
        35                  40                  45

Thr Ser Ala Thr Lys Thr Pro Ala Ser Ala Ser Thr Ser Ser Ser Val
    50                  55                  60

Asn Val Asp Thr Ser Asp Leu Pro Asp Ser Ser Ser Thr Val Val Asp
65                  70                  75                  80

Ser Thr Ser Ala Ser Ala Ser Val Val Ser Asp Ser Val Ala Val Pro
                85                  90                  95

Asp Thr Gly Ser Gln Phe Thr Ser Ser Ser Gly Ser Met Ser Ser Ser
            100                 105                 110
```

```
Phe Val Lys Ser Ser Leu Ala Ala Thr Thr Ser Asp Ala Ser Gly Ser
            115                 120                 125

Gln Ser Ala Ala Val Thr Ser Ala Thr Val Ser Ser Val Ala Thr Ser
    130                 135                 140

Ser Ser Ala Ser Ser Val Thr Thr Ala Thr Ser Glu Ser Ala Val Ile
145                 150                 155                 160

Ser Ser Ala Val Ser Asp Gly Tyr His Asp Glu Gly Asp Trp Val
                165                 170                 175

Tyr Tyr Arg Ala Gly Lys Lys Leu Val Gly Arg Gln Thr Ile Asp Thr
                180                 185                 190

Phe Ala Val Tyr Phe Asp Ala Asp Gly Lys Gln Val Lys Gly Asp Trp
            195                 200                 205

Arg Glu Ser Asp Gly Asn Arg Ala Tyr Tyr Asp Gly Gln Glu Gly Arg
        210                 215                 220

Ala Leu Thr Gln Thr Gln Ala Val Asn Gly Val Ile Tyr Gly Phe Asn
225                 230                 235                 240

Gln Ser Gly Tyr Gln Ile Lys Asn Asp Phe Gly Gln Thr Ala Asn Arg
                245                 250                 255

Asp Thr Tyr Tyr Phe Asp Ala Gln Gly His Val Val Thr Gly Ile Gln
            260                 265                 270

Thr Ile Ala Asn Lys Val Tyr Asp Phe Asp Glu Gln Gly Arg Met Leu
        275                 280                 285

Lys Gly Ile Ala Thr Ser Val Asp Asp Lys Met Met Tyr Phe Asp Asp
290                 295                 300

Gln Thr Gly Val Gly Gln Pro Ala Asp His Pro Glu Phe Asn Pro Glu
305                 310                 315                 320

Thr Glu Pro Val Pro Asp Asp Asn Ile Lys His Asn Ala Ala His Gly
                325                 330                 335

Thr Thr Pro Ala Asp Phe Asp Ser Met Ala Gly Tyr Leu Thr Ala Asp
            340                 345                 350

Thr Trp Tyr Arg Pro Thr Asp Ile Leu Glu Asn Gly Glu Thr Trp Arg
        355                 360                 365

Glu Ser Gln Pro Thr Glu Phe Arg Pro Leu Leu Ala Thr Trp Trp Pro
    370                 375                 380

Thr Lys Gln Thr Gln Ala Asp Tyr Val Asn Tyr Met Asn His Ala Leu
385                 390                 395                 400

Asp Met Ser Asn Ala Ser Val Ser Ala Ala Asp Ser Glu Ala Thr Leu
                405                 410                 415

Thr Ala Ala Thr Asp Ala Ile Gln Ala Ala Val Glu His Gln Ile Thr
            420                 425                 430

Val Arg Gln Ser Thr Ala Trp Leu Arg Glu Leu Met Ala Ala Phe Val
        435                 440                 445

Val Thr Gln Pro Gln Trp Asn Lys Thr Ser Glu Asp Val Asn Asp Asp
    450                 455                 460

His Leu Gln Gly Gly Ala Leu Thr Phe Glu Asn Gly Asp Thr Asp
465                 470                 475                 480

Ala Asn Ser Asp Tyr Arg Leu Met Asn Arg Thr Pro Thr Asn Gln Thr
                485                 490                 495

Gly Glu Arg Leu Tyr His Ile Asp Asp Ser Leu Gly Gly Tyr Glu Leu
            500                 505                 510

Leu Leu Ala Asn Asp Val Asp Asn Ser Asn Pro Gln Val Gln Ala Glu
        515                 520                 525
```

-continued

```
Gln Leu Asn Trp Leu Tyr Tyr Leu Met His Phe Gly Asp Ile Thr Ala
    530                 535                 540

Asp Asp Pro Asp Ala Asn Phe Asp Ala Ile Arg Ile Asp Ala Val Asp
545                 550                 555                 560

Asn Val Asp Ala Asp Leu Leu Gln Leu Ala Ala Gln Tyr Phe Arg Asp
                565                 570                 575

Ala Tyr Gly Met Ala Thr Thr Asp Ala Thr Ser Asn Lys His Leu Ser
            580                 585                 590

Ile Leu Glu Asp Trp Ser His Asn Asp Pro Ala Tyr Met Gln Ala His
        595                 600                 605

Gly Asn Asp Gln Leu Thr Met Asp Asp Tyr Met His Thr Gln Leu Ile
    610                 615                 620

Trp Ser Leu Thr Lys Pro Glu Ala Gln Arg Gly Thr Met Ala Arg Phe
625                 630                 635                 640

Met Asp Phe Tyr Leu Thr Asn Arg Ala Asn Asp Asp Thr Glu Asn Thr
                645                 650                 655

Ala Gln Pro Ser Tyr Ser Phe Val Arg Ala His Asp Ser Glu Val Gln
            660                 665                 670

Thr Val Ile Ala Glu Ile Val Thr Lys Leu His Pro Glu Ala Gly Asn
        675                 680                 685

Gly Leu Met Pro Thr Glu Glu Gln Met Ala Glu Ala Phe Lys Ile Tyr
    690                 695                 700

Asn Ala Asp Gln Lys Lys Ala Val Lys Thr Tyr Thr His Tyr Asn Met
705                 710                 715                 720

Pro Ser Ala Tyr Ala Met Leu Leu Thr Asn Lys Asp Val Ile Pro Arg
                725                 730                 735

Ile Tyr Tyr Gly Asp Leu Tyr Thr Asp Asp Gly Gln Phe Met Ala Thr
            740                 745                 750

Lys Ser Pro Tyr Phe Asp Ala Ile Ser Ala Met Leu Gln Ala Arg Thr
        755                 760                 765

Lys Tyr Val Ala Gly Gly Gln Thr Met Ala Val Asp Gln His Asp Val
    770                 775                 780

Leu Thr Ser Val Arg Phe Gly Lys Gly Ala Met Thr Ala Ser Asp Leu
785                 790                 795                 800

Gly Asn Ala Glu Thr Arg Thr Glu Gly Val Gly Leu Ile Ile Ser Asn
                805                 810                 815

Asn Pro Lys Leu Gln Leu Gly Gln Gln Asp Asn Val Val Leu His Met
            820                 825                 830

Gly Leu Ala His Ala Asn Gln Ala Phe Arg Ala Val Val Leu Thr Thr
        835                 840                 845

Ala Thr Gly Leu Thr Ile Tyr Asn Asp Asp Ala Pro Ile Arg Tyr
    850                 855                 860

Thr Asp Asn Lys Gly Asp Leu Ile Phe Asn Asn His Asp Val Tyr Gly
865                 870                 875                 880

Val Leu Asn Pro Gln Val Ser Gly Phe Leu Ala Met Trp Val Pro Thr
                885                 890                 895

Gly Ala Pro Ala Asn Gln Asp Ala Arg Ser Thr Ala Ser Thr Asn Ser
            900                 905                 910

Ser Thr Asp Gly Ser Ala Tyr His Ser Asn Ala Ala Leu Asp Ser Gln
        915                 920                 925

Val Ile Phe Glu Ser Phe Ser Asn Phe Gln Ala Met Pro Thr Ser His
    930                 935                 940

Asp Thr Tyr Thr Asn Val Val Leu Ala Asn His Ala Asp Gln Leu His
```

-continued

```
            945                 950                 955                 960
Asp Trp Gly Ile Thr Ser Val Gln Leu Ala Pro Gln Tyr Arg Ser Ser
                    965                 970                 975
Thr Asp Gly Thr Phe Leu Asp Ala Ile Ile Gln Asn Gly Tyr Ala Phe
                    980                 985                 990
Thr Asp Arg Tyr Asp Leu Gly Phe Gly Thr Pro Thr Lys Tyr Gly Asp
            995                 1000                1005
Asp Thr Asp Leu Arg Asn Val Ile Lys Ala Leu His Ala Asn Gly
    1010                1015                1020
Met Gln Val Met Ala Asp Phe Val Pro Asp Gln Leu Tyr Thr Leu
    1025                1030                1035
Pro Gly Lys Glu Leu Val Gln Val Thr Arg Thr Asn Asn Met Gly
    1040                1045                1050
Glu Pro Asp Thr His Ser Asp Ile Gln His Ile Leu Tyr Val Thr
    1055                1060                1065
Ser Thr Arg Gly Gly Gly Glu Tyr Gln Lys Gln Tyr Gly Gly Glu
    1070                1075                1080
Phe Leu Glu Arg Leu Arg Ala Leu Tyr Pro Asp Leu Phe Thr Thr
    1085                1090                1095
Arg Gln Ile Ser Thr Gly Gln Thr Ile Asp Asp Ser Val Lys Ile
    1100                1105                1110
Lys Glu Trp Ser Ala Lys Tyr Leu Asn Gly Thr Ala Ile Gln Gly
    1115                1120                1125
Arg Gly Ala Gly Tyr Val Leu Arg Asp Asn Gly Thr Asn Ala Tyr
    1130                1135                1140
Tyr Lys Val Thr Ala Asn Asp Gly Asn Val Asn Leu Pro Lys Gln
    1145                1150                1155
Leu Leu Gly Gln Pro Val Met Thr Gly Phe Tyr His Glu Ala Asp
    1160                1165                1170
Gly Tyr His Phe Glu Thr Leu Ser Gly Thr Ser Ala Lys Asp Ala
    1175                1180                1185
Phe Ile Met Gly Asp Asp Gly Ala Leu Tyr Tyr Phe Asp Asp Gln
    1190                1195                1200
Gly Val Met Val Thr Gly Lys Gln Arg Val His Gln Asp Gln Tyr
    1205                1210                1215
Phe Phe Leu Pro Asn Gly Ile Ala Leu Thr Asp Ala Phe Val Gln
    1220                1225                1230
Ser Ala Asp Gly Gln Arg Gln Tyr Tyr Asp Lys Thr Gly Arg Leu
    1235                1240                1245
Val Ile Asn Gln Tyr Val Thr Asp His Gln Ala Asn Ala Phe Arg
    1250                1255                1260
Val Asp Ala Asp Gly Asn Val Val Arg Asn Gln Ala Leu Thr Val
    1265                1270                1275
Asp Gly His Glu Gln Tyr Phe Gly Thr Asn Gly Val Gln Ala Lys
    1280                1285                1290
Ala Val Leu Ile Arg Thr Asp Asp Asn Gln Ala Arg Tyr Tyr Glu
    1295                1300                1305
Ala Asn Ser Gly Asn Leu Val Lys Gln Gln Phe Ile Leu Asp Thr
    1310                1315                1320
Asp Gly His Trp Leu Tyr Ala Asp Ala Ala Gly Asp Leu Ala Arg
    1325                1330                1335
Gly Gln Ile Thr Val Gly Gln Asp Thr Leu Tyr Phe Asp Asp Asn
    1340                1345                1350
```

Asn His Gln Val Lys Asp Asp Phe Val Tyr Asp Thr Asn Gly Val
1355                 1360                 1365

His Tyr Phe Asn Gly Thr Thr Gly Ala Glu Ile Lys Gln Asp Tyr
    1370                 1375                 1380

Ala Phe His Asp Gly Lys Trp Tyr Tyr Phe Asp Asp Leu Gly Arg
1385                 1390                 1395

Met Val Thr Gly Leu Gln Arg Ile Asn Gly Glu Tyr Arg Tyr Phe
1400                 1405                 1410

Asp Ala Asn Gly Val Gln Leu Lys Gly Gly Thr Val Thr Asp Pro
1415                 1420                 1425

Leu Thr His Gln Thr Tyr Thr Phe Asp Ala Gln Thr Gly Val Gly
1430                 1435                 1440

Thr Leu Val Thr Phe
1445

<210> SEQ ID NO 5
<211> LENGTH: 1422
<212> TYPE: PRT
<213> ORGANISM: Weissella cibaria
<220> FEATURE:
<221> NAME/KEY: MISC_FEATURE
<222> LOCATION: (1)..(1422)
<223> OTHER INFORMATION: mature 2919 gtf

<400> SEQUENCE: 5

Asp Thr Val Leu Pro Ser Glu Gln Arg Ala Thr Glu Thr Thr Gln Thr
1               5                   10                  15

Thr Gln Thr Ser Glu Asp Thr Ser Ala Thr Lys Thr Pro Ala Ser Ala
            20                  25                  30

Ser Thr Ser Ser Val Asn Val Asp Thr Ser Asp Leu Pro Asp Ser
        35                  40                  45

Ser Ser Thr Val Val Asp Ser Thr Ser Ala Ser Ala Ser Val Val Ser
    50                  55                  60

Asp Ser Val Ala Val Pro Asp Thr Gly Ser Gln Phe Thr Ser Ser Ser
65                  70                  75                  80

Gly Ser Met Ser Ser Ser Phe Val Lys Ser Ser Leu Ala Ala Thr Thr
                85                  90                  95

Ser Asp Ala Ser Gly Ser Gln Ser Ala Ala Val Thr Ser Ala Thr Val
            100                 105                 110

Ser Ser Val Ala Thr Ser Ser Ala Ser Ser Val Thr Thr Ala Thr
        115                 120                 125

Ser Glu Ser Ala Val Ile Ser Ser Ala Val Ser Asp Gly Tyr His Asp
130                 135                 140

Glu Gly Gly Asp Trp Val Tyr Tyr Arg Ala Gly Lys Lys Leu Val Gly
145                 150                 155                 160

Arg Gln Thr Ile Asp Thr Phe Ala Val Tyr Phe Asp Ala Asp Gly Lys
                165                 170                 175

Gln Val Lys Gly Asp Trp Arg Glu Ser Asp Gly Asn Arg Ala Tyr Tyr
            180                 185                 190

Asp Gly Gln Glu Gly Arg Ala Leu Thr Gln Thr Gln Ala Val Asn Gly
        195                 200                 205

Val Ile Tyr Gly Phe Asn Gln Ser Gly Tyr Gln Ile Lys Asn Asp Phe
    210                 215                 220

Gly Gln Thr Ala Asn Arg Asp Thr Tyr Tyr Phe Asp Ala Gln Gly His
225                 230                 235                 240

```
Val Val Thr Gly Ile Gln Thr Ile Ala Asn Lys Val Tyr Asp Phe Asp
            245                 250                 255

Glu Gln Gly Arg Met Leu Lys Gly Ile Ala Thr Ser Val Asp Asp Lys
        260                 265                 270

Met Met Tyr Phe Asp Asp Gln Thr Gly Val Gly Gln Pro Ala Asp His
            275                 280                 285

Pro Glu Phe Asn Pro Glu Thr Glu Pro Val Pro Asp Asp Asn Ile Lys
        290                 295                 300

His Asn Ala Ala His Gly Thr Thr Pro Ala Asp Phe Asp Ser Met Ala
305                 310                 315                 320

Gly Tyr Leu Thr Ala Asp Thr Trp Tyr Arg Pro Thr Asp Ile Leu Glu
            325                 330                 335

Asn Gly Glu Thr Trp Arg Glu Ser Gln Pro Thr Glu Phe Arg Pro Leu
        340                 345                 350

Leu Ala Thr Trp Trp Pro Thr Lys Gln Thr Gln Ala Asp Tyr Val Asn
            355                 360                 365

Tyr Met Asn His Ala Leu Asp Met Ser Asn Ala Ser Val Ser Ala Ala
        370                 375                 380

Asp Ser Glu Ala Thr Leu Thr Ala Ala Thr Asp Ala Ile Gln Ala Ala
385                 390                 395                 400

Val Glu His Gln Ile Thr Val Arg Gln Ser Thr Ala Trp Leu Arg Glu
            405                 410                 415

Leu Met Ala Ala Phe Val Val Thr Gln Pro Gln Trp Asn Lys Thr Ser
        420                 425                 430

Glu Asp Val Asn Asp Asp His Leu Gln Gly Gly Ala Leu Thr Phe Glu
            435                 440                 445

Asn Asn Gly Asp Thr Asp Ala Asn Ser Asp Tyr Arg Leu Met Asn Arg
450                 455                 460

Thr Pro Thr Asn Gln Thr Gly Glu Arg Leu Tyr His Ile Asp Asp Ser
465                 470                 475                 480

Leu Gly Gly Tyr Glu Leu Leu Leu Ala Asn Asp Val Asp Asn Ser Asn
            485                 490                 495

Pro Gln Val Gln Ala Glu Gln Leu Asn Trp Leu Tyr Tyr Leu Met His
        500                 505                 510

Phe Gly Asp Ile Thr Ala Asp Asp Pro Asp Ala Asn Phe Asp Ala Ile
            515                 520                 525

Arg Ile Asp Ala Val Asp Asn Val Asp Ala Asp Leu Leu Gln Leu Ala
        530                 535                 540

Ala Gln Tyr Phe Arg Asp Ala Tyr Gly Met Ala Thr Thr Asp Ala Thr
545                 550                 555                 560

Ser Asn Lys His Leu Ser Ile Leu Glu Asp Trp Ser His Asn Asp Pro
            565                 570                 575

Ala Tyr Met Gln Ala His Gly Asn Asp Gln Leu Thr Met Asp Asp Tyr
        580                 585                 590

Met His Thr Gln Leu Ile Trp Ser Leu Thr Lys Pro Glu Ala Gln Arg
            595                 600                 605

Gly Thr Met Ala Arg Phe Met Asp Phe Tyr Leu Thr Asn Arg Ala Asn
        610                 615                 620

Asp Asp Thr Glu Asn Thr Ala Gln Pro Ser Tyr Ser Phe Val Arg Ala
625                 630                 635                 640

His Asp Ser Glu Val Gln Thr Val Ile Ala Glu Ile Val Thr Lys Leu
            645                 650                 655

His Pro Glu Ala Gly Asn Gly Leu Met Pro Thr Glu Glu Gln Met Ala
```

```
                    660                 665                 670
Glu Ala Phe Lys Ile Tyr Asn Ala Asp Gln Lys Lys Ala Val Lys Thr
            675                 680                 685

Tyr Thr His Tyr Asn Met Pro Ser Ala Tyr Ala Met Leu Leu Thr Asn
        690                 695                 700

Lys Asp Val Ile Pro Arg Ile Tyr Tyr Gly Asp Leu Tyr Thr Asp Asp
705                 710                 715                 720

Gly Gln Phe Met Ala Thr Lys Ser Pro Tyr Phe Asp Ala Ile Ser Ala
                725                 730                 735

Met Leu Gln Ala Arg Thr Lys Tyr Val Ala Gly Gly Gln Thr Met Ala
            740                 745                 750

Val Asp Gln His Asp Val Leu Thr Ser Val Arg Phe Gly Lys Gly Ala
        755                 760                 765

Met Thr Ala Ser Asp Leu Gly Asn Ala Glu Thr Arg Thr Glu Gly Val
    770                 775                 780

Gly Leu Ile Ile Ser Asn Asn Pro Lys Leu Gln Leu Gly Gln Gln Asp
785                 790                 795                 800

Asn Val Val Leu His Met Gly Leu Ala His Ala Asn Gln Ala Phe Arg
                805                 810                 815

Ala Val Val Leu Thr Thr Ala Thr Gly Leu Thr Ile Tyr Asn Asp Asp
            820                 825                 830

Asp Ala Pro Ile Arg Tyr Thr Asp Asn Lys Gly Asp Leu Ile Phe Asn
        835                 840                 845

Asn His Asp Val Tyr Gly Val Leu Asn Pro Gln Val Ser Gly Phe Leu
    850                 855                 860

Ala Met Trp Val Pro Thr Gly Ala Pro Ala Asn Gln Asp Ala Arg Ser
865                 870                 875                 880

Thr Ala Ser Thr Asn Ser Ser Thr Asp Gly Ser Ala Tyr His Ser Asn
                885                 890                 895

Ala Ala Leu Asp Ser Gln Val Ile Phe Glu Ser Phe Ser Asn Phe Gln
            900                 905                 910

Ala Met Pro Thr Ser His Asp Thr Tyr Thr Asn Val Val Leu Ala Asn
        915                 920                 925

His Ala Asp Gln Leu His Asp Trp Gly Ile Thr Ser Val Gln Leu Ala
    930                 935                 940

Pro Gln Tyr Arg Ser Ser Thr Asp Gly Thr Phe Leu Asp Ala Ile Ile
945                 950                 955                 960

Gln Asn Gly Tyr Ala Phe Thr Asp Arg Tyr Asp Leu Gly Phe Gly Thr
                965                 970                 975

Pro Thr Lys Tyr Gly Asp Asp Thr Asp Leu Arg Asn Val Ile Lys Ala
            980                 985                 990

Leu His Ala Asn Gly Met Gln Val Met Ala Asp Phe Val Pro Asp Gln
        995                 1000                1005

Leu Tyr Thr Leu Pro Gly Lys Glu Leu Val Gln Val Thr Arg Thr
    1010                1015                1020

Asn Asn Met Gly Glu Pro Asp Thr His Ser Asp Ile Gln His Ile
    1025                1030                1035

Leu Tyr Val Thr Ser Thr Arg Gly Gly Gly Glu Tyr Gln Lys Gln
    1040                1045                1050

Tyr Gly Gly Glu Phe Leu Glu Arg Leu Arg Ala Leu Tyr Pro Asp
    1055                1060                1065

Leu Phe Thr Thr Arg Gln Ile Ser Thr Gly Gln Thr Ile Asp Asp
    1070                1075                1080
```

Ser Val Lys Ile Lys Glu Trp Ser Ala Lys Tyr Leu Asn Gly Thr
1085                1090                1095

Ala Ile Gln Gly Arg Gly Ala Gly Tyr Val Leu Arg Asp Asn Gly
    1100                1105                1110

Thr Asn Ala Tyr Tyr Lys Val Thr Ala Asn Asp Gly Asn Val Asn
1115                1120                1125

Leu Pro Lys Gln Leu Leu Gly Gln Pro Val Met Thr Gly Phe Tyr
    1130                1135                1140

His Glu Ala Asp Gly Tyr His Phe Glu Thr Leu Ser Gly Thr Ser
1145                1150                1155

Ala Lys Asp Ala Phe Ile Met Gly Asp Asp Gly Ala Leu Tyr Tyr
    1160                1165                1170

Phe Asp Asp Gln Gly Val Met Val Thr Gly Lys Gln Arg Val His
1175                1180                1185

Gln Asp Gln Tyr Phe Phe Leu Pro Asn Gly Ile Ala Leu Thr Asp
    1190                1195                1200

Ala Phe Val Gln Ser Ala Asp Gly Gln Arg Gln Tyr Tyr Asp Lys
1205                1210                1215

Thr Gly Arg Leu Val Ile Asn Gln Tyr Val Thr Asp His Gln Ala
    1220                1225                1230

Asn Ala Phe Arg Val Asp Ala Asp Gly Asn Val Arg Asn Gln
1235                1240                1245

Ala Leu Thr Val Asp Gly His Glu Gln Tyr Phe Gly Thr Asn Gly
    1250                1255                1260

Val Gln Ala Lys Ala Val Leu Ile Arg Thr Asp Asp Asn Gln Ala
1265                1270                1275

Arg Tyr Tyr Glu Ala Asn Ser Gly Asn Leu Val Lys Gln Gln Phe
    1280                1285                1290

Ile Leu Asp Thr Asp Gly His Trp Leu Tyr Ala Asp Ala Ala Gly
1295                1300                1305

Asp Leu Ala Arg Gly Gln Ile Thr Val Gly Gln Asp Thr Leu Tyr
    1310                1315                1320

Phe Asp Asp Asn Asn His Gln Val Lys Asp Asp Phe Val Tyr Asp
1325                1330                1335

Thr Asn Gly Val His Tyr Phe Asn Gly Thr Thr Gly Ala Glu Ile
    1340                1345                1350

Lys Gln Asp Tyr Ala Phe His Asp Gly Lys Trp Tyr Tyr Phe Asp
1355                1360                1365

Asp Leu Gly Arg Met Val Thr Gly Leu Gln Arg Ile Asn Gly Glu
    1370                1375                1380

Tyr Arg Tyr Phe Asp Ala Asn Gly Val Gln Leu Lys Gly Gly Thr
1385                1390                1395

Val Thr Asp Pro Leu Thr His Gln Thr Tyr Thr Phe Asp Ala Gln
    1400                1405                1410

Thr Gly Val Gly Thr Leu Val Thr Phe
1415                1420

<210> SEQ ID NO 6
<211> LENGTH: 4269
<212> TYPE: DNA
<213> ORGANISM: Artificial sequence
<220> FEATURE:
<223> OTHER INFORMATION: 2919 gtf with heterologous signal sequence

<400> SEQUENCE: 6

```
gacacagtcc ttccgtcaga acaaagagcc acggagacga cacagacaac acaaacaagc    60
gaagacacaa gcgccacaaa gacgcctgct agcgcttcaa cgagcagctc agtgaacgtg   120
gacacatcag atcttccgga cagctcaagc acggtggtgg attcaacgtc agcctcagca   180
agcgtcgtgt cagactcagt cgctgtccct gatacgggat cacagttcac atcatcaagc   240
ggcagcatgt caagcagctt tgttaaaagc tcactggcag ctacgacgtc agatgcttca   300
ggctcacaaa gcgccgctgt gacatcagca acagtttcaa gcgtggcgac gagctcatca   360
gcgtcatcag ttacaacagc cacgagcgaa tcagcggtta ttagctcagc agttagcgat   420
ggctatcacg atgaaggagg cgattgggtt tactacagag ctggcaaaaa actggttggc   480
agacaaacga ttgatacatt tgccgtttac ttcgatgcag atggaaaaca ggttaaagga   540
gactggagag agtcagacgg aaacagagcg tactatgatg ccaagaagg cagagccctt   600 acgcaaacac aggcagttaa cggagtcatc tatggattta atcaatcagg atatcagatt   660
aagaacgatt tcggccagac ggctaacaga gacacgtatt actttgatgc tcaaggacat   720
gtggttacgg gcatccagac aattgcaaat aaagtttatg atttcgatga acaaggaaga   780
atgctgaaag gaattgccac gtcagtcgac gataaaatga tgtatttcga cgaccaaacg   840
ggcgtgggcc aacctgccga ccacccctgag tttaatccgg aaacggagcc ggtcccggat   900
gacaacatta acataacgc tgcgcacgga acgacacctg ctgattttga tagcatggcc   960
ggatacctta cggcggatac atggtataga cctacagaca ttctggagaa tggcgaaaca  1020
tggagagaaa gccagcctac ggagttcaga ccgcttcttg ccacatggtg gcctacgaaa  1080
caaacgcaag cagattatgt taattacatg aaccatgctc tggatatgtc aaatgcgagc  1140
gtgagcgctg ccgatagcga ggcaacactt acagccgcga cggatgccat ccaagctgca  1200
gtcgaacatc aaattacagt gagacagtca acggcatggc ttagagaact tatggcggca  1260
tttgtcgtga cgcaaccgca gtggaataaa acatcagagg atgtcaacga cgatcacctg  1320
caaggaggag cgcttacatt cgaaaataac ggcgatacgg acgcaaatag cgattacaga  1380
cttatgaata aacgcctac aaaccaaaca ggagaaagac tttaccacat tgacgactca  1440
cttggaggat acgaactgct tctggccaac gatgttgata acagcaatcc tcaagtgcag  1500
gctgagcaac ttaattggct ttattacctg atgcattttg gcgatattac agctgacgac  1560
cctgacgcca acttcgacgc gattagaatc gatgcggtcg ataatgtcga cgcagacctt  1620
cttcaactgg ctgctcaata tttcagagac gcatacggaa tggcaacaac agacgctaca  1680
agcaataaac atctgtcaat tcttgaagac tggtcacata tgatccggc gtacatgcaa  1740 gctcatggaa acgatcaact tacgatggat gactatatgc acacacaact tatttggtca  1800
ctgacaaaac cggaggctca agaggaaca atggctagat ttatggactt ttatcttaca  1860
aatagagcga acgatgatac agaaaatacg gctcaacctt catattcatt cgttagagca  1920
catgattcag aagttcaaac agtgattgca gaaattgtta caaaactgca tcctgaggcg  1980
ggcaatggac tgatgccgac agaagagcaa atggcagaag cctttaagat ctataatgcc  2040
gatcagaaaa aagcagtgaa acatatataca cactacaata tgccttcagc ttatgcaatg  2100
ctgcttacga ataaagacgt cattcctaga atttactatg gagatcttta tacagatgat  2160
ggacaattca tggctacaaa gtcaccttat tttgacgcta tcagcgcgat gctgcaagcg  2220
agaacgaagt atgtcgcagg cggccagacg atggcagtgg atcagcacga cgtgcttaca  2280
agcgtgagat ttggcaaagg cgcaatgaca gcatcagacc tgggcaatgc agagacaaga  2340
```

-continued

| | |
|---|---|
| acggagggag ttggccttat catttcaaat aatccgaaac tgcaactggg ccagcaggat | 2400 |
| aacgtcgttc ttcatatggg cctggcgcac gcaaaccagg cctttagagc agttgttctt | 2460 |
| acaacagcga cgggcctgac aatctacaat gacgatgatg caccgattag atatacagac | 2520 |
| aataaaggcg acctgatttt caacaaccat gatgtctacg gcgtcctgaa cccgcaggtt | 2580 |
| tcaggcttcc tggccatgtg ggttcctaca ggcgcacctg ctaaccaaga tgctagatca | 2640 |
| acagcaagca caaactcatc aacggatggc tcagcatatc attcaaatgc tgcgctggat | 2700 |
| tcacaagtta ttttcgaatc attctcaaat ttccaagcaa tgccgacgtc acatgacaca | 2760 |
| tacacgaatg tggttctggc caaccacgcc gaccagcttc acgattgggg cattacatca | 2820 |
| gtgcagctgg caccgcagta tagaagctca acagacggca cgttcctgga tgcaattatc | 2880 |
| cagaatggct atgccttcac agatagatac gatcttggct ttggcacacc tacaaaatac | 2940 |
| ggcgacgaca cggatctgag aaatgtgatt aaggcgcttc atgccaacgg catgcaggtt | 3000 |
| atggccgact tcgtcccgga ccaactttat acacttccgg gaaaagagct ggtgcaagtc | 3060 |
| acgagaacga ataacatggg cgaacctgat acacactcag acattcaaca tattctgtac | 3120 |
| gttacgtcaa cgagaggcgg aggagaatat caaaaacagt atggcggcga gtttcttgaa | 3180 |
| agactgagag cactgtaccc tgaccttttt acgacaagac aaattagcac aggccaaaca | 3240 |
| attgacgatt cagtgaagat caaagagtgg tcagctaagt acctgaacgg cacagctatc | 3300 |
| caaggaagag gcgcaggcta tgttctgaga gataatggca caaatgccta ctacaaagtt | 3360 |
| acagcgaatg atggaaatgt caatcttcct aaacaacttc ttggacagcc ggttatgacg | 3420 |
| ggcttctacc acgaggccga tggatatcac ttcgagacac tgtcaggaac atcagccaag | 3480 |
| gatgcgttta tcatgggaga tgacggagcg ctttattact ttgatgacca aggcgttatg | 3540 |
| gtgacaggaa aacagagagt tcatcaagac cagtacttct ttctgcctaa cggaattgct | 3600 |
| ctgacagacg cgttcgttca atcagcagac ggacaaagac agtattatga caaaacggga | 3660 |
| agacttgtta tcaaccagta tgtgacagat caccaagcta atgcttttag agtcgatgct | 3720 |
| gatggcaacg tggttagaaa ccaagcactt acagttgatg gacacgaaca atatttcgga | 3780 |
| acaaatggag tccaggctaa agcggttctg attagaacag atgataatca agcgagatat | 3840 |
| tacgaagcta actcaggcaa tctggttaag caacaattca ttcttgacac agatggccac | 3900 |
| tggctgtacg ccgatgcagc cggagatctt gctagaggac agattacagt gggacaggat | 3960 |
| acactgtatt tcgacgataa taaccaccaa gttaaggatg attttgtcta tgatacaaac | 4020 |
| ggcgttcatt atttcaatgg aacgacagga gctgagatta acaagatta cgcatttcac | 4080 |
| gacggcaaat ggtactactt cgatgatctg ggaagaatgg ttacaggact gcaaagaatt | 4140 |
| aacgcgaat atagatattt tgacgctaat ggcgtccaac ttaagggagg aacagtcacg | 4200 |
| gaccctctta cacatcaaac atatacattt gatgctcaaa caggcgttgg aacgctggtc | 4260 |
| acgttttga | 4269 |

<210> SEQ ID NO 7
<211> LENGTH: 4392
<212> TYPE: DNA
<213> ORGANISM: Lactobacillus fermentum

<400> SEQUENCE: 7

| | |
|---|---|
| ttgcaagacg agtcacagaa gtttagaaaa aagatgtata agtccggaaa gttttgggta | 60 |
| gctgccggtg ctttgtttgt tgggctggca ttcgctggta acgcgcaggc agatactgta | 120 |
| ttaccaagtg aacaacgtgc aacacagacg acacagacga cacagaccag tgaagacacg | 180 |

```
tccgccacta agacgccggc atcggcgtcg acttcaagct cagacaatgt tgacacgagt      240
gacctgcctg acagtgcaag tgcggtggtt gatagtgcag ttacaagtac aagtacaagt      300
gcaagtgtag tgagtgatag cgtcgccgtg ccagatactg gatcacaatt tatgagttcg      360
tcagcgccag cgtcatcagc gtttgttaaa ccgtcactaa cgtcaacaac tagtggtgct      420
tccggcagtc agtcatcagc ggtgactagc gcaaacgata gttcggtggc aactagtagt      480
tcagcatctt cagtgacaac agccacaagt gaatcggctg tggtaagcag cgccgtgtca      540
gatggttacc atgatgaagg tggtgattgg gtctattatc gagctgggaa aaagttactc      600
ggtcgacaaa cgattgatac gtttgcggtt tactttgacg ccgatggcaa acaagtcaag      660
ggtgattggc gtgaaagtga tggtaaacgt gcgtattatg atgggcaaga aggacgagca      720
ttaacgcaaa cgcaagcagt caatggcgtt atctacggtt ttaatcaaag cggctatcaa      780
atcaagaatg atttcggcca aacagcgaat cgagatacgt attatttcga cgcacaaggt      840
catgttgtca cgggaatcca acaattgca acaaggttt atgattttga tgagcaaggt      900
cgaatgctga aaggcattgc cacgtcagtt gatgacaaga tgatgtattt tgatgatcaa      960
acaggtgttg acaaccggc tgatcatcct gaattcaacc ctgaaacgga accggttcct     1020
gacgacaata tcaaacataa tgcagcacat ggtacgacac cagaagattt tgattcgatg     1080
gctgactacc tgacggctga tacttggtat cgcccaaccg atattttgga aaatggtgag     1140
acgtggcgcg aatcgcaacc aactgaattt cgaccactgt tagcaacttg gtggccaaca     1200
aaacaaaccc aggccgatta cgtgaactac atgaatcacg cattagatat ggcaaatgca     1260
ggtgtgtcag ctgctgattc agaagccacg ttaactgcgg caaccgatgc tattcaagcg     1320
gttgttgagc accaaatcac ggtgcgtcaa tcaacggctt ggttacgtga attaatggcc     1380
gcatttgttg tgacacagcc acagtggaat aaaacaagtg aagatgtgaa tgatgatcat     1440
ttgcaaggtg gggcattaac atttgaaaat aacggcgaca cagacgctaa ttcggattat     1500
cgcctcatga accgcacgcc aacaaatcag actggcgaac gcttgtacca cattgatgac     1560
tcacttggtg gttacgaatt attgctggca aatgacgttg acaattcaaa tccacaagtt     1620
caggcagaac aattgaattg gttgtactac ttaatgcatt ttgggatat tacagctgat     1680 gatccggacg caaattttga tgccatacgg attgatgcgg tcgataatgt cgatgctgat     1740
ttacttcaac tagcagccca gtatttccgg gatgccatg gcatggctac aactgacgca     1800
acatcaaata gcatctttc aattcttgag gattggagcc ataacgatcc ggcgtatatg     1860
caagcacacg gcaatgatca attaacgatg gatgattata tgcacacaca gttgatttgg     1920
tcattaacca gcccgaggc acaacgcggg accatggcac gctttatgga cttctatctc     1980
accaaccgtg ctaatgatga tacagaaaac acggcgcaac ctagttactc gtttgtgcgt     2040
gcccatgata gcgaagtaca aacagtcatt gctgagatcg tgacgaagct gcatccagaa     2100
gcaggaaatg ggttaatgcc tacggaagaa caaatgcag aagcgtttaa gatttacaat     2160
gcggaccaaa agaaggccgt taagacttac acacattaca atatgccatc tgcatacgcc     2220
atgctgttaa cgaacaagga tgttattcca cgaatttact atggtgactt gtacactgat     2280
gatgggcaat tcatggcgac aaaatcacct tattttgatg cgatttcgac catgttacaa     2340
gcacgcacga gtatgtagc tggtggacag acgatggcgg ttgaccagca cgacgtcttg     2400
actagcgttc ggtttggtaa gggggccatg acggccaatg atttagggga tgctgagacc     2460
cggactgagg gtgtgggatt aattattagc aacaacccaa agttgcaatt gggacaacaa     2520
```

-continued

| | |
|---|---|
| gacaacgtgg tgttacacat gggacttgcg cacgcgaatc aggcattccg cgcagtcgta | 2580 |
| ctaacgaccg cgaccggatt aaccatttat aatgacgatg atgctccgat tcgttatacc | 2640 |
| gataataagg gtgatttaat tttcactaac catgacgtat atggcgtgtt gaatccacaa | 2700 |
| gtgtcaggct tcttggcaat gtgggtgcca actggtgcac cagcgaacca ggatgcgcga | 2760 |
| tctactgcgt caaccaacat gtcaacggat ggatctgcct accattctaa tgcggctttg | 2820 |
| gatagtcaag taatctttga atcattttcg aatttccagg ctatgccaac aagtcatgac | 2880 |
| acatacacca acgttgtgtt agccaatcat gctgaccagt tgcacgattg gggaataact | 2940 |
| tcggtacagt tagcaccaca ataccggtct caaccgacg gtaccttttt agacgcgatt | 3000 |
| attcaaaatg gctatgcctt cactgaccgt tatgatttag ggtttggtac gccaactaaa | 3060 |
| tacggggatg atacggattt gcggaacgtc atcaaagcat gcatgcaaa tggcatgcaa | 3120 |
| gtaatggctg attttgtgcc ggatcaattg tatacattac caggtaagga attggtacaa | 3180 |
| gtcacccgaa caaacaatat gggtgagcca gatacgcatt ctgacatcca acatattta | 3240 |
| tatgtgacga gcactcgtgg tggtggtgac tatcagaaac agtacggtgg tgagttcctt | 3300 |
| gcacgattgc gtgaacgata cccagattta tttacgacac gtcaaatttc gaccggacaa | 3360 |
| acaattgatg attcagtaaa aattaaagaa tggtcagcta agtatttgaa tggtaccgca | 3420 |
| attcaaggac gtggagctgg ctatgtgctg cgtgataatg gtacaaatgc ttattacaag | 3480 |
| gtgacagcaa atgacggtaa tgtgaactta ccaaagcaat tactcggcca accggtgatg | 3540 |
| accggattct atcacgaggc agatggttat cattttgaaa cattgagtgg tacgtcggcc | 3600 |
| aaagatgcct ttattatggg cgacgatggg gcactgtatt attttgatga tcagggtgtt | 3660 |
| atggtaacgg gtaagcaacg tgtgcaccaa gatcagtatt tcttcctgcc aaatggtatt | 3720 |
| gctttgacag atgctttcgt acaaactgct gatggtcaac gtcagtacta tgataaaaca | 3780 |
| ggtcgtctgg tcattaatca atatgtgact gaccaccaag cgaatgcgtt ccgggttgat | 3840 |
| gcagacggta acgttgtccg caatcaagct ttgactgttg acggccatga acaatatttc | 3900 |
| ggcacaaacg gtgtccaagc gaaagcagtg ctcattcgaa ctgacgataa tcaggcgcgc | 3960 |
| tactacgaag ccaatagtgg taatctcgtg aagcaacagt ttattcttga tacagatgga | 4020 |
| cattggttgt acgcggatgc tgcaggtgac ttggcacgcg gacaaattac aattggccaa | 4080 |
| gacacgttgt attttgatga taataatcac caggtaaaag atgatttcgt ctatgatact | 4140 |
| aacggtgtgc attatttaa tggcacaaca ggcgctgaaa tcaaacaaga ttacgcgttt | 4200 |
| catgatggca aatggtacta ttttgatgat ttgggacgaa tggtaaccgg cttgcagcgt | 4260 |
| attaatggtg agtatcgcta ttttgatgct aatggtgtgc aactaaaggg cggtaccgtg | 4320 |
| accgatccac taacgcacca aacgtacact tttgatgcga aaactggtgc tggtacgttg | 4380 |
| gtgacgattt aa | 4392 |

<210> SEQ ID NO 8
<211> LENGTH: 1463
<212> TYPE: PRT
<213> ORGANISM: Lactobacillus fermentum

<400> SEQUENCE: 8

Met Gln Asp Glu Ser Gln Lys Phe Arg Lys Lys Met Tyr Lys Ser Gly
1               5                   10                  15

Lys Phe Trp Val Ala Ala Gly Ala Leu Phe Val Gly Leu Ala Phe Ala
            20                  25                  30

Gly Asn Ala Gln Ala Asp Thr Val Leu Pro Ser Glu Gln Arg Ala Thr

```
                35                  40                  45
Gln Thr Thr Gln Thr Thr Gln Thr Ser Glu Asp Thr Ser Ala Thr Lys
 50                  55                  60

Thr Pro Ala Ser Ala Ser Thr Ser Ser Ser Asp Asn Val Asp Thr Ser
 65                  70                  75                  80

Asp Leu Pro Asp Ser Ala Ser Ala Val Val Asp Ser Ala Val Thr Ser
                 85                  90                  95

Thr Ser Thr Ser Ala Ser Val Val Ser Asp Ser Val Ala Val Pro Asp
            100                 105                 110

Thr Gly Ser Gln Phe Met Ser Ser Ala Pro Ala Ser Ser Ala Phe
        115                 120                 125

Val Lys Pro Ser Leu Thr Ser Thr Ser Gly Ala Ser Gly Ser Gln
    130                 135                 140

Ser Ser Ala Val Thr Ser Ala Asn Asp Ser Ser Val Ala Thr Ser Ser
145                 150                 155                 160

Ser Ala Ser Ser Val Thr Thr Ala Thr Ser Glu Ser Ala Val Val Ser
                165                 170                 175

Ser Ala Val Ser Asp Gly Tyr His Asp Glu Gly Gly Asp Trp Val Tyr
            180                 185                 190

Tyr Arg Ala Gly Lys Lys Leu Leu Gly Arg Gln Thr Ile Asp Thr Phe
        195                 200                 205

Ala Val Tyr Phe Asp Ala Asp Gly Lys Gln Val Lys Gly Asp Trp Arg
    210                 215                 220

Glu Ser Asp Gly Lys Arg Ala Tyr Tyr Asp Gly Gln Glu Gly Arg Ala
225                 230                 235                 240

Leu Thr Gln Thr Gln Ala Val Asn Gly Val Ile Tyr Gly Phe Asn Gln
                245                 250                 255

Ser Gly Tyr Gln Ile Lys Asn Asp Phe Gly Gln Thr Ala Asn Arg Asp
            260                 265                 270

Thr Tyr Tyr Phe Asp Ala Gln Gly His Val Val Thr Gly Ile Gln Thr
        275                 280                 285

Ile Ala Asn Lys Val Tyr Asp Phe Asp Glu Gln Gly Arg Met Leu Lys
    290                 295                 300

Gly Ile Ala Thr Ser Val Asp Asp Lys Met Met Tyr Phe Asp Asp Gln
305                 310                 315                 320

Thr Gly Val Gly Gln Pro Ala Asp His Pro Glu Phe Asn Pro Glu Thr
                325                 330                 335

Glu Pro Val Pro Asp Asp Asn Ile Lys His Asn Ala Ala His Gly Thr
            340                 345                 350

Thr Pro Glu Asp Phe Asp Ser Met Ala Asp Tyr Leu Thr Ala Asp Thr
        355                 360                 365

Trp Tyr Arg Pro Thr Asp Ile Leu Glu Asn Gly Glu Thr Trp Arg Glu
    370                 375                 380

Ser Gln Pro Thr Glu Phe Arg Pro Leu Leu Ala Thr Trp Pro Thr
385                 390                 395                 400

Lys Gln Thr Gln Ala Asp Tyr Val Asn Tyr Met Asn His Ala Leu Asp
                405                 410                 415

Met Ala Asn Ala Gly Val Ser Ala Ala Asp Ser Glu Ala Thr Leu Thr
            420                 425                 430

Ala Ala Thr Asp Ala Ile Gln Ala Val Val Glu His Gln Ile Thr Val
        435                 440                 445

Arg Gln Ser Thr Ala Trp Leu Arg Glu Leu Met Ala Ala Phe Val Val
    450                 455                 460
```

```
Thr Gln Pro Gln Trp Asn Lys Thr Ser Glu Asp Val Asn Asp Asp His
465                 470                 475                 480

Leu Gln Gly Gly Ala Leu Thr Phe Glu Asn Asn Gly Asp Thr Asp Ala
                485                 490                 495

Asn Ser Asp Tyr Arg Leu Met Asn Arg Thr Pro Thr Asn Gln Thr Gly
            500                 505                 510

Glu Arg Leu Tyr His Ile Asp Asp Ser Leu Gly Gly Tyr Glu Leu Leu
            515                 520                 525

Leu Ala Asn Asp Val Asp Asn Ser Asn Pro Gln Val Gln Ala Glu Gln
            530                 535                 540

Leu Asn Trp Leu Tyr Tyr Leu Met His Phe Gly Asp Ile Thr Ala Asp
545                 550                 555                 560

Asp Pro Asp Ala Asn Phe Asp Ala Ile Arg Ile Asp Ala Val Asp Asn
                565                 570                 575

Val Asp Ala Asp Leu Leu Gln Leu Ala Ala Gln Tyr Phe Arg Asp Ala
            580                 585                 590

Tyr Gly Met Ala Thr Thr Asp Ala Thr Ser Asn Lys His Leu Ser Ile
            595                 600                 605

Leu Glu Asp Trp Ser His Asn Asp Pro Ala Tyr Met Gln Ala His Gly
610                 615                 620

Asn Asp Gln Leu Thr Met Asp Asp Tyr Met His Thr Gln Leu Ile Trp
625                 630                 635                 640

Ser Leu Thr Lys Pro Glu Ala Gln Arg Gly Thr Met Ala Arg Phe Met
                645                 650                 655

Asp Phe Tyr Leu Thr Asn Arg Ala Asn Asp Asp Thr Glu Asn Thr Ala
            660                 665                 670

Gln Pro Ser Tyr Ser Phe Val Arg Ala His Asp Ser Glu Val Gln Thr
            675                 680                 685

Val Ile Ala Glu Ile Val Thr Lys Leu His Pro Glu Ala Gly Asn Gly
            690                 695                 700

Leu Met Pro Thr Glu Glu Gln Met Ala Glu Ala Phe Lys Ile Tyr Asn
705                 710                 715                 720

Ala Asp Gln Lys Lys Ala Val Lys Thr Tyr Thr His Tyr Asn Met Pro
                725                 730                 735

Ser Ala Tyr Ala Met Leu Leu Thr Asn Lys Asp Val Ile Pro Arg Ile
            740                 745                 750

Tyr Tyr Gly Asp Leu Tyr Thr Asp Asp Gly Gln Phe Met Ala Thr Lys
            755                 760                 765

Ser Pro Tyr Phe Asp Ala Ile Ser Thr Met Leu Gln Ala Arg Thr Lys
            770                 775                 780

Tyr Val Ala Gly Gly Gln Thr Met Ala Val Asp Gln His Asp Val Leu
785                 790                 795                 800

Thr Ser Val Arg Phe Gly Lys Gly Ala Met Thr Ala Asn Asp Leu Gly
                805                 810                 815

Asp Ala Glu Thr Arg Thr Glu Gly Val Gly Leu Ile Ile Ser Asn Asn
            820                 825                 830

Pro Lys Leu Gln Leu Gly Gln Gln Asp Asn Val Val Leu His Met Gly
            835                 840                 845

Leu Ala His Ala Asn Gln Ala Phe Arg Ala Val Val Leu Thr Thr Ala
            850                 855                 860

Thr Gly Leu Thr Ile Tyr Asn Asp Asp Asp Ala Pro Ile Arg Tyr Thr
865                 870                 875                 880
```

```
Asp Asn Lys Gly Asp Leu Ile Phe Thr Asn His Asp Val Tyr Gly Val
                885                 890                 895

Leu Asn Pro Gln Val Ser Gly Phe Leu Ala Met Trp Val Pro Thr Gly
        900                 905                 910

Ala Pro Ala Asn Gln Asp Ala Arg Ser Thr Ala Ser Thr Asn Met Ser
        915                 920                 925

Thr Asp Gly Ser Ala Tyr His Ser Asn Ala Ala Leu Asp Ser Gln Val
        930                 935                 940

Ile Phe Glu Ser Phe Ser Asn Phe Gln Ala Met Pro Thr Ser His Asp
945                 950                 955                 960

Thr Tyr Thr Asn Val Val Leu Ala Asn His Ala Asp Gln Leu His Asp
                965                 970                 975

Trp Gly Ile Thr Ser Val Gln Leu Ala Pro Gln Tyr Arg Ser Ser Thr
                980                 985                 990

Asp Gly Thr Phe Leu Asp Ala Ile Ile Gln Asn Gly Tyr Ala Phe Thr
        995                 1000                1005

Asp Arg Tyr Asp Leu Gly Phe Gly Thr Pro Thr Lys Tyr Gly Asp
    1010                1015                1020

Asp Thr Asp Leu Arg Asn Val Ile Lys Ala Leu His Ala Asn Gly
    1025                1030                1035

Met Gln Val Met Ala Asp Phe Val Pro Asp Gln Leu Tyr Thr Leu
    1040                1045                1050

Pro Gly Lys Glu Leu Val Gln Val Thr Arg Thr Asn Asn Met Gly
    1055                1060                1065

Glu Pro Asp Thr His Ser Asp Ile Gln His Ile Leu Tyr Val Thr
    1070                1075                1080

Ser Thr Arg Gly Gly Gly Asp Tyr Gln Lys Gln Tyr Gly Gly Glu
    1085                1090                1095

Phe Leu Ala Arg Leu Arg Glu Arg Tyr Pro Asp Leu Phe Thr Thr
    1100                1105                1110

Arg Gln Ile Ser Thr Gly Gln Thr Ile Asp Ser Val Lys Ile
    1115                1120                1125

Lys Glu Trp Ser Ala Lys Tyr Leu Asn Gly Thr Ala Ile Gln Gly
    1130                1135                1140

Arg Gly Ala Gly Tyr Val Leu Arg Asp Asn Gly Thr Asn Ala Tyr
    1145                1150                1155

Tyr Lys Val Thr Ala Asn Asp Gly Asn Val Asn Leu Pro Lys Gln
    1160                1165                1170

Leu Leu Gly Gln Pro Val Met Thr Gly Phe Tyr His Glu Ala Asp
    1175                1180                1185

Gly Tyr His Phe Glu Thr Leu Ser Gly Thr Ser Ala Lys Asp Ala
    1190                1195                1200

Phe Ile Met Gly Asp Asp Gly Ala Leu Tyr Tyr Phe Asp Asp Gln
    1205                1210                1215

Gly Val Met Val Thr Gly Lys Gln Arg Val His Gln Asp Gln Tyr
    1220                1225                1230

Phe Phe Leu Pro Asn Gly Ile Ala Leu Thr Asp Ala Phe Val Gln
    1235                1240                1245

Thr Ala Asp Gly Gln Arg Gln Tyr Tyr Asp Lys Thr Gly Arg Leu
    1250                1255                1260

Val Ile Asn Gln Tyr Val Thr Asp His Gln Ala Asn Ala Phe Arg
    1265                1270                1275

Val Asp Ala Asp Gly Asn Val Val Arg Asn Gln Ala Leu Thr Val
```

```
                    1280                1285                1290

Asp Gly His Glu Gln Tyr Phe Gly Thr Asn Gly Val Gln Ala Lys
    1295                1300                1305

Ala Val Leu Ile Arg Thr Asp Asp Asn Gln Ala Arg Tyr Tyr Glu
    1310                1315                1320

Ala Asn Ser Gly Asn Leu Val Lys Gln Gln Phe Ile Leu Asp Thr
    1325                1330                1335

Asp Gly His Trp Leu Tyr Ala Asp Ala Ala Gly Asp Leu Ala Arg
    1340                1345                1350

Gly Gln Ile Thr Ile Gly Gln Asp Thr Leu Tyr Phe Asp Asp Asn
    1355                1360                1365

Asn His Gln Val Lys Asp Asp Phe Val Tyr Asp Thr Asn Gly Val
    1370                1375                1380

His Tyr Phe Asn Gly Thr Thr Gly Ala Glu Ile Lys Gln Asp Tyr
    1385                1390                1395

Ala Phe His Asp Gly Lys Trp Tyr Tyr Phe Asp Asp Leu Gly Arg
    1400                1405                1410

Met Val Thr Gly Leu Gln Arg Ile Asn Gly Glu Tyr Arg Tyr Phe
    1415                1420                1425

Asp Ala Asn Gly Val Gln Leu Lys Gly Gly Thr Val Thr Asp Pro
    1430                1435                1440

Leu Thr His Gln Thr Tyr Thr Phe Asp Ala Lys Thr Gly Ala Gly
    1445                1450                1455

Thr Leu Val Thr Ile
    1460

<210> SEQ ID NO 9
<211> LENGTH: 1426
<212> TYPE: PRT
<213> ORGANISM: Lactobacillus fermentum
<220> FEATURE:
<221> NAME/KEY: MISC_FEATURE
<222> LOCATION: (1)..(1426)
<223> OTHER INFORMATION: mature 2918 gtf

<400> SEQUENCE: 9

Asp Thr Val Leu Pro Ser Glu Gln Arg Ala Thr Gln Thr Thr Gln Thr
1               5                  10                  15

Thr Gln Thr Ser Glu Asp Thr Ser Ala Thr Lys Thr Pro Ala Ser Ala
            20                  25                  30

Ser Thr Ser Ser Ser Asp Asn Val Asp Thr Ser Asp Leu Pro Asp Ser
        35                  40                  45

Ala Ser Ala Val Val Asp Ser Ala Val Thr Ser Thr Ser Thr Ser Ala
    50                  55                  60

Ser Val Val Ser Asp Val Ala Val Pro Asp Thr Gly Ser Gln Phe
65                  70                  75                  80

Met Ser Ser Ser Ala Pro Ala Ser Ser Ala Phe Val Lys Pro Ser Leu
                85                  90                  95

Thr Ser Thr Thr Ser Gly Ala Ser Gly Ser Gln Ser Ser Ala Val Thr
            100                 105                 110

Ser Ala Asn Asp Ser Ser Val Ala Thr Ser Ser Ser Ala Ser Ser Val
        115                 120                 125

Thr Thr Ala Thr Ser Glu Ser Ala Val Val Ser Ser Ala Val Ser Asp
    130                 135                 140

Gly Tyr His Asp Glu Gly Gly Asp Trp Val Tyr Tyr Arg Ala Gly Lys
145                 150                 155                 160
```

```
Lys Leu Leu Gly Arg Gln Thr Ile Asp Thr Phe Ala Val Tyr Phe Asp
                165                 170                 175

Ala Asp Gly Lys Gln Val Lys Gly Asp Trp Arg Glu Ser Asp Gly Lys
            180                 185                 190

Arg Ala Tyr Tyr Asp Gly Gln Glu Gly Arg Ala Leu Thr Gln Thr Gln
        195                 200                 205

Ala Val Asn Gly Val Ile Tyr Gly Phe Asn Gln Ser Gly Tyr Gln Ile
    210                 215                 220

Lys Asn Asp Phe Gly Gln Thr Ala Asn Arg Asp Thr Tyr Tyr Phe Asp
225                 230                 235                 240

Ala Gln Gly His Val Val Thr Gly Ile Gln Thr Ile Ala Asn Lys Val
                245                 250                 255

Tyr Asp Phe Asp Glu Gln Gly Arg Met Leu Lys Gly Ile Ala Thr Ser
                260                 265                 270

Val Asp Asp Lys Met Met Tyr Phe Asp Asp Gln Thr Gly Val Gly Gln
            275                 280                 285

Pro Ala Asp His Pro Glu Phe Asn Pro Glu Thr Glu Pro Val Pro Asp
        290                 295                 300

Asp Asn Ile Lys His Asn Ala Ala His Gly Thr Thr Pro Glu Asp Phe
305                 310                 315                 320

Asp Ser Met Ala Asp Tyr Leu Thr Ala Asp Thr Trp Tyr Arg Pro Thr
                325                 330                 335

Asp Ile Leu Glu Asn Gly Glu Thr Trp Arg Glu Ser Gln Pro Thr Glu
                340                 345                 350

Phe Arg Pro Leu Leu Ala Thr Trp Trp Pro Thr Lys Gln Thr Gln Ala
            355                 360                 365

Asp Tyr Val Asn Tyr Met Asn His Ala Leu Asp Met Ala Asn Ala Gly
        370                 375                 380

Val Ser Ala Ala Asp Ser Glu Ala Thr Leu Thr Ala Ala Thr Asp Ala
385                 390                 395                 400

Ile Gln Ala Val Val Glu His Gln Ile Thr Val Arg Gln Ser Thr Ala
                405                 410                 415

Trp Leu Arg Glu Leu Met Ala Ala Phe Val Val Thr Gln Pro Gln Trp
                420                 425                 430

Asn Lys Thr Ser Glu Asp Val Asn Asp Asp His Leu Gln Gly Gly Ala
            435                 440                 445

Leu Thr Phe Glu Asn Asn Gly Asp Thr Asp Ala Asn Ser Asp Tyr Arg
        450                 455                 460

Leu Met Asn Arg Thr Pro Thr Asn Gln Thr Gly Glu Arg Leu Tyr His
465                 470                 475                 480

Ile Asp Asp Ser Leu Gly Gly Tyr Glu Leu Leu Leu Ala Asn Asp Val
                485                 490                 495

Asp Asn Ser Asn Pro Gln Val Gln Ala Glu Gln Leu Asn Trp Leu Tyr
            500                 505                 510

Tyr Leu Met His Phe Gly Asp Ile Thr Ala Asp Pro Asp Ala Asn
        515                 520                 525

Phe Asp Ala Ile Arg Ile Asp Ala Val Asp Asn Val Asp Ala Asp Leu
530                 535                 540

Leu Gln Leu Ala Ala Gln Tyr Phe Arg Asp Ala Tyr Gly Met Ala Thr
545                 550                 555                 560

Thr Asp Ala Thr Ser Asn Lys His Leu Ser Ile Leu Glu Asp Trp Ser
                565                 570                 575
```

His Asn Asp Pro Ala Tyr Met Gln Ala His Gly Asn Asp Gln Leu Thr
            580                 585                 590

Met Asp Asp Tyr Met His Thr Gln Leu Ile Trp Ser Leu Thr Lys Pro
        595                 600                 605

Glu Ala Gln Arg Gly Thr Met Ala Arg Phe Met Asp Phe Tyr Leu Thr
    610                 615                 620

Asn Arg Ala Asn Asp Asp Thr Glu Asn Thr Ala Gln Pro Ser Tyr Ser
625                 630                 635                 640

Phe Val Arg Ala His Asp Ser Glu Val Gln Thr Val Ile Ala Glu Ile
                645                 650                 655

Val Thr Lys Leu His Pro Glu Ala Gly Asn Gly Leu Met Pro Thr Glu
            660                 665                 670

Glu Gln Met Ala Glu Ala Phe Lys Ile Tyr Asn Ala Asp Gln Lys Lys
        675                 680                 685

Ala Val Lys Thr Tyr Thr His Tyr Asn Met Pro Ser Ala Tyr Ala Met
    690                 695                 700

Leu Leu Thr Asn Lys Asp Val Ile Pro Arg Ile Tyr Tyr Gly Asp Leu
705                 710                 715                 720

Tyr Thr Asp Asp Gly Gln Phe Met Ala Thr Lys Ser Pro Tyr Phe Asp
                725                 730                 735

Ala Ile Ser Thr Met Leu Gln Ala Arg Thr Lys Tyr Val Ala Gly Gly
            740                 745                 750

Gln Thr Met Ala Val Asp Gln His Asp Val Leu Thr Ser Val Arg Phe
        755                 760                 765

Gly Lys Gly Ala Met Thr Ala Asn Asp Leu Gly Asp Ala Glu Thr Arg
    770                 775                 780

Thr Glu Gly Val Gly Leu Ile Ile Ser Asn Asn Pro Lys Leu Gln Leu
785                 790                 795                 800

Gly Gln Gln Asp Asn Val Val Leu His Met Gly Leu Ala His Ala Asn
                805                 810                 815

Gln Ala Phe Arg Ala Val Val Leu Thr Thr Ala Thr Gly Leu Thr Ile
            820                 825                 830

Tyr Asn Asp Asp Asp Ala Pro Ile Arg Tyr Thr Asp Asn Lys Gly Asp
        835                 840                 845

Leu Ile Phe Thr Asn His Asp Val Tyr Gly Val Leu Asn Pro Gln Val
    850                 855                 860

Ser Gly Phe Leu Ala Met Trp Val Pro Thr Gly Ala Pro Ala Asn Gln
865                 870                 875                 880

Asp Ala Arg Ser Thr Ala Ser Thr Asn Met Ser Thr Asp Gly Ser Ala
                885                 890                 895

Tyr His Ser Asn Ala Ala Leu Asp Ser Gln Val Ile Phe Glu Ser Phe
            900                 905                 910

Ser Asn Phe Gln Ala Met Pro Thr Ser His Asp Thr Tyr Thr Asn Val
        915                 920                 925

Val Leu Ala Asn His Ala Asp Gln Leu His Asp Trp Gly Ile Thr Ser
    930                 935                 940

Val Gln Leu Ala Pro Gln Tyr Arg Ser Ser Thr Asp Gly Thr Phe Leu
945                 950                 955                 960

Asp Ala Ile Ile Gln Asn Gly Tyr Ala Phe Thr Asp Arg Tyr Asp Leu
                965                 970                 975

Gly Phe Gly Thr Pro Thr Lys Tyr Gly Asp Thr Asp Leu Arg Asn
            980                 985                 990

Val Ile Lys Ala Leu His Ala Asn  Gly Met Gln Val Met  Ala Asp Phe

```
            995                 1000                1005
Val Pro Asp Gln Leu Tyr Thr Leu Pro Gly Lys Glu Leu Val Gln
        1010                1015                1020

Val Thr Arg Thr Asn Asn Met Gly Glu Pro Asp Thr His Ser Asp
        1025                1030                1035

Ile Gln His Ile Leu Tyr Val Thr Ser Thr Arg Gly Gly Gly Asp
        1040                1045                1050

Tyr Gln Lys Gln Tyr Gly Gly Glu Phe Leu Ala Arg Leu Arg Glu
        1055                1060                1065

Arg Tyr Pro Asp Leu Phe Thr Thr Arg Gln Ile Ser Thr Gly Gln
        1070                1075                1080

Thr Ile Asp Asp Ser Val Lys Ile Lys Glu Trp Ser Ala Lys Tyr
        1085                1090                1095

Leu Asn Gly Thr Ala Ile Gln Gly Arg Gly Ala Gly Tyr Val Leu
        1100                1105                1110

Arg Asp Asn Gly Thr Asn Ala Tyr Tyr Lys Val Thr Ala Asn Asp
        1115                1120                1125

Gly Asn Val Asn Leu Pro Lys Gln Leu Leu Gly Gln Pro Val Met
        1130                1135                1140

Thr Gly Phe Tyr His Glu Ala Asp Gly Tyr His Phe Glu Thr Leu
        1145                1150                1155

Ser Gly Thr Ser Ala Lys Asp Ala Phe Ile Met Gly Asp Asp Gly
        1160                1165                1170

Ala Leu Tyr Tyr Phe Asp Asp Gln Gly Val Met Val Thr Gly Lys
        1175                1180                1185

Gln Arg Val His Gln Asp Gln Tyr Phe Phe Leu Pro Asn Gly Ile
        1190                1195                1200

Ala Leu Thr Asp Ala Phe Val Gln Thr Ala Asp Gly Gln Arg Gln
        1205                1210                1215

Tyr Tyr Asp Lys Thr Gly Arg Leu Val Ile Asn Gln Tyr Val Thr
        1220                1225                1230

Asp His Gln Ala Asn Ala Phe Arg Val Asp Ala Asp Gly Asn Val
        1235                1240                1245

Val Arg Asn Gln Ala Leu Thr Val Asp Gly His Glu Gln Tyr Phe
        1250                1255                1260

Gly Thr Asn Gly Val Gln Ala Lys Ala Val Leu Ile Arg Thr Asp
        1265                1270                1275

Asp Asn Gln Ala Arg Tyr Tyr Glu Ala Asn Ser Gly Asn Leu Val
        1280                1285                1290

Lys Gln Gln Phe Ile Leu Asp Thr Asp Gly His Trp Leu Tyr Ala
        1295                1300                1305

Asp Ala Ala Gly Asp Leu Ala Arg Gly Gln Ile Thr Ile Gly Gln
        1310                1315                1320

Asp Thr Leu Tyr Phe Asp Asp Asn Asn His Gln Val Lys Asp Asp
        1325                1330                1335

Phe Val Tyr Asp Thr Asn Gly Val His Tyr Phe Asn Gly Thr Thr
        1340                1345                1350

Gly Ala Glu Ile Lys Gln Asp Tyr Ala Phe His Asp Gly Lys Trp
        1355                1360                1365

Tyr Tyr Phe Asp Asp Leu Gly Arg Met Val Thr Gly Leu Gln Arg
        1370                1375                1380

Ile Asn Gly Glu Tyr Arg Tyr Phe Asp Ala Asn Gly Val Gln Leu
        1385                1390                1395
```

Lys Gly  Gly Thr Val Thr  Asp Pro Leu Thr His Gln  Thr Tyr Thr
    1400              1405                  1410

Phe Asp  Ala Lys Thr Gly Ala  Gly Thr Leu Val Thr  Ile
    1415              1420                 1425

<210> SEQ ID NO 10
<211> LENGTH: 4281
<212> TYPE: DNA
<213> ORGANISM: Artificial sequence
<220> FEATURE:
<223> OTHER INFORMATION: 2918 gtf with heterologous signal sequence

<400> SEQUENCE: 10

| | | | | | |
|---|---|---|---|---|---|
| gatacagtgc | tgcctagcga | gcaaagagca | acacagacga | cacaaacaac | gcagacatca | 60 |
| gaggatacga | gcgcgacgaa | gacaccggca | agcgcatcaa | cgtcaagcag | cgataacgtg | 120 |
| gatacgtcag | atcttccgga | tagcgccagc | gcagttgtcg | attcagcggt | tacatcaaca | 180 |
| agcacgtcag | cctcagtggt | gagcgatagc | gttgcagtcc | cggatacggg | atcacaattt | 240 |
| atgtcatcat | cagctcctgc | gagcagcgcg | tttgttaaac | ctagccttac | gtcaacgacg | 300 |
| tcaggagcga | gcggctcaca | gagctcagca | gtgacaagcg | ccaatgattc | aagcgtcgct | 360 |
| acaagctcat | cagcttcatc | agttacgaca | gcaacaagcg | agtcagccgt | tgtctcaagc | 420 |
| gcggtctcag | acggctatca | tgacgaagga | ggagattggg | tttactacag | agcaggaaaa | 480 |
| aaactgcttg | gaagacagac | aattgatacg | tttgctgttt | actttgatgc | tgacggaaaa | 540 |
| caagtgaaag | gcgactggag | agaatcagat | ggaaagagag | cgtattatga | tggacaagaa | 600 |
| ggaagagccc | ttacgcaaac | gcaagccgtt | aatggagtga | tctatggatt | caatcaatca | 660 |
| ggataccaga | tcaaaaacga | ttttggccag | acagcgaaca | gagatacata | ctacttcgac | 720 |
| gcacaaggcc | atgtggttac | aggcatccaa | acaatcgcga | ataaagttta | tgacttcgat | 780 |
| gaacaaggca | gaatgcttaa | aggaattgcc | acatcagtcg | atgacaagat | gatgtatttt | 840 |
| gacgatcaaa | caggcgtggg | acaacctgca | gatcaccctg | agtttaaccc | ggaaacagaa | 900 |
| ccggtgcctg | acgataacat | caagcataat | gcagcccacg | gcacaacacc | tgaagatttt | 960 |
| gatagcatgg | cggactatct | gacagctgat | acatggtata | gacctacaga | tattctggag | 1020 |
| aatggagaaa | catggagaga | gagccaaccg | acggaattta | gaccgctgct | ggcaacgtgg | 1080 |
| tggcctacaa | aacagacaca | agcagattat | gtgaactata | tgaaccacgc | acttgacatg | 1140 |
| gctaatgctg | gcgttagcgc | tgcggattca | gaggcaacac | ttacagcggc | tacggatgcc | 1200 |
| attcaggctg | ttgttgagca | ccaaattacg | gttagacaaa | gcacggcctg | gcttagagaa | 1260 |
| cttatggcgg | cttttgttgt | tacacaacct | caatggaata | agacgagcga | agatgtcaat | 1320 |
| gatgatcacc | ttcaaggagg | cgcactgaca | tttgagaata | acgagacac | agatgcaaat | 1380 |
| agcgattata | gacttatgaa | tagaacaccg | acaaatcaaa | cgggcgagag | actttatcat | 1440 |
| attgatgact | cactgggagg | ctacgagctg | cttcttgcaa | acgatgtgga | caactcaaac | 1500 |
| ccgcaggttc | aggcggaaca | acttaactgg | ctttactatc | ttatgcattt | cggagatatt | 1560 |
| acagccgatg | acccggatgc | taactttgac | gcgatcagaa | ttgacgccgt | tgataatgtc | 1620 |
| gacgctgacc | tgcttcagct | tgctgcccaa | tactttagag | atgcatatgg | aatgccaca | 1680 |
| acagacgcca | cgagcaataa | acacctttca | atccttgagg | attggagcca | taacgatcct | 1740 |
| gcttatatgc | aggcacatgg | aaaatgaccag | cttacaatgg | atgactacat | gcacacacaa | 1800 |
| ctgatttggt | cactgacgaa | accggaagca | caaagaggaa | cgatggcaag | atttatggac | 1860 |

```
tttttatctta caaatagagc taacgatgat acagaaaaca cagcgcaacc ttcatattca    1920
tttgttagag cacacgactc agaagtgcag acagttattg cagaaattgt tacgaaactt    1980
cacccggagg caggcaacgg ccttatgcct acggaggaac agatggcaga ggcgtttaag    2040
atctacaatg cagaccaaaa gaaagcggtg aaaacatata cacactataa catgccttca    2100
gcctacgcta tgctgctgac aaataaggat gtgattccta gaatctacta cggcgatctt    2160
tacacgacg acggccagtt catggcaaca aagtcaccgt atttcgatgc aatttcaaca    2220
atgctgcaag caagaacaaa atatgttgca ggcggacaaa cgatggcggt tgaccaacat    2280
gatgtcctga cgagcgtgag atttggcaaa ggcgcgatga cagcaaatga ccttggagac    2340
gcggaaacga gaacagaggg cgtgggactg atcatcagca acaaccctaa gctgcaactg    2400
ggacagcagg ataacgtggt ccttcatatg ggcctggcac acgcgaatca ggctttcaga    2460
gcagtcgtgc ttacaacagc cacaggactg acgatctaca cgacgatga cgctcctatt    2520
agatatacgg acaataaggg cgacctgatc tttacgaatc acgatgttta cggcgttctg    2580
aacccgcagg ttagcggctt ccttgctatg tgggttccga cgggcgcacc tgccaatcaa    2640
gacgcaagaa gcacggcttc aacgaatatg tcaacggatg gatcagctta tcattcaaac    2700
gcagctctgg attcacaagt tatctttgag tcatttagca actttcaagc aatgccgaca    2760
tcacacgata catacacgaa tgttgtcctt gcaaaccatg cagaccaact tcacgattgg    2820
ggaattacgt cagtgcaact tgcaccgcaa tatagatcaa gcacagacgg aacgtttctg    2880
gatgcaatta ttcaaaatgg atatgctttt acagatagat atgatcttgg ctttggaaca    2940
cctacgaagt acgcgacga cacggacctg agaaatgtga tcaaagccct tcatgcaaac    3000
ggcatgcaag tcatggcaga ttttgttcct gatcaactgt acacacttcc gggcaaagaa    3060
ctggttcaag tgacaagaac aaataacatg ggcgaaccgg atacacacag cgatattcaa    3120
cacatcctgt atgttacatc aacaagagga ggcggagact atcagaaaca atatggcggc    3180
gaatttctgg ctagacttag agaaagatac ccggaccttt ttacgacgag acaaattagc    3240
acaggccaaa caattgacga cagcgttaag attaaggagt ggtcagcgaa atatctgaac    3300
ggcacagcaa ttcaaggcag aggcgctggc tatgttctga gagataatgg aacgaatgca    3360
tactataaag ttacggccaa tgatggaaac gtcaatcttc ctaagcaact gctgggccag    3420
ccggttatga caggcttcta tcacgaagca gacggctacc acttcgagac actgtcaggc    3480
acatcagcca aggacgcatt tatcatggga gatgatggcg cactgtacta tttcgatgac    3540
caaggcgtga tggttacagg aaaacaaaga gttcatcagg atcaatactt ttttctgccg    3600
aatggcatcg ctctgacgga cgctttcgtt caaacagctg atggacagag acagtactac    3660
gataaaacag gcagactggt tattaaccaa tatgtgacag accatcaggc gaatgccttc    3720
agagttgatg cggacggaaa tgtcgttaga aaccaagcac ttacagtgga cggacatgaa    3780
cagtatttcg gcacgaacgg agtgcaggca aaagcagttc tgattagaac ggacgataat    3840
caagcgagat attatgaggc aaattcaggc aatctggtga acaacaatt tatccttgac    3900
acagatggcc actggctgta cgcagacgca gcaggcgatc ttgctagagg ccagattaca    3960
atcggccagg atacgctgta ttttgatgat aacaatcacc aagttaaaga tgacttcgtt    4020
tatgatacga atggagtcca ttactttaat ggcacaacag gagcagagat taaacaagat    4080
tacgcattcc atgacggcaa atggtactac ttcgacgacc tgggaagaat ggtcacggga    4140
cttcaaagaa ttaatggaga gtatagatac tttgacgcga acggcgtcca actgaaagga    4200
ggcacagtga cggatcctct gacacatcaa acatatacat ttgatgcaaa aacgggagcc    4260
```

```
ggcacgcttg ttacaatttg a                                          4281
```

<210> SEQ ID NO 11
<211> LENGTH: 4521
<212> TYPE: DNA
<213> ORGANISM: Streptococcus sobrinus

<400> SEQUENCE: 11

```
atggaaagaa aattgcatta caaattacac aaggtaaaaa aacagtgggt aacgattgcc     60
gttgcctctg ctggtttggc tagcattgtt ggtgctggtt cattaagcca aactgtttct    120
gccgatgact tagccaagga acaagctgcg gctagtcaac aaaaggcagc agccaatcag    180
aatgaggacg aagtggcttc tgatgcagct gatactgcta gtgcaaaagc gacttccgaa    240
aaagaagttg tccaatcttc tgatacaaat tcagaaacta accaagttga aactaaagat    300
caagctagcg ctaaggaaag tgctgacgca gtagccaagc aagcaccaca agctggccct    360
gcaaccacta gccaggttgc aagctcagaa agcagctctg tagcgcctag caaggaagct    420
gataaggcag ctgctggatc agttagccaa atgaagaag aagcagccct atcgcttgcc     480
aatattaaaa agattgatgg taagtattac tatgttatgg cagacggttc ttataagaag    540
aactttgcca ttacagttga tggtcaaatg ctttactttg atgccaaaac aggtgccctg    600
tcttcaacct ctacctattc tttcagtcaa ggtttgacac caattgtttc tgatttctca    660
gtcaacaaca aggctttcga ttcttctgaa aagagttttg aattggttga tggctatttg    720
acagctgaaa gctggtaccg tcctgctaag attcttgaaa atggtaaaac ttgggttgat    780
tctaaagaaa ctgacctacg cccagttctg atgagctggt ggccaaacaa ggatacgcaa    840
gttgcctacc ttaactacat gagcaaggca cttggtggca aggaagaatt cacaactgaa    900
acctcccaat tgaccttgaa tacagccgct gagttgattc aagctaaaat tgaagctcgc    960
gtttctaaag aacaaggaac aaagtggttg cgtgaagcta tggcagcctt cgttgctacc   1020
caatctcgtt ggaataagga cagcgaacaa tacgataagg ctgaccacct gcaaggcgga   1080
gccctgctct ataccaataa caacttgaca gagtgggcaa attcaaactg gcgcctgctt   1140
aaccgtaccc caactcgtca agatggtaaa acccattact ctaaggctga caaatacggt   1200
ggttatgaat tcctcttggc caacgacgtg ataactcta acccagtcgt tcaagcggaa    1260
atgctcaacc aaatccacta cctcatgaac tggggtgaaa ttgtgatggg tgataagaat   1320
gccaactttg atggtattcg tgtcgatgcc gtggataacg tcaatgcaga tactctgcaa   1380
ctctacacca actactttaa ttctgtttat ggtgtcaaca agtctgaagc caagccctg    1440
gctcacatct cagtcttgga agcatggtct tacaatgata atgactataa ccaagacacc   1500
aacgggctg ccctggctat ggacaatggt ctacgctttt ccctgcttta taccttgacc    1560
cgtccgatca atgaacggac acctggtatg tcaaccctga ttaaatcaga atatggtttg   1620
actgaccgga ctaagaatga taagtatgga gatacccaac catcttatgt ttttgttcgg   1680
gcgcatgact cagaagtgca aaccgttatt gcacaaatca tcaaggaaaa aattgatcca   1740
acaaccgatg gtttcacctt caccttggac caattgaaac aggcctttga aatctacaac   1800
aaggatatga atagtgttaa caagcactat acccactata tatcccagc agcctacgct    1860
gtcatgttgt ctaatatgga atccgtaacc cgggtttact atggtgaccct cttcaccgat   1920
gatggtcaat acatggcatc taaatctcca tattatgatg ccatcaacac tctcttgcgg   1980
gctcgcattc gttacgcagc cggtggtcaa attatggaac acaattccta caaaccatca   2040
```

| | |
|---|---|
| gcagccatga aggcagctca tccagatgct ggtaatgtcc ttggtaacag cgaagtcttg | 2100 |
| gtatcggttc gtttcggtca agatgtcatg tctgccgatg atatgactgg tggtaagctg | 2160 |
| gctaagacct ctggtatgtt caccctgatt tctaacaacc ctgaattgga attggatgtc | 2220 |
| aatgaagaaa tcaaggttaa cgttggtaaa atccatgctg ccaagccta ccgtcccttg | 2280 |
| cttttgacaa ctgataaggg tctgcaaaag tatctcaatg attctgatac caagttgacc | 2340 |
| aagattgctg acaaggatgg tttcattacc ttcaagggta gcgaaatcaa gggttacaaa | 2400 |
| caagtcgaag tcaatggtta cctctcagtt tgggtaccag ttggtgctaa ggctgaccaa | 2460 |
| gacattcgtg tggcccttc aacagcggct aagggtgaaa aggccaagac ttacacagct | 2520 |
| agccaagctt tggaatcgca attaatctac gaaggcttct caaacttcca agattttgtt | 2580 |
| caaaaagatt cccaatacac caacaagaag attgctgaaa atactgacct cttcaaggct | 2640 |
| tggggtgtta cctcatttga aatggcacca caatacgttt cagcaaccga tggaaccttc | 2700 |
| ctggattcta tcattgaaaa cggttatgcc ttcaccgacc gttatgacct tgccatgagc | 2760 |
| aagaacaata aatacggttc taaggaagat ttggccaacg ccctcaaggc ccttcacgca | 2820 |
| gctggtattc aagccattgc tgactgggta ccagaccaaa tttaccaact gcctggtaag | 2880 |
| gaagttgtta ccgctagccg ggttgacaac tacggtcgtg tgaaagttga ccaaccacta | 2940 |
| gttgaaaaac tttatctggc caacaccaag agctcaggaa aagatttcca agctaaatac | 3000 |
| ggtggtgaat cttagcaga actgcaaaag aaatatcctg aaatgttcac gactaagatg | 3060 |
| atttcaactg gtaaaaccat tgatccatct gtcaaattga agaatggtc tgctaagtac | 3120 |
| ttcaacggaa ccaacgtcct tgatcgtggt acggactata tcctcagtga tgaaggtact | 3180 |
| ggtaaatact ttaccgtcaa tgaaaaaggt gacttcttac ctgcctcatt gactggtaat | 3240 |
| aaggatgcca agactggttt ctacaacgat ggtaagggca ttgtttacta cacaaccgcc | 3300 |
| ggtaacaagg ctagatcagc cttcgtaaca gaagcaggta ataccctatta cttcgactac | 3360 |
| accggccata tggtaacagg ccctaacgtt attaacacta aattctatta cttcttgcca | 3420 |
| aatggtatca tgcttaagga tgctattaag caggatgaaa aaggtcgttc cgtatactac | 3480 |
| ggtaagactg tgttatgta caagggtggc cgcgataatg aatggttcgc catgacagac | 3540 |
| tctaagggtc aaatgcgttt ccgtcacttt gacaggtacg gcttcatgtc tatcggtttg | 3600 |
| gtaaccatca accaaaatgt tcagtattat gatgaaaatg gtttccaagt taaaggtgaa | 3660 |
| tttgtaaccg atcaggatgg acaaacccgt tacttcgacc aaggttcagg taacttggtt | 3720 |
| aagggacaat tcctcaacaa ggatggcaac tggtactacc ttgatgacca agggctagtt | 3780 |
| gctaaaggag ctcagacaat taaaggtcaa aagctttact ttgacacaaa aaccggtgtc | 3840 |
| caagttaaag gggattttgt aacggataaa gatggcaata ccttcttta cagtggagat | 3900 |
| actggcgatt taatccttgg tcagttcttc tcaactggaa ataacgcttg gttctatgct | 3960 |
| gatgaaaatg gtcatgtcgc taagggagct aagactatca gaggtcagaa gctctacttt | 4020 |
| gatacaaaaa caggtcagca agctaaggga cgctttatcc gtgatgacaa gggggttcgt | 4080 |
| tactatgatg ctgacacagg taccttggta accaacgctt tccttgaaac taaggctggt | 4140 |
| tctaaccaat ggtattacat gggagcagat ggttatgctg tcaagggga ccagaccata | 4200 |
| aaaaatcagc acatgtattt tgatgctgaa actggccaac aagctaaggg aattatagtg | 4260 |
| acagatgcca atggtcgcaa gtatttctat gatactttta ctggcagtcg tgttgtaaac | 4320 |
| caatttgttt tggttaatgg aaattggtat ttctttggtt atgatggagc tgcagtaaca | 4380 |
| ggtttccatg atatcaaggg acaacacctt tacttcaatt ccgatggaac acaggccaaa | 4440 |

```
gggactacgg taaaaattgg caatcgcagc tataccttttg atgctcacac tggtgagctg      4500
acatctgttc attatggctg a                                                 4521

<210> SEQ ID NO 12
<211> LENGTH: 1506
<212> TYPE: PRT
<213> ORGANISM: Streptococcus sobrinus

<400> SEQUENCE: 12
```

| Met | Glu | Arg | Lys | Leu | His | Tyr | Lys | Leu | His | Lys | Val | Lys | Lys | Gln | Trp |
|---|---|---|---|---|---|---|---|---|---|---|---|---|---|---|---|
| 1 | | | | 5 | | | | | 10 | | | | | 15 | |

| Val | Thr | Ile | Ala | Val | Ala | Ser | Ala | Gly | Leu | Ala | Ser | Ile | Val | Gly | Ala |
|---|---|---|---|---|---|---|---|---|---|---|---|---|---|---|---|
| | | | 20 | | | | | 25 | | | | | 30 | | |

| Gly | Ser | Leu | Ser | Gln | Thr | Val | Ser | Ala | Asp | Asp | Leu | Ala | Lys | Glu | Gln |
|---|---|---|---|---|---|---|---|---|---|---|---|---|---|---|---|
| | | | 35 | | | | | 40 | | | | | 45 | | |

| Ala | Ala | Ala | Ser | Gln | Gln | Lys | Ala | Ala | Ala | Asn | Gln | Asn | Glu | Asp | Glu |
|---|---|---|---|---|---|---|---|---|---|---|---|---|---|---|---|
| | 50 | | | | | 55 | | | | | 60 | | | | |

| Val | Ala | Ser | Asp | Ala | Ala | Asp | Thr | Ala | Ser | Ala | Lys | Ala | Thr | Ser | Glu |
|---|---|---|---|---|---|---|---|---|---|---|---|---|---|---|---|
| 65 | | | | | 70 | | | | | 75 | | | | | 80 |

| Lys | Glu | Val | Val | Gln | Ser | Ser | Asp | Thr | Asn | Ser | Glu | Thr | Asn | Gln | Val |
|---|---|---|---|---|---|---|---|---|---|---|---|---|---|---|---|
| | | | | 85 | | | | | 90 | | | | | 95 | |

| Glu | Thr | Lys | Asp | Gln | Ala | Ser | Ala | Lys | Glu | Ser | Ala | Asp | Ala | Val | Ala |
|---|---|---|---|---|---|---|---|---|---|---|---|---|---|---|---|
| | | | 100 | | | | | 105 | | | | | 110 | | |

| Lys | Gln | Ala | Pro | Gln | Ala | Gly | Pro | Ala | Thr | Thr | Ser | Gln | Val | Ala | Ser |
|---|---|---|---|---|---|---|---|---|---|---|---|---|---|---|---|
| | | 115 | | | | | 120 | | | | | 125 | | | |

| Ser | Glu | Ser | Ser | Ser | Val | Ala | Pro | Ser | Lys | Glu | Ala | Asp | Lys | Ala | Ala |
|---|---|---|---|---|---|---|---|---|---|---|---|---|---|---|---|
| | 130 | | | | | 135 | | | | | 140 | | | | |

| Ala | Gly | Ser | Val | Ser | Gln | Asn | Glu | Glu | Ala | Ala | Leu | Ser | Leu | Ala |
|---|---|---|---|---|---|---|---|---|---|---|---|---|---|---|
| 145 | | | | | 150 | | | | | 155 | | | | | 160 |

| Asn | Ile | Lys | Lys | Ile | Asp | Gly | Lys | Tyr | Tyr | Val | Met | Ala | Asp | Gly |
|---|---|---|---|---|---|---|---|---|---|---|---|---|---|---|
| | | | | 165 | | | | | 170 | | | | | 175 |

| Ser | Tyr | Lys | Lys | Asn | Phe | Ala | Ile | Thr | Val | Asp | Gly | Gln | Met | Leu | Tyr |
|---|---|---|---|---|---|---|---|---|---|---|---|---|---|---|---|
| | | | 180 | | | | | 185 | | | | | 190 | | |

| Phe | Asp | Ala | Lys | Thr | Gly | Ala | Leu | Ser | Ser | Thr | Ser | Tyr | Ser | Phe |
|---|---|---|---|---|---|---|---|---|---|---|---|---|---|---|
| | | 195 | | | | | 200 | | | | | 205 | | | |

| Ser | Gln | Gly | Leu | Thr | Pro | Ile | Val | Ser | Asp | Phe | Ser | Val | Asn | Asn | Lys |
|---|---|---|---|---|---|---|---|---|---|---|---|---|---|---|---|
| | 210 | | | | | 215 | | | | | 220 | | | | |

| Ala | Phe | Asp | Ser | Ser | Glu | Lys | Ser | Phe | Glu | Leu | Val | Asp | Gly | Tyr | Leu |
|---|---|---|---|---|---|---|---|---|---|---|---|---|---|---|---|
| 225 | | | | | 230 | | | | | 235 | | | | | 240 |

| Thr | Ala | Glu | Ser | Trp | Tyr | Arg | Pro | Ala | Lys | Ile | Leu | Glu | Asn | Gly | Lys |
|---|---|---|---|---|---|---|---|---|---|---|---|---|---|---|---|
| | | | | 245 | | | | | 250 | | | | | 255 | |

| Thr | Trp | Val | Asp | Ser | Lys | Glu | Thr | Asp | Leu | Arg | Pro | Val | Leu | Met | Ser |
|---|---|---|---|---|---|---|---|---|---|---|---|---|---|---|---|
| | | | 260 | | | | | 265 | | | | | 270 | | |

| Trp | Trp | Pro | Asn | Lys | Asp | Thr | Gln | Val | Ala | Tyr | Leu | Asn | Tyr | Met | Ser |
|---|---|---|---|---|---|---|---|---|---|---|---|---|---|---|---|
| | | 275 | | | | | 280 | | | | | 285 | | | |

| Lys | Ala | Leu | Gly | Gly | Lys | Glu | Glu | Phe | Thr | Thr | Glu | Thr | Ser | Gln | Leu |
|---|---|---|---|---|---|---|---|---|---|---|---|---|---|---|---|
| | 290 | | | | | 295 | | | | | 300 | | | | |

| Thr | Leu | Asn | Thr | Ala | Ala | Glu | Leu | Ile | Gln | Ala | Lys | Ile | Glu | Ala | Arg |
|---|---|---|---|---|---|---|---|---|---|---|---|---|---|---|---|
| 305 | | | | | 310 | | | | | 315 | | | | | 320 |

| Val | Ser | Lys | Glu | Gln | Gly | Thr | Lys | Trp | Leu | Arg | Glu | Ala | Met | Ala | Ala |
|---|---|---|---|---|---|---|---|---|---|---|---|---|---|---|---|
| | | | 325 | | | | | 330 | | | | | 335 | | |

| Phe | Val | Ala | Thr | Gln | Ser | Arg | Trp | Asn | Lys | Asp | Ser | Glu | Gln | Tyr | Asp |
|---|---|---|---|---|---|---|---|---|---|---|---|---|---|---|---|
| | | | 340 | | | | | 345 | | | | | 350 | | |

```
Lys Ala Asp His Leu Gln Gly Gly Ala Leu Leu Tyr Thr Asn Asn
        355                 360                 365
Leu Thr Glu Trp Ala Asn Ser Asn Trp Arg Leu Leu Asn Arg Thr Pro
370                 375                 380
Thr Arg Gln Asp Gly Lys Thr His Tyr Ser Lys Ala Asp Lys Tyr Gly
385                 390                 395                 400
Gly Tyr Glu Phe Leu Leu Ala Asn Asp Val Asp Asn Ser Asn Pro Val
                405                 410                 415
Val Gln Ala Glu Met Leu Asn Gln Ile His Tyr Leu Met Asn Trp Gly
            420                 425                 430
Glu Ile Val Met Gly Asp Lys Asn Ala Asn Phe Asp Gly Ile Arg Val
        435                 440                 445
Asp Ala Val Asp Asn Val Asn Ala Asp Thr Leu Gln Leu Tyr Thr Asn
    450                 455                 460
Tyr Phe Asn Ser Val Tyr Gly Val Asn Lys Ser Glu Ala Gln Ala Leu
465                 470                 475                 480
Ala His Ile Ser Val Leu Glu Ala Trp Ser Tyr Asn Asp Asn Asp Tyr
                485                 490                 495
Asn Gln Asp Thr Asn Gly Ala Ala Leu Ala Met Asp Asn Gly Leu Arg
                500                 505                 510
Phe Ser Leu Leu Tyr Thr Leu Thr Arg Pro Ile Asn Glu Arg Thr Pro
            515                 520                 525
Gly Met Ser Thr Leu Ile Lys Ser Glu Tyr Gly Leu Thr Asp Arg Thr
            530                 535                 540
Lys Asn Asp Lys Tyr Gly Asp Thr Gln Pro Ser Tyr Val Phe Val Arg
545                 550                 555                 560
Ala His Asp Ser Glu Val Gln Thr Val Ile Ala Gln Ile Ile Lys Glu
                565                 570                 575
Lys Ile Asp Pro Thr Thr Asp Gly Phe Thr Phe Thr Leu Asp Gln Leu
                580                 585                 590
Lys Gln Ala Phe Glu Ile Tyr Asn Lys Asp Met Asn Ser Val Asn Lys
                595                 600                 605
His Tyr Thr His Tyr Asn Ile Pro Ala Ala Tyr Ala Val Met Leu Ser
        610                 615                 620
Asn Met Glu Ser Val Thr Arg Val Tyr Tyr Gly Asp Leu Phe Thr Asp
625                 630                 635                 640
Asp Gly Gln Tyr Met Ala Ser Lys Ser Pro Tyr Tyr Asp Ala Ile Asn
                645                 650                 655
Thr Leu Leu Arg Ala Arg Ile Arg Tyr Ala Ala Gly Gly Gln Ile Met
            660                 665                 670
Glu His Asn Ser Tyr Lys Pro Ser Ala Ala Met Lys Ala Ala His Pro
            675                 680                 685
Asp Ala Gly Asn Val Leu Gly Asn Ser Glu Val Leu Val Ser Val Arg
    690                 695                 700
Phe Gly Gln Asp Val Met Ser Asp Asp Met Thr Gly Gly Lys Leu
705                 710                 715                 720
Ala Lys Thr Ser Gly Met Phe Thr Leu Ile Ser Asn Asn Pro Glu Leu
                725                 730                 735
Glu Leu Asp Val Asn Glu Glu Ile Lys Val Asn Val Gly Lys Ile His
                740                 745                 750
Ala Gly Gln Ala Tyr Arg Pro Leu Leu Leu Thr Thr Asp Lys Gly Leu
            755                 760                 765
Gln Lys Tyr Leu Asn Asp Ser Asp Thr Lys Leu Thr Lys Ile Ala Asp
```

```
                770             775             780
Lys Asp Gly Phe Ile Thr Phe Lys Gly Ser Glu Ile Lys Gly Tyr Lys
785             790             795             800

Gln Val Glu Val Asn Gly Tyr Leu Ser Val Trp Val Pro Val Gly Ala
                805             810             815

Lys Ala Asp Gln Asp Ile Arg Val Ala Pro Ser Thr Ala Ala Lys Gly
                820             825             830

Glu Lys Ala Lys Thr Tyr Thr Ala Ser Gln Ala Leu Glu Ser Gln Leu
            835             840             845

Ile Tyr Glu Gly Phe Ser Asn Phe Gln Asp Phe Val Gln Lys Asp Ser
850             855             860

Gln Tyr Thr Asn Lys Lys Ile Ala Glu Asn Thr Asp Leu Phe Lys Ala
865             870             875             880

Trp Gly Val Thr Ser Phe Glu Met Ala Pro Gln Tyr Val Ser Ala Thr
                885             890             895

Asp Gly Thr Phe Leu Asp Ser Ile Ile Glu Asn Gly Tyr Ala Phe Thr
                900             905             910

Asp Arg Tyr Asp Leu Ala Met Ser Lys Asn Asn Lys Tyr Gly Ser Lys
            915             920             925

Glu Asp Leu Ala Asn Ala Leu Lys Ala Leu His Ala Ala Gly Ile Gln
930             935             940

Ala Ile Ala Asp Trp Val Pro Asp Gln Ile Tyr Gln Leu Pro Gly Lys
945             950             955             960

Glu Val Val Thr Ala Ser Arg Val Asp Asn Tyr Gly Arg Val Lys Val
                965             970             975

Asp Gln Pro Leu Val Glu Lys Leu Tyr Leu Ala Asn Thr Lys Ser Ser
                980             985             990

Gly Lys Asp Phe Gln Ala Lys Tyr  Gly Gly Glu Phe Leu  Ala Glu Leu
            995             1000            1005

Gln Lys  Lys Tyr Pro Glu Met  Phe Thr Thr Lys Met  Ile Ser Thr
    1010            1015            1020

Gly Lys  Thr Ile Asp Pro Ser  Val Lys Leu Lys Glu  Trp Ser Ala
    1025            1030            1035

Lys Tyr  Phe Asn Gly Thr Asn  Val Leu Asp Arg Gly  Thr Asp Tyr
    1040            1045            1050

Ile Leu  Ser Asp Glu Gly Thr  Gly Lys Tyr Phe Thr  Val Asn Glu
    1055            1060            1065

Lys Gly  Asp Phe Leu Pro Ala  Ser Leu Thr Gly Asn  Lys Asp Ala
    1070            1075            1080

Lys Thr  Gly Phe Tyr Asn Asp  Gly Lys Gly Ile Val  Tyr Tyr Thr
    1085            1090            1095

Thr Ala  Gly Asn Lys Ala Arg  Ser Ala Phe Val Thr  Glu Ala Gly
    1100            1105            1110

Asn Thr  Tyr Tyr Phe Asp Tyr  Thr Gly His Met Val  Thr Gly Pro
    1115            1120            1125

Asn Val  Ile Asn Thr Lys Phe  Tyr Tyr Phe Leu Pro  Asn Gly Ile
    1130            1135            1140

Met Leu  Lys Asp Ala Ile Lys  Gln Asp Glu Lys Gly  Arg Ser Val
    1145            1150            1155

Tyr Tyr  Gly Lys Thr Gly Val  Met Tyr Lys Gly Arg  Arg Asp Asn
    1160            1165            1170

Glu Trp  Phe Ala Met Thr Asp  Ser Lys Gly Gln Met  Arg Phe Arg
    1175            1180            1185
```

```
His Phe Asp Arg Tyr Gly Phe Met Ser Ile Gly Leu Val Thr Ile
    1190                1195                1200

Asn Gln Asn Val Gln Tyr Tyr Asp Glu Asn Gly Phe Gln Val Lys
    1205                1210                1215

Gly Glu Phe Val Thr Asp Gln Asp Gly Gln Thr Arg Tyr Phe Asp
    1220                1225                1230

Gln Gly Ser Gly Asn Leu Val Lys Gly Gln Phe Leu Asn Lys Asp
    1235                1240                1245

Gly Asn Trp Tyr Tyr Leu Asp Asp Gln Gly Leu Val Ala Lys Gly
    1250                1255                1260

Ala Gln Thr Ile Lys Gly Gln Lys Leu Tyr Phe Asp Thr Lys Thr
    1265                1270                1275

Gly Val Gln Val Lys Gly Asp Phe Val Thr Asp Lys Asp Gly Asn
    1280                1285                1290

Thr Phe Phe Tyr Ser Gly Asp Thr Gly Asp Leu Ile Leu Gly Gln
    1295                1300                1305

Phe Phe Ser Thr Gly Asn Asn Ala Trp Phe Tyr Ala Asp Glu Asn
    1310                1315                1320

Gly His Val Ala Lys Gly Ala Lys Thr Ile Arg Gly Gln Lys Leu
    1325                1330                1335

Tyr Phe Asp Thr Lys Thr Gly Gln Gln Ala Lys Gly Arg Phe Ile
    1340                1345                1350

Arg Asp Asp Lys Gly Val Arg Tyr Tyr Asp Ala Asp Thr Gly Thr
    1355                1360                1365

Leu Val Thr Asn Ala Phe Leu Glu Thr Lys Ala Gly Ser Asn Gln
    1370                1375                1380

Trp Tyr Tyr Met Gly Ala Asp Gly Tyr Ala Val Lys Gly Asn Gln
    1385                1390                1395

Thr Ile Lys Asn Gln His Met Tyr Phe Asp Ala Glu Thr Gly Gln
    1400                1405                1410

Gln Ala Lys Gly Ile Ile Val Thr Asp Ala Asn Gly Arg Lys Tyr
    1415                1420                1425

Phe Tyr Asp Thr Phe Thr Gly Ser Arg Val Val Asn Gln Phe Val
    1430                1435                1440

Leu Val Asn Gly Asn Trp Tyr Phe Phe Gly Tyr Asp Gly Ala Ala
    1445                1450                1455

Val Thr Gly Phe His Asp Ile Lys Gly Gln His Leu Tyr Phe Asn
    1460                1465                1470

Ser Asp Gly Thr Gln Ala Lys Gly Thr Thr Val Lys Ile Gly Asn
    1475                1480                1485

Arg Ser Tyr Thr Phe Asp Ala His Thr Gly Glu Leu Thr Ser Val
    1490                1495                1500

His Tyr Gly
    1505

<210> SEQ ID NO 13
<211> LENGTH: 1465
<212> TYPE: PRT
<213> ORGANISM: Streptococcus sobrinus
<220> FEATURE:
<221> NAME/KEY: MISC_FEATURE
<222> LOCATION: (1)..(1465)
<223> OTHER INFORMATION: mature 2920 gtf

<400> SEQUENCE: 13
```

```
Asp Asp Leu Ala Lys Glu Gln Ala Ala Ala Ser Gln Gln Lys Ala Ala
1               5                   10                  15

Ala Asn Gln Asn Glu Asp Glu Val Ala Ser Asp Ala Ala Asp Thr Ala
                20                  25                  30

Ser Ala Lys Ala Thr Ser Glu Lys Glu Val Val Gln Ser Ser Asp Thr
            35                  40                  45

Asn Ser Glu Thr Asn Gln Val Glu Thr Lys Asp Gln Ala Ser Ala Lys
        50                  55                  60

Glu Ser Ala Asp Ala Val Ala Lys Gln Ala Pro Gln Ala Gly Pro Ala
65                  70                  75                  80

Thr Thr Ser Gln Val Ala Ser Ser Glu Ser Ser Val Ala Pro Ser
                85                  90                  95

Lys Glu Ala Asp Lys Ala Ala Ala Gly Ser Val Ser Gln Asn Glu Glu
                100                 105                 110

Glu Ala Ala Leu Ser Leu Ala Asn Ile Lys Lys Ile Asp Gly Lys Tyr
            115                 120                 125

Tyr Tyr Val Met Ala Asp Gly Ser Tyr Lys Lys Asn Phe Ala Ile Thr
        130                 135                 140

Val Asp Gly Gln Met Leu Tyr Phe Asp Ala Lys Thr Gly Ala Leu Ser
145                 150                 155                 160

Ser Thr Ser Thr Tyr Ser Phe Ser Gln Gly Leu Thr Pro Ile Val Ser
                165                 170                 175

Asp Phe Ser Val Asn Asn Lys Ala Phe Asp Ser Ser Glu Lys Ser Phe
                180                 185                 190

Glu Leu Val Asp Gly Tyr Leu Thr Ala Glu Ser Trp Tyr Arg Pro Ala
            195                 200                 205

Lys Ile Leu Glu Asn Gly Lys Thr Trp Val Asp Ser Lys Glu Thr Asp
        210                 215                 220

Leu Arg Pro Val Leu Met Ser Trp Trp Pro Asn Lys Asp Thr Gln Val
225                 230                 235                 240

Ala Tyr Leu Asn Tyr Met Ser Lys Ala Leu Gly Gly Lys Glu Glu Phe
                245                 250                 255

Thr Thr Glu Thr Ser Gln Leu Thr Leu Asn Thr Ala Ala Glu Leu Ile
                260                 265                 270

Gln Ala Lys Ile Glu Ala Arg Val Ser Lys Glu Gln Gly Thr Lys Trp
            275                 280                 285

Leu Arg Glu Ala Met Ala Ala Phe Val Ala Thr Gln Ser Arg Trp Asn
        290                 295                 300

Lys Asp Ser Glu Gln Tyr Asp Lys Ala Asp His Leu Gln Gly Gly Ala
305                 310                 315                 320

Leu Leu Tyr Thr Asn Asn Asn Leu Thr Glu Trp Ala Asn Ser Asn Trp
                325                 330                 335

Arg Leu Leu Asn Arg Thr Pro Thr Arg Gln Asp Gly Lys Thr His Tyr
                340                 345                 350

Ser Lys Ala Asp Lys Tyr Gly Gly Tyr Glu Phe Leu Leu Ala Asn Asp
            355                 360                 365

Val Asp Asn Ser Asn Pro Val Val Gln Ala Glu Met Leu Asn Gln Ile
        370                 375                 380

His Tyr Leu Met Asn Trp Gly Glu Ile Val Met Gly Asp Lys Asn Ala
385                 390                 395                 400

Asn Phe Asp Gly Ile Arg Val Asp Ala Val Asp Asn Val Asn Ala Asp
                405                 410                 415

Thr Leu Gln Leu Tyr Thr Asn Tyr Phe Asn Ser Val Tyr Gly Val Asn
```

-continued

```
                420             425             430
Lys Ser Glu Ala Gln Ala Leu Ala His Ile Ser Val Leu Glu Ala Trp
            435                 440                 445

Ser Tyr Asn Asp Asn Asp Tyr Asn Gln Asp Thr Asn Gly Ala Ala Leu
    450                 455                 460

Ala Met Asp Asn Gly Leu Arg Phe Ser Leu Leu Tyr Thr Leu Thr Arg
465                 470                 475                 480

Pro Ile Asn Glu Arg Thr Pro Gly Met Ser Thr Leu Ile Lys Ser Glu
                485                 490                 495

Tyr Gly Leu Thr Asp Arg Thr Lys Asn Asp Lys Tyr Gly Asp Thr Gln
            500                 505                 510

Pro Ser Tyr Val Phe Val Arg Ala His Asp Ser Glu Val Gln Thr Val
    515                 520                 525

Ile Ala Gln Ile Ile Lys Glu Lys Ile Asp Pro Thr Thr Asp Gly Phe
530                 535                 540

Thr Phe Thr Leu Asp Gln Leu Lys Gln Ala Phe Glu Ile Tyr Asn Lys
545                 550                 555                 560

Asp Met Asn Ser Val Asn Lys His Tyr Thr His Tyr Asn Ile Pro Ala
                565                 570                 575

Ala Tyr Ala Val Met Leu Ser Asn Met Glu Ser Val Thr Arg Val Tyr
            580                 585                 590

Tyr Gly Asp Leu Phe Thr Asp Asp Gly Gln Tyr Met Ala Ser Lys Ser
    595                 600                 605

Pro Tyr Tyr Asp Ala Ile Asn Thr Leu Leu Arg Ala Arg Ile Arg Tyr
    610                 615                 620

Ala Ala Gly Gly Gln Ile Met Glu His Asn Ser Tyr Lys Pro Ser Ala
625                 630                 635                 640

Ala Met Lys Ala Ala His Pro Asp Ala Gly Asn Val Leu Gly Asn Ser
                645                 650                 655

Glu Val Leu Val Ser Val Arg Phe Gly Gln Asp Val Met Ser Ala Asp
            660                 665                 670

Asp Met Thr Gly Gly Lys Leu Ala Lys Thr Ser Gly Met Phe Thr Leu
    675                 680                 685

Ile Ser Asn Asn Pro Glu Leu Glu Leu Asp Val Asn Glu Glu Ile Lys
    690                 695                 700

Val Asn Val Gly Lys Ile His Ala Gly Gln Ala Tyr Arg Pro Leu Leu
705                 710                 715                 720

Leu Thr Thr Asp Lys Gly Leu Gln Lys Tyr Leu Asn Asp Ser Asp Thr
                725                 730                 735

Lys Leu Thr Lys Ile Ala Asp Lys Asp Gly Phe Ile Thr Phe Lys Gly
            740                 745                 750

Ser Glu Ile Lys Gly Tyr Lys Gln Val Glu Val Asn Gly Tyr Leu Ser
    755                 760                 765

Val Trp Val Pro Val Gly Ala Lys Ala Asp Gln Asp Ile Arg Val Ala
770                 775                 780

Pro Ser Thr Ala Ala Lys Gly Glu Lys Ala Lys Thr Tyr Thr Ala Ser
785                 790                 795                 800

Gln Ala Leu Glu Ser Gln Leu Ile Tyr Glu Gly Phe Ser Asn Phe Gln
                805                 810                 815

Asp Phe Val Gln Lys Asp Ser Gln Tyr Thr Asn Lys Lys Ile Ala Glu
            820                 825                 830

Asn Thr Asp Leu Phe Lys Ala Trp Gly Val Thr Ser Phe Glu Met Ala
    835                 840                 845
```

-continued

```
Pro Gln Tyr Val Ser Ala Thr Asp Gly Thr Phe Leu Asp Ser Ile Ile
    850                 855                 860

Glu Asn Gly Tyr Ala Phe Thr Asp Arg Tyr Asp Leu Ala Met Ser Lys
865                 870                 875                 880

Asn Asn Lys Tyr Gly Ser Lys Glu Asp Leu Ala Asn Ala Leu Lys Ala
                885                 890                 895

Leu His Ala Ala Gly Ile Gln Ala Ile Ala Asp Trp Val Pro Asp Gln
            900                 905                 910

Ile Tyr Gln Leu Pro Gly Lys Glu Val Val Thr Ala Ser Arg Val Asp
        915                 920                 925

Asn Tyr Gly Arg Val Lys Val Asp Gln Pro Leu Val Glu Lys Leu Tyr
    930                 935                 940

Leu Ala Asn Thr Lys Ser Ser Gly Lys Asp Phe Gln Ala Lys Tyr Gly
945                 950                 955                 960

Gly Glu Phe Leu Ala Glu Leu Gln Lys Lys Tyr Pro Glu Met Phe Thr
                965                 970                 975

Thr Lys Met Ile Ser Thr Gly Lys Thr Ile Asp Pro Ser Val Lys Leu
            980                 985                 990

Lys Glu Trp Ser Ala Lys Tyr Phe Asn Gly Thr Asn Val Leu Asp Arg
        995                 1000                1005

Gly Thr Asp Tyr Ile Leu Ser Asp Glu Gly Thr Gly Lys Tyr Phe
        1010                1015                1020

Thr Val Asn Glu Lys Gly Asp Phe Leu Pro Ala Ser Leu Thr Gly
        1025                1030                1035

Asn Lys Asp Ala Lys Thr Gly Phe Tyr Asn Asp Gly Lys Gly Ile
        1040                1045                1050

Val Tyr Tyr Thr Thr Ala Gly Asn Lys Ala Arg Ser Ala Phe Val
        1055                1060                1065

Thr Glu Ala Gly Asn Thr Tyr Tyr Phe Asp Tyr Thr Gly His Met
        1070                1075                1080

Val Thr Gly Pro Asn Val Ile Asn Thr Lys Phe Tyr Tyr Phe Leu
        1085                1090                1095

Pro Asn Gly Ile Met Leu Lys Asp Ala Ile Lys Gln Asp Glu Lys
        1100                1105                1110

Gly Arg Ser Val Tyr Tyr Lys Thr Gly Val Met Tyr Lys Gly
        1115                1120                1125

Gly Arg Asp Asn Glu Trp Phe Ala Met Thr Asp Ser Lys Gly Gln
        1130                1135                1140

Met Arg Phe Arg His Phe Asp Arg Tyr Gly Phe Met Ser Ile Gly
        1145                1150                1155

Leu Val Thr Ile Asn Gln Asn Val Gln Tyr Tyr Asp Glu Asn Gly
        1160                1165                1170

Phe Gln Val Lys Gly Glu Phe Val Thr Asp Gln Asp Gly Gln Thr
        1175                1180                1185

Arg Tyr Phe Asp Gln Gly Ser Gly Asn Leu Val Lys Gly Gln Phe
        1190                1195                1200

Leu Asn Lys Asp Gly Asn Trp Tyr Tyr Leu Asp Asp Gln Gly Leu
        1205                1210                1215

Val Ala Lys Gly Ala Gln Thr Ile Lys Gly Gln Lys Leu Tyr Phe
        1220                1225                1230

Asp Thr Lys Thr Gly Val Gln Val Lys Gly Asp Phe Val Thr Asp
        1235                1240                1245
```

```
Lys Asp Gly Asn Thr Phe Phe Tyr Ser Gly Asp Thr Gly Asp Leu
    1250                1255                1260

Ile Leu Gly Gln Phe Phe Ser Thr Gly Asn Asn Ala Trp Phe Tyr
1265                1270                1275

Ala Asp Glu Asn Gly His Val Ala Lys Gly Ala Lys Thr Ile Arg
    1280                1285                1290

Gly Gln Lys Leu Tyr Phe Asp Thr Lys Thr Gly Gln Gln Ala Lys
1295                1300                1305

Gly Arg Phe Ile Arg Asp Asp Lys Gly Val Arg Tyr Tyr Asp Ala
    1310                1315                1320

Asp Thr Gly Thr Leu Val Thr Asn Ala Phe Leu Glu Thr Lys Ala
1325                1330                1335

Gly Ser Asn Gln Trp Tyr Tyr Met Gly Ala Asp Gly Tyr Ala Val
    1340                1345                1350

Lys Gly Asn Gln Thr Ile Lys Asn Gln His Met Tyr Phe Asp Ala
1355                1360                1365

Glu Thr Gly Gln Gln Ala Lys Gly Ile Ile Val Thr Asp Ala Asn
    1370                1375                1380

Gly Arg Lys Tyr Phe Tyr Asp Thr Phe Thr Gly Ser Arg Val Val
1385                1390                1395

Asn Gln Phe Val Leu Val Asn Gly Asn Trp Tyr Phe Phe Gly Tyr
    1400                1405                1410

Asp Gly Ala Ala Val Thr Gly Phe His Asp Ile Lys Gly Gln His
1415                1420                1425

Leu Tyr Phe Asn Ser Asp Gly Thr Gln Ala Lys Gly Thr Thr Val
    1430                1435                1440

Lys Ile Gly Asn Arg Ser Tyr Thr Phe Asp Ala His Thr Gly Glu
1445                1450                1455

Leu Thr Ser Val His Tyr Gly
    1460                1465

<210> SEQ ID NO 14
<211> LENGTH: 4398
<212> TYPE: DNA
<213> ORGANISM: Artificial sequence
<220> FEATURE:
<223> OTHER INFORMATION: 2920 gtf with heterologous signal sequence

<400> SEQUENCE: 14
gatgacctgg cgaaggaaca agcagccgcc tcacagcaaa aagcagcggc taaccagaat      60
gaagacgaag ttgcatcaga tgcagccgat acagctagcg ccaaagccac gtcagagaaa     120
gaagtggttc agtcaagcga tacaaactca gaaacaaatc aggttgagac gaaagaccaa     180
gcatcagcta aggagagcgc agacgcagtc gcgaaacaag ctcctcaagc aggaccggca     240
acaacgtcac aggtcgccag ctcagagagc agcagcgtgg caccgagcaa ggaggctgac     300
aaggctgccg caggctcagt ctcacagaac gaggaggagg cagcccttc acttgccaac     360 atcaagaaga ttgacggaaa atactattac gttatggccg atggaagcta caagaaaaac     420
tttgcgatta cggttgatgg acagatgctt tactttgacg caaaaacagg cgcactttca     480
tcaacgagca cgtatagctt ttcacaaggc ctgacgccga ttgtctcaga ctttagcgtg     540
aacaataagg ctttcgattc atcagaaaag tcatttgaac ttgtggacgg ctacctgaca     600
gccgaaagct ggtacagacc ggccaaaatc ctggaaaacg aaagacgtg gtcgactca      660 aaagaaacag atcttagacc tgtcctgatg tcatggtggc cgaacaaaga cacacaagtc     720
```

```
gcatatctga attacatgtc aaaagctctg ggaggcaaag aagagtttac gacagagaca    780
tcacaactga cactgaatac agcggcagaa cttatccagg cgaagatcga agctagagtg    840
agcaaagagc agggcacaaa atggctgaga gaagcaatgg cagcatttgt ggcgacgcaa    900
tcaagatgga ataaagattc agagcaatat gataaagcag atcatcttca aggcggagct    960
ctgctgtaca caaacaacaa ccttacagaa tgggctaatt caaattggag actgcttaat   1020
agaacaccga cgagacagga tggaaaaaca cattactcaa aggcagataa gtatggcgga   1080
tatgagtttc tgctggctaa tgatgtcgat aactcaaatc cggttgtcca agctgaaatg   1140
cttaaccaaa ttcattatct tatgaattgg ggcgaaattg ttatgggcga taagaatgct   1200
aacttcgacg gaatcagagt tgatgcagtt gacaacgtta atgcagatac actgcagctt   1260
tatacaaatt actttaatag cgtttatgga gtcaacaagt cagaagcaca ggcccttgca   1320
catatttcag tccttgaggc atggtcatat aatgataacg actataatca ggatacgaat   1380
ggcgcagcac ttgcgatgga taatggcctg agattctcac ttctgtatac gcttacaaga   1440
ccgattaatg aaagaacgcc tggcatgagc acactgatta gagcgaata cggactgacg   1500 gatagaacga aaaacgacaa gtacggcgac acgcaaccta gctatgtctt cgttagagca   1560
catgatagcg aggttcaaac ggttattgcc caaattatca aggagaaaat cgatcctaca   1620
acagatggct ttacatttac gctggatcaa ctgaagcaag ccttcgaaat ctataacaag   1680
gacatgaact cagtgaataa gcactacacg cattacaata ttcctgctgc atacgctgtt   1740
atgctgagca acatggaaag cgtgacaaga gtgtactacg gcgacctttt tacggatgac   1800
ggccagtata tggcaagcaa gtcacccttat tatgatgcta tcaatacact tcttagagcg   1860
agaattagat acgccgctgg aggacaaatc atggaacata attcatataa gccgagcgcc   1920
gcaatgaaag ctgcacaccc ggacgccggc aacgtcctgg gcaattcaga ggtcctggtc   1980
tcagtgagat tcggccaaga cgtgatgtca gcagatgata tgacaggcgg aaaacttgcg   2040
aaaacatcag gcatgtttac gcttattagc aataacccgg aactggaact tgacgttaat   2100
gaggagatca aagtgaatgt gggcaaaatc catgctggac aagcttatag accgcttctg   2160
cttacaacag ataagggact tcagaagtac cttaatgatt cagacacaaa actgacgaag   2220
atcgctgaca agacggatt cattacattc aaaggatcag aaattaaggg ctataaacaa   2280
gttgaggtta atggctacct ttcagtttgg gtcccggttg gcgctaaagc agaccaagat   2340
attagagttg ccccgagcac agccgcaaaa ggagaaaagg ctaaaacgta tacagcatca   2400
caggctctgg aatcacagct tatctatgaa ggcttctcaa actttcaaga ctttgttcaa   2460
aaagatagcc aatatacgaa taagaaaatt gcagagaaca cagacctgtt taaagcatgg   2520
ggagttacgt cattcgagat ggctcctcaa tatgttagcg caacggatgg cacattcctg   2580
gattcaatca ttgaaaacgg ctatgcattc acagacagat acgaccttgc tatgagcaag   2640
aataacaaat atggatcaaa agaggatctg gctaacgcac ttaaggcact tcacgcagct   2700
ggcattcaag ctattgcgga ttgggtgcct gaccaaatct accaactgcc gggcaaagag   2760
gttgtgacag ccagcagagt ggataactat ggcagagtta aggtggacca gccgcttgtc   2820
gagaagctgt atctggcgaa tacgaaatca tcaggaaaag atttccaggc taagtacggc   2880
ggagagttcc ttgcggagct gcagaagaaa tacccggaga tgttcacgac aaaaatgatc   2940
agcacaggaa agacaatcga cccgtcagtg aagctgaaag agtggtcagc caagtacttc   3000
aatggaacga acgtgctgga tagaggcaca gactatattc ttagcgatga gggaacggga   3060
aagtatttca cagtcaacga gaagggcgat ttcctgcctg cgagccttac aggcaacaag   3120
```

```
gatgccaaaa caggcttta caatgacgga aaaggaattg tttactacac aacagctgga      3180
aacaaggcta gaagcgcgtt cgtgacagag gctggcaaca catactattt cgactatacg      3240
ggccacatgg tgacaggacc gaatgttatc aacacgaagt tctattactt tcttcctaac      3300
ggcatcatgc tgaaggacgc aattaagcaa gatgaaaagg gaagaagcgt ttattacggc      3360
aagacaggag ttatgtacaa gggcggcaga gataacgaat ggtttgcaat gacagactca      3420
aagggacaga tgagatttag acatttcgat agatatggct tcatgtcaat ggacttgtt      3480 acaatcaacc agaatgttca atactatgat gagaatggct ttcaggtgaa aggcgaattt      3540
gtcacagatc aggatggaca aacgagatac ttcgaccaag gctcaggcaa tcttgttaaa      3600
ggacagtttc ttaacaaaga tggaaattgg tattatctgg atgatcaagg actggttgct      3660
aaaggagctc aaacgattaa aggccaaaaa ctgtattttg atacgaagac gggcgtgcag      3720
gttaagggag attttgtgac ggacaaggac ggcaatacat tcttctatag cggagatacg      3780
ggagatctga ttctgggaca attcttttca acgggcaata atgcatggtt ttatgcggac      3840
gagaacggac acgtcgccaa aggcgcaaaa acaatcagag gacagaagct ttacttcgat      3900
acaaaaacgg acaacaagc caagggcaga ttcatcagag acgacaaggg agtcagatac      3960
tacgatgcag acacgggcac actggttaca aacgcatttc tggagacgaa ggcgggaagc      4020
aatcagtggt actacatggg cgctgatgga tatgccgtga agggaaacca gacgatcaag      4080
aaccagcata tgtactttga cgctgaaaca ggacagcaag ctaagggaat catcgttacg      4140
gacgcgaacg gcagaaaata cttctatgac acgtttacgg gctcaagagt tgttaatcaa      4200
ttcgttcttg tgaacggaaa ctggtacttt tttggatacg atggagcagc agttacagga      4260
ttccacgata tcaagggcca acatctttat ttcaactcag acggaacgca agcgaaaggc      4320
acgacagtta agatcggaaa tagaagctac acattcgacg cacacacagg cgagcttaca      4380
tcagtccatt acggatga                                                    4398
```

<210> SEQ ID NO 15
<211> LENGTH: 4360
<212> TYPE: DNA
<213> ORGANISM: Streptococcus downei

<400> SEQUENCE: 15

```
atgatttca tggaaagaaa attacattac aaattacaca aggtcaagaa gcagtgggtg       60
accatcgctg tcgcctctgc tggtttggcc agcgtagtcg gtgctggctc cttgagccaa      120
accgtttctg ctgacgatct tgctaaggac caagcggcag cgactgagca aaaggcatca      180
gccaatcagg aaaagaaga agtagtttct gatcaggttg acacgaccag tgccaaagca      240
acctctgaga aggaagttgc tcaagcttcg gacactagtt cagaagccaa ccaagttcca      300
gcccaagaag aaagaaggc tgaaaaggca gctgctcctg cgacagcgac accagctcca      360
cagactggtg caaaaaacag ccaaacagct agttcagaag caccagcgac aagcaatcaa      420
gcaagtgaga cagctgaaac tggtgcctta agccaaaaag aagaagcagc agttcttcg      480 cttgataata tcaagaagat tgatggaaag tattactatg ttatggcaga cggctcttat      540
aagaagaact tgccattac tgttgatggg caatgctttt actttgatgc caaaacaggt      600
gccctgtctt caacctctac ctattctttc agtcaaggt tgacaccaat tgtttctgat      660
ttctcagtca acaataaggc tttcgattct tctgaaaaga gttttgaact ggtagatggt      720
tacctgacag ctgaaagctg gtaccgtcct gctaagattc ttgaaaatgg caagacctgg      780
```

```
gtggactcca aagaaactga ccttcgtcca gttctcatga gctggtggcc aaacaaggat    840
acccaagttg cctacctcaa ctatatgtcc aaggcgcttg gtggcaagga agagtttaca    900
acagaaacct ctcaaacaac cttgaataca gctgctgagt tgattcaaac caagattgaa    960
gctcgtattt ctaaggaaca agggaccaaa tggcttcgtg aagctatggc tgcttttgta   1020
gcgactcagt ctcgttggag ttacgctagt gagcaatttg ataaaaacga ccacttgcaa   1080
ggtggtgctc tcctttatac taataataaa ttgacccaat gggcagattc taactatcgt   1140
ttgcttaacc gcaccccta ccgacaggat ggcaagcctc attattctaa agctgacgaa    1200
tacggtggtt acgaattcct cttggctaat gacgtggata ctccaaccc agtcgttcaa    1260 gcggaaatgc tcaaccaaat ccactacctg atgaactggg gctctattgt catgaatgac   1320
aaggatgcca actttgatgg tatccgtgtg gatgcgtgg ataatgtcaa tgcggatacc    1380
ctgcaactct acactaacta ttttaattcg gtttatggtg tcaacaagtc agaagcccaa   1440
gccctagctc acatttcagt attagaagct tggtcttata tgataatga ctataaccaa    1500 gataccaatg gtgcggcctt ggctatggac aatggtctac gcttctccct gctttatacc   1560
ctgacacgtc cacttaatga gcggactcct ggtatgtcaa ccttgattaa gtcacaatat   1620
ggtttgactg accggaccaa ggatgacaag tatggcgata ctcagccatc ctatgtcttt   1680
gttcgggctc atgactcaga agtgcaaacc gttattgcgc aaatcatcaa gaaaaaatt    1740 gatccaacga ctgatggctt taccttcacc ttggaccaat gaaacaggc ctttgacatc    1800 tacaataagg atatgaatag tgttgataag cactataccc actacaatat tccagcagcc   1860
tacgctgtta tgttgtccaa catggaatca gtaactcggg tttactatgg agacctcttt   1920
accgatgatg gtcaatacat ggaaaccaag tctccttact acgatgctat caataccctc   1980
cttagggccc ggattcgtta cgccgctggt ggtcaaacca tggaacacaa ttcctataag   2040
gcatcagcag ctatgaaagc taaaaatcct gatagtggta gtgtgcttgg caacagcgaa   2100
gttcttgtct ctgttcgttt tggtcaagat gtgatgtctg ctgacgatat gactggtggt   2160
aagctggcta aacctctgg tatgttcagc ctgatttcca caaccctga attagaattg    2220 gatgccaatg aagaaatcag ggtcaatgtt ggtaagattc atgctggtca aacctaccgt   2280
ccattgcttt tgacaaccga taagggtctg caaaagtacc tcaatgattc tgatactaag   2340
ctgaccaagg ttgccgataa ggatggttat atcaccttca agggcagtga atcaagggc    2400 tacaagcagg ttgaagtcaa tggttacctt tctgtttggg taccagtcgg cgcaaaggca   2460
gatcaagata ttcgtgtggc agcttcaact aaggttaatg gtaaggatga caagacttat   2520
acagctagtc aagccttaga atcacaatta atctacgaag gtttctcaaa cttccaagat   2580
ttcgttaaga aggactccca atataccaat aagaagattg ctgaaaatac cgacctcttt   2640
aaggcctggg gcgtgacctc atttgaaatg gcgccacaat acgtttccgc aactgatggt   2700
accttcctgg attctattat tgaaaatggt tatgccttca ccgaccgtta tgaccttgcc   2760
atgagcaaga acaacaagta cggttctaag gaagacttgg ccaatgctct taaggccctc   2820
cacgctgctg gtatccaagc tatcgcagac tgggttccag accaaattta ccaactccca   2880
ggtaaggaag tggtaactgc aagtcgtgtt gataactatg ccgtgttaa gattgaccaa    2940 ccattggttg aaaaactta cttggccaat accaagagct caggaaaaga cttccaggct   3000
aaatatggtg gtgaattctt agaagacctg caaaagcaat accctgaaat gtttaccgct   3060
aagatgattt caaccggtaa aaccattgat ccatctgtca aattgaagga atggtcagct   3120
aagtacttga acggaacaaa tgttctgggt cgtggtacag actatgtcct cagcgatgaa   3180
```

-continued

```
ggaactggca aatacttcac tgttaatgaa aagggtgact tcctaccagc agccctgaca    3240 ggtgatpggg aagccaagac tggtttctac aatgatggta agggaatgac ctactataca    3300
acggctggta acaaggctaa atctgccttt gtaaccgtag ctggaaatac ctattacttt    3360
gactatactg gttatatggt aacaggacca aacacgatta acagcaaatt ctattacttc    3420
ctgccaaatg gggtaatgct caaggatgct attaagcaag atgagttggg ccgttcggtt    3480
tactatggta aaactggtac catgtacaag gcgacagata atctcaatg gtttgccatg     3540 accgactcta agggtcaaca acgcttccgt cactttgacc gcttcggtat catgtctgta    3600
ggactggtta ccatcaatgg tagtgttcaa tattacgatg aagaaggctt ccaagttaag    3660
ggcgaatttg tcactgataa ggatggtcaa acccgttact ttgacgaagg ttctggtaat    3720
ctggttaagg accgcttcct caataaggat ggcaagtggt actatcttga tgataaaggc    3780
ttgctggtca agggggctca aaccattaag ggtcaaaaac tctactttga caccaagacc    3840
ggtgcccaag tcaagggtga ctttgttgcc gacaaggatg caacctgac cttctatagt     3900 ggtgatagtg gtcaaatggt tcaaagtgat ttcttctcaa caggaaataa tgcttggttc    3960
tatgccgatg aaaatggtca tgtcgctaag ggagctaaga ctatcagagg tcagaagctc    4020
tactttgata caaaaacagg tcagcaagct aagggacgct ttatccgtga tgacaagggg    4080
gttcgttact atgatgctga cacaggtgcc ttgtaaccaa acgctttcct tgaaactaag    4140
gctggttcta accaatggta ttacatggga gcagatggtt atgctgtcaa ggggaaccag    4200
accataaaaa atcagcacat gtattttgat gctgaaactg ccaacaagc taagggaatt     4260 atagtgacag atgccaatgg tcgcaagtat ttctatgata cttttactgg cagtcgtgtt    4320
gtaaaccaat ttgttttggt taatggaaat tggtatttct                           4360
```

<210> SEQ ID NO 16
<211> LENGTH: 1453
<212> TYPE: PRT
<213> ORGANISM: Streptococcus downei

<400> SEQUENCE: 16

```
Met Ile Phe Met Glu Arg Lys Leu His Tyr Lys Leu His Lys Val Lys
1               5                  10                  15

Lys Gln Trp Val Thr Ile Ala Val Ala Ser Ala Gly Leu Ala Ser Val
            20                  25                  30

Val Gly Ala Gly Ser Leu Ser Gln Thr Val Ser Ala Asp Asp Leu Ala
        35                  40                  45

Lys Asp Gln Ala Ala Ala Thr Glu Gln Lys Ala Ser Ala Asn Gln Glu
    50                  55                  60

Lys Glu Glu Val Val Ser Asp Gln Val Asp Thr Thr Ser Ala Lys Ala
65                  70                  75                  80

Thr Ser Glu Lys Glu Val Ala Gln Ala Ser Asp Thr Ser Ser Glu Ala
                85                  90                  95

Asn Gln Val Pro Ala Gln Glu Glu Lys Lys Ala Glu Lys Ala Ala Ala
            100                 105                 110

Pro Ala Thr Ala Thr Pro Ala Pro Gln Thr Gly Ala Lys Asn Ser Gln
        115                 120                 125

Thr Ala Ser Ser Glu Ala Pro Ala Thr Ser Asn Gln Ala Ser Glu Thr
    130                 135                 140

Ala Glu Thr Gly Ala Leu Ser Gln Lys Glu Glu Ala Ala Val Leu Ser
145                 150                 155                 160
```

```
Leu Asp Asn Ile Lys Lys Ile Asp Gly Lys Tyr Tyr Tyr Val Met Ala
            165                 170                 175
Asp Gly Ser Tyr Lys Lys Asn Phe Ala Ile Thr Val Asp Gly Gln Met
            180                 185                 190
Leu Tyr Phe Asp Ala Lys Thr Gly Ala Leu Ser Ser Thr Ser Thr Tyr
            195                 200                 205
Ser Phe Ser Gln Gly Leu Thr Pro Ile Val Ser Asp Phe Ser Val Asn
            210                 215                 220
Asn Lys Ala Phe Asp Ser Ser Glu Lys Ser Phe Glu Leu Val Asp Gly
225                 230                 235                 240
Tyr Leu Thr Ala Glu Ser Trp Tyr Arg Pro Ala Lys Ile Leu Glu Asn
            245                 250                 255
Gly Lys Thr Trp Val Asp Ser Lys Glu Thr Asp Leu Arg Pro Val Leu
            260                 265                 270
Met Ser Trp Trp Pro Asn Lys Asp Thr Gln Val Ala Tyr Leu Asn Tyr
            275                 280                 285
Met Ser Lys Ala Leu Gly Gly Lys Glu Glu Phe Thr Thr Glu Thr Ser
            290                 295                 300
Gln Thr Thr Leu Asn Thr Ala Ala Glu Leu Ile Gln Thr Lys Ile Glu
305                 310                 315                 320
Ala Arg Ile Ser Lys Glu Gln Gly Thr Lys Trp Leu Arg Glu Ala Met
            325                 330                 335
Ala Ala Phe Val Ala Thr Gln Ser Arg Trp Ser Tyr Ala Ser Glu Gln
            340                 345                 350
Phe Asp Lys Asn Asp His Leu Gln Gly Gly Ala Leu Leu Tyr Thr Asn
            355                 360                 365
Asn Lys Leu Thr Gln Trp Ala Asp Ser Asn Tyr Arg Leu Leu Asn Arg
            370                 375                 380
Thr Pro Thr Arg Gln Asp Gly Lys Pro His Tyr Ser Lys Ala Asp Glu
385                 390                 395                 400
Tyr Gly Gly Tyr Glu Phe Leu Leu Ala Asn Asp Val Asp Asn Ser Asn
            405                 410                 415
Pro Val Val Gln Ala Glu Met Leu Asn Gln Ile His Tyr Leu Met Asn
            420                 425                 430
Trp Gly Ser Ile Val Met Asn Asp Lys Asp Ala Asn Phe Asp Gly Ile
            435                 440                 445
Arg Val Asp Ala Val Asp Asn Val Asn Ala Asp Thr Leu Gln Leu Tyr
            450                 455                 460
Thr Asn Tyr Phe Asn Ser Val Tyr Gly Val Asn Lys Ser Glu Ala Gln
465                 470                 475                 480
Ala Leu Ala His Ile Ser Val Leu Glu Ala Trp Ser Tyr Asn Asp Asn
            485                 490                 495
Asp Tyr Asn Gln Asp Thr Asn Gly Ala Ala Leu Ala Met Asp Asn Gly
            500                 505                 510
Leu Arg Phe Ser Leu Leu Tyr Thr Leu Thr Arg Pro Leu Asn Glu Arg
            515                 520                 525
Thr Pro Gly Met Ser Thr Leu Ile Lys Ser Gln Tyr Gly Leu Thr Asp
            530                 535                 540
Arg Thr Lys Asp Asp Lys Tyr Gly Asp Thr Gln Pro Ser Tyr Val Phe
545                 550                 555                 560
Val Arg Ala His Asp Ser Glu Val Gln Thr Val Ile Ala Gln Ile Ile
            565                 570                 575
Lys Lys Lys Ile Asp Pro Thr Thr Asp Gly Phe Thr Phe Thr Leu Asp
```

-continued

```
                580                 585                 590
Gln Leu Lys Gln Ala Phe Asp Ile Tyr Asn Lys Asp Met Asn Ser Val
            595                 600                 605
Asp Lys His Tyr Thr His Tyr Asn Ile Pro Ala Ala Tyr Ala Val Met
            610                 615                 620
Leu Ser Asn Met Glu Ser Val Thr Arg Val Tyr Tyr Gly Asp Leu Phe
625                 630                 635                 640
Thr Asp Asp Gly Gln Tyr Met Glu Thr Lys Ser Pro Tyr Tyr Asp Ala
                645                 650                 655
Ile Asn Thr Leu Leu Arg Ala Arg Ile Arg Tyr Ala Ala Gly Gly Gln
            660                 665                 670
Thr Met Glu His Asn Ser Tyr Lys Ala Ser Ala Ala Met Lys Ala Lys
            675                 680                 685
Asn Pro Asp Ser Gly Ser Val Leu Gly Asn Ser Glu Val Leu Val Ser
            690                 695                 700
Val Arg Phe Gly Gln Asp Val Met Ser Ala Asp Asp Met Thr Gly Gly
705                 710                 715                 720
Lys Leu Ala Lys Thr Ser Gly Met Phe Ser Leu Ile Ser Asn Asn Pro
                725                 730                 735
Glu Leu Glu Leu Asp Ala Asn Glu Glu Ile Arg Val Asn Val Gly Lys
            740                 745                 750
Ile His Ala Gly Gln Thr Tyr Arg Pro Leu Leu Thr Thr Asp Lys
            755                 760                 765
Gly Leu Gln Lys Tyr Leu Asn Asp Ser Asp Thr Lys Leu Thr Lys Val
            770                 775                 780
Ala Asp Lys Asp Gly Tyr Ile Thr Phe Lys Gly Ser Glu Ile Lys Gly
785                 790                 795                 800
Tyr Lys Gln Val Glu Val Asn Gly Tyr Leu Ser Val Trp Val Pro Val
                805                 810                 815
Gly Ala Lys Ala Asp Gln Asp Ile Arg Val Ala Ala Ser Thr Lys Val
            820                 825                 830
Asn Gly Lys Asp Asp Lys Thr Tyr Thr Ala Ser Gln Ala Leu Glu Ser
            835                 840                 845
Gln Leu Ile Tyr Glu Gly Phe Ser Asn Phe Gln Asp Phe Val Lys Lys
            850                 855                 860
Asp Ser Gln Tyr Thr Asn Lys Lys Ile Ala Glu Asn Thr Asp Leu Phe
865                 870                 875                 880
Lys Ala Trp Gly Val Thr Ser Phe Glu Met Ala Pro Gln Tyr Val Ser
                885                 890                 895
Ala Thr Asp Gly Thr Phe Leu Asp Ser Ile Ile Glu Asn Gly Tyr Ala
            900                 905                 910
Phe Thr Asp Arg Tyr Asp Leu Ala Met Ser Lys Asn Asn Lys Tyr Gly
            915                 920                 925
Ser Lys Glu Asp Leu Ala Asn Ala Leu Lys Ala Leu His Ala Ala Gly
            930                 935                 940
Ile Gln Ala Ile Ala Asp Trp Val Pro Asp Gln Ile Tyr Gln Leu Pro
945                 950                 955                 960
Gly Lys Glu Val Val Thr Ala Ser Arg Val Asp Asn Tyr Gly Arg Val
                965                 970                 975
Lys Ile Asp Gln Pro Leu Val Glu Lys Leu Tyr Leu Ala Asn Thr Lys
            980                 985                 990
Ser Ser Gly Lys Asp Phe Gln Ala Lys Tyr Gly Gly Glu Phe Leu Glu
            995                 1000                1005
```

```
Asp Leu Gln Lys Gln Tyr Pro Glu Met Phe Thr Ala Lys Met Ile
    1010            1015                1020

Ser Thr Gly Lys Thr Ile Asp Pro Ser Val Lys Leu Lys Glu Trp
    1025            1030                1035

Ser Ala Lys Tyr Leu Asn Gly Thr Asn Val Leu Gly Arg Gly Thr
    1040            1045                1050

Asp Tyr Val Leu Ser Asp Glu Gly Thr Gly Lys Tyr Phe Thr Val
    1055            1060                1065

Asn Glu Lys Gly Asp Phe Leu Pro Ala Ala Leu Thr Gly Asp Arg
    1070            1075                1080

Glu Ala Lys Thr Gly Phe Tyr Asn Asp Gly Lys Gly Met Thr Tyr
    1085            1090                1095

Tyr Thr Thr Ala Gly Asn Lys Ala Lys Ser Ala Phe Val Thr Val
    1100            1105                1110

Ala Gly Asn Thr Tyr Tyr Phe Asp Tyr Thr Gly Tyr Met Val Thr
    1115            1120                1125

Gly Pro Asn Thr Ile Asn Ser Lys Phe Tyr Tyr Phe Leu Pro Asn
    1130            1135                1140

Gly Val Met Leu Lys Asp Ala Ile Lys Gln Asp Glu Leu Gly Arg
    1145            1150                1155

Ser Val Tyr Tyr Gly Lys Thr Gly Thr Met Tyr Lys Ala Thr Asp
    1160            1165                1170

Lys Ser Gln Trp Phe Ala Met Thr Asp Ser Lys Gly Gln Gln Arg
    1175            1180                1185

Phe Arg His Phe Asp Arg Phe Gly Ile Met Ser Val Gly Leu Val
    1190            1195                1200

Thr Ile Asn Gly Ser Val Gln Tyr Tyr Asp Glu Glu Gly Phe Gln
    1205            1210                1215

Val Lys Gly Glu Phe Val Thr Asp Lys Asp Gly Gln Thr Arg Tyr
    1220            1225                1230

Phe Asp Glu Gly Ser Gly Asn Leu Val Lys Asp Arg Phe Leu Asn
    1235            1240                1245

Lys Asp Gly Lys Trp Tyr Tyr Leu Asp Asp Lys Gly Leu Leu Val
    1250            1255                1260

Lys Gly Ala Gln Thr Ile Lys Gly Gln Lys Leu Tyr Phe Asp Thr
    1265            1270                1275

Lys Thr Gly Ala Gln Val Lys Gly Asp Phe Val Ala Asp Lys Asp
    1280            1285                1290

Gly Asn Leu Thr Phe Tyr Ser Gly Asp Ser Gly Gln Met Val Gln
    1295            1300                1305

Ser Asp Phe Phe Ser Thr Gly Asn Asn Ala Trp Phe Tyr Ala Asp
    1310            1315                1320

Glu Asn Gly His Val Ala Lys Gly Ala Lys Thr Ile Arg Gly Gln
    1325            1330                1335

Lys Leu Tyr Phe Asp Thr Lys Thr Gly Gln Gln Ala Lys Gly Arg
    1340            1345                1350

Phe Ile Arg Asp Asp Lys Gly Val Arg Tyr Tyr Asp Ala Asp Thr
    1355            1360                1365

Gly Ala Leu Val Thr Asn Ala Phe Leu Glu Thr Lys Ala Gly Ser
    1370            1375                1380

Asn Gln Trp Tyr Tyr Met Gly Ala Asp Gly Tyr Ala Val Lys Gly
    1385            1390                1395
```

-continued

```
Asn Gln Thr Ile Lys Asn Gln His Met Tyr Phe Asp Ala Glu Thr
    1400                1405                1410

Gly Gln Gln Ala Lys Gly Ile Ile Val Thr Asp Ala Asn Gly Arg
    1415                1420                1425

Lys Tyr Phe Tyr Asp Thr Phe Thr Gly Ser Arg Val Val Asn Gln
    1430                1435                1440

Phe Val Leu Val Asn Gly Asn Trp Tyr Phe
    1445                1450

<210> SEQ ID NO 17
<211> LENGTH: 1409
<212> TYPE: PRT
<213> ORGANISM: Streptococcus downei
<220> FEATURE:
<221> NAME/KEY: MISC_FEATURE
<222> LOCATION: (1)..(1409)
<223> OTHER INFORMATION: mature 2921 gtf

<400> SEQUENCE: 17

Asp Asp Leu Ala Lys Asp Gln Ala Ala Thr Glu Gln Lys Ala Ser
1               5                   10                  15

Ala Asn Gln Glu Lys Glu Glu Val Val Ser Asp Gln Val Asp Thr Thr
                20                  25                  30

Ser Ala Lys Ala Thr Ser Glu Lys Glu Val Ala Gln Ala Ser Asp Thr
                35                  40                  45

Ser Ser Glu Ala Asn Gln Val Pro Ala Gln Glu Lys Lys Ala Glu
    50                  55                  60

Lys Ala Ala Ala Pro Ala Thr Ala Thr Pro Ala Pro Gln Thr Gly Ala
65                  70                  75                  80

Lys Asn Ser Gln Thr Ala Ser Ser Glu Ala Pro Ala Thr Ser Asn Gln
                85                  90                  95

Ala Ser Glu Thr Ala Glu Thr Gly Ala Leu Ser Gln Lys Glu Glu Ala
                100                 105                 110

Ala Val Leu Ser Leu Asp Asn Ile Lys Lys Ile Asp Gly Lys Tyr Tyr
                115                 120                 125

Tyr Val Met Ala Asp Gly Ser Tyr Lys Lys Asn Phe Ala Ile Thr Val
    130                 135                 140

Asp Gly Gln Met Leu Tyr Phe Asp Ala Lys Thr Gly Ala Leu Ser Ser
145                 150                 155                 160

Thr Ser Thr Tyr Ser Phe Ser Gln Gly Leu Thr Pro Ile Val Ser Asp
                165                 170                 175

Phe Ser Val Asn Asn Lys Ala Phe Asp Ser Ser Glu Lys Ser Phe Glu
                180                 185                 190

Leu Val Asp Gly Tyr Leu Thr Ala Glu Ser Trp Tyr Arg Pro Ala Lys
                195                 200                 205

Ile Leu Glu Asn Gly Lys Thr Trp Val Asp Ser Lys Glu Thr Asp Leu
    210                 215                 220

Arg Pro Val Leu Met Ser Trp Trp Pro Asn Lys Asp Thr Gln Val Ala
225                 230                 235                 240

Tyr Leu Asn Tyr Met Ser Lys Ala Leu Gly Gly Lys Glu Glu Phe Thr
                245                 250                 255

Thr Glu Thr Ser Gln Thr Thr Leu Asn Thr Ala Ala Glu Leu Ile Gln
                260                 265                 270

Thr Lys Ile Glu Ala Arg Ile Ser Lys Glu Gln Gly Thr Lys Trp Leu
                275                 280                 285

Arg Glu Ala Met Ala Ala Phe Val Ala Thr Gln Ser Arg Trp Ser Tyr
```

```
            290                 295                 300
Ala Ser Glu Gln Phe Asp Lys Asn Asp His Leu Gln Gly Gly Ala Leu
305                 310                 315                 320

Leu Tyr Thr Asn Asn Lys Leu Thr Gln Trp Ala Asp Ser Asn Tyr Arg
                325                 330                 335

Leu Leu Asn Arg Thr Pro Thr Arg Gln Asp Gly Lys Pro His Tyr Ser
            340                 345                 350

Lys Ala Asp Glu Tyr Gly Gly Tyr Glu Phe Leu Leu Ala Asn Asp Val
        355                 360                 365

Asp Asn Ser Asn Pro Val Val Gln Ala Glu Met Leu Asn Gln Ile His
    370                 375                 380

Tyr Leu Met Asn Trp Gly Ser Ile Val Met Asn Asp Lys Asp Ala Asn
385                 390                 395                 400

Phe Asp Gly Ile Arg Val Asp Ala Val Asp Asn Val Asn Ala Asp Thr
                405                 410                 415

Leu Gln Leu Tyr Thr Asn Tyr Phe Asn Ser Val Tyr Gly Val Asn Lys
            420                 425                 430

Ser Glu Ala Gln Ala Leu Ala His Ile Ser Val Leu Glu Ala Trp Ser
        435                 440                 445

Tyr Asn Asp Asn Asp Tyr Asn Gln Asp Thr Asn Gly Ala Ala Leu Ala
    450                 455                 460

Met Asp Asn Gly Leu Arg Phe Ser Leu Leu Tyr Thr Leu Thr Arg Pro
465                 470                 475                 480

Leu Asn Glu Arg Thr Pro Gly Met Ser Thr Leu Ile Lys Ser Gln Tyr
                485                 490                 495

Gly Leu Thr Asp Arg Thr Lys Asp Asp Lys Tyr Gly Asp Thr Gln Pro
            500                 505                 510

Ser Tyr Val Phe Val Arg Ala His Asp Ser Glu Val Gln Thr Val Ile
        515                 520                 525

Ala Gln Ile Ile Lys Lys Lys Ile Asp Pro Thr Thr Asp Gly Phe Thr
    530                 535                 540

Phe Thr Leu Asp Gln Leu Lys Gln Ala Phe Asp Ile Tyr Asn Lys Asp
545                 550                 555                 560

Met Asn Ser Val Asp Lys His Tyr Thr His Tyr Asn Ile Pro Ala Ala
                565                 570                 575

Tyr Ala Val Met Leu Ser Asn Met Glu Ser Val Thr Arg Val Tyr Tyr
            580                 585                 590

Gly Asp Leu Phe Thr Asp Asp Gly Gln Tyr Met Glu Thr Lys Ser Pro
        595                 600                 605

Tyr Tyr Asp Ala Ile Asn Thr Leu Leu Arg Ala Arg Ile Arg Tyr Ala
    610                 615                 620

Ala Gly Gly Gln Thr Met Glu His Asn Ser Tyr Lys Ala Ser Ala Ala
625                 630                 635                 640

Met Lys Ala Lys Asn Pro Asp Ser Gly Val Leu Gly Asn Ser Glu
                645                 650                 655

Val Leu Val Ser Val Arg Phe Gly Gln Asp Val Met Ser Ala Asp Asp
            660                 665                 670

Met Thr Gly Gly Lys Leu Ala Lys Thr Ser Gly Met Phe Ser Leu Ile
        675                 680                 685

Ser Asn Asn Pro Glu Leu Glu Leu Asp Ala Asn Glu Glu Ile Arg Val
    690                 695                 700

Asn Val Gly Lys Ile His Ala Gly Gln Thr Tyr Arg Pro Leu Leu Leu
705                 710                 715                 720
```

```
Thr Thr Asp Lys Gly Leu Gln Lys Tyr Leu Asn Asp Ser Asp Thr Lys
            725                 730                 735
Leu Thr Lys Val Ala Asp Lys Asp Gly Tyr Ile Thr Phe Lys Gly Ser
            740                 745                 750
Glu Ile Lys Gly Tyr Lys Gln Val Glu Val Asn Gly Tyr Leu Ser Val
            755                 760                 765
Trp Val Pro Val Gly Ala Lys Ala Asp Gln Asp Ile Arg Val Ala Ala
            770                 775                 780
Ser Thr Lys Val Asn Gly Lys Asp Asp Lys Thr Tyr Thr Ala Ser Gln
785                 790                 795                 800
Ala Leu Glu Ser Gln Leu Ile Tyr Glu Gly Phe Ser Asn Phe Gln Asp
                    805                 810                 815
Phe Val Lys Lys Asp Ser Gln Tyr Thr Asn Lys Lys Ile Ala Glu Asn
                    820                 825                 830
Thr Asp Leu Phe Lys Ala Trp Gly Val Thr Ser Phe Glu Met Ala Pro
                    835                 840                 845
Gln Tyr Val Ser Ala Thr Asp Gly Thr Phe Leu Asp Ser Ile Ile Glu
                    850                 855                 860
Asn Gly Tyr Ala Phe Thr Asp Arg Tyr Asp Leu Ala Met Ser Lys Asn
865                 870                 875                 880
Asn Lys Tyr Gly Ser Lys Glu Asp Leu Ala Asn Ala Leu Lys Ala Leu
                    885                 890                 895
His Ala Ala Gly Ile Gln Ala Ile Ala Asp Trp Val Pro Asp Gln Ile
                    900                 905                 910
Tyr Gln Leu Pro Gly Lys Glu Val Thr Ala Ser Arg Val Asp Asn
                    915                 920                 925
Tyr Gly Arg Val Lys Ile Asp Gln Pro Leu Val Glu Lys Leu Tyr Leu
                    930                 935                 940
Ala Asn Thr Lys Ser Ser Gly Lys Asp Phe Gln Ala Lys Tyr Gly Gly
945                 950                 955                 960
Glu Phe Leu Glu Asp Leu Gln Lys Gln Tyr Pro Glu Met Phe Thr Ala
                    965                 970                 975
Lys Met Ile Ser Thr Gly Lys Thr Ile Asp Pro Ser Val Lys Leu Lys
                    980                 985                 990
Glu Trp Ser Ala Lys Tyr Leu Asn Gly Thr Asn Val Leu Gly Arg Gly
                    995                 1000                1005
Thr Asp Tyr Val Leu Ser Asp Glu Gly Thr Gly Lys Tyr Phe Thr
        1010                1015                1020
Val Asn Glu Lys Gly Asp Phe Leu Pro Ala Ala Leu Thr Gly Asp
        1025                1030                1035
Arg Glu Ala Lys Thr Gly Phe Tyr Asn Asp Gly Lys Gly Met Thr
        1040                1045                1050
Tyr Tyr Thr Thr Ala Gly Asn Lys Ala Lys Ser Ala Phe Val Thr
        1055                1060                1065
Val Ala Gly Asn Thr Tyr Tyr Phe Asp Tyr Thr Gly Tyr Met Val
        1070                1075                1080
Thr Gly Pro Asn Thr Ile Asn Ser Lys Phe Tyr Tyr Phe Leu Pro
        1085                1090                1095
Asn Gly Val Met Leu Lys Asp Ala Ile Lys Gln Asp Glu Leu Gly
        1100                1105                1110
Arg Ser Val Tyr Tyr Gly Lys Thr Gly Thr Met Tyr Lys Ala Thr
        1115                1120                1125
```

```
Asp Lys Ser Gln Trp Phe Ala Met Thr Asp Ser Lys Gly Gln Gln
    1130                1135                1140
Arg Phe Arg His Phe Asp Arg Phe Gly Ile Met Ser Val Gly Leu
    1145                1150                1155
Val Thr Ile Asn Gly Ser Val Gln Tyr Tyr Asp Glu Glu Gly Phe
    1160                1165                1170
Gln Val Lys Gly Glu Phe Val Thr Asp Lys Asp Gly Gln Thr Arg
    1175                1180                1185
Tyr Phe Asp Glu Gly Ser Gly Asn Leu Val Lys Asp Arg Phe Leu
    1190                1195                1200
Asn Lys Asp Gly Lys Trp Tyr Tyr Leu Asp Asp Lys Gly Leu Leu
    1205                1210                1215
Val Lys Gly Ala Gln Thr Ile Lys Gly Gln Lys Leu Tyr Phe Asp
    1220                1225                1230
Thr Lys Thr Gly Ala Gln Val Lys Gly Asp Phe Val Ala Asp Lys
    1235                1240                1245
Asp Gly Asn Leu Thr Phe Tyr Ser Gly Asp Ser Gly Gln Met Val
    1250                1255                1260
Gln Ser Asp Phe Phe Ser Thr Gly Asn Asn Ala Trp Phe Tyr Ala
    1265                1270                1275
Asp Glu Asn Gly His Val Ala Lys Gly Ala Lys Thr Ile Arg Gly
    1280                1285                1290
Gln Lys Leu Tyr Phe Asp Thr Lys Thr Gly Gln Gln Ala Lys Gly
    1295                1300                1305
Arg Phe Ile Arg Asp Asp Lys Gly Val Arg Tyr Tyr Asp Ala Asp
    1310                1315                1320
Thr Gly Ala Leu Val Thr Asn Ala Phe Leu Glu Thr Lys Ala Gly
    1325                1330                1335
Ser Asn Gln Trp Tyr Tyr Met Gly Ala Asp Gly Tyr Ala Val Lys
    1340                1345                1350
Gly Asn Gln Thr Ile Lys Asn Gln His Met Tyr Phe Asp Ala Glu
    1355                1360                1365
Thr Gly Gln Gln Ala Lys Gly Ile Ile Val Thr Asp Ala Asn Gly
    1370                1375                1380
Arg Lys Tyr Phe Tyr Asp Thr Phe Thr Gly Ser Arg Val Val Asn
    1385                1390                1395
Gln Phe Val Leu Val Asn Gly Asn Trp Tyr Phe
    1400                1405

<210> SEQ ID NO 18
<211> LENGTH: 4230
<212> TYPE: DNA
<213> ORGANISM: Artificial sequence
<220> FEATURE:
<223> OTHER INFORMATION: 2921 gtf with heterologous signal sequence

<400> SEQUENCE: 18
gatgatctgg caaaggacca agcggctgcc acggaacaga aggcatcagc gaatcaagaa      60
aaggaggaag ttgtttcaga tcaagttgat acgacaagcg ccaaagcaac gtcagaaaaa     120
gaggtggcac aggctagcga tacatcatca gaggccaacc aggttccggc ccaagaggaa     180
aagaaagccg agaaggccgc agcacctgcg acagctacgc cggcaccgca acgggagcc      240 aaaaatagcc aaacagcctc aagcgaggca ccggctacat caatcaagc atcgaaacg       300 gcggaaacag gcgcactgtc acaaaaggaa gaagcagctg tcctttcact tgataatatc     360
```

```
aaaaagattg acggaaaata ctactatgtt atggctgatg gatcatataa gaaaaacttt    420
gcgattacag tcgatggcca aatgctgtat tttgatgcaa aaacaggagc tctttcaagc    480
acatcaacat attcattttc acaaggcctg acaccgattg ttagcgactt ctcagtcaat    540
aacaaggcat ttgatagcag cgagaaatca ttcgaacttg tggatggata tcttacggcc    600
gagagctggt acagaccggc aaaaattctg gagaatggaa agacgtgggt tgattcaaaa    660
gagacggacc ttagaccggt gctgatgtca tggtggccga ataaggatac gcaggttgcc    720
tacctgaact atatgtcaaa agcacttggc ggcaaagagg agtttacaac ggagacatca    780
caaacgacac ttaacacggc tgctgaactt atccagacga gatcgaggc aagaattagc    840 aaagaacaag gaacgaagtg gcttagagaa gctatggccg catttgttgc tacgcagtca    900
agatggtcat atgcgtcaga gcagttcgat aaaaacgatc accttcaagg cggagcactt    960
ctgtacacaa ataataagct gacacaatgg gctgactcaa actatagact gcttaacaga   1020
acgcctacga gacaggatgg aaaacctcat tacagcaaag cagacgagta tggaggctat   1080
gagttcctgc ttgcaaatga cgtcgataac tcaaatccgg tggttcaggc agagatgctt   1140
aatcaaattc actatcttat gaactggggc tcaattgtta tgaatgataa ggacgcgaat   1200
ttcgatggaa ttagagtgga tgcggttgac aatgttaatg cggacacact tcaactgtat   1260
acgaattact ttaactcagt ttacggcgtt aacaaatcag aagctcaggc acttgctcat   1320
atcagcgttc ttgaagcatg gagctacaac gacaatgatt acaatcagga tacaaatggc   1380
gctgcactgg ccatggataa tggacttaga ttcagccttc tttacacact gacaagaccg   1440
cttaacgaga gaacacctgg catgtcaaca cttattaagt cacaatatgg ccttacagac   1500
agaacaaaag acgataagta cggcgacacg caaccgtcat acgtgtttgt tagagctcac   1560
gacagcgaag ttcaaacagt tattgctcag attattaaga gaaaaattga tccgacaaca   1620
gacggattca catttacact ggaccaactt aaacaagcct tcgatatcta taacaaagat   1680
atgaatagcg ttgataaaca ttacacgcac tacaatattc ctgcagcata cgctgtcatg   1740
ctgtcaaaca tggaatcagt tacaagagtc tattatggcg acctgtttac agatgacggc   1800
caatatatgg aaacaaaatc accgtactat gacgccatta atacactgct gagagccaga   1860
atcagatatg cagctggcgg acaaacaatg gaacacaaca gctataaggc gtcagctgcg   1920
atgaaggcga aaaaccctga tagcggctca gtccttggca attcagaagt tctggttagc   1980
gttagatttg gacaagatgt gatgagcgct gacgatatga caggaggcaa acttgctaag   2040
acgtcaggaa tgttctcact gatttcaaat aatccggaac tggaacttga cgctaatgaa   2100
gagatcagag tgaatgttgg aaaaatccat gccggccaaa cgtacagacc tcttctgctt   2160 acgcacagata agggcctgca aaagtatctt aatgactcag acacgaaact tacgaaggtt   2220
gcagataaag atggctatat tacatttaag ggctcagaga ttaaaggcta taaacaggtt   2280
gaagttaatg gctacctgag cgtctgggtg ccggttggcg ctaaagcaga ccaagacatc   2340
agagtcgcag cttcaacaaa agtcaatgga aaggatgata gacgtacac ggcaagccaa   2400 gcacttgagt cacagcttat ttacgagggc ttctcaaatt tccaagattt cgttaagaaa   2460
gattcacaat atacaaataa gaaaatcgcg gaaaatacag atcttttcaa gcatggggc   2520 gttacatcat ttgaaatggc gcctcagtat gttagcgcaa cagatggcac atttctggat   2580
agcattatcg agaatggata tgcatttacg gatagatatg acctggccat gtcaaaaaac   2640
aacaaatacg gatcaaaaga ggatcttgct aatgcgctta agctctgca cgcagctggc   2700 attcaagcca ttgcggattg ggttcctgat caaatctacc aacttcctgg caaggaggtt   2760
```

-continued

```
gttacagcat caagagtcga caattacggc agagtgaaga tcgaccaacc tctggtggaa    2820
aagctgtatc tggctaacac aaagagctca ggcaaagatt ttcaggcgaa atatggcgga    2880
gaatttcttg aagacctgca gaaacagtat cctgaaatgt ttacagcgaa aatgatttca    2940
acaggaaaaa cgattgatcc tagcgttaaa cttaaggagt ggtcagccaa atacctgaat    3000
ggaacaaacg tgctgggaag aggcacagat tatgttcttt cagatgaggg aacgggcaaa    3060
tactttacgg tcaatgagaa aggcgatttc ctgccggctg cacttacagg cgatagagaa    3120
gcaaagacag gattctataa tgacggcaaa ggcatgacgt attacacaac ggccggaaat    3180
aaggcgaaga gcgcgttcgt tacagtggcg ggcaacacat actactttga ttatacggga    3240
tatatggtta caggacctaa tacaattaac agcaagtttt actatttcct tcctaatggc    3300
gttatgctga aggatgcaat taagcaggat gaacttggaa gatcagtcta ctatggcaaa    3360
acgggaacaa tgtataaggc aacggataaa tcacagtggt tcgccatgac agatagcaag    3420
ggacaacaga gattcagaca ttttgataga ttcggaatca tgagcgttgg acttgtcacg    3480
attaatggaa gcgtccagta ttacgacgaa gaaggctttc aagttaaggg agagttcgtg    3540
acggacaaag atggacagac gagatatttt gacgagggaa gcggcaacct ggttaaggac    3600
agattcctga acaaggacgg aaagtggtat taccttgacg ataagggact gcttgtcaag    3660
ggagctcaaa caatcaaggg ccagaaactt tatttcgata caaaaacagg agcgcaagtc    3720
aaaggagact ttgtggctga taaggatgga aacctgacgt tttatagcgg cgattcagga    3780
caaatggtgc agtcagactt ctttagcaca ggcaacaatg catggtttta tgcagatgaa    3840
aacggacatg ttgcaaaagg cgcgaagaca atcagaggcc aaaaactgta cttcgacacg    3900
aagacgggac agcaggccaa gggcagattc attagagatg acaaaggcgt gagatactat    3960
gatgcagaca caggcgcact ggtcacaaat gctttcctgg aaacgaaggc tggctcaaat    4020
cagtggtact acatgggagc cgatggatac gcggtgaagg gcaaccagac gatcaagaat    4080
cagcacatgt actttgacgc ggagacgggc caacaagcta agggcatcat cgtcacagat    4140
gcaaatggca gaaagtactt ctatgacacg ttcacgggca gcagagttgt taaccaattt    4200
gttctggtga acggcaattg gtactttga                                      4230
```

ENZYMATICALLY POLYMERIZED GELLING DEXTRANS

This application claims the benefit of U.S. Provisional Application No. 62/075,460 (filed Nov. 5, 2014), which is incorporated herein by reference in its entirety.

FIELD OF INVENTION

The present disclosure is in the field of polysaccharides. For example, the disclosure pertains to certain dextran polymers, reactions comprising glucosyltransferase enzymes that synthesize these polymers, and use of the polymers in various applications.

REFERENCE TO SEQUENCE LISTING SUBMITTED ELECTRONICALLY

The official copy of the sequence listing is submitted electronically via EFS-Web as an ASCII formatted sequence listing with a file named 20151105_CL6294USNP_SequenceListing.txt created on Nov. 5, 2015, and having a size of 164 kilobytes and is filed concurrently with the specification. The sequence listing contained in this ASCII-formatted document is part of the specification and is herein incorporated by reference in its entirety.

BACKGROUND

Driven by a desire to find new structural polysaccharides using enzymatic syntheses or genetic engineering of microorganisms, researchers have discovered polysaccharides that are biodegradable and can be made economically from renewably sourced feedstocks. One such family of polysaccharides are alpha-glucans, which are polymers comprising glucose monomers linked by alpha-glycosidic bonds.

Dextrans represent a family of complex, branched alpha-glucans generally comprising chains of alpha-1,6-linked glucose monomers, with periodic side chains (branches) linked to the straight chains by alpha-1,3-linkage (Ioan et al., *Macromolecules* 33:5730-5739). Production of dextrans is typically done through fermentation of sucrose with bacteria (e.g., *Leuconostoc* or *Streptococcus* species), where sucrose serves as the source of glucose for dextran polymerization (Naessens et al., *J. Chem. Technol. Biotechnol.* 80:845-860; Sarwat et al., *Int. J. Biol. Sci.* 4:379-386; Onilude et al., *Int. Food Res. J.* 20:1645-1651). Although dextrans are used in several applications given their high solubility in water (e.g., adjuvants, stabilizers), this high solubility can negatively affect their general utility as thickening agents in hydrocolloid applications.

Thus, there is interest in developing new, higher viscosity dextran polymers that are more amenable to high viscosity applications. In turn, there is also interest in identifying glucosyltransferase enzymes that can synthesize such dextran polymers.

SUMMARY OF INVENTION

In one embodiment, the disclosure concerns a composition comprising dextran that comprises:
(i) about 87-93 wt % glucose linked at positions 1 and 6;
(ii) about 0.1-1.2 wt % glucose linked at positions 1 and 3;
(iii) about 0.1-0.7 wt % glucose linked at positions 1 and 4;
(iv) about 7.7-8.6 wt % glucose linked at positions 1, 3 and 6; and
(v) about 0.4-1.7 wt % glucose linked at:
(a) positions 1, 2 and 6, or
(b) positions 1, 4 and 6;
wherein the weight-average molecular weight (Mw) of the dextran is about 50-200 million Daltons, the z-average radius of gyration of the dextran is about 200-280 nm, and the dextran optionally is not a product of a *Leuconostoc mesenteroides* glucosyltransferase enzyme.

In another embodiment, the dextran comprises: (i) about 89.5-90.5 wt % glucose linked at positions 1 and 6; (ii) about 0.4-0.9 wt % glucose linked at positions 1 and 3; (iii) about 0.3-0.5 wt % glucose linked at positions 1 and 4; (iv) about 8.0-8.3 wt % glucose linked at positions 1, 3 and 6; and (v) about 0.7-1.4 wt % glucose linked at: (a) positions 1, 2 and 6, or (b) positions 1, 4 and 6.

In another embodiment, the dextran comprises chains (long chains) linked together within a branching structure, wherein said chains are similar in length and comprise substantially alpha-1,6-glucosidic linkages. The average length of the chains is about 10-50 monomeric units in another embodiment.

In another embodiment, the dextran is a product of a glucosyltransferase enzyme comprising an amino acid sequence that is at least 90% identical to SEQ ID NO:1, SEQ ID NO:2, SEQ ID NO:5, SEQ ID NO:9, SEQ ID NO:13, or SEQ ID NO:17.

In another embodiment, the composition is an aqueous composition having a viscosity of at least about 25 cPs.

In another embodiment, the Mw of the dextran is about 80-120 million Daltons.

In another embodiment, the z-average radius of gyration of the dextran is about 230-250 nm.

In another embodiment, the composition is in the form of a food product, personal care product, pharmaceutical product, household product, or industrial product. In another embodiment, the composition is in the form of a confectionery.

In another embodiment, the disclosure concerns a method for increasing the viscosity of an aqueous composition. This method comprises contacting at least one dextran compound as disclosed herein with an aqueous composition. The contacting step in this method results in increasing the viscosity of the aqueous composition, in comparison to the viscosity of the aqueous composition before the contacting step.

In another embodiment, the disclosure concerns a method of treating a material. This method comprises contacting a material with an aqueous composition comprising at least one dextran compound disclosed herein.

In another embodiment, the disclosure concerns an enzymatic reaction comprising water, sucrose and a glucosyltransferase enzyme comprising an amino acid sequence that is at least 90% identical to SEQ ID NO:1, SEQ ID NO:2, SEQ ID NO:5, SEQ ID NO:9, SEQ ID NO:13, or SEQ ID NO:17, wherein the glucosyltransferase enzyme synthesizes a dextran compound as disclosed herein.

In another embodiment, the disclosure concerns a method of producing dextran comprising the step of contacting at least water, sucrose, and a glucosyltransferase enzyme comprising an amino acid sequence that is at least 90% identical to SEQ ID NO:1, SEQ ID NO:2, SEQ ID NO:5, SEQ ID NO:9, SEQ ID NO:13, or SEQ ID NO:17, thereby producing dextran as disclosed herein. This dextran can optionally be isolated.

In another embodiment, the viscosity of the dextran produced in the method is increased by decreasing the amount of sucrose in step (a).

BRIEF DESCRIPTION OF THE DRAWINGS AND SEQUENCES

FIG. 1: HPLC analysis of sucrose consumption by a glucosyltransferase reaction comprising 100 g/L sucrose and a 0768 gtf (SEQ ID NO:1). Refer to Example 2.

Figure 2A:
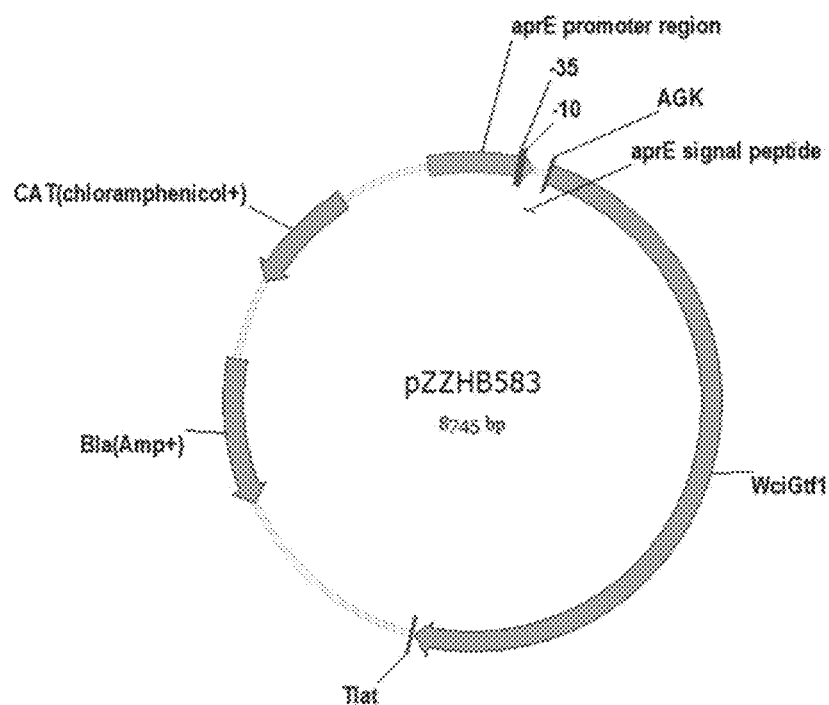

FIG. 2A: Map of plasmid pZZHB583 used to express 2919 gtf (SEQ ID NO:5) in *B. subtilis*. Refer to Example 3.

Figure 2B:
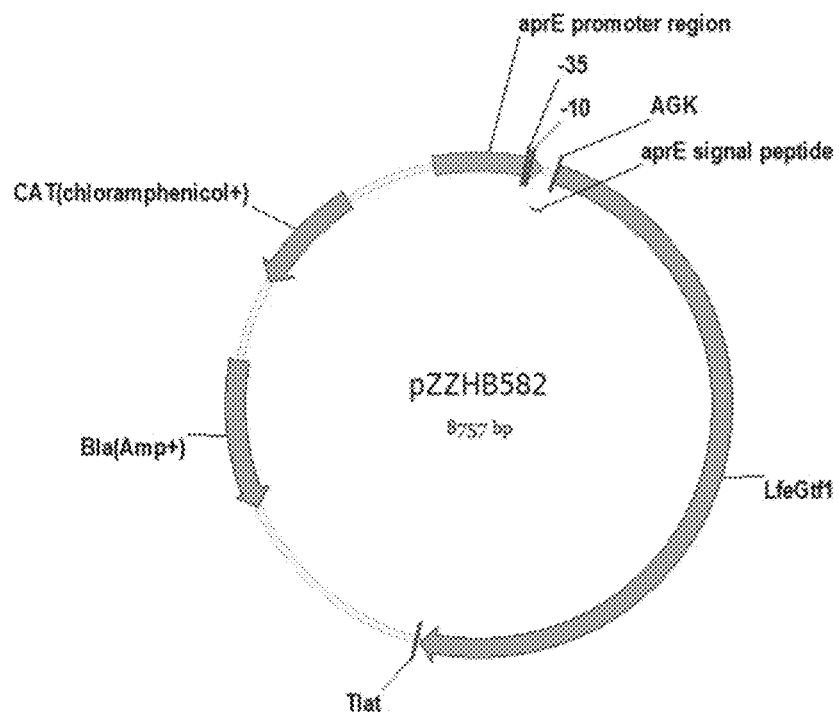

FIG. 2B: Map of plasmid pZZHB582 used to express 2918 gtf (SEQ ID NO:9) in *B. subtilis*. Refer to Example 4.

Figure 2C:
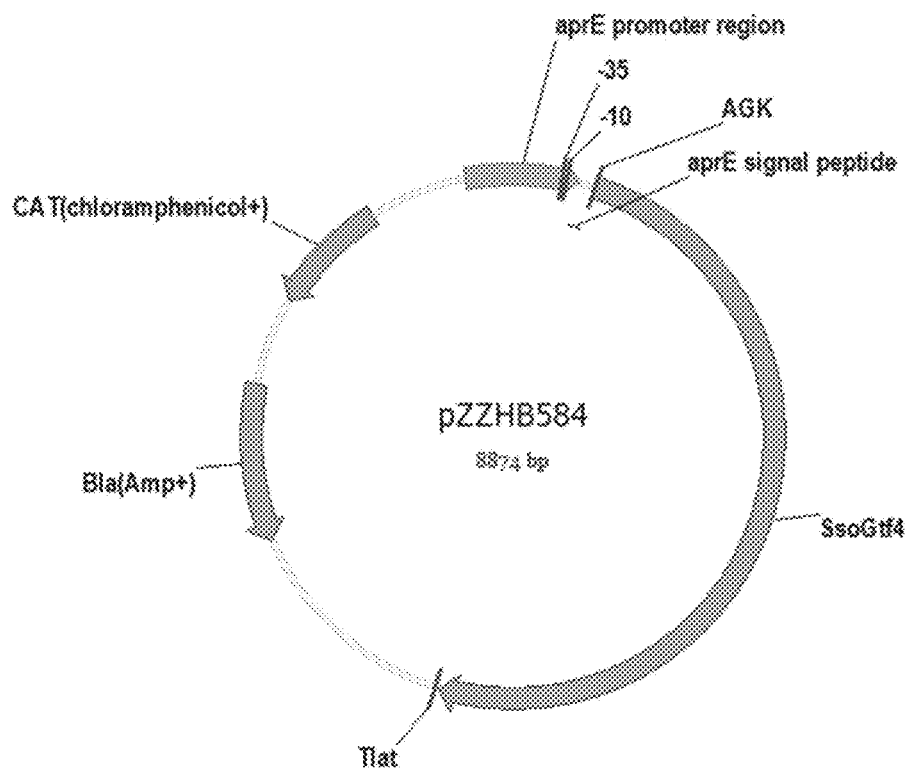

FIG. 2C: Map of plasmid pZZHB584 used to express 2920 gtf (SEQ ID NO:13) in *B. subtilis*. Refer to Example 5.

Figure 2D:
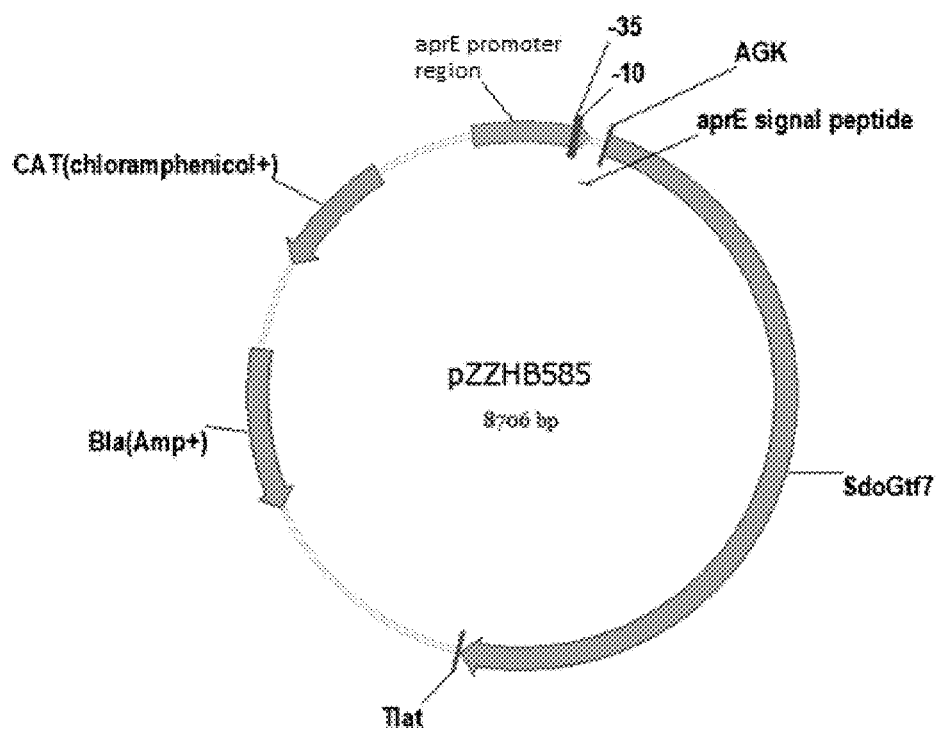

FIG. 2D: Map of plasmid pZZHB585 used to express 2921 (SEQ ID NO:17) gtf in *B. subtilis*. Refer to Example 6.

Figure 3:
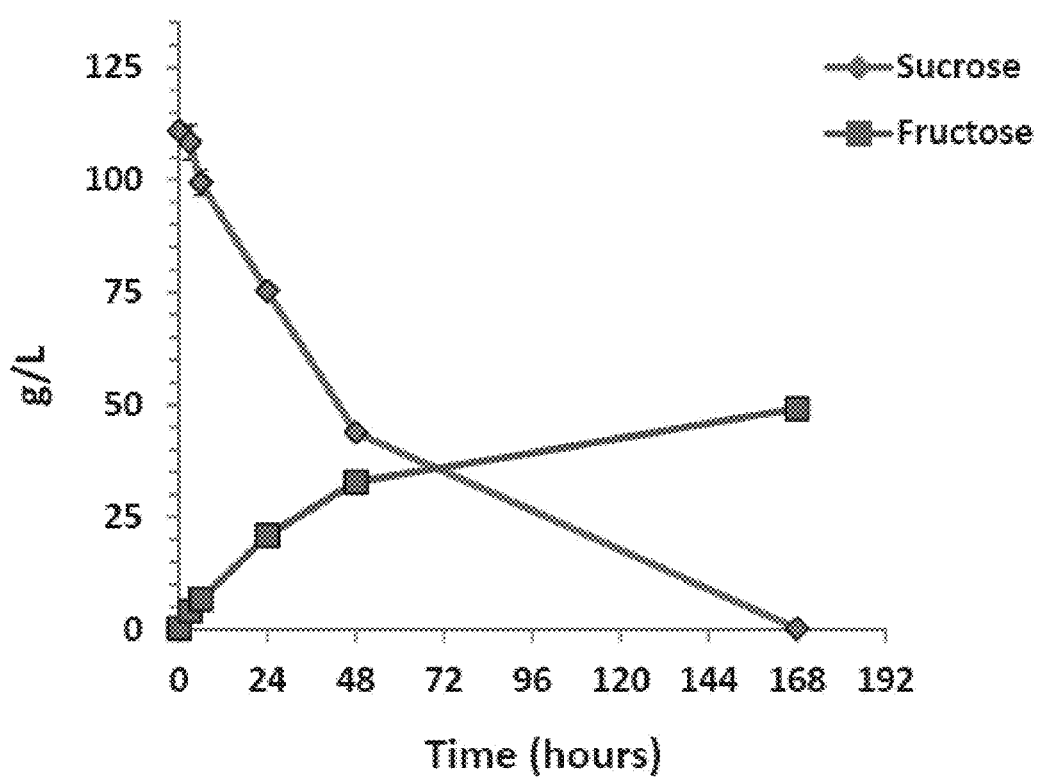

FIG. 3: HPLC analysis of sucrose consumption by a reaction comprising a commercially available dextran sucrase. Refer to Example 7.

TABLE 1

Summary of Nucleic Acid and Protein SEQ ID Numbers

| Description | Nucleic acid SEQ ID NO. | Protein SEQ ID NO. |
|---|---|---|
| "0768 gtf", *Leuconostoc pseudomesenteroides*. Mature form of GENBANK Identification No. 497964659. | | 1 (1447 aa) |
| "0768 gtf", *Leuconostoc pseudomesenteroides*. Mature form of GENBANK Identification No. 497964659, but including a start methionine and additional N- and C-terminal amino acids. | | 2 (1457 aa) |
| WciGtf1, *Weissella cibaria*. Full length form comprising signal sequence. GENBANK Accession No. ZP_08417432 (amino acid sequence). | 3 (4347 bases) | 4 (1448 aa) |
| "2919 gtf", *Weissella cibaria*. Mature form of GENBANK Identification No. ZP_08417432. | | 5 (1422 aa) |
| "2919 gtf", *Weissella cibaria*. Sequence optimized for expression in *B. subtilis*. Encodes 2919 gtf with a heterologous signal sequence and additional N-terminal amino acids. | 6 (4269 bases) | |
| LfeGtf1, *Lactobacillus fermentum*. Full length form comprising signal sequence. GENBANK Accession No. AAU08008 (amino acid sequence). | 7 (4392 bases) | 8 (1463 aa) |
| "2918 gtf", *Lactobacillus fermentum*. Mature form of GENBANK Identification No. AAU08008. | | 9 (1426 aa) |
| "2918 gtf", *Lactobacillus fermentum*. Sequence optimized for expression in *B. subtilis*. Encodes 2918 gtf with a heterologous signal sequence and additional N-terminal amino acids. | 10 (4281 bases) | |
| SsoGtf4, *Streptococcus sobrinus*. Full length form comprising signal sequence. GENBANK Accession No. AAX76986 (amino acid sequence). | 11 (4521 bases) | 12 (1506 aa) |
| "2920 gtf", *Streptococcus sobrinus*. Mature form of GENBANK Identification No. AAX76986. | | 13 (1465 aa) |
| "2920 gtf", *Streptococcus sobrinus*. Sequence optimized for expression in *B. subtilis*. Encodes 2920 gtf with a heterologous signal sequence and additional N-terminal amino acids. | 14 (4398 bases) | |
| SdoGtf7, *Streptococcus downei*. Full length form comprising signal sequence. GENBANK Accession No. ZP_08549987.1 (amino acid sequence). | 15 (4360 bases) | 16 (1453 aa) |
| "2921 gtf", *Streptococcus downei*. Mature form of GENBANK Identification No. ZP_08549987.1. | | 17 (1409 aa) |
| "2921 gtf", *Streptococcus downei*. Sequence optimized for expression in *B. subtilis*. Encodes 2921 gtf with a heterologous signal sequence and additional N-terminal amino acids. | 18 (4230 bases) | |

DETAILED DESCRIPTION

The disclosures of all cited patent and non-patent literature are incorporated herein by reference in their entirety.

Unless otherwise disclosed, the terms "a" and "an" as used herein are intended to encompass one or more (i.e., at least one) of a referenced feature.

The term "glucan" herein refers to a polysaccharide of D-glucose monomers that are linked by glucosidic linkages, which are a type of glycosidic linkage. An "alpha-glucan" herein refers to a glucan in which the constituent D-glucose monomers are alpha-D-glucose monomers.

The terms "dextran", "dextran polymer", "dextran compound" and the like are used interchangeably herein and refer to complex, branched alpha-glucans generally comprising chains of substantially (mostly) alpha-1,6-linked glucose monomers, with side chains (branches) linked mainly by alpha-1,3-linkage. The term "gelling dextran" herein refers to the ability of one or more dextrans disclosed herein to form a viscous solution or gel-like composition (i) during enzymatic dextran synthesis and, optionally, (ii) when such synthesized dextran is isolated (e.g., >90% pure) and then placed in an aqueous composition.

Dextran "long chains" herein can comprise "substantially [or mostly] alpha-1,6-glucosidic linkages", meaning that they can have at least about 98.0% alpha-1,6-glucosidic linkages in some aspects. Dextran herein can comprise a "branching structure" (branched structure) in some aspects. It is contemplated that in this structure, long chains branch from other long chains, likely in an iterative manner (e.g., a long chain can be a branch from another long chain, which in turn can itself be a branch from another long chain, and so on). It is contemplated that long chains in this structure can be "similar in length", meaning that the length (DP [degree of polymerization]) of at least 70% of all the long chains in a branching structure is within plus/minus 30% of the mean length of all the long chains of the branching structure.

Dextran in some embodiments can also comprise "short chains" branching from the long chains, typically being one to three glucose monomers in length, and comprising less than about 10% of all the glucose monomers of a dextran polymer. Such short chains typically comprise alpha-1,2-, alpha-1,3-, and/or alpha-1,4-glucosidic linkages (it is believed that there can also be a small percentage of such non-alpha-1,6 linkages in long chains in some aspects).

The terms "glycosidic linkage" and "glycosidic bond" are used interchangeably herein and refer to the covalent bond that joins a carbohydrate molecule to another carbohydrate molecule. The terms "glucosidic linkage" and "glucosidic bond" are used interchangeably herein and refer to a glycosidic linkage between two glucose molecules. The term "alpha-1,6-glucosidic linkage" as used herein refers to the covalent bond that joins alpha-D-glucose molecules to each other through carbons 1 and 6 on adjacent alpha-D-glucose rings. The term "alpha-1,3-glucosidic linkage" as used herein refers to the covalent bond that joins alpha-D-glucose molecules to each other through carbons 1 and 3 on adjacent alpha-D-glucose rings. The term "alpha-1,2-glucosidic linkage" as used herein refers to the covalent bond that joins alpha-D-glucose molecules to each other through carbons 1 and 2 on adjacent alpha-D-glucose rings. The term "alpha-1,4-glucosidic linkage" as used herein refers to the covalent bond that joins alpha-D-glucose molecules to each other through carbons 1 and 4 on adjacent alpha-D-glucose rings. Herein, "alpha-D-glucose" will be referred to as "glucose."

All glucosidic linkages disclosed herein are alpha-glucosidic linkages, except where otherwise noted.

"Glucose (glucose monomers) linked at positions 1 and 6" herein refers to a glucose monomer of dextran in which only carbons 1 and 6 of the glucose monomer are involved in respective glucosidic linkages with two adjacent glucose monomers. This definition likewise applies to glucose (i) "linked at positions 1 and 3", and (ii) "linked at positions 1 and 4", taking into account, accordingly, the different carbon positions involved in each respective linkage.

"Glucose (glucose monomers) linked at positions 1, 3 and 6" herein refers to a glucose monomer of dextran in which carbons 1, 3 and 6 of the glucose monomer are involved in respective glucosidic linkages with three adjacent glucose monomers. A glucose linked only at positions 1, 3 and 6 is a branch point. This definition likewise applies to glucose linked at (i) positions 1, 2 and 6, and (ii) positions 1, 4 and 6, but taking into account, accordingly, the different carbon positions involved in each respective linkage.

Glucose positions (glucose carbon positions) 1, 2, 3, 4 and 6 herein are as known in the art (depicted in the following structure):

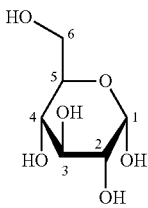

The glycosidic linkage profile of a dextran herein can be determined using any method known in the art. For example, a linkage profile can be determined using methods that use nuclear magnetic resonance (NMR) spectroscopy (e.g., $^{13}$C NMR or $^1$H NMR). These and other methods that can be used are disclosed in *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, Fla., 2005), which is incorporated herein by reference.

The term "sucrose" herein refers to a non-reducing disaccharide composed of an alpha-D-glucose molecule and a beta-D-fructose molecule linked by an alpha-1,2-glycosidic bond. Sucrose is known commonly as table sugar.

The "molecular weight" of dextran herein can be represented as number-average molecular weight (Mn) or as weight-average molecular weight (Mw), the units of which are in Daltons or grams/mole. Alternatively, molecular weight can be represented as DPw (weight average degree of polymerization) or DPn (number average degree of polymerization). Various means are known in the art for calculating these molecular weight measurements such as with high-pressure liquid chromatography (HPLC), size exclusion chromatography (SEC), or gel permeation chromatography (GPC).

The term "radius of gyration" (Rg) herein refers to the mean radius of dextran, and is calculated as the root-mean-square distance of a dextran molecule's components (atoms) from the molecule's center of gravity. Rg can be provided in Angstrom or nanometer (nm) units, for example. The "z-average radius of gyration" of dextran herein refers to the Rg of dextran as measured using light scattering (e.g., MALS). Methods for measuring z-average Rg are known and can be used herein, accordingly. For example, z-average Rg can be measured as disclosed in U.S. Pat. No. 7,531,073, U.S. Patent Appl. Publ. Nos. 2010/0003515 and 2009/0046274, Wyatt (*Anal. Chim. Acta* 272:1-40), and Mori and Barth (Size Exclusion Chromatography, Springer-Verlag, Berlin, 1999), all of which are incorporated herein by reference.

The terms "glucosyltransferase enzyme", "gtf enzyme", "gtf enzyme catalyst", "gtf", "glucansucrase" and the like are used interchangeably herein. The activity of a gtf enzyme herein catalyzes the reaction of the substrate sucrose to make the products glucan and fructose. A gtf enzyme that produces a dextran (a type of glucan) can also be referred to as a dextransucrase. Other products (byproducts) of a gtf reaction can include glucose (where glucose is hydrolyzed from the glucosyl-gtf enzyme intermediate complex), and various soluble oligosaccharides (e.g., DP2-DP7) such as leucrose. Wild type forms of glucosyltransferase enzymes generally contain (in the N-terminal to C-terminal direction) a signal peptide, a variable domain, a catalytic domain, and a glucan-binding domain. A gtf herein is classified under the glycoside hydrolase family 70 (GH70) according to the CAZy (Carbohydrate-Active EnZymes) database (Cantarel et al., *Nucleic Acids Res.* 37:D233-238, 2009).

The terms "glucosyltransferase catalytic domain" and "catalytic domain" are used interchangeably herein and refer to the domain of a glucosyltransferase enzyme that provides glucan-producing activity to the glucosyltransferase enzyme.

The terms "gtf reaction", "gtf reaction solution", "glucosyltransferase reaction", "enzymatic reaction", "dextran synthesis reaction", "dextran reaction" and the like are used interchangeably herein and refer to a reaction that is performed by a glucosyltransferase enzyme. A gtf reaction as used herein generally refers to a reaction initially comprising at least one active glucosyltransferase enzyme in a solution comprising sucrose and water, and optionally other components. Other components that can be in a gtf reaction after it has commenced include fructose, glucose, soluble oligosaccharides (e.g., DP2-DP7) such as leucrose, and dextran products. It is in a gtf reaction where the step of contacting water, sucrose and a glucosyltransferase enzyme is performed. The term "under suitable gtf reaction conditions" as used herein, refers to gtf reaction conditions that support conversion of sucrose to dextran via glucosyltransferase enzyme activity. A gtf reaction herein is not naturally occurring.

A "control" gtf reaction as used herein can refer to a reaction using a glucosyltransferase not comprising an amino acid sequence that is at least 90% identical to SEQ ID NO:1, SEQ ID NO:2, SEQ ID NO:5, SEQ ID NO:9, SEQ ID NO:13, or SEQ ID NO:17. All the other features (e.g., sucrose concentration, temperature, pH, time) of a control reaction solution can be the same as the reaction to which it is being compared.

The "percent dry solids" of a gtf reaction refers to the wt % of all the sugars in a gtf reaction. The percent dry solids of a gtf reaction can be calculated, for example, based on the amount of sucrose used to prepare the reaction.

The "yield" of dextran by a gtf reaction herein represents the weight of dextran product expressed as a percentage of the weight of sucrose substrate that is converted in the reaction. For example, if 100 g of sucrose in a reaction solution is converted to products, and 10 g of the products is dextran, the yield of the dextran would be 10%. This yield calculation can be considered as a measure of selectivity of the reaction toward dextran.

The terms "percent by volume", "volume percent", "vol %", "v/v %" and the like are used interchangeably herein.

The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein.

The terms "polynucleotide", "polynucleotide sequence", and "nucleic acid sequence" are used interchangeably herein. These terms encompass nucleotide sequences and the like. A polynucleotide may be a polymer of DNA or RNA that is single- or double-stranded, that optionally contains synthetic, non-natural or altered nucleotide bases. A polynucleotide may be comprised of one or more segments of cDNA, genomic DNA, synthetic DNA, or mixtures thereof.

The term "gene" as used herein refers to a DNA polynucleotide sequence that expresses an RNA (RNA is transcribed from the DNA polynucleotide sequence) from a coding region (coding sequence), which RNA can be a messenger RNA (encoding a protein) or a non-protein-coding RNA. A gene may refer to the coding region alone, or may include regulatory sequences upstream and/or downstream to the coding region (e.g., promoters, 5'-untranslated regions, 3'-transcription terminator regions). A coding region encoding a protein can alternatively be referred to herein as an "open reading frame" (ORF). A gene that is "native" or "endogenous" refers to a gene as found in nature with its own regulatory sequences; such a gene is located in its natural location in the genome of a host cell. A "chimeric" gene refers to any gene that is not a native gene, comprising regulatory and coding sequences that are not found together in nature (i.e., the regulatory and coding regions are heterologous with each other). Accordingly, a chimeric gene may comprise regulatory sequences and coding sequences that are derived from different sources, or regulatory sequences and coding sequences derived from the same source, but arranged in a manner different than that found in nature. A "foreign" or "heterologous" gene refers to a gene that is introduced into a host organism by gene transfer. Foreign genes can comprise native genes inserted into a non-native organism, native genes introduced into a new location within the native host, or chimeric genes. Polynucleotide sequences in certain embodiments disclosed herein are heterologous. A "transgene" is a gene that has been introduced into the genome by a transformation procedure. A "codon-optimized" open reading frame has its frequency of codon usage designed to mimic the frequency of preferred codon usage of the host cell.

The term "recombinant" or "heterologous" as used herein refers to an artificial combination of two otherwise separated segments of sequence, e.g., by chemical synthesis or by the manipulation of isolated segments of nucleic acids by genetic engineering techniques. The terms "recombinant", "transgenic", "transformed", "engineered" or "modified for exogenous gene expression" are used interchangeably herein.

A native amino acid sequence or polynucleotide sequence is naturally occurring, whereas a non-native amino acid sequence or polynucleotide sequence does not occur in nature.

"Regulatory sequences" as used herein refer to nucleotide sequences located upstream of a gene's transcription start site (e.g., promoter), 5' untranslated regions, and 3' non-coding regions, and which may influence the transcription, processing or stability, or translation of an RNA transcribed from the gene. Regulatory sequences herein may include promoters, enhancers, silencers, 5' untranslated leader sequences, introns, polyadenylation recognition sequences, RNA processing sites, effector binding sites, stem-loop structures, and other elements involved in regulation of gene expression. One or more regulatory elements herein may be heterologous to a coding region herein.

Methods for preparing recombinant constructs/vectors herein can follow standard recombinant DNA and molecular cloning techniques as described by J. Sambrook and D. Russell (*Molecular Cloning: A Laboratory Manual*, 3rd Edition, Cold Spring Harbor Laboratory Press, Cold Spring Harbor, N.Y., 2001); T. J. Silhavy et al. (*Experiments with Gene Fusions*, Cold Spring Harbor Laboratory Press, Cold Spring Harbor, N.Y., 1984); and F. M. Ausubel et al. (*Short Protocols in Molecular Biology*, 5th Ed. Current Protocols, John Wiley and Sons, Inc., NY, 2002).

The terms "sequence identity" or "identity" as used herein with respect to polynucleotide or polypeptide sequences refer to the nucleic acid bases or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining percent complementarity of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

The Basic Local Alignment Search Tool (BLAST) algorithm, which is available online at the National Center for Biotechnology Information (NCBI) website, may be used, for example, to measure percent identity between or among two or more of the polynucleotide sequences (BLASTN algorithm) or polypeptide sequences (BLASTP algorithm) disclosed herein. Alternatively, percent identity between sequences may be performed using a Clustal algorithm (e.g., ClustalW, ClustalV, or Clustal-Omega). For multiple alignments using a Clustal method of alignment, the default values may correspond to GAP PENALTY=10 and GAP LENGTH PENALTY=10. Default parameters for pairwise alignments and calculation of percent identity of protein sequences using a Clustal method may be KTUPLE=1, GAP PENALTY=3, WINDOW=5 and DIAGONALS SAVED=5. For nucleic acids, these parameters may be KTUPLE=2, GAP PENALTY=5, WINDOW=4 and DIAGONALS SAVED=4. Alternatively still, percent identity between sequences may be performed using an EMBOSS algorithm (e.g., needle) with parameters such as GAP OPEN=10, GAP EXTEND=0.5, END GAP PENALTY=false, END GAP OPEN=10, END GAP EXTEND=0.5 using a BLOSUM matrix (e.g., BLOSUM62).

Various polypeptide amino acid sequences and polynucleotide sequences are disclosed herein as features of certain embodiments. Variants of these sequences that are at least about 70-85%, 85-90%, or 90%-95% identical to the sequences disclosed herein can be used. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence may have the same function/activity of the disclosed sequence, or at least about 85%, 86%, 87%, 88%, 89%, 90%, 91%, 92%, 93%, 94%, 95%, 96%, 97%, 98%, or 99% of the function/activity of the disclosed sequence. Any polypeptide amino acid sequence disclosed herein not beginning with a methionine can typically further comprise at least a start-methionine at the N-terminus of the amino acid sequence. Any polypeptide amino acid sequence disclosed herein beginning with a methionine can optionally be considered without this methionine residue (i.e., a polypeptide sequence can be referred to in reference to the position-2 residue to the C-terminal residue of the sequence).

The term "isolated" as used herein refers to any cellular component that has been completely or partially purified from its native source (e.g., an isolated polynucleotide or polypeptide molecule). In some instances, an isolated polynucleotide or polypeptide molecule is part of a greater composition, buffer system or reagent mix. For example, an isolated polynucleotide or polypeptide molecule can be comprised within a cell or organism in a heterologous manner. Another example is an isolated glucosyltransferase enzyme or reaction. "Isolated" herein can also characterize a dextran compound. As such, dextran compounds of the present disclosure are synthetic, man-made compounds, and/or exhibit properties not believed to naturally occur.

An "aqueous composition" herein has a liquid component that comprises at least about 10 wt % water, for example. Examples of aqueous compositions include mixtures, solutions, dispersions (e.g., colloidal dispersions), suspensions and emulsions, for example. Aqueous compositions in certain embodiments comprise dextran that is dissolved in the aqueous composition (i.e., in solution, and typically has viscosity).

As used herein, the term "colloidal dispersion" refers to a heterogeneous system having a dispersed phase and a dispersion medium, i.e., microscopically dispersed insoluble particles are suspended throughout another substance (e.g., an aqueous composition such as water or aqueous solution). An example of a colloidal dispersion herein is a hydrocolloid. All, or a portion of, the particles of a colloidal dispersion such as a hydrocolloid can comprise certain dextran compounds of the present disclosure. The terms "dispersant" and "dispersion agent" are used interchangeably herein to refer to a material that promotes the formation and/or stabilization of a dispersion.

The terms "hydrocolloid" and "hydrogel" are used interchangeably herein. A hydrocolloid refers to a colloid system in which water is the dispersion medium.

The term "aqueous solution" herein refers to a solution in which the solvent comprises water. An aqueous solution can serve as a dispersant in certain aspects herein. Dextran compounds in certain embodiments can be dissolved, dispersed, or mixed within an aqueous solution.

The terms "dispersant", "dispersion agent" and the like are used interchangeably herein to refer to a material that promotes the formation and stabilization of a dispersion of one substance in another. A "dispersion" herein refers to an aqueous composition comprising one or more particles (e.g., any ingredient of a personal care product, pharmaceutical product, food product, household product, or industrial product disclosed herein) that are scattered, or uniformly scattered, throughout the aqueous composition.

The term "viscosity" as used herein refers to the measure of the extent to which a fluid or an aqueous composition such as a hydrocolloid resists a force tending to cause it to flow. Various units of viscosity that can be used herein include centipoise (cPs) and Pascal-second (Pa·s). A centipoise is one one-hundredth of a poise; one poise is equal to 0.100 kg·m$^{-1}$·s$^{-1}$. Thus, the terms "viscosity modifier", "viscosity-modifying agent" and the like as used herein refer to anything that can alter/modify the viscosity of a fluid or aqueous composition.

The term "shear thinning behavior" as used herein refers to a decrease in the viscosity of an aqueous composition as shear rate increases. The term "shear thickening behavior" as used herein refers to an increase in the viscosity of an aqueous composition as shear rate increases. "Shear rate" herein refers to the rate at which a progressive shearing deformation is applied to an aqueous composition. A shearing deformation can be applied rotationally.

The term "contacting" as used herein with respect to methods of increasing the viscosity of an aqueous composition refers to any action that results in bringing together an aqueous composition with a dextran. Contacting can be performed by any means known in the art, such as dissolving, mixing, shaking, or homogenization, for example.

The terms "confectionery", "confection", "sweets", "sweetmeat", "candy" and the like are used interchangeably herein. A confectionary refers to any flavored food product having a sweet taste, the consistency of which may be hard or soft, which is typically consumed by sucking and/or by chewing within the oral cavity. A confectionary can contain sugar or otherwise be sugar-free.

The terms "fabric", "textile", "cloth" and the like are used interchangeably herein to refer to a woven material having a network of natural and/or artificial fibers. Such fibers can be thread or yarn, for example.

A "fabric care composition" herein is any composition suitable for treating fabric in some manner. Examples of such a composition include laundry detergents and fabric softeners.

The terms "heavy duty detergent", "all-purpose detergent" and the like are used interchangeably herein to refer to a detergent useful for regular washing of white and colored textiles at any temperature. The terms "low duty detergent" or "fine fabric detergent" are used interchangeably herein to refer to a detergent useful for the care of delicate fabrics such as viscose, wool, silk, microfiber or other fabric requiring special care. "Special care" can include conditions of using excess water, low agitation, and/or no bleach, for example.

A "detergent composition" herein typically comprises at least one surfactant (detergent compound) and/or at least one builder. A "surfactant" herein refers to a substance that tends to reduce the surface tension of a liquid in which the substance is dissolved. A surfactant may act as a detergent, wetting agent, emulsifier, foaming agent, and/or dispersant, for example.

The terms "anti-redeposition agent", "anti-soil redeposition agent", "anti-greying agent" and the like herein refer to agents that help keep soils from redepositing onto clothing in laundry wash water after these soils have been removed, therefore preventing greying/discoloration of laundry. Anti-redeposition agents can function by helping keep soil dispersed in wash water and/or by blocking attachment of soil onto fabric surfaces.

An "oral care composition" herein is any composition suitable for treating an soft or hard surface in the oral cavity such as dental (teeth) and/or gum surfaces.

The term "adsorption" herein refers to the adhesion of a compound (e.g., dextran herein) to the surface of a material.

The terms "cellulase", "cellulase enzyme" and the like are used interchangeably herein to refer to an enzyme that hydrolyzes beta-1,4-D-glucosidic linkages in cellulose, thereby partially or completely degrading cellulose. Cellulase can alternatively be referred to as "beta-1,4-glucanase", for example, and can have endocellulase activity (EC 3.2.1.4), exocellulase activity (EC 3.2.1.91), or cellobiase activity (EC 3.2.1.21). "Cellulose" refers to an insoluble polysaccharide having a linear chain of beta-1,4-linked D-glucose monomeric units.

There is interest in developing new, high viscosity dextran polymers, which are more amenable to gelling applications. In turn, there is also interest in identifying glucosyltransferase enzymes that can synthesize such dextran polymers.

Embodiments of the present disclosure concern a composition comprising a dextran that comprises:
  (i) about 87-93 wt % glucose linked at positions 1 and 6;
  (ii) about 0.1-1.2 wt % glucose linked at positions 1 and 3;
  (iii) about 0.1-0.7 wt % glucose linked at positions 1 and 4;
  (iv) about 7.7-8.6 wt % glucose linked at positions 1, 3 and 6; and
  (v) about 0.4-1.7 wt % glucose linked at: (a) positions 1, 2 and 6, or (b) positions 1, 4 and 6.

The weight-average molecular weight (Mw) and z-average radius of gyration of such dextran is about 50-200 million Daltons and about 200-280 nm, respectively. Also, such dextran optionally is not a product of a *Leuconostoc mesenteroides* glucosyltransferase enzyme.

An example of this composition is a glucosyltransferase reaction in which a dextran with the above linkage, weight and size profile is synthesized. Significantly, this dextran exhibits high viscosity in aqueous compositions, even at relatively low concentrations of the dextran. It is believed that this high viscosity profile is unique in comparison to viscosity profiles of previously disclosed dextran polymers.

A dextran herein can comprise (i) about 87-93 wt % glucose linked only at positions 1 and 6; (ii) about 0.1-1.2 wt % glucose linked only at positions 1 and 3; (iii) about 0.1-0.7 wt % glucose linked only at positions 1 and 4; (iv) about 7.7-8.6 wt % glucose linked only at positions 1, 3 and 6; and (v) about 0.4-1.7 wt % glucose linked only at: (a) positions 1, 2 and 6, or (b) positions 1, 4 and 6. In certain embodiments, a dextran can comprise (i) about 89.5-90.5 wt % glucose linked only at positions 1 and 6; (ii) about 0.4-0.9 wt % glucose linked only at positions 1 and 3; (iii) about 0.3-0.5 wt % glucose linked only at positions 1 and 4; (iv) about 8.0-8.3 wt % glucose linked only at positions 1, 3 and 6; and (v) about 0.7-1.4 wt % glucose linked only at: (a) positions 1, 2 and 6, or (b) positions 1, 4 and 6.

A dextran in some aspects of the present disclosure can comprise about 87, 87.5, 88, 88.5, 89, 89.5, 90, 90.5, 91, 91.5, 92, 92.5, or 93 wt % glucose linked only at positions 1 and 6. There can be about 87-92.5, 87-92, 87-91.5, 87-91, 87-90.5, 87-90, 87.5-92.5, 87.5-92, 87.5-91.5, 87.5-91, 87.5-90.5, 87.5-90, 88-92.5, 88-92, 88-91.5, 88-91, 88-90.5, 88-90, 88.5-92.5, 88.5-92, 88.5-91.5, 88.5-91, 88.5-90.5, 88.5-90, 89-92.5, 89-92, 89-91.5, 89-91, 89-90.5, 89-90, 89.5-92.5, 89.5-92, 89.5-91.5, 89.5-91, or 89.5-90.5 wt % glucose linked only at positions 1 and 6, in some instances.

A dextran in some aspects can comprise about 0.1, 0.2, 0.3, 0.4, 0.5, 0.6, 0.7, 0.8, 0.9, 1.0, 1.1, or 1.2 wt % glucose linked only at positions 1 and 3. There can be about 0.1-1.2, 0.1-1.0, 0.1-0.8, 0.3-1.2, 0.3-1.0, 0.3-0.8, 0.4-1.2, 0.4-1.0, 0.4-0.8, 0.5-1.2, 0.5-1.0, 0.5-0.8, 0.6-1.2, 0.6-1.0, or 0.6-0.8 wt % glucose linked only at positions 1 and 3, in some instances.

A dextran in some aspects can comprise about 0.1, 0.2, 0.3, 0.4, 0.5, 0.6, or 0.7 wt % glucose linked only at positions 1 and 4. There can be about 0.1-0.7, 0.1-0.6, 0.1-0.5, 0.1-0.4, 0.2-0.7, 0.2-0.6, 0.2-0.5, 0.2-0.4, 0.3-0.7, 0.3-0.6, 0.3-0.5, or 0.3-0.4 wt % glucose linked only at positions 1 and 4, in some instances.

A dextran in some aspects can comprise about 7.7, 7.8, 7.9, 8.0, 8.1, 8.2, 8.3, 8.4, 8.5, or 8.6 wt % glucose linked only at positions 1, 3 and 6. There can be about 7.7-8.6, 7.7-8.5, 7.7-8.4, 7.7-8.3, 7.7-8.2, 7.8-8.6, 7.8-8.5, 7.8-8.4, 7.8-8.3, 7.8-8.2, 7.9-8.6, 7.9-8.5, 7.9-8.4, 7.9-8.3, 7.9-8.2, 8.0-8.6, 8.0-8.5, 8.0-8.4, 8.0-8.3, 8.0-8.2, 8.1-8.6, 8.1-8.5, 8.1-8.1, 8.1-8.3,or 8.1-8.2 wt % glucose linked only at positions 1, 3 and 6, in some instances.

A dextran in some aspects can comprise about 0.4, 0.5, 0.6, 0.7, 0.8, 0.9, 1.0, 1.1, 1.2, 1.3, 1.4, 1.5, 1.6, or 1.7 wt % glucose linked only at (a) positions 1, 2 and 6, or (b) positions 1, 4 and 6. There can be about 0.4-1.7, 0.4-1.6, 0.4-1.5, 0.4-1.4, 0.4-1.3, 0.5-1.7, 0.5-1.6, 0.5-1.5, 0.5-1.4, 0.5-1.3, 0.6-1.7, 0.6-1.6, 0.6-1.5, 0.6-1.4, 0.6-1.3, 0.7-1.7, 0.7-1.6, 0.7-1.5, 0.7-1.4, 0.7-1.3, 0.8-1.7, 0.8-1.6, 0.8-1.5, 0.8-1.4, 0.8-1.3 wt % glucose linked only at (a) positions 1, 2 and 6, or (b) positions 1, 4 and 6, in some instances.

The glucosidic linkage profile of dextran can be determined using dextran produced following any protocol disclosed herein. An example of a suitable linkage determination protocol can be similar to, or the same as, the protocol disclosed in Example 9: For example, an 0768 gtf enzyme reaction that has been deactivated by heating the reaction at about 70-90° C. (e.g., 80° C.) for about 5-30 minutes (e.g., 10 minutes) is placed into dialysis tubing (e.g., made with regenerated cellulose) with an MWCO of 12-14 kDa (e.g., Spectra/Por® 4 Dialysis Tubing, Part No. 132706, Spectrum Laboratories, Inc.). The deactivated reaction is then dialyzed against a large volume of water (e.g., 3-5 L) at about 20-25° C. (room temp) over about 4-10 days (e.g., 7 days); this water can be exchanged every day during the dialysis. The dextran product is then (i) precipitated by mixing the dialyzed deactivated reaction with about 1-2× (1.5×) reaction volume of 100% methanol, (ii) washed at least two times with the same volume of 100% methanol, and (iii) dried at about 40-50° C. (e.g., 45° C.) (optionally under a vacuum). A dissolvable amount of dry dextran is dissolved in dimethyl sulfoxide (DMSO) or DMSO/5% LiCl, after which all free hydroxyl groups are methylated (e.g., by sequential addition of a NaOH/DMSO slurry followed with iodomethane). The methylated dextran is then extracted (e.g., into methylene chloride) and hydrolyzed to monomeric units using aqueous trifluoroacetic acid (TFA) at about 110-125° C. (e.g., 120° C.). The TFA is then evaporated and reductive ring opening is done using sodium borodeuteride. The hydroxyl groups created by hydrolyzing the glycosidic linkages are then acetylated by treating with acetyl chloride and TFA at a temperature of about 40-60° C. (e.g., 50° C.). Next, the derivatizing reagents are evaporated and the resulting methylated/acetylated monomers are reconstituted in acetonitrile; this preparation is then analyzed by GC/MS using an appropriate column (e.g., biscyanopropyl cyanopropylphenyl polysiloxane). The relative positioning of the methyl and acetyl functionalities render species with distinctive retention time indices and mass spectra that can be compared to published databases. In this way, the derivatives of the monomeric units indicate how each monomer was originally linked in the dextran polymer.

It is believed that dextran herein may be a branched structure in which there are long chains (containing mostly or all alpha-1,6-linkages) that iteratively branch from each other (e.g., a long chain can be a branch from another long chain, which in turn can itself be a branch from another long chain, and so on). The branched structure may also comprise short branches from the long chains; these short chains are believed to mostly comprise alpha-1,3 and -1,4 linkages, for example. Branch points in the dextran, whether from a long chain branching from another long chain, or a short chain branching from a long chain, appear to comprise alpha-1,3, -1,4, or -1,2 linkages off of a glucose involved in alpha-1,6 linkage. On average, about 20%, 21%, 22%, 23%, 24%, 25%, 26%, 27%, 28%, 29%, 30%, 15-35%, 15-30%, 15-25%, 15-20%, 20-35%, 20-30%, 20-25%, 25-35%, or 25-30% of all branch points of dextran in some embodiments branch into long chains. Most (>98% or 99%) or all the other branch points branch into short chains.

The long chains of a dextran branching structure can be similar in length in some aspects. By being similar in length, it is meant that the length (DP) of at least 70%, 75%, 80%, 85%, or 90% of all the long chains in a branching structure is within plus/minus 15% (or 10%, 5%) of the mean length of all the long chains of the branching structure. In some aspects, the mean length (average length) of the long chains is about 10-50 DP (i.e., 10-50 glucose monomers). For example, the mean individual length of the long chains can be about 10, 15, 16, 17, 18, 19, 20, 21, 22, 23, 24, 25, 30, 35, 40, 45, 50, 10-50, 10-40, 10-30, 10-25, 10-20, 15-50, 15-40, 15-30, 15-25, 15-20, 20-50, 20-40, 20-30, or 20-25 DP.

Dextran long chains in certain embodiments can comprise substantially alpha-1,6-glucosidic linkages and a small amount (less than 2.0%) of alpha-1,3- and/or alpha-1,4-glucosidic linkages. For example, dextran long chains can comprise about, or at least about, 98%, 98.25%, 98.5%, 98.75%, 99%, 99.25%, 99.5%, 99.75%, or 99.9% alpha-1, 6-glucosidic linkages. A dextran long chain in certain embodiments does not comprise alpha-1,4-glucosidic linkages (i.e., such a long chain has mostly alpha-1,6 linkages and a small amount of alpha-1,3 linkages). Conversely, a dextran long chain in some embodiments does not comprise alpha-1,3-glucosidic linkages (i.e., such a long chain has mostly alpha-1,6 linkages and a small amount of alpha-1,4 linkages). Any dextran long chain of the above embodiments may further not comprise alpha-1,2-glucosidic linkages, for example. Still in some aspects, a dextran long chain can comprise 100% alpha-1,6-glucosidic linkages (excepting the linkage used by such long chain to branch from another chain).

Short chains of a dextran molecule in some aspects are one to three glucose monomers in length and comprise less than about 5-10% of all the glucose monomers of the dextran polymer. At least about 90%, 91%, 92%, 93%, 94%, 95%, 96%, 97%, 98%, 99%, or all of, short chains herein are 1-3 glucose monomers in length. The short chains of a dextran molecule can comprise less than about 10%, 9%, 8%, 7%, 6%, 5%, 4%, 3%, 2%, or 1% of all the glucose monomers of the dextran molecule, for example.

Short chains of a dextran molecule in some aspects can comprise alpha-1,2-, alpha-1,3-, and/or alpha-1,4-glucosidic linkages. Short chains, when considered all together (not individually) may comprise (i) all three of these linkages, or (ii) alpha-1,3- and alpha-1,4-glucosidic linkages, for example. It is believed that short chains of a dextran molecule herein can be heterogeneous (i.e., showing some variation in linkage profile) or homogeneous (i.e., sharing similar or same linkage profile) with respect to the other short chains of the dextran.

Dextran in certain embodiments can have an Mw of about, or at least about, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 million (or any integer between 50 and 200 million) (or any range between two of these values). The Mw of dextran can be about 50-200, 60-200, 70-200, 80-200, 90-200, 100-200, 110-200, 120-200, 50-180, 60-180, 70-180, 80-180, 90-180, 100-180, 110-180, 120-180, 50-160, 60-160, 70-160, 80-160, 90-160, 100-160, 110-160, 120-160, 50-140, 60-140, 70-140, 80-140, 90-140, 100-140, 110-140, 120-140, 50-120, 60-120, 70-120, 80-120, 90-120, 100-120, 110-120, 50-110, 60-110, 70-110, 80-110, 90-110, 100-110, 50-100, 60-100, 70-100, 80-100, 90-100, or 95-105 million, for example. Any of these Mw's can be represented in DPw, if desired, by dividing Mw by 162.14.

The z-average radius of gyration of a dextran herein can be about 200-280 nm. For example, the z-average Rg can be about 200, 205, 210, 215, 220, 225, 230, 235, 240, 245, 250, 255, 260, 265, 270, 275, or 280 nm (or any integer between 200-280 nm). As other examples, the z-average Rg can be about 200-280, 200-270, 200-260, 200-250, 200-240, 200-230, 220-280, 220-270, 220-260, 220-250, 220-240, 220-230, 230-280, 230-270, 230-260, 230-250, 230-240, 240-280, 240-270, 240-260, 240-250, 250-280, 250-270, or 250-260 nm.

The Mw and/or z-average Rg of dextran in some aspects can be measured following a protocol similar to, or the same as, the protocol disclosed in Example 9. For example, a Mw and/or z-average Rg herein can be measured by first dissolving dextran produced by an 0768 gtf at 0.4-0.6 mg/mL (e.g., ~0.5 mg/mL) in 0.05-1.0 M (e.g., ~0.075 M) Tris (hydroxymethyl)aminomethane buffer with 150-250 ppm (e.g., ~200 ppm) $NaN_3$. Solvation of dry dextran can be achieved by shaking for 12-18 hours at 45-55° C. (e.g., ~50° C.). The resulting dextran solution can be entered into a suitable flow injection chromatographic apparatus comprising a separation module (e.g., Alliance™ 2695 separation module from Waters Corporation, Milford, Mass.) coupled with three online detectors: a differential refractometer (e.g., Waters 2414 refractive index detector), a multiangle light scattering (MALS) photometer (e.g., Heleos™-2 18-angle multiangle MALS photometer) equipped with a quasielastic light scatering (QELS) detector (e.g., QELS detector from Wyatt Technologies, Santa Barbara, Calif.), and a differential capillary viscometer (e.g., ViscoStar™ differential capillary viscometer from Wyatt). Two suitable size-exclusion columns (e.g., AQUAGEL-OH GUARD columns from Agilent Technologies, Santa Clara, Calif.) can be used to separate the dextran polymer peak from the injection peak, where the mobile phase can be the same as the sample solvent (above), the flow rate can be about 0.2 mL/min, the injection volumes can be about 0.1 mL, and column temperature can be about 30° C. Suitable software can be used for data acquisition (e.g., Empower™ version 3 software from Waters) and for multidetector data reduction (Astra™ version 6 software from Wyatt). MALS data can provide weight-average molecular weight (Mw) and z-average radius of gyration (Rg), and QELS data can provide z-average hydrodynamic radius, for example.

A dextran herein can be a product of a glucosyltransferase enzyme comprising, or consisting of, an amino acid sequence that is 100% identical to, or at least 90%, 91%, 92%, 93%, 94%, 95%, 96%, 97%, 98%, or 99% identical to, SEQ ID NO:1, SEQ ID NO:2, SEQ ID NO:5, SEQ ID NO:9, SEQ ID NO:13, or SEQ ID NO:17 (and have gtf activity). Non-limiting examples of a glucosyltransferase enzyme comprising SEQ ID NO:1 (or a related sequence) include glucosyltransferase enzymes comprising, or consisting of, an amino acid sequence that is 100% identical to, or at least 90%, 91%, 92%, 93%, 94%, 95%, 96%, 97%, 98%, or 99% identical to, SEQ ID NO:2 (and have gtf activity). Production of dextran can be accomplished with a gtf reaction as disclosed herein, for example. Dextran as disclosed in the instant detailed description (e.g., molecular weight, linkage and branching profile) can optionally be characterized as a product of a glucosyltransferase enzyme comprising or consisting of SEQ ID NO:1 or 2 (or a related sequence thereof that is at least 90% identical [above]). In some other embodiments, a glucosyltransferase enzyme comprises or consists of an amino acid sequence that is 100% identical to, or at least 90%, 91%, 92%, 93%, 94%, 95%, 96%, 97%, 98%, or 99% identical to, the secreted portion (i.e., signal peptide removed) of the amino acid sequence encoded by SEQ ID NO:6, 10, 14, or 18.

A glucosyltransferase enzyme herein may be from various microbial sources, such as a bacteria or fungus. Examples of bacterial glucosyltransferase enzymes are those derived from a *Streptococcus* species, *Leuconostoc* species, *Lactobacillus* species, or *Weissella* species. Examples of *Streptococcus* species include *S. sobrinus, S. downei, S. salivarius, S. dentirousetti, S. mutans, S. oralis, S. gallolyticus* and *S. sanguinis*. Examples of *Leuconostoc* species include *L. pseudomesenteroides, L. mesenteroides, L. amelibiosum, L. argentinum, L. carnosum, L. citreum, L. cremoris, L. dextranicum* and *L. fructosum*. Examples of *Lactobacillus* species include *L. fermentum, L. acidophilus, L. delbrueckii, L. helveticus, L. salivarius, L. casei, L. curvatus, L. plantarum, L. sakei, L. brevis, L. buchneri* and *L. reuteri*. Examples of *Weissella* species include *W. cibaria, W. confusa, W. halotolerans, W. hellenica, W. kandleri, W. kimchii, W. koreensis, W. minor, W. paramesenteroides, W. soli* and *W. thailandensis*. A glucosyltransferase in some aspects is not from *L. mesenteroides*.

Examples of glucosyltransferase enzymes herein can be any of the amino acid sequences disclosed herein and that further include 1-300 (or any integer there between [e.g., 10, 15, 20, 25, 30, 35, 40, 45, or 50]) residues on the N-terminus and/or C-terminus. Such additional residues may be from a corresponding wild type sequence from which the glucosyltransferase enzyme is derived, or may be a heterologous sequence such as an epitope tag (at either N- or C-terminus) or a heterologous signal peptide (at N-terminus), for example.

A glucosyltransferase enzyme used to produce dextran herein is typically in a mature form lacking an N-terminal signal peptide. An expression system for producing a mature glucosyltransferase enzyme herein may employ an enzyme-encoding polynucleotide that further comprises sequence encoding an N-terminal signal peptide to direct extra-cellular secretion. The signal peptide in such embodiments is cleaved from the enzyme during the secretion process. The signal peptide may either be native or heterologous to the glucosyltransferase. An example of a signal peptide useful herein is one from a bacterial (e.g., a *Bacillus* species such as *B. subtilis*) or fungal species. An example of a bacterial signal peptide is an aprE signal peptide, such as one from *Bacillus* (e.g., *B. subtilis*, see Vogtentanz et al., *Protein Expr. Purif.* 55:40-52, which is incorporated herein by reference).

SEQ ID NO:1, SEQ ID NO:5, SEQ ID NO:9, SEQ ID NO:13 and SEQ ID NO:17 are examples of mature glucosyltransferase enzymes that lack an N-terminal signal peptide. Since these and related amino acid sequences do not begin with a methionine residue, it would be understood that an N-terminal start-methionine is preferably added to the sequence (directly or via an intervening heterologous amino acid sequence such as an epitope) if expressing any of these enzymes without using a signal peptide (such as with an expression system where the enzyme is expressed intracellularly and obtained from a cell lysate).

A glucosyltransferase enzyme in certain embodiments can be produced by any means known in the art. For example, a glucosyltransferase enzyme can be produced recombinantly in a heterologous expression system, such as a microbial heterologous expression system. Examples of heterologous expression systems include bacterial (e.g., *E. coli* such as TOP10, MG1655, or BL21 DE3; *Bacillus* sp. such as *B. subtilis*) and eukaryotic (e.g., yeasts such as *Pichia* sp. and *Saccharomyces* sp.) expression systems.

A glucosyltransferase enzyme disclosed herein may be used in any purification state (e.g., pure or non-pure). For example, the glucosyltransferase enzyme may be purified and/or isolated prior to its use. Examples of glucosyltransferase enzymes that are non-pure include those in the form of a cell lysate. A cell lysate or extract may be prepared from a bacteria (e.g., *E. coli*) used to heterologously express the enzyme. For example, the bacteria may be subjected to disruption using a French pressure cell. In alternative embodiments, bacteria may be homogenized with a homogenizer (e.g., APV, Rannie, Gaulin). A glucosyltransferase enzyme is typically soluble in these types of preparations. A bacterial cell lysate, extract, or homogenate herein may be used at about 0.15-0.3% (v/v) in a reaction for producing dextran from sucrose.

A heterologous gene expression system for expressing a glucosyltransferase enzyme herein can be designed for protein secretion, for example. A glucosyltransferase enzyme typically comprises a signal peptide in such embodiments. A glucosyltransferase enzyme in some embodiments does not occur in nature; for example, an enzyme herein is not believed to be one that is naturally secreted (i.e., mature form) from a microbe (from which the glucosyltransferase enzyme herein could possibly have been derived).

The activity of a glucosyltransferase enzyme herein can be determined using any method known in the art. For example, glucosyltransferase enzyme activity can be determined by measuring the production of reducing sugars (fructose and glucose) in a reaction containing sucrose (~50 g/L), dextran T10 (~1 mg/mL) and potassium phosphate buffer (~pH 6.5, 50 mM), where the solution is held at ~22-25° C. for ~24-30 hours. The reducing sugars can be measured by adding 0.01 mL of the reaction to a mixture containing ~1 N NaOH and ~0.1% triphenyltetrazolium chloride and then monitoring the increase in absorbance at $OD_{480\ nm}$ for ~five minutes. Also for instance, a unit of an enzyme such as gtf 0768 (comprising SEQ ID NO:1) herein can be defined as the amount of enzyme required to consume 1 g of sucrose in 1 hour at 26° C., pH 6.5, and with 100 g/L of sucrose.

A dextran as presently disclosed can be a product of a glucosyltransferase as comprised in a glucosyltransferase reaction.

The temperature of a glucosyltransferase reaction herein can be controlled, if desired. In certain embodiments, the temperature is between about 5° C. to about 50° C. The temperature in certain other embodiments is between about 20° C. to about 40° C. Alternatively, the temperature may be about 20, 21, 22, 23, 24, 25, 26, 27, 28, 29, 30, 31, 32, 33, 34, 35, 36, 37, 38, 39, or 40° C. The temperature of a glucosyltransferase reaction herein may be maintained using various means known in the art. For example, the temperature can be maintained by placing the vessel containing the reaction in an air or water bath incubator set at the desired temperature.

The initial concentration of sucrose in a glucosyltransferase reaction herein can be about 20 g/L to 900 g/L, 20 g/L to 400 g/L, 75 g/L to 175 g/L, or 50 g/L to 150 g/L. The initial concentration of sucrose can be about 20, 30, 40, 50, 60, 70, 80, 90, 100, 110, 120, 130, 140, 150, 160, 200, 300, 400, 500, 600, 700, 800, 900, 50-150, 75-125, 90-110, 50-500, 100-500, 200-500, 300-500, 400-500, 50-400, 100-400, 200-400, 300-400, 50-300, 100-300, 200-300, 50-200, 100-200, or 50-100 g/L (or any integer between 20 and 900 g/L), for example. "Initial concentration of sucrose" refers to the sucrose concentration in a gtf reaction just after all the reaction components have been added (at least water, sucrose, glucosyltransferase enzyme).

Sucrose used in a glucosyltransferase reaction herein can be highly pure (≥99.5%) or be of any other purity or grade. For example, sucrose can have a purity of at least 99.0%, or can be reagent grade sucrose. As another example, incompletely refined sucrose can be used. Incompletely refined sucrose herein refers to sucrose that has not been processed to white refined sucrose. Thus, incompletely refined sucrose can be completely unrefined or partially refined. Examples of unrefined sucrose are "raw sucrose" ("raw sugar") and solutions thereof. Examples of partially refined sucrose have not gone through one, two, three, or more crystallization steps. The ICUMSA (International Commission for Uniform Methods of Sugar Analysis) of incompletely refined sucrose herein can be greater than 150, for example. Sucrose herein may be derived from any renewable sugar source such as sugar cane, sugar beets, cassava, sweet sorghum, or corn. Suitable forms of sucrose useful herein are crystalline form or non-crystalline form (e.g., syrup, cane juice, beet juice), for example. Additional suitable forms of incompletely refined sucrose are disclosed in U.S. Appl. Publ. No. 2015/0275256, which is incorporated herein by reference.

Methods of determining ICUMSA values for sucrose are well known in the art and disclosed by the International Commission for Uniform Methods of Sugar Analysis in *ICUMSA Methods of Sugar Analysis: Official and Tentative Methods Recommended by the International Commission for Uniform Methods of Sugar Analysis (ICUMSA)* (Ed. H. C. S. de Whalley, Elsevier Pub. Co., 1964), for example, which is incorporated herein by reference. ICUMSA can be measured, for example, by ICUMSA Method GS1/3-7 as described by R. J. McCowage, R. M. Urquhart and M. L. Burge (*Determination of the Solution Colour of Raw Sugars, Brown Sugars and Coloured Syrups at pH 7.0—Official*, Verlag Dr Albert Bartens, 2011 revision), which is incorporated herein by reference.

The pH of a glucosyltransferase reaction in certain embodiments can be between about 4.0 to about 8.0. Alternatively, the pH can be about 4.0, 4.5, 5.0, 5.5, 6.0, 6.5, 7.0, 7.5, or 8.0. The pH can be adjusted or controlled by the addition or incorporation of a suitable buffer, including but not limited to: phosphate, tris, citrate, or a combination thereof. Buffer concentration in a gtf reaction can be from 0 mM to about 100 mM, or about 10, 20, or 50 mM, for example.

A glucosyltransferase reaction can be contained within any vessel suitable for applying one or more of the reaction conditions disclosed herein. For example, a glucosyltransferase reaction herein may be in a stainless steel, plastic, or glass vessel or container of a size suitable to contain a particular reaction. Such a vessel can optionally be equipped with a stirring device.

A glucosyltransferase reaction herein can optionally be agitated via stirring or orbital shaking, for example. Such agitation can be at about 50, 60, 70, 80, 90, 100, 110, 120, 130, 140, 150, 50-150, 60-140, 70-130, 80-120, or 90-110 rpm, for example.

The concentration of glucosyltransferase enzyme in a reaction can be at least about 15, 20, 25, 30, 35, or 40 U/L, for example. In some embodiments, 15-35, 15-30, 15-25, 20-35, 20-30, 20-25, 25-35, 25-30, or 30-35 U/L of glucosyltransferase can be used.

A glucosyltransferase reaction herein can take about 2, 3, 4, 5, 6, 7, 8, 9, 10, 12, 18, 24, 30, 36, 48, 60, 72, 84, 96, 18-30, 20-28, or 22-26 hours to complete. Reaction time may depend, for example, on certain parameters such as the amount of sucrose and glucosyltransferase enzyme used in the reaction.

All the features herein defining a glucosyltransferase reaction can be combined, accordingly. Simply as an example, a reaction using an 0768 glucosyltransferase (comprising SEQ ID NO:1 or related sequence thereof) can initially contain 90-110 g/L (e.g., ~100 g/L) sucrose, 10-30 mM (e.g., ~20 mM) sodium phosphate buffer at pH 6.0-7.0 (e.g., ~pH 6.5), and 20-30 U/L (e.g., ~25 U/L) enzyme. Such a reaction can be held for about 20-28 hours (e.g., ~24 hours) with 50-150 rpm (e.g., ~100 rpm) shaking at 24-28° C. (e.g., ~26° C.).

In some embodiments, a glucosyltransferase reaction comprising a gtf 0768 enzyme (SEQ ID NO:1 or related sequences) and any amount of sucrose disclosed herein can be complete (e.g., 95% or more initially provided sucrose depleted) in less than about 24, 22, 20, 18, or 16 hours after initiating the reaction. Depletion of sucrose in such a reaction can be about, or at least about, 3, 4, 5, 6, 7, 8, 9, or 10 times faster than a same or similar reaction, but which comprises a *Leuconostoc mesenteroides* dextran sucrase instead of a gtf 0768 enzyme, for example.

A composition comprising a dextran herein can be non-aqueous (e.g., a dry composition). Examples of such embodiments include powders, granules, microcapsules, flakes, or any other form of particulate matter. Other examples include larger compositions such as pellets, bars, kernels, beads, tablets, sticks, or other agglomerates. A non-aqueous or dry composition herein typically has less than 3, 2, 1, 0.5, or 0.1 wt % water comprised therein. The amount of dextran herein in a non-aqueous or dry composition can be about, or at least about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, or 99.9 wt %, for example. A non-aqueous composition herein can be in the form of a household product, personal care product, pharmaceutical product, industrial product, or food product, for example.

In certain embodiments of the present disclosure, a composition comprising a dextran can be an aqueous composition having a viscosity of about, or at least about, 25 cPs. Alternatively, an aqueous composition herein can have a viscosity of about, or at least about, 25, 50, 75, 100, 250, 500, 750, 1000, 2000, 3000, 4000, 5000, 6000, 7000, 8000, 9000, 10000, 11000, 12000, 13000, 14000, 15000, 16000, 17000, 18000, 19000, 20000, 25000, 30000, 35000, 40000, 45000, or 50000 cPs (or any integer between 25 and 50000 cPs), for example. Examples of aqueous compositions include hydrocolloids and aqueous solutions.

Viscosity can be measured with an aqueous composition herein at any temperature between about 3° C. to about 110° C. (or any integer between 3 and 110° C.). Alternatively, viscosity can be measured at a temperature between about 4° C. to 30° C., or about 20° C. to 25° C., for example. Viscosity can be measured at atmospheric pressure (about 760 torr) or any other higher or lower pressure.

The viscosity of an aqueous composition disclosed herein can be measured using a viscometer or rheometer, or using any other means known in the art. It would be understood by those skilled in the art that a viscometer or rheometer can be used to measure the viscosity of aqueous compositions herein that exhibits rheological behavior (i.e., having viscosities that vary with flow conditions). The viscosity of such embodiments can be measured at a rotational shear rate of about 0.1 to 1000 rpm (revolutions per minute), for example. Alternatively, viscosity can be measured at a rotational shear rate of about 10, 60, 150, 250, or 600 rpm.

In certain embodiments, viscosity can be measured with an aqueous composition in which the constituent dextran was synthesized. For example, viscosity can be measured for a gtf reaction herein that is at or near completion. Viscosity can thus be measured with an aqueous composition in which the constituent dextran is not purified (e.g., other components in the composition, aside from water, are present at greater than 1, 5, or 10 wt %); such a composition can contain one or more salts, buffers, proteins (e.g., gtf enzymes), sugars (e.g., fructose, glucose, leucrose, oligosaccharides).

The pH of an aqueous composition disclosed herein can be between about 2.0 to about 12.0, for example. Alternatively, pH can be about 2.0, 3.0, 4.0, 5.0, 6.0, 7.0, 8.0, 9.0, 10.0, 11.0, 12.0; or between 5.0 to about 12.0; or between about 4.0 and 8.0; or between about 5.0 and 8.0, for example.

An aqueous composition herein such as a hydrocolloid or aqueous solution can comprise a solvent having about, or at least about, 10 wt % water. In other embodiments, a solvent is about, or at least about, 20, 30, 40, 50, 60, 70, 80, 90, or 100 wt % water (or any integer value between 10 and 100 wt %), for example.

A dextran herein can be present in an aqueous composition at a wt % of about, or at least about, 0.01, 0.05, 0.1, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 wt %, for example. Example 8 below demonstrates that dextran in certain aspects provides high viscosity to aqueous solutions at relatively low concentrations of the dextran. Thus, certain embodiments of the present disclosure are drawn to aqueous compositions with less than about 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or 0.5 wt % dextran herein.

An aqueous composition herein can comprise other components in addition to dextran. For example, an aqueous composition can comprise one or more salts such as a sodium salt (e.g., NaCl, $Na_2SO_4$). Other non-limiting examples of salts include those having (i) an aluminum, ammonium, barium, calcium, chromium (II or III), copper (I or II), iron (II or III), hydrogen, lead (II), lithium, magnesium, manganese (II or III), mercury (I or II), potassium, silver, sodium strontium, tin (II or IV), or zinc cation, and (ii) an acetate, borate, bromate, bromide, carbonate, chlorate, chloride, chlorite, chromate, cyanamide, cyanide, dichromate, dihydrogen phosphate, ferricyanide, ferrocyanide, fluoride, hydrogen carbonate, hydrogen phosphate, hydrogen sulfate, hydrogen sulfide, hydrogen sulfite, hydride, hydroxide, hypochlorite, iodate, iodide, nitrate, nitride, nitrite, oxalate, oxide, perchlorate, permanganate, peroxide, phosphate, phosphide, phosphite, silicate, stannate, stannite, sulfate, sulfide, sulfite, tartrate, or thiocyanate anion. Thus, any salt having a cation from (i) above and an anion from (ii) above can be in an aqueous composition, for example. A salt can be present in an aqueous composition herein at a wt % of about 0.01 to about 10.00 (or any hundredth increment between 0.01 and 10.00), for example.

A composition herein may optionally contain one or more active enzymes. Non-limiting examples of suitable enzymes include proteases, cellulases, hemicellulases, peroxidases, lipolytic enzymes (e.g., metallolipolytic enzymes), xylanases, lipases, phospholipases, esterases (e.g., arylesterase, polyesterase), perhydrolases, cutinases, pectinases, pectate lyases, mannanases, keratinases, reductases, oxidases (e.g., choline oxidase), phenoloxidases, lipoxygenases, ligninases, pullulanases, tannases, pentosanases, malanases, beta-glucanases, arabinosidases, hyaluronidases, chondroitinases, laccases, metalloproteinases, amadoriases, glucoamylases, arabinofuranosidases, phytases, isomerases, transferases and amylases. If an enzyme(s) is included, it may be comprised in a composition herein at about 0.0001-0.1 wt % (e.g., 0.01-0.03 wt %) active enzyme (e.g., calculated as pure enzyme protein), for example.

A cellulase herein can have endocellulase activity (EC 3.2.1.4), exocellulase activity (EC 3.2.1.91), or cellobiase activity (EC 3.2.1.21). A cellulase herein is an "active cellulase" having activity under suitable conditions for maintaining cellulase activity; it is within the skill of the art to determine such suitable conditions.

A cellulase herein may be derived from any microbial source, such as a bacteria or fungus. Chemically-modified cellulases or protein-engineered mutant cellulases are included. Suitable cellulases include, but are not limited to, cellulases from the genera *Bacillus, Pseudomonas, Streptomyces, Trichoderma, Humicola, Fusarium, Thielavia* and *Acremonium*. As other examples, a cellulase may be derived from *Humicola insolens, Myceliophthora thermophila* or *Fusarium oxysporum*; these and other cellulases are disclosed in U.S. Pat. Nos. 4,435,307, 5,648,263, 5,691,178, 5,776,757 and 7,604,974, which are all incorporated herein by reference. Exemplary *Trichoderma reesei* cellulases are disclosed in U.S. Pat. Nos. 4,689,297, 5,814,501, 5,324,649, and International Patent Appl. Publ. Nos. WO92/06221 and WO92/06165, all of which are incorporated herein by reference. Exemplary *Bacillus cellulases* are disclosed in U.S. Pat. No. 6,562,612, which is incorporated herein by reference. A cellulase, such as any of the foregoing, preferably is in a mature form lacking an N-terminal signal peptide. Commercially available cellulases useful herein include CELLUZYME® and CAREZYME® (Novozymes A/S); CLAZINASE® and PURADAX® HA (DuPont Industrial Biosciences), and KAC-500(B)® (Kao Corporation).

Alternatively, a cellulase herein may be produced by any means known in the art, such as described in U.S. Pat. Nos. 4,435,307, 5,776,757 and 7,604,974, which are incorporated herein by reference. For example, a cellulase may be produced recombinantly in a heterologous expression system, such as a microbial or fungal heterologous expression system. Examples of heterologous expression systems include bacterial (e.g., *E. coli, Bacillus* sp.) and eukaryotic systems. Eukaryotic systems can employ yeast (e.g., *Pichia* sp., *Saccharomyces* sp.) or fungal (e.g., *Trichoderma* sp. such as *T. reesei, Aspergillus* species such as *A. niger*) expression systems, for example.

One or more cellulases can be directly added as an ingredient when preparing a composition disclosed herein. Alternatively, one or more cellulases can be indirectly (inadvertently) provided in the disclosed composition. For example, cellulase can be provided in a composition herein by virtue of being present in a non-cellulase enzyme preparation used for preparing a composition. Cellulase in compositions in which cellulase is indirectly provided thereto can be present at about 0.1-10 ppb (e.g., less than 1 ppm), for example. A contemplated benefit of a composition herein, by virtue of employing a dextran compound, is that non-cellulase enzyme preparations that might have background cellulase activity can be used without concern that the desired effects of the dextran will be negated by the background cellulase activity.

A cellulase in certain embodiments can be thermostable. Cellulase thermostability refers to the ability of the enzyme to retain activity after exposure to an elevated temperature (e.g. about 60-70° C.) for a period of time (e.g., about 30-60 minutes). The thermostability of a cellulase can be measured by its half-life (t½) given in minutes, hours, or days, during which time period half the cellulase activity is lost under defined conditions.

A cellulase in certain embodiments can be stable to a wide range of pH values (e.g. neutral or alkaline pH such as pH of ~7.0 to ~11.0). Such enzymes can remain stable for a predetermined period of time (e.g., at least about 15 min., 30 min., or 1 hour) under such pH conditions.

At least one, two, or more cellulases may be included in the composition. The total amount of cellulase in a composition herein typically is an amount that is suitable for the purpose of using cellulase in the composition (an "effective amount"). For example, an effective amount of cellulase in a composition intended for improving the feel and/or appearance of a cellulose-containing fabric is an amount that produces measurable improvements in the feel of the fabric (e.g., improving fabric smoothness and/or appearance, removing pills and fibrils which tend to reduce fabric appearance sharpness). As another example, an effective amount of cellulase in a fabric stonewashing composition herein is that amount which will provide the desired effect (e.g., to produce a worn and faded look in seams and on fabric panels). The amount of cellulase in a composition herein can also depend on the process parameters in which the composition is employed (e.g., equipment, temperature, time, and the like) and cellulase activity, for example. The effective concentration of cellulase in an aqueous composition in which a fabric is treated can be readily determined by a skilled artisan. In fabric care processes, cellulase can be present in an aqueous composition (e.g., wash liquor) in which a fabric is treated in a concentration that is minimally about 0.01-0.1 ppm total cellulase protein, or about 0.1-10 ppb total cellulase protein (e.g., less than 1 ppm), to maximally about 100, 200, 500, 1000, 2000, 3000, 4000, or 5000 ppm total cellulase protein, for example.

Dextran polymers provided herein are believed to be mostly or completely stable (resistant) to being degraded by cellulase. For example, the percent degradation of a dextran herein by one or more cellulases is believed to be less than 10%, 9%, 8%, 7%, 6%, 5%, 4%, 3%, 2%, or 1%, or is 0%. Such percent degradation can be determined, for example, by comparing the molecular weight of dextran polymer before and after treatment with a cellulase for a period of time (e.g., ~24 hours).

Aqueous compositions in certain embodiments are believed to have shear thinning behavior or shear thickening behavior. Shear thinning behavior is observed as a decrease in viscosity of the aqueous composition as shear rate increases, whereas shear thickening behavior is observed as an increase in viscosity of the aqueous composition as shear rate increases. Modification of the shear thinning behavior or shear thickening behavior of an aqueous composition herein can be due to the admixture of a dextran to the aqueous composition. Thus, one or more dextran compounds of the present disclosure can be added to an aqueous composition to modify its rheological profile (i.e., the flow properties of an aqueous liquid, solution, or mixture are modified). Also, one or more dextran compounds can be added to an aqueous composition to modify its viscosity.

The rheological properties of aqueous compositions herein can be observed by measuring viscosity over an increasing rotational shear rate (e.g., from about 0.1 rpm to about 1000 rpm). For example, shear thinning behavior of an aqueous composition disclosed herein can be observed as a decrease in viscosity (cPs) by about, or at least about, 5%, 10%, 15%, 20%, 25%, 30%, 35%, 40%, 45%, 50%, 55%, 60%, 65%, 70%, 75%, 80%, 85%, 90%, or 95% (or any integer between 5% and 95%) as the rotational shear rate increases from about 10 rpm to 60 rpm, 10 rpm to 150 rpm, 10 rpm to 250 rpm, 60 rpm to 150 rpm, 60 rpm to 250 rpm, or 150 rpm to 250 rpm. As another example, shear thickening behavior of an aqueous composition disclosed herein can be observed as an increase in viscosity (cPs) by about, or at least about, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, or 200% (or any integer between 5% and 200%) as the rotational shear rate increases from about 10 rpm to 60 rpm, 10 rpm to 150 rpm, 10 rpm to 250 rpm, 60 rpm to 150 rpm, 60 rpm to 250 rpm, or 150 rpm to 250 rpm.

An aqueous composition disclosed herein can be in the form of, and/or comprised in, a food product, personal care product, pharmaceutical product, household product, or industrial product, such as any of those products described below. Dextran compounds herein can be used as thickening agents in each of these products. Such a thickening agent may be used in conjunction with one or more other types of thickening agents if desired, such as those disclosed in U.S.

Pat. No. 8,541,041, the disclosure of which is incorporated herein by reference in its entirety.

Dextran compounds disclosed herein are believed to be useful for providing one or more of the following physical properties to a personal care product, pharmaceutical product, household product, industrial product, or food product: thickening, freeze/thaw stability, lubricity, moisture retention and release, texture, consistency, shape retention, emulsification, binding, suspension, dispersion, gelation, reduced mineral hardness, for example. Examples of a concentration or amount of a dextran in a product can be any of the weight percentages provided herein, for example.

Personal care products herein are not particularly limited and include, for example, skin care compositions, cosmetic compositions, antifungal compositions, and antibacterial compositions. Personal care products herein may be in the form of, for example, lotions, creams, pastes, balms, ointments, pomades, gels, liquids, combinations of these and the like. The personal care products disclosed herein can include at least one active ingredient, if desired. An active ingredient is generally recognized as an ingredient that causes an intended pharmacological effect.

In certain embodiments, a skin care product can be applied to skin for addressing skin damage related to a lack of moisture. A skin care product may also be used to address the visual appearance of skin (e.g., reduce the appearance of flaky, cracked, and/or red skin) and/or the tactile feel of the skin (e.g., reduce roughness and/or dryness of the skin while improved the softness and subtleness of the skin). A skin care product typically may include at least one active ingredient for the treatment or prevention of skin ailments, providing a cosmetic effect, or for providing a moisturizing benefit to skin, such as zinc oxide, petrolatum, white petrolatum, mineral oil, cod liver oil, lanolin, dimethicone, hard fat, vitamin A, allantoin, calamine, kaolin, glycerin, or colloidal oatmeal, and combinations of these. A skin care product may include one or more natural moisturizing factors such as ceramides, hyaluronic acid, glycerin, squalane, amino acids, cholesterol, fatty acids, triglycerides, phospholipids, glycosphingolipids, urea, linoleic acid, glycosaminoglycans, mucopolysaccharide, sodium lactate, or sodium pyrrolidone carboxylate, for example. Other ingredients that may be included in a skin care product include, without limitation, glycerides, apricot kernel oil, canola oil, squalane, squalene, coconut oil, corn oil, jojoba oil, jojoba wax, lecithin, olive oil, safflower oil, sesame oil, shea butter, soybean oil, sweet almond oil, sunflower oil, tea tree oil, shea butter, palm oil, cholesterol, cholesterol esters, wax esters, fatty acids, and orange oil.

A personal care product herein can also be in the form of makeup, lipstick, mascara, rouge, foundation, blush, eyeliner, lip liner, lip gloss, other cosmetics, sunscreen, sun block, nail polish, nail conditioner, bath gel, shower gel, body wash, face wash, lip balm, skin conditioner, cold cream, moisturizer, body spray, soap, body scrub, exfoliant, astringent, scruffing lotion, depilatory, permanent waving solution, antidandruff formulation, antiperspirant composition, deodorant, shaving product, pre-shaving product, aftershaving product, cleanser, skin gel, rinse, dentifrice composition, toothpaste, or mouthwash, for example. An example of a personal care product (e.g., a cleanser, soap, scrub, cosmetic) comprises a carrier or exfoliation agent (e.g., jojoba beads [jojoba ester beads]) (e.g., about 1-10, 3-7, 4-6, or 5 wt %); such an agent may optionally be dispersed within the product.

A personal care product in some aspects can be a hair care product. Examples of hair care products herein include shampoo, hair conditioner (leave-in or rinse-out), cream rinse, hair dye, hair coloring product, hair shine product, hair serum, hair anti-frizz product, hair split-end repair product, mousse, hair spray, and styling gel. A hair care product can be in the form of a liquid, paste, gel, solid, or powder in some embodiments. A hair care product as presently disclosed typically comprises one or more of the following ingredients, which are generally used to formulate hair care products: anionic surfactants such as polyoxyethylenelauryl ether sodium sulfate; cationic surfactants such as stearyltrimethylammonium chloride and/or distearyltrimethylammonium chloride; nonionic surfactants such as glyceryl monostearate, sorbitan monopalmitate and/or polyoxyethylenecetyl ether; wetting agents such as propylene glycol, 1,3-butylene glycol, glycerin, sorbitol, pyroglutamic acid salts, amino acids and/or trimethylglycine; hydrocarbons such as liquid paraffins, petrolatum, solid paraffins, squalane and/or olefin oligomers; higher alcohols such as stearyl alcohol and/or cetyl alcohol; superfatting agents; antidandruff agents; disinfectants; anti-inflammatory agents; crude drugs; water-soluble polymers such as methyl cellulose, hydroxycellulose and/or partially deacetylated chitin (in addition to one or more dextrans as disclosed herein); antiseptics such as paraben; ultra-violet light absorbers; pearling agents; pH adjustors; perfumes; and pigments.

A pharmaceutical product herein can be in the form of an emulsion, liquid, elixir, gel, suspension, solution, cream, or ointment, for example. Also, a pharmaceutical product herein can be in the form of any of the personal care products disclosed herein, such as an antibacterial or antifungal composition. A pharmaceutical product can further comprise one or more pharmaceutically acceptable carriers, diluents, and/or pharmaceutically acceptable salts. A dextran compound disclosed herein can also be used in capsules, encapsulants, tablet coatings, and as an excipients for medicaments and drugs.

Non-limiting examples of food products herein include vegetable, meat, and soy patties; reformed seafood; reformed cheese sticks; cream soups; gravies and sauces; salad dressing; mayonnaise; onion rings; jams, jellies, and syrups; pie filling; potato products such as French fries and extruded fries; batters for fried foods, pancakes/waffles and cakes; pet foods; confectioneries (candy); beverages; frozen desserts; ice cream; cultured dairy products such as cottage cheese, yogurt, cheeses, and sour creams; cake icing and glazes; whipped topping; leavened and unleavened baked goods; and the like.

In certain embodiments, dextran herein can be comprised in a foodstuff or any other ingestible material (e.g., enteral pharmaceutical preparation) in an amount that provides the desired degree of thickening and/or dispersion. For example, the concentration or amount of dextran in a product can be about 0.1-3 wt %, 0.1-4 wt %, 0.1-5 wt %, or 0.1-10 wt %.

A household and/or industrial product herein can be in the form of drywall tape-joint compounds; mortars; grouts; cement plasters; spray plasters; cement stucco; adhesives; pastes; wall/ceiling texturizers; binders and processing aids for tape casting, extrusion forming, injection molding and ceramics; spray adherents and suspending/dispersing aids for pesticides, herbicides, and fertilizers; fabric care products such as fabric softeners and laundry detergents; hard surface cleaners; air fresheners; polymer emulsions; gels such as water-based gels; surfactant solutions; paints such as water-based paints; protective coatings; adhesives; sealants and caulks; inks such as water-based ink; metal-working fluids; or emulsion-based metal cleaning fluids used in electroplating, phosphatizing, galvanizing and/or general metal cleaning operations, for example.

A dextran compound disclosed herein can be comprised in a personal care product, pharmaceutical product, household product, or industrial product in an amount that provides a desired degree of thickening and/or dispersion, for example. Examples of a concentration or amount of a dextran compound in a product can be any of the weight percentages provided above, for example.

An aqueous composition in some aspects can comprise about 0.5-2.0 wt % dextran herein (e.g., ~1.0 wt %), about 15-25 wt % (e.g., ~20 wt %) of moisturizer such as oil (e.g., mineral oil), about 4-6 wt % (~5 wt %) surfactant/emulsifier (e.g., one or both of sorbitan monooleate or polysorbate 80, such as ~2.6 wt % sorbitan monooleate and ~2.4 wt % polysorbate 80), optionally 0.25-1.0 wt % (e.g., 0.5 wt %) preservative (e.g., preservative comprising one or more of propylene glycol, diazolidinyl urea, methylparaben, or propylparaben [e.g., Germaben® II]), and optionally one or more other ingredients. Such compositions can be in the form of an emulsion, for example. In these and some other related aspects, dextran as presently disclosed can be used as a substitute for compounds (e.g., xanthan gum, crosslinked polyacrylic acid polymers such as Carbopol® Ultrez 10) typically used to provide viscosity to certain consumer products such as personal care (e.g., lotion), food, and/or pharmaceutical products. Still in some aspects the sensory experience rating of an aqueous composition (e.g., personal care item such as lotion), as measured by ASTM E1490-3 ("Standard Practice for Descriptive Skinfeel Analysis of Creams and Lotions", ASTM International, West Conshohocken, Pa., 2003, DOI: 10.1520/E1490-03, incorporated herein by reference), can be less than about 8, 7, or 6, where each of rub-out sliminess, afterfeel stickiness, pick-up stringiness and pick-up stickiness are measured in the evaluation.

A food product herein can be in the form of a confectionery, for example. A confectionary herein can contain one or more sugars (e.g., sucrose, fructose, dextrose) for sweetening, or otherwise be sugar-free.

Examples of confectioneries herein include boiled sugars (hard boiled candies [i.e., hard candy]), dragees, jelly candies, gums, licorice, chews, caramels, toffee, fudge, chewing gums, bubble gums, nougat, chewy pastes, halawa, tablets, lozenges, icing, frosting, pudding, and gels (e.g., fruit gels, gelatin dessert). Other examples of confectioneries include aerated confectioneries such as marshmallows, and baked confectioneries.

A confectionery herein can optionally be prepared with chocolate, in any form (e.g., bars, candies, bonbons, truffles, lentils). A confectionary can be coated with chocolate, sugar-coated, candied, glazed, and/or film-coated, for example. Film-coating processes typically comprise applying to the surface of a confectionery a film-forming liquid composition which becomes, after drying, a protective film. This film-coating serves, for example, to protect the active principles contained in the confectionery; to protect the confectionery itself from moisture, shocks, and/or friability; and/or to confer the confectionery attractive visual properties (e.g., shine, uniform color, smooth surface).

In certain embodiments, a confectionery can be filled with a filling that is liquid, pasty, solid, or powdered. Dextran herein can be comprised in such a filling, in which case dextran is optionally also included in the confectionery component being filled.

A confectionery herein is optionally sugar-free, comprising no sugar and typically instead having one or more artificial and/or non-sugar sweeteners (optionally non-caloric) (e.g., aspartame, saccharin, STEVIA, SUCRALOSE). A sugar-free confectionery in certain embodiments can comprise one or more polyols (e.g., erythritol, glycerol, lactitol, mannitol, maltitol, xylitol), soluble fibers, and/or proteins in place of sugar.

A food product herein can be in the form of a pet food, for example. A pet food herein can be a food for a domesticated animal such as a dog or cat (or any other companion animal), for example. A pet food in certain embodiments provides to a domestic animal one or more of the following: necessary dietary requirements, treats (e.g., dog biscuits), food supplements. Examples of pet food include dry pet food (e.g., kernels, kibbles), semi-moist compositions, wet pet food (e.g., canned pet food), or any combination thereof. Wet pet food typically has a moisture content over 65%. Semi-moist pet food typically has a moisture content of 20-65% and can include humectants such as propylene glycol, potassium sorbate, and ingredients that prevent microbial growth (bacteria and mold). Dry pet food typically has a moisture content less than 20% and its processing usually includes extruding, drying and/or baking. A pet food can optionally be in the form of a gravy, yogurt, powder, suspension, chew, or treat (e.g., biscuits); all these compositions can also be used as pet food supplements, if desired. Pet treats can be semi-moist chewable treats; dry treats; chewable bones; baked, extruded or stamped treats; or confection treats, for example. Examples of pet food compositions/formulations in which a dextran herein can be added include those disclosed in U.S. Patent Appl. Publ. Nos. 2013/0280352 and 2010/0159103, and U.S. Pat. No. 6,977,084, which are all incorporated herein by reference.

Compositions disclosed herein can be in the form of a fabric care composition. A fabric care composition herein can be used for hand wash, machine wash and/or other purposes such as soaking and/or pretreatment of fabrics, for example. A fabric care composition may take the form of, for example, a laundry detergent; fabric conditioner; any wash-, rinse-, or dryer-added product; unit dose or spray. Fabric care compositions in a liquid form may be in the form of an aqueous composition as disclosed herein. In other aspects, a fabric care composition can be in a dry form such as a granular detergent or dryer-added fabric softener sheet. Other non-limiting examples of fabric care compositions herein include: granular or powder-form all-purpose or heavy-duty washing agents; liquid, gel or paste-form all-purpose or heavy-duty washing agents; liquid or dry fine-fabric (e.g. delicates) detergents; cleaning auxiliaries such as bleach additives, "stain-stick", or pre-treatments; substrate-laden products such as dry and wetted wipes, pads, or sponges; sprays and mists.

A detergent composition herein may be in any useful form, e.g., as powders, granules, pastes, bars, unit dose, or liquid. A liquid detergent may be aqueous, typically containing up to about 70 wt % of water and 0 wt % to about 30 wt % of organic solvent. It may also be in the form of a compact gel type containing only about 30 wt % water.

A detergent composition herein typically comprises one or more surfactants, wherein the surfactant is selected from nonionic surfactants, anionic surfactants, cationic surfactants, ampholytic surfactants, zwitterionic surfactants, semi-polar nonionic surfactants and mixtures thereof. In some embodiments, the surfactant is present at a level of from about 0.1% to about 60%, while in alternative embodiments the level is from about 1% to about 50%, while in still further embodiments the level is from about 5% to about 40%, by weight of the detergent composition. A detergent will usually contain 0 wt % to about 50 wt % of an anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. In addition, a detergent composition may optionally contain 0 wt % to about 40 wt % of a nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO92/06154, which is incorporated herein by reference).

A detergent composition herein typically comprises one or more detergent builders or builder systems. One or more oxidized poly alpha-1,3-glucan compounds can be included as a builder, for example. In some aspects, oxidized poly alpha-1,3-glucan can be included as a co-builder, in which it is used together with one or more additional builders such as any disclosed herein. Oxidized poly alpha-1,3-glucan compounds for use herein are disclosed in U.S. Patent Appl. Publ. No. 2015/0259439. In some embodiments incorporating at least one builder, the cleaning compositions comprise at least about 1%, from about 3% to about 60%, or even from about 5% to about 40%, builder by weight of the composition. Builders (in addition to oxidized poly alpha-1,3-glucan) include, but are not limited to, alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present disclosure. Additional examples of a detergent builder or complexing agent include zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst).

In some embodiments, builders form water-soluble hardness ion complexes (e.g., sequestering builders), such as citrates and polyphosphates (e.g., sodium tripolyphosphate and sodium tripolyphosphate hexahydrate, potassium tripolyphosphate, and mixed sodium and potassium tripolyphosphate, etc.). It is contemplated that any suitable builder will find use in the present disclosure, including those known in the art (See, e.g., EP2100949).

In some embodiments, suitable builders can include phosphate builders and non-phosphate builders. In some embodiments, a builder is a phosphate builder. In some embodiments, a builder is a non-phosphate builder. A builder can be used in a level of from 0.1% to 80%, or from 5% to 60%, or from 10% to 50%, by weight of the composition. In some embodiments, the product comprises a mixture of phosphate and non-phosphate builders. Suitable phosphate builders include mono-phosphates, di-phosphates, tri-polyphosphates or oligomeric-polyphosphates, including the alkali metal salts of these compounds, including the sodium salts.

In some embodiments, a builder can be sodium tripolyphosphate (STPP). Additionally, the composition can comprise carbonate and/or citrate, preferably citrate that helps to achieve a neutral pH composition. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above mentioned compounds include ammonium and/or alkali metal salts, i.e., lithium, sodium, and potassium salts, including sodium salts. Suitable polycarboxylic acids include acyclic, alicyclic, hetero-cyclic and aromatic carboxylic acids, wherein in some embodiments, they can contain at least two carboxyl groups which are in each case separated from one another by, in some instances, no more than two carbon atoms.

A detergent composition herein can comprise at least one chelating agent. Suitable chelating agents include, but are not limited to, copper, iron and/or manganese chelating agents and mixtures thereof. In embodiments in which at least one chelating agent is used, the composition comprises from about 0.1% to about 15%, or even from about 3.0% to about 10%, chelating agent by weight of the composition.

A detergent composition herein can comprise at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

A detergent composition herein can comprise one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. Additional dye transfer inhibiting agents include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents examples of which include ethylene-diamine-tetraacetic acid (EDTA); diethylene triamine penta methylene phosphonic acid (DTPMP); hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetracetic acid (PDT A); 2-hydroxypyridine-N-oxide (HPNO); or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof; N-hydroxyethyl ethylenediaminetriacetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP) and derivatives thereof, which can be used alone or in combination with any of the above. In embodiments in which at least one dye transfer inhibiting agent is used, a composition herein may comprise from about 0.0001% to about 10%, from about 0.01% to about 5%, or even from about 0.1% to about 3%, by weight of the composition.

A detergent composition herein can comprise silicates. In some of these embodiments, sodium silicates (e.g., sodium disilicate, sodium metasilicate, and/or crystalline phyllosilicates) find use. In some embodiments, silicates are present at a level of from about 1% to about 20% by weight of the composition. In some embodiments, silicates are present at a level of from about 5% to about 15% by weight of the composition.

A detergent composition herein can comprise dispersants. Suitable water-soluble organic materials include, but are not limited to the homo- or co-polymeric acids or their salts, in which the polycarboxylic acid comprises at least two carboxyl radicals separated from each other by not more than two carbon atoms.

A detergent composition herein may additionally comprise one or more enzymes. Examples of enzymes include proteases, cellulases, hemicellulases, peroxidases, lipolytic enzymes (e.g., metallolipolytic enzymes), xylanases, lipases, phospholipases, esterases (e.g., arylesterase, polyesterase), perhydrolases, cutinases, pectinases, pectate lyases, mannanases, keratinases, reductases, oxidases (e.g., choline oxidase, phenoloxidase), phenoloxidases, lipoxygenases, ligninases, pullulanases, tannases, pentosanases, malanases, beta-glucanases, arabinosidases, hyaluronidases, chondroitinases, laccases, metalloproteinases, amadoriases, glucoamylases, alpha-amylases, beta-amylases, galactosidases, galactanases, catalases, carageenases, hyaluronidases, keratinases, lactases, ligninases, peroxidases, phosphatases, polygalacturonases, pullulanases, rhamnogalactouronases, tannases, transglutaminases, xyloglucanases, xylosidases, metalloproteases, arabinofuranosidases, phytases, isomerases, transferases and/or amylases in any combination.

Any cellulase disclosed above is contemplated for use in the disclosed detergent compositions. Suitable cellulases include, but are not limited to Humicola insolens cellulases (See e.g., U.S. Pat. No. 4,435,307). Exemplary cellulases contemplated for use herein are those having color care benefit for a textile. Examples of cellulases that provide a color care benefit are disclosed in EP0495257, EP0531372, EP531315, WO96/11262, WO96/29397, WO94/07998; WO98/12307; WO95/24471, WO98/08940, and U.S. Pat. Nos. 5,457,046, 5,686,593 and 5,763,254,all of which are incorporated herein by reference. Examples of commercially available cellulases useful in a detergent include CELLUSOFT®, CELLUCLEAN®, CELLUZYME®, and CAREZYME® (Novo Nordisk A/S and Novozymes A/S); CLAZINASE®, PURADAX HA®, and REVITALENZ™ (DuPont Industrial Biosciences); BIOTOUCH® (AB Enzymes); and KAC-500(B)™ (Kao Corporation). Additional cellulases are disclosed in, e.g., U.S. Pat. No. 7,595,182, U.S. Pat. No. 8,569,033, U.S. Pat. No. 7,138,263, U.S. Pat. No. 3,844,890, U.S. Pat. No. 4,435,307, U.S. Pat. No. 4,435,307, and GB2095275.

In some embodiments, a detergent composition can comprise one or more enzymes (e.g., any disclosed herein), each at a level from about 0.00001% to about 10% by weight of the composition and the balance of cleaning adjunct materials by weight of composition. In some other embodiments, a detergent composition can also comprise each enzyme at a level of about 0.0001% to about 10%, about 0.001% to about 5%, about 0.001% to about 2%, or about 0.005% to about 0.5%, by weight of the composition.

Suitable proteases include those of animal, vegetable or microbial origin. In some embodiments, microbial proteases are used. In some embodiments, chemically or genetically modified mutants are included. In some embodiments, the protease is a serine protease, preferably an alkaline microbial protease or a trypsin-like protease. Examples of alkaline proteases include subtilisins, especially those derived from Bacillus (e.g., subtilisin, lentus, amyloliquefaciens, subtilisin Carlsberg, subtilisin 309, subtilisin 147 and subtilisin 168). Additional examples include those mutant proteases described in U.S. Pat. Nos. RE34606, 5,955,340, 5,700,676, 6,312,936 and 6,482,628, all of which are incorporated herein by reference. Additional protease examples include, but are not limited to, trypsin (e.g., of porcine or bovine origin), and the Fusarium protease described in WO89/06270. In some embodiments, commercially available protease enzymes include, but are not limited to, MAXATASE®, MAXACAL™, MAXAPEM™, OPTICLEAN®, OPTIMASE®, PROPERASE®, PURAFECT®, PURAFECT® OXP, PURAMAX™, EXCELLASE™, PREFERENZ™ proteases (e.g. P100, P110, P280), EFFECTENZ™ proteases (e.g. P1000, P1050, P2000), EXCELLENZ™ proteases (e.g. P1000), ULTIMASE®, and PURAFAST™ (Genencor); ALCALASE®, SAVINASE®, PRIMASE®, DURAZYM™, POLARZYME®, OVOZYME®, KANNASE®, LIQUANASE®, NEUTRASE®, RELASE® and ESPERASE® (Novozymes); BLAP™ and BLAP™ variants (Henkel Kommanditgesellschaft auf Aktien, Duesseldorf, Germany), and KAP (*B. alkalophilus* subtilisin; Kao Corp., Tokyo, Japan). Various proteases are described in WO95/23221, WO92/21760, WO09/149200, WO09/149144, WO09/149145, WO11/072099, WO10/056640, WO10/056653, WO11/140364, WO12/151534, U.S. Pat. Publ. No. 2008/0090747, and U.S. Pat. Nos. 5,801,039, 5,340,735, 5,500,364, 5,855,625, RE34606, 5,955,340, 5,700,676, 6,312,936, 6,482,628, 8,530,219, and various other patents. In some further embodiments, neutral metalloproteases find use in the present disclosure, including but not limited to, the neutral metalloproteases described in WO1999014341, WO1999033960, WO1999014342, WO1999034003, WO2007044993, WO2009058303 and WO2009058661, all of which are incorporated herein by reference. Exemplary metalloproteases include nprE, the recombinant form of neutral metalloprotease expressed in *Bacillus subtilis* (See e.g., WO07/044993), and PMN, the purified neutral metalloprotease from *Bacillus amyloliquefaciens*.

Suitable mannanases include, but are not limited to, those of bacterial or fungal origin. Chemically or genetically modified mutants are included in some embodiments. Various mannanases are known which find use in the present disclosure (See, e.g., U.S. Pat. Nos. 6,566,114, 6,602,842, and 6,440,991, all of which are incorporated herein by reference). Commercially available mannanases that find use in the present disclosure include, but are not limited to MANNASTAR®, PURABRITE™, and MANNAWAY®.

Suitable lipases include those of bacterial or fungal origin. Chemically modified, proteolytically modified, or protein engineered mutants are included. Examples of useful lipases include those from the genera *Humicola* (e.g., *H. lanuginosa*, EP258068 and EP305216; *H. insolens*, WO96/13580), *Pseudomonas* (e.g., *P. alcaligenes* or *P. pseudoalcaligenes*, EP218272; *P. cepacia*, EP331376; *P. stutzeri*, GB1372034; *P. fluorescens* and *Pseudomonas* sp. strain SD 705, WO95/06720 and WO96/27002; *P. wisconsinensis*, WO96/12012); and *Bacillus* (e.g., *B. subtilis*, Dartois et al., *Biochemica et Biophysica Acta* 1131:253-360; *B. stearothermophilus*, JP64/744992; *B. pumilus*, WO91/16422). Furthermore, a number of cloned lipases find use in some embodiments of the present disclosure, including but not limited to, *Penicillium camembertii* lipase (See, Yamaguchi et al., Gene 103: 61-67 [1991]), *Geotricum candidum* lipase (See, Schimada et al., J. Biochem., 106:383-388 [1989]), and various *Rhizopus* lipases such as *R. delemar* lipase (See, Hass et al., Gene 109:117-113 [1991]), a *R. niveus* lipase (Kugimiya et al., Biosci. Biotech. Biochem. 56:716-719 [1992]) and *R.*

*oryzae* lipase. Additional lipases useful herein include, for example, those disclosed in WO92/05249, WO94/01541, WO95/35381, WO96/00292, WO95/30744, WO94/25578, WO95/14783, WO95/22615, WO97/04079, WO97/07202, EP407225 and EP260105. Other types of lipase polypeptide enzymes such as cutinases also find use in some embodiments of the present disclosure, including but not limited to, cutinase derived from *Pseudomonas mendocina* (See, WO88/09367), and cutinase derived from *Fusarium solani pisi* (See, WO90/09446). Examples of certain commercially available lipase enzymes useful herein include M1 LIPASE™, LUMA FAST™, and LIPOMAX™ (Genencor); LIPEX®, LIPOLASE® and LIPOLASE® ULTRA (Novozymes); and LIPASE P™ "Amano" (Amano Pharmaceutical Co. Ltd., Japan).

Suitable polyesterases include, for example, those disclosed in WO01/34899, WO01/14629 and U.S. Pat. No. 6,933,140.

A detergent composition herein can also comprise 2,6-beta-D-fructan hydrolase, which is effective for removal/cleaning of certain biofilms present on household and/or industrial textiles/laundry.

Suitable amylases include, but are not limited to those of bacterial or fungal origin. Chemically or genetically modified mutants are included in some embodiments. Amylases that find use in the present disclosure, include, but are not limited to, alpha-amylases obtained from *B. licheniformis* (See e.g., GB1296839). Additional suitable amylases include those disclosed in WO9510603, WO9526397, WO9623874, WO9623873, WO9741213, WO9919467, WO0060060, WO0029560, WO9923211, WO9946399, WO0060058, WO0060059, WO9942567, WO0114532, WO02092797, WO0166712, WO0188107, WO0196537, WO0210355, WO9402597, WO0231124, WO9943793, WO9943794, WO2004113551, WO2005001064, WO2005003311, WO0164852, WO2006063594, WO2006066594, WO2006066596, WO2006012899, WO2008092919, WO2008000825, WO2005018336, WO2005066338, WO2009140504, WO2005019443, WO2010091221, WO2010088447, WO0134784, WO2006012902, WO2006031554, WO2006136161, WO2008101894, WO2010059413, WO2011098531, WO2011080352, WO2011080353, WO2011080354, WO2011082425, WO2011082429, WO2011076123, WO2011087836, WO2011076897, WO94183314, WO9535382, WO9909183, WO9826078, WO9902702, WO9743424, WO9929876, WO9100353, WO9605295, WO9630481, WO9710342, WO2008088493, WO2009149419, WO2009061381, WO2009100102, WO2010104675, WO2010117511, and WO2010115021, all of which are incorporated herein by reference.

Suitable amylases include, for example, commercially available amylases such as STAINZYME®, STAINZYME PLUS®, NATALASE®, DURAMYL®, TERMAMYL®, TERMAMYL ULTRA®, FUNGAMYL® and BAN™ (Novo Nordisk A/S and Novozymes A/S); RAPIDASE®, POWERASE®, PURASTAR® and PREFERENZ™ (DuPont Industrial Biosciences).

Suitable peroxidases/oxidases contemplated for use in the compositions include those of plant, bacterial or fungal origin. Chemically modified or protein engineered mutants are included. Examples of peroxidases useful herein include those from the genus *Coprinus* (e.g., *C. cinereus*, WO93/24618, WO95/10602, and WO98/15257), as well as those referenced in WO2005056782, WO2007106293, WO2008063400, WO2008106214, and WO2008106215.

Commercially available peroxidases useful herein include, for example, GUARDZYME™ (Novo Nordisk A/S and Novozymes A/S).

In some embodiments, peroxidases are used in combination with hydrogen peroxide or a source thereof (e.g., a percarbonate, perborate or persulfate) in the compositions of the present disclosure. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO94/12621 and WO95/01426). Suitable peroxidases/oxidases include, but are not limited to, those of plant, bacterial or fungal origin. Chemically or genetically modified mutants are included in some embodiments.

Enzymes that may be comprised in a detergent composition herein may be stabilized using conventional stabilizing agents, e.g., a polyol such as propylene glycol or glycerol; a sugar or sugar alcohol; lactic acid; boric acid or a boric acid derivative (e.g., an aromatic borate ester).

A detergent composition in certain embodiments may comprise one or more other types of polymers in addition to a dextran as disclosed herein. Examples of other types of polymers useful herein include carboxymethyl cellulose (CMC), poly(vinylpyrrolidone) (PVP), polyethylene glycol (PEG), poly(vinyl alcohol) (PVA), polycarboxylates such as polyacrylates, maleic/acrylic acid copolymers and lauryl methacrylate/acrylic acid copolymers.

A detergent composition herein may contain a bleaching system. For example, a bleaching system can comprise an $H_2O_2$ source such as perborate or percarbonate, which may be combined with a peracid-forming bleach activator such as tetraacetylethylenediamine (TAED) or nonanoyloxybenzenesulfonate (NOBS). Alternatively, a bleaching system may comprise peroxyacids (e.g., amide, imide, or sulfone type peroxyacids). Alternatively still, a bleaching system can be an enzymatic bleaching system comprising perhydrolase, for example, such as the system described in WO2005/056783.

A detergent composition herein may also contain conventional detergent ingredients such as fabric conditioners, clays, foam boosters, suds suppressors, anti-corrosion agents, soil-suspending agents, anti-soil redeposition agents, dyes, bactericides, tarnish inhibitors, optical brighteners, or perfumes. The pH of a detergent composition herein (measured in aqueous solution at use concentration) is usually neutral or alkaline (e.g., pH of about 7.0 to about 11.0).

It is believed that a dextran herein can be included as an anti-redeposition agent and/or clay soil removal agent in a detergent composition such as a fabric care composition, if desired (such agents can optionally be characterized as whiteness maintenance agents in certain aspects). Examples of other suitable anti-redeposition and/or clay soil removal agents herein include polyethoxy zwitterionic surfactants, water-soluble copolymers of acrylic or methacrylic acid with acrylic or methacrylic acid-ethylene oxide condensates (e.g., U.S. Pat. No. 3,719,647), cellulose derivatives such as carboxymethylcellulose and hydroxypropylcellulose (e.g., U.S. Pat. Nos. 3,597,416 and 3,523,088), and mixtures comprising nonionic alkyl polyethoxy surfactant, polyethoxy alkyl quaternary cationic surfactant and fatty amide surfactant (e.g., U.S. Pat. No. 4,228,044). Non-limiting examples of other suitable anti-redeposition and clay soil removal agents are disclosed in U.S. Pat. Nos. 4,597,898 and 4,891,160, and Int. Pat. Appl. Publ. No. WO95/32272, all of which are incorporated herein by reference.

Particular forms of detergent compositions that can be adapted for purposes disclosed herein are disclosed in, for example, US20090209445A1, US20100081598A1, U.S. Pat. No. 7,001,878B2, EP1504994B1, WO2001085888A2, WO2003089562A1, WO2009098659A1, WO2009098660A1, WO2009112992A1, WO2009124160A1, WO2009152031A1, WO2010059483A1, WO2010088112A1, WO2010090915A1, WO2010135238A1, WO2011094687A1, WO2011094690A1, WO2011127102A1, WO2011163428A1, WO2008000567A1, WO2006045391A1, WO2006007911A1, WO2012027404A1, EP1740690B1, WO2012059336A1, U.S. Pat. No. 6,730,646B1, WO2008087426A1, WO2010116139A1, and WO2012104613A1, all of which are incorporated herein by reference.

Laundry detergent compositions herein can optionally be heavy duty (all purpose) laundry detergent compositions. Exemplary heavy duty laundry detergent compositions comprise a detersive surfactant (10%-40% wt/wt), including an anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof), and optionally non-ionic surfactant (selected from a group of linear or branched or random chain, substituted or unsubstituted alkyl alkoxylated alcohol, e.g., C8-C18 alkyl ethoxylated alcohols and/or C6-C12 alkyl phenol alkoxylates), where the weight ratio of anionic detersive surfactant (with a hydrophilic index (Hlc) of from 6.0 to 9) to non-ionic detersive surfactant is greater than 1:1. Suitable detersive surfactants also include cationic detersive surfactants (selected from a group of alkyl pyridinium compounds, alkyl quaternary ammonium compounds, alkyl quaternary phosphonium compounds, alkyl ternary sulphonium compounds, and/or mixtures thereof); zwitterionic and/or amphoteric detersive surfactants (selected from a group of alkanolamine sulpho-betaines); ampholytic surfactants; semi-polar non-ionic surfactants and mixtures thereof.

A detergent herein such as a heavy duty laundry detergent composition may optionally include, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated C1-C6 carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: C4-C25 alkyl group, polypropylene, polybutylene, vinyl ester of a saturated C1-C6 mono-carboxylic acid, C1-C6 alkyl ester of acrylic or methacrylic acid, and mixtures thereof.

A detergent herein such as a heavy duty laundry detergent composition may optionally include additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and co-polymers thereof in random or block configuration, for example REPEL-O-TEX SF, SF-2 AND SRP6, TEX-CARE SRA100, SRA300, SRN100, SRN170, SRN240, SRN300 AND SRN325, MARLOQUEST SL), anti-redeposition agent(s) herein (0.1 wt % to 10 wt %), include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); and polymeric carboxylate (such as maleate/acrylate random copolymer or polyacrylate homopolymer).

A detergent herein such as a heavy duty laundry detergent composition may optionally further include saturated or unsaturated fatty acids, preferably saturated or unsaturated C12-C24 fatty acids (0 wt % to 10 wt %); deposition aids in addition to a dextran compound disclosed herein (examples for which include polysaccharides, cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic starch, cationic polyacylamides, and mixtures thereof.

A detergent herein such as a heavy duty laundry detergent composition may optionally further include dye transfer inhibiting agents, examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents, examples of which include ethylene-diamine-tetraacetic acid (EDTA), diethylene triamine penta methylene phosphonic acid (DTPMP), hydroxy-ethane diphosphonic acid (HEDP), ethylenediamine N,N'-disuccinic acid (EDDS), methyl glycine diacetic acid (MGDA), diethylene triamine penta acetic acid (DTPA), propylene diamine tetracetic acid (PDTA), 2-hydroxypyridine-N-oxide (HPNO), or methyl glycine diacetic acid (MGDA), glutamic acid N,N-diacetic acid (N,N-dicarboxymethyl glutamic acid tetrasodium salt (GLDA), nitrilotriacetic acid (NTA), 4,5-dihydroxy-m-benzenedisulfonic acid, citric acid and any salts thereof, N-hydroxyethylethylenediaminetriacetic acid (HEDTA), triethylenetetraaminehexaacetic acid (TTNA), N-hydroxyethyliminodiacetic acid (HEIDA), dihydroxyethylglycine (DHEG), ethylenediaminetetrapropionic acid (EDTP), and derivatives thereof.

A detergent herein such as a heavy duty laundry detergent composition may optionally include silicone or fatty-acid based suds suppressors; hueing dyes, calcium and magnesium cations, visual signaling ingredients, anti-foam (0.001 wt % to about 4.0 wt %), and/or a structurant/thickener (0.01 wt % to 5 wt %) selected from the group consisting of diglycerides and triglycerides, ethylene glycol distearate, microcrystalline cellulose, microfiber cellulose, biopolymers, xanthan gum, gellan gum, and mixtures thereof). Such structurant/thickener would be, in certain embodiments, in addition to the one or more dextran compounds comprised in the detergent. A structurant can also be referred to as a structural agent.

A detergent herein can be in the form of a heavy duty dry/solid laundry detergent composition, for example. Such a detergent may include: (i) a detersive surfactant, such as any anionic detersive surfactant disclosed herein, any non-ionic detersive surfactant disclosed herein, any cationic detersive surfactant disclosed herein, any zwitterionic and/or amphoteric detersive surfactant disclosed herein, any ampholytic surfactant, any semi-polar non-ionic surfactant, and mixtures thereof; (ii) a builder, such as any phosphate-free builder (e.g., zeolite builders in the range of 0 wt % to less than 10 wt %), any phosphate builder (e.g., sodium tri-polyphosphate in the range of 0 wt % to less than 10 wt %), citric acid, citrate salts and nitrilotriacetic acid, any silicate salt (e.g., sodium or potassium silicate or sodium meta-silicate in the range of 0 wt % to less than 10 wt %); any carbonate salt (e.g., sodium carbonate and/or sodium bicarbonate in the range of 0 wt % to less than 80 wt %), and mixtures thereof; (iii) a bleaching agent, such as any photobleach (e.g., sulfonated zinc phthalocyanines, sulfonated aluminum phthalocyanines, xanthenes dyes, and mixtures thereof), any hydrophobic or hydrophilic bleach activator (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, nonanoyloxybenzene sulfonate-NOBS, nitrile quats, and mixtures thereof), any source of hydrogen peroxide (e.g., inorganic perhydrate salts, examples of which include mono or tetra hydrate sodium salt of perborate, percarbonate, persulfate, perphosphate, or persilicate), any preformed hydrophilic and/or hydrophobic peracids (e.g., percarboxylic acids and salts, percarbonic acids and salts, perimidic acids and salts, peroxymonosulfuric acids and salts, and mixtures thereof); and/or (iv) any other components such as a bleach catalyst (e.g., imine bleach boosters examples of which include iminium cations and polyions, iminium zwitterions, modified amines, modified amine oxides, N-sulphonyl imines, N-phosphonyl imines, N-acyl imines, thiadiazole dioxides, perfluoroimines, cyclic sugar ketones, and mixtures thereof), and a metal-containing bleach catalyst (e.g., copper, iron, titanium, ruthenium, tungsten, molybdenum, or manganese cations along with an auxiliary metal cations such as zinc or aluminum and a sequestrate such as EDTA, ethylenediaminetetra (methylenephosphonic acid).

Compositions disclosed herein can be in the form of a dishwashing detergent composition, for example. Examples of dishwashing detergents include automatic dishwashing detergents (typically used in dishwasher machines) and hand-washing dish detergents. A dishwashing detergent composition can be in any dry or liquid/aqueous form as disclosed herein, for example. Components that may be included in certain embodiments of a dishwashing detergent composition include, for example, one or more of a phosphate; oxygen- or chlorine-based bleaching agent; non-ionic surfactant; alkaline salt (e.g., metasilicates, alkali metal hydroxides, sodium carbonate); any active enzyme disclosed herein; anti-corrosion agent (e.g., sodium silicate); anti-foaming agent; additives to slow down the removal of glaze and patterns from ceramics; perfume; anti-caking agent (in granular detergent); starch (in tablet-based detergents); gelling agent (in liquid/gel based detergents); and/or sand (powdered detergents).

Dishwashing detergents such as an automatic dishwasher detergent or liquid dishwashing detergent can comprise (i) a non-ionic surfactant, including any ethoxylated non-ionic surfactant, alcohol alkoxylated surfactant, epoxy-capped poly(oxyalkylated) alcohol, or amine oxide surfactant present in an amount from 0 to 10 wt %; (ii) a builder, in the range of about 5-60 wt %, including any phosphate builder (e.g., mono-phosphates, di-phosphates, tri-polyphosphates, other oligomeric-polyphosphates, sodium tripolyphosphate-STPP), any phosphate-free builder (e.g., amino acid-based compounds including methyl-glycine-diacetic acid [MGDA] and salts or derivatives thereof, glutamic-N,N-diacetic acid [GLDA] and salts or derivatives thereof, iminodisuccinic acid (IDS) and salts or derivatives thereof, carboxy methyl inulin and salts or derivatives thereof, nitrilotriacetic acid [NTA], diethylene triamine penta acetic acid [DTPA], B-alaninediacetic acid [B-ADA] and salts thereof), homopolymers and copolymers of poly-carboxylic acids and partially or completely neutralized salts thereof, monomeric polycarboxylic acids and hydroxycarboxylic acids and salts thereof in the range of 0.5 wt % to 50 wt %, or sulfonated/carboxylated polymers in the range of about 0.1 wt % to about 50 wt %; (iii) a drying aid in the range of about 0.1 wt % to about 10 wt % (e.g., polyesters, especially anionic polyesters, optionally together with further monomers with 3 to 6 functionalities—typically acid, alcohol or ester functionalities which are conducive to polycondensation, polycarbonate-, polyurethane- and/or polyurea-polyorganosiloxane compounds or precursor compounds thereof, particularly of the reactive cyclic carbonate and urea type); (iv) a silicate in the range from about 1 wt % to about 20 wt % (e.g., sodium or potassium silicates such as sodium disilicate, sodium meta-silicate and crystalline phyllosilicates); (v) an inorganic bleach (e.g., perhydrate salts such as perborate, percarbonate, perphosphate, persulfate and per-silicate salts) and/or an organic bleach (e.g., organic per-oxyacids such as diacyl- and tetraacylperoxides, especially diperoxydodecanedioic acid, diperoxytetradecanedioic acid, and diperoxyhexadecanedioic acid); (vi) a bleach activator (e.g., organic peracid precursors in the range from about 0.1 wt % to about 10 wt %) and/or bleach catalyst (e.g., manganese triazacyclononane and related complexes; Co, Cu, Mn, and Fe bispyridylamine and related complexes; and pentamine acetate cobalt (III) and related complexes); (vii) a metal care agent in the range from about 0.1 wt % to 5 wt % (e.g., benzatriazoles, metal salts and complexes, and/or silicates); and/or (viii) any active enzyme disclosed herein in the range from about 0.01 to 5.0 mg of active enzyme per gram of automatic dishwashing detergent composition, and an enzyme stabilizer component (e.g., oligosaccharides, polysaccharides, and inorganic divalent metal salts).

Various examples of detergent formulations comprising at least one dextran herein are disclosed below (1-19):

1) A detergent composition formulated as a granulate having a bulk density of at least 600 g/L comprising: linear alkylbenzenesulfonate (calculated as acid) at about 7-12 wt %; alcohol ethoxysulfate (e.g., C12-18 alcohol, 1-2 ethylene oxide [EO]) or alkyl sulfate (e.g., C16-18) at about 1-4 wt %; alcohol ethoxylate (e.g., C14-15 alcohol) at about 5-9 wt %; sodium carbonate at about 14-20 wt %; soluble silicate (e.g., $Na_2O$ $2SiO_2$) at about 2-6 wt %; zeolite (e.g., $NaAlSiO_4$) at about 15-22 wt %; sodium sulfate at about 0-6 wt %; sodium citrate/citric acid at about 0-15 wt %; sodium perborate at about 11-18 wt %; TAED at about 2-6 wt %; dextran herein up to about 2 wt %; other polymers (e.g., maleic/acrylic acid copolymer, PVP, PEG) at about 0-3 wt %; optionally an enzyme(s) (calculated as pure enzyme protein) at about 0.0001-0.1 wt %; and minor ingredients (e.g., suds suppressors, perfumes, optical brightener, photobleach) at about 0-5 wt %.

2) A detergent composition formulated as a granulate having a bulk density of at least 600 g/L comprising: linear alkylbenzenesulfonate (calculated as acid) at about 6-11 wt %; alcohol ethoxysulfate (e.g., C12-18 alcohol, 1-2 EO) or alkyl sulfate (e.g., C16-18) at about 1-3 wt %; alcohol ethoxylate (e.g., C14-15 alcohol) at about 5-9 wt %; sodium carbonate at about 15-21 wt %; soluble silicate (e.g., $Na_2O$ $2SiO_2$) at about 1-4 wt %; zeolite (e.g., $NaAlSiO_4$) at about 24-34 wt %; sodium sulfate at about 4-10 wt %; sodium citrate/citric acid at about 0-15 wt %; sodium perborate at about 11-18 wt %; TAED at about 2-6 wt %; dextran herein up to about 2 wt %; other polymers (e.g., maleic/acrylic acid copolymer, PVP, PEG) at about 1-6 wt %; optionally an enzyme(s) (calculated as pure enzyme protein) at about 0.0001-0.1 wt %; and minor ingredients (e.g., suds suppressors, perfumes, optical brightener, photobleach) at about 0-5 wt %.

3) A detergent composition formulated as a granulate having a bulk density of at least 600 g/L comprising: linear alkylbenzenesulfonate (calculated as acid) at about 5-9 wt %; alcohol ethoxysulfate (e.g., C12-18 alcohol, 7 EO) at about 7-14 wt %; soap as fatty acid (e.g., C16-22 fatty acid) at about 1-3 wt %; sodium carbonate at about 10-17 wt %; soluble silicate (e.g., $Na_2O\ 2SiO_2$) at about 3-9 wt %; zeolite (e.g., $NaAlSiO_4$) at about 23-33 wt %; sodium sulfate at about 0-4 wt %; sodium perborate at about 8-16 wt %; TAED at about 2-8 wt %; phosphonate (e.g., EDTMPA) at about 0-1 wt %; dextran herein up to about 2 wt %; other polymers (e.g., maleic/acrylic acid copolymer, PVP, PEG) at about 0-3 wt %; optionally an enzyme(s) (calculated as pure enzyme protein) at about 0.0001-0.1 wt %; and minor ingredients (e.g., suds suppressors, perfumes, optical brightener) at about 0-5 wt %.

4) A detergent composition formulated as a granulate having a bulk density of at least 600 g/L comprising: linear alkylbenzenesulfonate (calculated as acid) at about 8-12 wt %; alcohol ethoxylate (e.g., C12-18 alcohol, 7 EO) at about 10-25 wt %; sodium carbonate at about 14-22 wt %; soluble silicate (e.g., $Na_2O\ 2SiO_2$) at about 1-5 wt %; zeolite (e.g., $NaAlSiO_4$) at about 25-35 wt %; sodium sulfate at about 0-10 wt %; sodium perborate at about 8-16 wt %; TAED at about 2-8 wt %; phosphonate (e.g., EDTMPA) at about 0-1 wt %; dextran herein up to about 2 wt %; other polymers (e.g., maleic/acrylic acid copolymer, PVP, PEG) at about 1-3 wt %; optionally an enzyme(s) (calculated as pure enzyme protein) at about 0.0001-0.1 wt %; and minor ingredients (e.g., suds suppressors, perfumes) at about 0-5 wt %.

5) An aqueous liquid detergent composition comprising: linear alkylbenzenesulfonate (calculated as acid) at about 15-21 wt %; alcohol ethoxylate (e.g., C12-18 alcohol, 7 EO; or C12-15 alcohol, 5 EO) at about 12-18 wt %; soap as fatty acid (e.g., oleic acid) at about 3-13 wt %; alkenylsuccinic acid (C12-14) at about 0-13 wt %; aminoethanol at about 8-18 wt %; citric acid at about 2-8 wt %; phosphonate at about 0-3 wt %; dextran herein up to about 2 wt %; other polymers (e.g., PVP, PEG) at about 0-3 wt %; borate at about 0-2 wt %; ethanol at about 0-3 wt %; propylene glycol at about 8-14 wt %; optionally an enzyme(s) (calculated as pure enzyme protein) at about 0.0001-0.1 wt %; and minor ingredients (e.g., dispersants, suds suppressors, perfume, optical brightener) at about 0-5 wt %.

6) An aqueous structured liquid detergent composition comprising: linear alkylbenzenesulfonate (calculated as acid) at about 15-21 wt %; alcohol ethoxylate (e.g., C12-18 alcohol, 7 EO; or C12-15 alcohol, 5 EO) at about 3-9 wt %; soap as fatty acid (e.g., oleic acid) at about 3-10 wt %; zeolite (e.g., $NaAlSiO_4$) at about 14-22 wt %; potassium citrate about 9-18 wt %; borate at about 0-2 wt %; dextran herein up to about 2 wt %; other polymers (e.g., PVP, PEG) at about 0-3 wt %; ethanol at about 0-3 wt %; anchoring polymers (e.g., lauryl methacrylate/acrylic acid copolymer, molar ratio 25:1, MW 3800) at about 0-3 wt %; glycerol at about 0-5 wt %; optionally an enzyme(s) (calculated as pure enzyme protein) at about 0.0001-0.1 wt %; and minor ingredients (e.g., dispersants, suds suppressors, perfume, optical brightener) at about 0-5 wt %.

7) A detergent composition formulated as a granulate having a bulk density of at least 600 g/L comprising: fatty alcohol sulfate at about 5-10 wt %, ethoxylated fatty acid monoethanolamide at about 3-9 wt %; soap as fatty acid at about 0-3 wt %; sodium carbonate at about 5-10 wt %; soluble silicate (e.g., $Na_2O\ 2SiO_2$) at about 1-4 wt %; zeolite (e.g., $NaAlSiO_4$) at about 20-40 wt %; sodium sulfate at about 2-8 wt %; sodium perborate at about 12-18 wt %; TAED at about 2-7 wt %; dextran herein up to about 2 wt %; other polymers (e.g., maleic/acrylic acid copolymer, PEG) at about 1-5 wt %; optionally an enzyme(s) (calculated as pure enzyme protein) at about 0.0001-0.1 wt %; and minor ingredients (e.g., optical brightener, suds suppressors, perfumes) at about 0-5 wt %.

8) A detergent composition formulated as a granulate comprising: linear alkylbenzenesulfonate (calculated as acid) at about 8-14 wt %; ethoxylated fatty acid monoethanolamide at about 5-11 wt %; soap as fatty acid at about 0-3 wt %; sodium carbonate at about 4-10 wt %; soluble silicate (e.g., $Na_2O\ 2SiO_2$) at about 1-4 wt %; zeolite (e.g., $NaAlSiO_4$) at about 30-50 wt %; sodium sulfate at about 3-11 wt %; sodium citrate at about 5-12 wt %; dextran herein up to about 2 wt %; other polymers (e.g., PVP, maleic/acrylic acid copolymer, PEG) at about 1-5 wt %; optionally an enzyme(s) (calculated as pure enzyme protein) at about 0.0001-0.1 wt %; and minor ingredients (e.g., suds suppressors, perfumes) at about 0-5 wt %.

9) A detergent composition formulated as a granulate comprising: linear alkylbenzenesulfonate (calculated as acid) at about 6-12 wt %; nonionic surfactant at about 1-4 wt %; soap as fatty acid at about 2-6 wt %; sodium carbonate at about 14-22 wt %; zeolite (e.g., $NaAlSiO_4$) at about 18-32 wt %; sodium sulfate at about 5-20 wt %; sodium citrate at about 3-8 wt %; sodium perborate at about 4-9 wt %; bleach activator (e.g., NOBS or TAED) at about 1-5 wt %; dextran herein up to about 2 wt %; other polymers (e.g., polycarboxylate or PEG) at about 1-5 wt %; optionally an enzyme(s) (calculated as pure enzyme protein) at about 0.0001-0.1 wt %; and minor ingredients (e.g., optical brightener, perfume) at about 0-5 wt %.

10) An aqueous liquid detergent composition comprising: linear alkylbenzenesulfonate (calculated as acid) at about 15-23 wt %; alcohol ethoxysulfate (e.g., C12-15 alcohol, 2-3 EO) at about 8-15 wt %; alcohol ethoxylate (e.g., C12-15 alcohol, 7 EO; or C12-15 alcohol, 5 EO) at about 3-9 wt %; soap as fatty acid (e.g., lauric acid) at about 0-3 wt %; aminoethanol at about 1-5 wt %; sodium citrate at about 5-10 wt %; hydrotrope (e.g., sodium toluenesulfonate) at about 2-6 wt %; borate at about 0-2 wt %; dextran herein up to about 1 wt %; ethanol at about 1-3 wt %; propylene glycol at about 2-5 wt %; optionally an enzyme(s) (calculated as pure enzyme protein) at about 0.0001-0.1 wt %; and minor ingredients (e.g., dispersants, perfume, optical brighteners) at about 0-5 wt %.

11) An aqueous liquid detergent composition comprising: linear alkylbenzenesulfonate (calculated as acid) at about 20-32 wt %; alcohol ethoxylate (e.g., C12-15 alcohol, 7 EO; or C12-15 alcohol, 5 EO) at about 6-12 wt %; aminoethanol at about 2-6 wt %; citric acid at about 8-14 wt %; borate at about 1-3 wt %; dextran herein up to about 2 wt %; ethanol at about 1-3 wt %; propylene glycol at about 2-5 wt %; other polymers (e.g., maleic/acrylic acid copolymer, anchoring polymer such as lauryl methacrylate/acrylic acid copolymer) at about 0-3 wt %; glycerol at about 3-8 wt %; optionally an enzyme(s) (calculated as pure enzyme protein) at about 0.0001-0.1 wt %; and minor ingredients (e.g., hydrotropes, dispersants, perfume, optical brighteners) at about 0-5 wt %.

12) A detergent composition formulated as a granulate having a bulk density of at least 600 g/L comprising: anionic surfactant (e.g., linear alkylbenzenesulfonate, alkyl sulfate, alpha-olefinsulfonate, alpha-sulfo fatty acid methyl esters, alkanesulfonates, soap) at about 25-40 wt %; nonionic surfactant (e.g., alcohol ethoxylate) at about 1-10 wt %; sodium carbonate at about 8-25 wt %; soluble silicate (e.g., $Na_2O$ $2SiO_2$) at about 5-15 wt %; sodium sulfate at about 0-5 wt %; zeolite ($NaAlSiO_4$) at about 15-28 wt %; sodium perborate at about 0-20 wt %; bleach activator (e.g., TAED or NOBS) at about 0-5 wt %; dextran herein up to about 2 wt %; optionally an enzyme(s) (calculated as pure enzyme protein) at about 0.0001-0.1 wt %; and minor ingredients (e.g., perfume, optical brighteners) at about 0-3 wt %.

13) Detergent compositions as described in (1)-(12) above, but in which all or part of the linear alkylbenzenesulfonate is replaced by C12-C18 alkyl sulfate.

14) A detergent composition formulated as a granulate having a bulk density of at least 600 g/L comprising: C12-C18 alkyl sulfate at about 9-15 wt %; alcohol ethoxylate at about 3-6 wt %; polyhydroxy alkyl fatty acid amide at about 1-5 wt %; zeolite (e.g., $NaAlSiO_4$) at about 10-20 wt %; layered disilicate (e.g., SK56 from Hoechst) at about 10-20 wt %; sodium carbonate at about 3-12 wt %; soluble silicate (e.g., $Na_2O$ $2SiO_2$) at 0-6 wt %; sodium citrate at about 4-8 wt %; sodium percarbonate at about 13-22 wt %; TAED at about 3-8 wt %; dextran herein up to about 2 wt %; other polymers (e.g., polycarboxylates and PVP) at about 0-5 wt %; optionally an enzyme(s) (calculated as pure enzyme protein) at about 0.0001-0.1 wt %; and minor ingredients (e.g., optical brightener, photobleach, perfume, suds suppressors) at about 0-5 wt %.

15) A detergent composition formulated as a granulate having a bulk density of at least 600 g/L comprising: C12-C18 alkyl sulfate at about 4-8 wt %; alcohol ethoxylate at about 11-15 wt %; soap at about 1-4 wt %; zeolite MAP or zeolite A at about 35-45 wt %; sodium carbonate at about 2-8 wt %; soluble silicate (e.g., $Na_2O$ $2SiO_2$) at 0-4 wt %; sodium percarbonate at about 13-22 wt %; TAED at about 1-8 wt %; dextran herein up to about 3 wt %; other polymers (e.g., polycarboxylates and PVP) at about 0-3 wt %; optionally an enzyme(s) (calculated as pure enzyme protein) at about 0.0001-0.1 wt %; and minor ingredients (e.g., optical brightener, phosphonate, perfume) at about 0-3 wt %.

16) Detergent formulations as described in (1)-(15) above, but that contain a stabilized or encapsulated peracid, either as an additional component or as a substitute for an already specified bleach system(s).

17) Detergent compositions as described in (1), (3), (7), (9) and (12) above, but in which perborate is replaced by percarbonate.

18) Detergent compositions as described in (1), (3), (7), (9), (12), (14) and (15) above, but that additionally contain a manganese catalyst. A manganese catalyst, for example, is one of the compounds described by Hage et al. (1994, *Nature* 369:637-639), which is incorporated herein by reference.

19) Detergent compositions formulated as a non-aqueous detergent liquid comprising a liquid non-ionic surfactant (e.g., a linear alkoxylated primary alcohol), a builder system (e.g., phosphate), dextran herein, optionally an enzyme(s), and alkali. The detergent may also comprise an anionic surfactant and/or bleach system.

It is believed that numerous commercially available detergent formulations can be adapted to include a dextran compound disclosed herein. Examples include PUREX® ULTRAPACKS (Henkel), FINISH® QUANTUM (Reckitt Benckiser), CLOROX™ 2 PACKS (Clorox), OXICLEAN MAX FORCE POWER PAKS (Church & Dwight), TIDE® STAIN RELEASE, CASCADE® ACTIONPACS, and TIDE® PODS™ (Procter & Gamble).

Compositions disclosed herein can be in the form of an oral care composition, for example. Examples of oral care compositions include dentifrices, toothpaste, mouth wash, mouth rinse, chewing gum, and edible strips that provide some form of oral care (e.g., treatment or prevention of cavities [dental caries], gingivitis, plaque, tartar, and/or periodontal disease). An oral care composition can also be for treating an "oral surface", which encompasses any soft or hard surface within the oral cavity including surfaces of the tongue, hard and soft palate, buccal mucosa, gums and dental surfaces. A "dental surface" herein is a surface of a natural tooth or a hard surface of artificial dentition including a crown, cap, filling, bridge, denture, or dental implant, for example.

An oral care composition herein can comprise about 0.01-15.0 wt % (e.g., ~0.1-10 wt % or ~0.1-5.0 wt %, ~0.1-2.0 wt %) of one or more dextran ether compounds as disclosed herein, for example. One or more dextran ether compounds comprised in an oral care composition can sometimes be provided therein as a thickening agent and/or dispersion agent, which may be useful to impart a desired consistency and/or mouth feel to the composition. One or more other thickening or dispersion agents can also be provided in an oral care composition herein, such as a carboxyvinyl polymer, carrageenan (e.g., L-carrageenan), natural gum (e.g., karaya, xanthan, gum arabic, tragacanth), colloidal magnesium aluminum silicate, or colloidal silica, for example.

An oral care composition herein may be a toothpaste or other dentifrice, for example. Such compositions, as well as any other oral care composition herein, can additionally comprise, without limitation, one or more of an anticaries agent, antimicrobial or antibacterial agent, anticalculus or tartar control agent, surfactant, abrasive, pH-modifying agent, foam modulator, humectant, flavorant, sweetener, pigment/colorant, whitening agent, and/or other suitable components. Examples of oral care compositions to which one or more dextran compounds can be added are disclosed in U.S. Patent Appl. Publ. Nos. 2006/0134025, 2002/0022006 and 2008/0057007, which are incorporated herein by reference.

An anticaries agent herein can be an orally acceptable source of fluoride ions. Suitable sources of fluoride ions include fluoride, monofluorophosphate and fluorosilicate salts as well as amine fluorides, including olaflur (N'-octadecyltrimethylendiamine-N,N,N'-tris(2-ethanol)-dihydrofluoride), for example. An anticaries agent can be present in an amount providing a total of about 100-20000 ppm, about 200-5000 ppm, or about 500-2500 ppm, fluoride ions to the composition, for example. In oral care compositions in which sodium fluoride is the sole source of fluoride ions, an amount of about 0.01-5.0 wt %, about 0.05-1.0 wt %, or about 0.1-0.5 wt %, sodium fluoride can be present in the composition, for example.

An antimicrobial or antibacterial agent suitable for use in an oral care composition herein includes, for example, phenolic compounds (e.g., 4-allylcatechol; p-hydroxybenzoic acid esters such as benzylparaben, butylparaben, ethylparaben, methylparaben and propylparaben; 2-benzylphenol; butylated hydroxyanisole; butylated hydroxytoluene; capsaicin; carvacrol; creosol; eugenol; guaiacol; halogenated bisphenolics such as hexachlorophene and bromochlorophene; 4-hexylresorcinol; 8-hydroxyquinoline and salts thereof; salicylic acid esters such as menthyl salicylate, methyl salicylate and phenyl salicylate; phenol; pyrocatechol; salicylanilide; thymol; halogenated diphenylether compounds such as triclosan and triclosan monophosphate), copper (II) compounds (e.g., copper (II) chloride, fluoride, sulfate and hydroxide), zinc ion sources (e.g., zinc acetate, citrate, gluconate, glycinate, oxide, and sulfate), phthalic acid and salts thereof (e.g., magnesium monopotassium phthalate), hexetidine, octenidine, sanguinarine, benzalkonium chloride, domiphen bromide, alkylpyridinium chlorides (e.g. cetylpyridinium chloride, tetradecylpyridinium chloride, N-tetradecyl-4-ethylpyridinium chloride), iodine, sulfonamides, bisbiguanides (e.g., alexidine, chlorhexidine, chlorhexidine digluconate), piperidino derivatives (e.g., delmopinol, octapinol), magnolia extract, grapeseed extract, rosemary extract, menthol, geraniol, citral, eucalyptol, antibiotics (e.g., augmentin, amoxicillin, tetracycline, doxycycline, minocycline, metronidazole, neomycin, kanamycin, clindamycin), and/or any antibacterial agents disclosed in U.S. Pat. No. 5,776,435, which is incorporated herein by reference. One or more antimicrobial agents can optionally be present at about 0.01-10 wt % (e.g., 0.1-3 wt %), for example, in the disclosed oral care composition.

An anticalculus or tartar control agent suitable for use in an oral care composition herein includes, for example, phosphates and polyphosphates (e.g., pyrophosphates), polyaminopropanesulfonic acid (AMPS), zinc citrate trihydrate, polypeptides (e.g., polyaspartic and polyglutamic acids), polyolefin sulfonates, polyolefin phosphates, diphosphonates (e.g., azacycloalkane-2,2-diphosphonates such as azacycloheptane-2,2-diphosphonic acid), N-methyl azacyclopentane-2,3-diphosphonic acid, ethane-1-hydroxy-1,1-diphosphonic acid (EHDP), ethane-1-amino-1,1-diphosphonate, and/or phosphonoalkane carboxylic acids and salts thereof (e.g., their alkali metal and ammonium salts). Useful inorganic phosphate and polyphosphate salts include, for example, monobasic, dibasic and tribasic sodium phosphates, sodium tripolyphosphate, tetrapolyphosphate, mono-, di-, tri- and tetra-sodium pyrophosphates, disodium dihydrogen pyrophosphate, sodium trimetaphosphate, sodium hexametaphosphate, or any of these in which sodium is replaced by potassium or ammonium. Other useful anticalculus agents in certain embodiments include anionic polycarboxylate polymers (e.g., polymers or copolymers of acrylic acid, methacrylic, and maleic anhydride such as polyvinyl methyl ether/maleic anhydride copolymers). Still other useful anticalculus agents include sequestering agents such as hydroxycarboxylic acids (e.g., citric, fumaric, malic, glutaric and oxalic acids and salts thereof) and aminopolycarboxylic acids (e.g., EDTA). One or more anticalculus or tartar control agents can optionally be present at about 0.01-50 wt % (e.g., about 0.05-25 wt % or about 0.1-15 wt %), for example, in the disclosed oral care composition.

A surfactant suitable for use in an oral care composition herein may be anionic, non-ionic, or amphoteric, for example. Suitable anionic surfactants include, without limitation, water-soluble salts of $C_{8-20}$ alkyl sulfates, sulfonated monoglycerides of $C_{8-20}$ fatty acids, sarcosinates, and taurates. Examples of anionic surfactants include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable non-ionic surfactants include, without limitation, poloxamers, polyoxyethylene sorbitan esters, fatty alcohol ethoxylates, alkylphenol ethoxylates, tertiary amine oxides, tertiary phosphine oxides, and dialkyl sulfoxides. Suitable amphoteric surfactants include, without limitation, derivatives of $C_{8-20}$ aliphatic secondary and tertiary amines having an anionic group such as a carboxylate, sulfate, sulfonate, phosphate or phosphonate. An example of a suitable amphoteric surfactant is cocoamidopropyl betaine. One or more surfactants are optionally present in a total amount of about 0.01-10 wt % (e.g., about 0.05-5.0 wt % or about 0.1-2.0 wt %), for example, in the disclosed oral care composition.

An abrasive suitable for use in an oral care composition herein may include, for example, silica (e.g., silica gel, hydrated silica, precipitated silica), alumina, insoluble phosphates, calcium carbonate, and resinous abrasives (e.g., a urea-formaldehyde condensation product). Examples of insoluble phosphates useful as abrasives herein are orthophosphates, polymetaphosphates and pyrophosphates, and include dicalcium orthophosphate dihydrate, calcium pyrophosphate, beta-calcium pyrophosphate, tricalcium phosphate, calcium polymetaphosphate and insoluble sodium polymetaphosphate. One or more abrasives are optionally present in a total amount of about 5-70 wt % (e.g., about 10-56 wt % or about 15-30 wt %), for example, in the disclosed oral care composition. The average particle size of an abrasive in certain embodiments is about 0.1-30 microns (e.g., about 1-20 microns or about 5-15 microns).

An oral care composition in certain embodiments may comprise at least one pH-modifying agent. Such agents may be selected to acidify, make more basic, or buffer the pH of a composition to a pH range of about 2-10 (e.g., pH ranging from about 2-8, 3-9, 4-8, 5-7, 6-10, or 7-9). Examples of pH-modifying agents useful herein include, without limitation, carboxylic, phosphoric and sulfonic acids; acid salts (e.g., monosodium citrate, disodium citrate, monosodium malate); alkali metal hydroxides (e.g. sodium hydroxide, carbonates such as sodium carbonate, bicarbonates, sesquicarbonates); borates; silicates; phosphates (e.g., monosodium phosphate, trisodium phosphate, pyrophosphate salts); and imidazole.

A foam modulator suitable for use in an oral care composition herein may be a polyethylene glycol (PEG), for example. High molecular weight PEGs are suitable, including those having an average molecular weight of about 200000-7000000 (e.g., about 500000-5000000 or about 1000000-2500000), for example. One or more PEGs are optionally present in a total amount of about 0.1-10 wt % (e.g. about 0.2-5.0 wt % or about 0.25-2.0 wt %), for example, in the disclosed oral care composition.

An oral care composition in certain embodiments may comprise at least one humectant. A humectant in certain embodiments may be a polyhydric alcohol such as glycerin, sorbitol, xylitol, or a low molecular weight PEG. Most suitable humectants also may function as a sweetener herein. One or more humectants are optionally present in a total amount of about 1.0-70 wt % (e.g., about 1.0-50 wt %, about 2-25 wt %, or about 5-15 wt %), for example, in the disclosed oral care composition.

A natural or artificial sweetener may optionally be comprised in an oral care composition herein. Examples of suitable sweeteners include dextrose, sucrose, maltose, dextrin, invert sugar, mannose, xylose, ribose, fructose, levulose, galactose, corn syrup (e.g., high fructose corn syrup or corn syrup solids), partially hydrolyzed starch, hydrogenated starch hydrolysate, sorbitol, mannitol, xylitol, maltitol, isomalt, aspartame, neotame, saccharin and salts thereof, dipeptide-based intense sweeteners, and cyclamates. One or more sweeteners are optionally present in a total amount of about 0.005-5.0 wt %, for example, in the disclosed oral care composition.

A natural or artificial flavorant may optionally be comprised in an oral care composition herein. Examples of suitable flavorants include vanillin; sage; marjoram; parsley oil; spearmint oil; cinnamon oil; oil of wintergreen (methylsalicylate); peppermint oil; clove oil; bay oil; anise oil; eucalyptus oil; citrus oils; fruit oils; essences such as those derived from lemon, orange, lime, grapefruit, apricot, banana, grape, apple, strawberry, cherry, or pineapple; bean- and nut-derived flavors such as coffee, cocoa, cola, peanut, or almond; and adsorbed and encapsulated flavorants. Also encompassed within flavorants herein are ingredients that provide fragrance and/or other sensory effect in the mouth, including cooling or warming effects. Such ingredients include, without limitation, menthol, menthyl acetate, menthyl lactate, camphor, eucalyptus oil, eucalyptol, anethole, eugenol, cassia, oxanone, Irisone®, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), and menthone glycerol acetal (MGA). One or more flavorants are optionally present in a total amount of about 0.01-5.0 wt % (e.g., about 0.1-2.5 wt %), for example, in the disclosed oral care composition.

An oral care composition in certain embodiments may comprise at least one bicarbonate salt. Any orally acceptable bicarbonate can be used, including alkali metal bicarbonates such as sodium or potassium bicarbonate, and ammonium bicarbonate, for example. One or more bicarbonate salts are optionally present in a total amount of about 0.1-50 wt % (e.g., about 1-20 wt %), for example, in the disclosed oral care composition.

An oral care composition in certain embodiments may comprise at least one whitening agent and/or colorant. A suitable whitening agent is a peroxide compound such as any of those disclosed in U.S. Pat. No. 8,540,971, which is incorporated herein by reference. Suitable colorants herein include pigments, dyes, lakes and agents imparting a particular luster or reflectivity such as pearling agents, for example. Specific examples of colorants useful herein include talc; mica; magnesium carbonate; calcium carbonate; magnesium silicate; magnesium aluminum silicate; silica; titanium dioxide; zinc oxide; red, yellow, brown and black iron oxides; ferric ammonium ferrocyanide; manganese violet; ultramarine; titaniated mica; and bismuth oxychloride. One or more colorants are optionally present in a total amount of about 0.001-20 wt % (e.g., about 0.01-10 wt % or about 0.1-5.0 wt %), for example, in the disclosed oral care composition.

Additional components that can optionally be included in an oral composition herein include one or more enzymes (above), vitamins, and anti-adhesion agents, for example. Examples of vitamins useful herein include vitamin C, vitamin E, vitamin B5, and folic acid. Examples of suitable anti-adhesion agents include solbrol, ficin, and quorum-sensing inhibitors.

The present disclosure also concerns a method for increasing the viscosity of an aqueous composition. This method comprises contacting at least one dextran compound as presently disclosed with the aqueous composition. The contacting step in this method results in increasing the viscosity of the aqueous composition, in comparison to the viscosity of the aqueous composition before the contacting step.

An aqueous composition herein can be water (e.g., deionized water), an aqueous solution, or a hydrocolloid, for example. The viscosity of an aqueous composition before the contacting step, measured at about 20-25° C., can be about 0-10000 cPs (or any integer between 0-10000 cPs), for example. Since the aqueous composition can be a hydrocolloid or the like in certain embodiments, it should be apparent that the method can be used to increase the viscosity of aqueous compositions that are already viscous.

Contacting dextran herein with an aqueous composition increases the viscosity of the aqueous composition in certain embodiments. This increase in viscosity can be an increase of at least about 1%, 10%, 100%, 1000%, 100000%, or 1000000% (or any integer between 1% and 1000000%), for example, compared to the viscosity of the aqueous composition before the contacting step. It should be apparent that very large percent increases in viscosity can be obtained with the disclosed method when the aqueous composition has little to no viscosity before the contacting step. An increase in viscosity can be determined, for example, by comparing the viscosity of the aqueous composition obtained by the method (i.e., after the contacting step) with the viscosity of the aqueous composition as it had existed before the method (i.e., before the contacting step).

Contacting dextran herein with an aqueous composition increases the shear thinning behavior or shear thickening behavior of the aqueous composition in certain embodiments. Thus, dextran rheologically modifies the aqueous composition in these embodiments. The increase in shear thinning behavior or shear thickening behavior can be an increase of at least about 1%, 10%, 100%, 1000%, 100000%, or 1000000% (or any integer between 1% and 1000000%), for example, compared to the shear thinning behavior or shear thickening behavior of the aqueous composition before the contacting step. It should be apparent that very large percent increases in rheologic modification can be obtained with the disclosed method when the aqueous composition has little to no rheologic behavior before the contacting step.

The contacting step in a method for increasing the viscosity of an aqueous composition can be performed by mixing or dissolving any dextran as presently disclosed in the aqueous composition by any means known in the art. For example, mixing or dissolving can be performed manually or with a machine (e.g., industrial mixer or blender, orbital shaker, stir plate, homogenizer, sonicator, bead mill). Mixing or dissolving can comprise a homogenization step in certain embodiments. Homogenization (as well as any other type of mixing) can be performed for about 5 to 60, 5 to 30, 10 to 60, 10 to 30, 5 to 15, or 10 to 15 seconds (or any integer between 5 and 60 seconds), or longer periods of time as necessary to mix dextran with the aqueous composition. A homogenizer can be used at about 5000 to 30000 rpm, 10000 to 30000 rpm, 15000 to 30000 rpm, 15000 to 25000 rpm, or 20000 rpm (or any integer between 5000 and 30000 rpm), for example.

After a dextran herein is mixed with or dissolved into an aqueous composition, the resulting aqueous composition may be filtered, or may not be filtered. For example, an aqueous composition prepared with a homogenization step may or may not be filtered.

Certain embodiments of the above method can be used to prepare an aqueous composition disclosed herein, such as a food product (e.g., a confectionery such as a candy filling), pharmaceutical product (e.g., excipient), household product (e.g., laundry detergent, fabric softener, dishwasher detergent), personal care product (e.g., a water-containing dentifrice such as toothpaste), or industrial product.

The present disclosure also concerns a method of treating a material. This method comprises contacting a material with an aqueous composition comprising at least one dextran compound as disclosed herein.

A material contacted with an aqueous composition in a contacting method herein can comprise a fabric in certain embodiments. A fabric herein can comprise natural fibers, synthetic fibers, semi-synthetic fibers, or any combination thereof. A semi-synthetic fiber herein is produced using naturally occurring material that has been chemically derivatized, an example of which is rayon. Non-limiting examples of fabric types herein include fabrics made of (i) cellulosic fibers such as cotton (e.g., broadcloth, canvas, chambray, chenille, chintz, corduroy, cretonne, damask, denim, flannel, gingham, jacquard, knit, matelassé, oxford, percale, poplin, plissé, sateen, seersucker, sheers, terry cloth, twill, velvet), rayon (e.g., viscose, modal, lyocell), linen, and Tencel®; (ii) proteinaceous fibers such as silk, wool and related mammalian fibers; (iii) synthetic fibers such as polyester, acrylic, nylon, and the like; (iv) long vegetable fibers from jute, flax, ramie, coir, kapok, sisal, henequen, abaca, hemp and sunn; and (v) any combination of a fabric of (i)-(iv). Fabric comprising a combination of fiber types (e.g., natural and synthetic) include those with both a cotton fiber and polyester, for example. Materials/articles containing one or more fabrics herein include, for example, clothing, curtains, drapes, upholstery, carpeting, bed linens, bath linens, tablecloths, sleeping bags, tents, car interiors, etc. Other materials comprising natural and/or synthetic fibers include, for example, non-woven fabrics, paddings, paper, and foams.

An aqueous composition that is contacted with a fabric can be, for example, a fabric care composition (e.g., laundry detergent, fabric softener). Thus, a treatment method in certain embodiments can be considered a fabric care method or laundry method if employing a fabric care composition therein. A fabric care composition herein is contemplated to effect one or more of the following fabric care benefits (i.e., surface substantive effects): wrinkle removal, wrinkle reduction, wrinkle resistance, fabric wear reduction, fabric wear resistance, fabric pilling reduction, extended fabric life, fabric color maintenance, fabric color fading reduction, reduced dye transfer, fabric color restoration, fabric soiling reduction, fabric soil release, fabric shape retention, fabric smoothness enhancement, anti-redeposition of soil on fabric, anti-greying of laundry, improved fabric hand/handle, and/or fabric shrinkage reduction.

Examples of conditions (e.g., time, temperature, wash/rinse volumes) for conducting a fabric care method or laundry method herein are disclosed in WO1997/003161 and U.S. Pat. Nos. 4,794,661, 4,580,421 and 5,945,394, which are incorporated herein by reference. In other examples, a material comprising fabric can be contacted with an aqueous composition herein: (i) for at least about 5, 10, 20, 30, 40, 50, 60, 70, 80, 90, 100, 110, or 120 minutes; (ii) at a temperature of at least about 10, 15, 20, 25, 30, 35, 40, 45, 50, 55, 60, 65, 70, 75, 80, 85, 90, or 95° C. (e.g., for laundry wash or rinse: a "cold" temperature of about 15-30° C., a "warm" temperature of about 30-50° C., a "hot" temperature of about 50-95° C.); (iii) at a pH of about 2, 3, 4, 5, 6, 7, 8, 9, 10, 11, or 12 (e.g., pH range of about 2-12, or about 3-11); (iv) at a salt (e.g., NaCl) concentration of at least about 0.5, 1.0, 1.5, 2.0, 2.5, 3.0, 3.5, or 4.0 wt %; or any combination of (i)-(iv).

The contacting step in a fabric care method or laundry method can comprise any of washing, soaking, and/or rinsing steps, for example. Contacting a material or fabric in still further embodiments can be performed by any means known in the art, such as dissolving, mixing, shaking, spraying, treating, immersing, flushing, pouring on or in, combining, painting, coating, applying, affixing to, and/or communicating an effective amount of a dextran compound herein with the fabric or material. In still further embodiments, contacting may be used to treat a fabric to provide a surface substantive effect. As used herein, the term "fabric hand" or "handle" refers to a person's tactile sensory response towards fabric which may be physical, physiological, psychological, social or any combination thereof. In one embodiment, the fabric hand may be measured using a PhabrOmeter® System for measuring relative hand value (available from Nu Cybertek, Inc. Davis, Calif.) (American Association of Textile Chemists and Colorists (AATCC test method "202-2012, Relative Hand Value of Textiles: Instrumental Method")).

In certain embodiments of treating a material comprising fabric, a dextran compound component(s) of the aqueous composition adsorbs to the fabric. This feature is believed to render dextran compounds herein useful as anti-redeposition agents and/or anti-greying agents in fabric care compositions disclosed (in addition to their viscosity-modifying effect). An anti-redeposition agent or anti-greying agent herein helps keep soil from redepositing onto clothing in wash water after the soil has been removed. It is further contemplated that adsorption of one or more dextran compounds herein to a fabric enhances mechanical properties of the fabric.

Adsorption of a dextran compound to a fabric herein can be measured using a colorimetric technique (e.g., Dubois et al., 1956, *Anal. Chem.* 28:350-356; Zemljič et al., 2006, *Lenzinger Berichte* 85:68-76; both incorporated herein by reference), for example, or any other method known in the art.

Other materials that can be contacted in the above treatment method include surfaces that can be treated with a dish detergent (e.g., automatic dishwashing detergent or hand dish detergent). Examples of such materials include surfaces of dishes, glasses, pots, pans, baking dishes, utensils and flatware made from ceramic material, china, metal, glass, plastic (e.g., polyethylene, polypropylene, polystyrene, etc.) and wood (collectively referred to herein as "tableware"). Thus, the treatment method in certain embodiments can be considered a dishwashing method or tableware washing method, for example. Examples of conditions (e.g., time, temperature, wash volume) for conducting a dishwashing or tableware washing method herein are disclosed in U.S. Pat. No. 8,575,083, which is incorporated herein by reference. In other examples, a tableware article can be contacted with an aqueous composition herein under a suitable set of conditions such as any of those disclosed above with regard to contacting a fabric-comprising material.

Other materials that can be contacted in the above treatment method include oral surfaces such as any soft or hard surface within the oral cavity including surfaces of the tongue, hard and soft palate, buccal mucosa, gums and dental surfaces (e.g., natural tooth or a hard surface of artificial dentition such as a crown, cap, filling, bridge, denture, or dental implant). Thus, a treatment method in certain embodiments can be considered an oral care method or dental care method, for example. Conditions (e.g., time, temperature) for contacting an oral surface with an aqueous composition herein should be suitable for the intended purpose of making such contact. Other surfaces that can be contacted in a treatment method also include a surface of the integumentary system such as skin, hair or nails.

Thus, certain embodiments of the present disclosure concern material (e.g., fabric) that comprises a dextran compound herein. Such material can be produced following a material treatment method as disclosed herein, for example. A material may comprise a dextran compound in certain embodiments if the compound is adsorbed to, or otherwise in contact with, the surface of the material.

Certain embodiments of a method of treating a material herein further comprise a drying step, in which a material is dried after being contacted with the aqueous composition. A drying step can be performed directly after the contacting step, or following one or more additional steps that might follow the contacting step (e.g., drying of a fabric after being rinsed, in water for example, following a wash in an aqueous composition herein). Drying can be performed by any of several means known in the art, such as air drying (e.g., ~20-25° C.), or at a temperature of at least about 30, 40, 50, 60, 70, 80, 90, 100, 120, 140, 160, 170, 175, 180, or 200° C., for example. A material that has been dried herein typically has less than 3, 2, 1, 0.5, or 0.1 wt % water comprised therein. Fabric is a preferred material for conducting an optional drying step.

An aqueous composition used in a treatment method herein can be any aqueous composition disclosed herein, such as in the above embodiments or in the below Examples. Thus, the dextran component(s) of an aqueous composition can be any as disclosed herein. Examples of aqueous compositions include detergents (e.g., laundry detergent or dish detergent) and water-containing dentifrices such as toothpaste.

The present disclosure also concerns an enzymatic reaction comprising water, sucrose and a glucosyltransferase enzyme comprising, or consisting of, an amino acid sequence that is at least 90% identical to SEQ ID NO:1, SEQ ID NO:2, SEQ ID NO:5, SEQ ID NO:9, SEQ ID NO:13, or SEQ ID NO:17. The glucosyltransferase enzyme synthesizes dextran as presently disclosed. Significantly, dextran synthesized in this gtf reaction exhibits high viscosity in aqueous compositions, even at relatively low concentrations of the dextran. It is believed that this high viscosity profile is unique in comparison to viscosity profiles of previously disclosed dextran polymers.

Dextran synthesized in an enzymatic reaction herein can be as characterized (e.g., molecular weight, linkage and branching profile) in the above disclosure regarding dextran as produced by a glucosyltransferase enzyme. A glucosyltransferase enzyme in an enzymatic reaction herein can be as characterized in the above disclosure regarding dextran as produced by a glucosyltransferase enzyme.

One or more different glucosyltransferase enzymes may be used in an enzymatic reaction herein. A single glucosyltransferase enzyme (e.g., gtf 0768) is used in some cases, as opposed to situations in which multiple enzymes may be present (e.g., a bacterial or yeast fermentation). An enzymatic reaction can be as characterized (e.g., initial sucrose concentration and sucrose type, pH, temperature, time) in the above disclosure regarding dextran as produced by a glucosyltransferase enzyme. Also, any features presently disclosed of a method of producing dextran can apply to a glucosyltransferase reaction.

The present disclosure also concerns a method for producing dextran comprising the step of contacting at least water, sucrose, and a glucosyltransferase enzyme comprising an amino acid sequence that is at least 90% identical to SEQ ID NO:1, SEQ ID NO:2, SEQ ID NO:5, SEQ ID NO:9, SEQ ID NO:13, or SEQ ID NO:17. This contacting step results in production of dextran as presently disclosed. Dextran produced in the contacting step can optionally be isolated.

Dextran synthesized in a synthesis method herein can be as characterized (e.g., molecular weight, linkage and branching profile) in the above disclosure regarding dextran as produced by a glucosyltransferase enzyme. A glucosyltransferase enzyme in a synthesis method herein can be as characterized in the above disclosure regarding dextran as produced by a glucosyltransferase enzyme. Any features of an enzymatic reaction as disclosed above can apply to the instant synthesis method.

The contacting step in a method herein of producing dextran comprises providing an enzymatic reaction comprising water, sucrose and any glucosyltransferase enzyme disclosed herein. The contacting step of the disclosed method can be performed in any number of ways. For example, the desired amount of sucrose can first be dissolved in water (optionally, other components may also be added at this stage of preparation, such as buffer components), followed by addition of one or more glucosyltransferase enzymes. The solution may be kept still, or agitated via stirring or orbital shaking, for example.

The reaction can be, and typically is, cell-free. Thus, a dextran herein is not isolated from a cell, such as a bacteria (e.g., L. mesenteroides), in some aspects.

Completion of a glucosyltransferase reaction in certain embodiments can be gauged, for example, by determining whether reaction viscosity is no longer increasing and/or by measuring the amount of sucrose left in the reaction (residual sucrose), where a percent sucrose consumption of over about 90% can indicate reaction completion. Typically, a reaction of the disclosed process can take about 2, 3, 4, 5, 6, 7, 8, 9, 10, 12, 18, 24, 30, 36, 48, 60, 72, 84, or 96 hours to complete. Reaction time may depend, for example, on certain parameters such as the amount of sucrose and glucosyltransferase enzyme used in the reaction.

The yield of dextran produced in a glucosyltransferase reaction in certain embodiments can be about, or at least about, 10%, 15%, 20%, 25%, 30%, 35%, 40%, or 45%, based on the weight of the sucrose used in the reaction.

Dextran produced in the disclosed method may optionally be isolated. For example, dextran may be precipitated with alcohol (e.g., 90-100% methanol, ethanol, or isopropanol) and then separated from the supernatant, which may comprise water, fructose, and optionally one or more of residual sucrose and byproduct (e.g., glucose; leucrose and other soluble oligosaccharides). Such separation can be by centrifugation or filtration, for example. Precipitated dextran can optionally be washed one or more times (e.g., 2-4 times; 2, 3, 4 or more times) with alcohol (e.g., 70-100%, or at least 70%, 80%, 90%, 95%, or 100% methanol, ethanol, or isopropanol). In other examples, dextran isolation can comprise using an ultrafiltration and/or dialysis technique (i.e., a molecular weight cut-off technique), such as disclosed in U.S. Patent Appl. Publ. No. 2014/0142294 and U.S. Pat. No. 6,977,249, which are incorporated herein by reference. Measurements of certain dextran features herein (e.g., linkage profile, molecular weight) can be made with dextran isolated as above, if desired.

A dextran synthesis method herein is believed to be useful for producing dextran with increased or decreased viscosity, depending on the amount of sucrose used in the method. In general, the lower the sucrose concentration used in a glucosyltransferase reaction, the higher the viscosity of the dextran product, and vice versa. Any sucrose concentration disclosed herein can be used in a glucosyltransferase reaction, where the dextran product of the reaction has a viscosity that is greater than that of a dextran product produced in a reaction comprising a higher sucrose concentration, and vice versa. In certain aspects, any viscosity disclosed herein can be used to characterize embodiments of this method, and an increase in viscosity can be at least about 2-, 3-, 4-, 5-, 6-, 7-, 8-, 9-, 10-, 20-, 50-, 100-, 150-, 200-, or 250-fold higher. A glucosyltransferase enzyme in certain embodiments of this method can be gtf 0768 (comprising SEQ ID NO:1 or related sequences).

Non-limiting examples of compositions and methods disclosed herein include:

1. A composition comprising dextran, wherein the dextran comprises:
   (i) about 87-93 wt % glucose linked at positions 1 and 6;
   (ii) about 0.1-1.2 wt % glucose linked at positions 1 and 3;
   (iii) about 0.1-0.7 wt % glucose linked at positions 1 and 4;
   (iv) about 7.7-8.6 wt % glucose linked at positions 1, 3 and 6; and
   (v) about 0.4-1.7 wt % glucose linked at:
      (a) positions 1, 2 and 6, or
      (b) positions 1, 4 and 6;
   wherein the weight-average molecular weight (Mw) of the dextran is about 50-200 million Daltons, the z-average radius of gyration of the dextran is about 200-280 nm, and the dextran optionally is not a product of a *Leuconostoc mesenteroides* glucosyltransferase enzyme.

2. The composition of embodiment 1, wherein the dextran comprises:
   (i) about 89.5-90.5 wt % glucose linked at positions 1 and 6;
   (ii) about 0.4-0.9 wt % glucose linked at positions 1 and 3;
   (iii) about 0.3-0.5 wt % glucose linked at positions 1 and 4;
   (iv) about 8.0-8.3 wt % glucose linked at positions 1, 3 and 6; and
   (v) about 0.7-1.4 wt % glucose linked at:
      (a) positions 1, 2 and 6, or
      (b) positions 1, 4 and 6.

3. The composition of embodiment 1 or 2, wherein the dextran comprises chains linked together within a branching structure, wherein the chains are similar in length and comprise substantially alpha-1,6-glucosidic linkages.

4. The composition of embodiment 1, 2, or 3, wherein the average length of the chains is about 10-50 monomeric units.

5. The composition of embodiment 1, 2, 3, or 4, wherein the dextran is a product of a glucosyltransferase enzyme comprising an amino acid sequence that is at least 90% identical to SEQ ID NO:1, SEQ ID NO:2, SEQ ID NO:5, SEQ ID NO:9, SEQ ID NO:13, or SEQ ID NO:17.

6. The composition of embodiment 1, 2, 3, 4, or 5, wherein the composition is an aqueous composition having a viscosity of at least about 25 cPs.

7. The composition of embodiment 1, 2, 3, 4, 5, or 6, wherein the Mw of the dextran is about 80-120 million Daltons.

8. The composition of embodiment 1, 2, 3, 4, 5, 6, or 7, wherein the z-average radius of gyration of the dextran is about 230-250 nm.

9. The composition of embodiment 1, 2, 3, 4, 5, 6, 7, or 8, wherein the composition is in the form of a food product, personal care product, pharmaceutical product, household product, or industrial product.

10. The composition of embodiment 9, wherein the composition is in the form of a confectionery.

11. A method for increasing the viscosity of an aqueous composition, the method comprising: contacting dextran according to any of embodiments 1-8 with the aqueous composition, wherein the viscosity of the aqueous composition is increased by the dextran compared to the viscosity of the aqueous composition before the contacting step.

12. A method of treating a material, the method comprising: contacting a material with an aqueous composition comprising dextran according to any of embodiments 1-8.

13. An enzymatic reaction comprising water, sucrose and a glucosyltransferase enzyme comprising an amino acid sequence that is at least 90% identical to SEQ ID NO:1, SEQ ID NO:2, SEQ ID NO:5, SEQ ID NO:9, SEQ ID NO:13, or SEQ ID NO:17, wherein the glucosyltransferase enzyme synthesizes dextran according to any of embodiments 1-8.

14. A method for producing dextran, the method comprising:
   a) contacting at least water, sucrose, and a glucosyltransferase enzyme comprising an amino acid sequence that is at least 90% identical to SEQ ID NO:1, SEQ ID NO:2, SEQ ID NO:5, SEQ ID NO:9, SEQ ID NO:13, or SEQ ID NO:17, whereby dextran according to any of embodiments 1-8 is produced; and
   b) optionally, isolating the dextran produced in step (a).

15. The method of embodiment 14, wherein the viscosity of the dextran produced in the method is increased by decreasing the amount of sucrose in step (a).

EXAMPLES

The present disclosure is further defined in Examples 1-6 and 8-11. It should be understood that these Examples, while indicating certain preferred aspects of the disclosure, are given by way of illustration only. From the above discussion and these Examples, one skilled in the art can ascertain the essential characteristics of this disclosure, and without departing from the spirit and scope thereof, can make various changes and modifications to adapt the disclosure to various uses and conditions.

General Methods

Cloning and Expression of Glucosyltransferase Enzymes in *Bacillus subtilis*

Each glucosyltransferase used in Examples 3-6 was prepared as follows.

A plasmid encoding the gtf enzyme (pZZHB582, pZZHB583, pZZHB584, or pZZHB585, which allow for gtf expression and secretion from *B. subtilis*; see FIGS. 2A-D) was amplified using Illustra TempliPhi® 100 Amplification Kit (GE Healthcare Life Sciences, NJ). Competent *B. subtilis* cells (ΔspoIIE, ΔaprE, ΔnprE, degUHy32, ΔscoC, ΔnprB, Δvpr, Δepr, ΔwprA, Δmpr, ΔispA, Δbpr) were transformed with the amplification product. Cells were plated on Luria Agar plates supplemented with 5 ppm chloramphenicol. Colonies from the transformation plate were inoculated into 5 mL LB medium and incubated at 37° C. overnight. Aliquots (25-50 μL) from each culture were then transferred to 250-mL shake flasks containing 30 mL of Grant's II Medium supplemented with 5 ppm chloramphenicol and incubated at 30° C. with shaking (280 rpm) for 24 hours. Cells were harvested by centrifugation at 14000 rpm for 1 hour. Supernatants were analyzed by SDS-PAGE for secreted gtf product and further dialyzed three times against a solution containing 20 mM Tris, pH 7.5 for a total of 20 hours. Dialyzed samples were aliquoted at 25 mL per 50-mL conical centrifuge tube, and the tubes were placed at an angle at −80° C. for about 1 hour. Once the samples were frozen, the tube lid was removed and replaced with PARAFILM that was pierced 5-10 times with a high-gauge needle. The PARAFILM-covered frozen samples were lyophilized in a FreeZone® Freeze Dry System (Labconco Corp., Kansas City, Mo.) according to the manufacturer's instruction.

Stock Solutions of Glucosyltransferase Enzymes

An enzyme stock solution was made for each gtf by adding 10 mL of molecular grade $H_2O$ into each 50-mL conical centrifuge tube containing lyophilized enzyme powder.

Example 1

Expression of a Glucosyltransferase (0768) in *E. coli* and Production of Active Crude Enzyme Lysate This Example describes expression of a mature glucosyltransferase (gtf) enzyme in *E. coli*. Crude cell lysate of an *E. coli* expression strain was produced and showed gel product-forming activity in the presence of sucrose.

A putative YG repeat-containing hydrolase (categorized in GENBANK under GI number 339480768, but now having GI number 497964659) with 1484 amino acids was identified from *Leuconostoc pseudomesenteroides* strain KCTC3652 by whole genome shotgun sequencing. This putative glucosyltransferase (designated herein as gtf 0768) belongs to the GH70 family of glycosyl hydrolases containing a glucan-binding domain. The N-terminal 37 amino acid segment of gtf 0768 was deduced as the signal peptide of the enzyme by the SIGNALP 4.0 program (Petersen et al., *Nature Methods* 8:785-786). The mature form of gtf 0768 is represented by SEQ ID NO:1.

To construct a plasmid for bacterial expression of gtf 0768, a DNA sequence encoding a mature form of the gtf without the signal peptide was synthesized by GenScript USA Inc. (Piscataway, N.J.). The synthesized sequence was subcloned into the NheI and HindIII sites of the pET23D+ vector (NOVAGEN®; Merck KGaA, Darmstadt, Germany). The 0768 gtf (SEQ ID NO:2) encoded by this construct included a start methionine and 3 additional amino acids (Ala-Ser-Ala) at the N-terminus, and 6 histidine residues at the C-terminus, compared to the wild type mature (predicted) form of gtf 0768 (SEQ ID NO:1) (i.e., SEQ ID NO:1 is comprised in SEQ ID NO:2). The plasmid construct was sequence-confirmed and transformed into *E. coli* BL21 DE3 host cells with ampicillin selection, resulting in expression strain EC0052.

Cells of EC0052 and a control strain containing only empty pET23D+ vector were grown in LB medium with 100 µg/mL ampicillin to $OD_{600}$ ~0.5, and then induced with 1 mM IPTG at 37° C. for 3 hours or alternatively induced at 23° C. overnight. Following this induction period, cells were collected by centrifugation at 4000×g for 10 min and resuspended in PBS buffer pH 6.8. The cells were then lysed by passing through a French Press at 14,000 psi (~96.53 MPa) twice, after which cell debris was pelleted by centrifugation at 15,000×g for 20 min. The supernatants of each crude cell lysate were aliquoted and frozen at −80° C.

The activity of crude cell lysate from EC0052 cells was checked by reaction with sucrose. A control reaction was set up similarly using cell lysate prepared from cells containing the empty vector. Each sucrose reaction was set up using 10% (v/v) of cell lysate with 100 g/L sucrose, 10 mM sodium citrate pH 5, and 1 mM $CaCl_2$. After incubation of the reactions at 37° C. for a few hours, a gel-like product, believed to be a dextran, was formed in the tube in which EC0052 cell lysate had been added. No gel-like product was formed in the control reaction. HPLC analysis confirmed that sucrose was consumed in the reaction containing EC0052 cell lysate, and not in the control reaction. This result suggested that the EC0052 crude cell lysate expressed active gtf 0768 enzyme, and that this gtf produced a dextran product having high viscosity.

Thus, reactions comprising water, sucrose and an enzyme comprising SEQ ID NO:1 synthesized a gelling product, believed to be a dextran. This result demonstrated that gtf 0768 likely has glucosyltransferase activity.

Example 2

Reaction of Sucrose with Gtf 0768 and Analysis of a Gelling Dextran Reaction Product This Example describes additional reactions comprising water, sucrose and gtf 0768, supplementing the results provided in Example 1. Also, this Example provides glycosidic linkage analysis of the gelling product synthesized by gtf 0768, showing that this product is a type of dextran.

Reagents for preparing gtf reactions:
Sucrose (Sigma Prod. No. S-9378).
Sodium phosphate buffer stock (200 mM) (pH 5.5): prepare 250 mL in water using sodium phosphate monobasic monohydrate (Sigma Prod. No. S9638) and sodium phosphate dibasic heptahydrate (Sigma Prod. No. S9390), accordingly.
Gtf 0768 enzyme solution (cell lysate as prepared in Example 1).

Conditions of three gtf reactions:

A 1000-mL reaction was prepared containing 2.72 g of sodium phosphate buffer stock (pH 5.5), 100 g/L sucrose, and 2 mL of gtf 0768 enzyme solution. The reaction was stirred at 26° C. for 20 hours, and became viscous. The gtf enzyme was deactivated by heating the reaction at 80° C. for 10 minutes. The deactivated viscous reaction was then mixed with 3 liters of 100% methanol to precipitate the viscous product. A white precipitate was formed, which was then filtered, followed by four washes with 120 ml of 100% methanol. The solid product was dried at room temperature under vacuum in an oven for 72 hours.

A 725-mL reaction was prepared containing 1.97 g of sodium phosphate buffer, 300 g/L sucrose, and 1.45 mL of gtf 0768 enzyme solution. The reaction was stirred at 26° C. for 20 hours, and became viscous. The gtf enzyme was deactivated by adding methanol to the reaction mixture. The deactivated reaction was then mixed with 3 liters of 100% methanol to precipitate the viscous product. A white precipitate was formed, which was then filtered, followed by four washes with 120 mL of 100% methanol. The solid product was dried at room temperature under vacuum in an oven for 72 hours.

A 200-mL reaction was prepared containing 0.544 g of sodium phosphate buffer, 400 g/L sucrose, and 0.4 mL of gtf 0768 enzyme solution. The reaction was stirred at 26° C. for 20 hours, and became viscous. The gtf enzyme was deactivated by adding methanol to the reaction mixture. The deactivated reaction was then mixed with 3 liters of 100% methanol to precipitate the viscous product. A white precipitate was formed, which was then filtered, followed by four washes with 120 mL of 100% methanol. The solid product was dried at room temperature under vacuum in an oven for 72 hours.

A 200-mL reaction was prepared containing 0.544 g of sodium phosphate buffer, 800 g/L sucrose, and 0.4 mL of gtf 0768 enzyme solution. The reaction was stirred at 26° C. for 20 hours, and became viscous. The gtf enzyme was deactivated by adding methanol to the reaction mixture. The deactivated reaction was then mixed with 3 liters of 100% methanol to precipitate the viscous product. A white precipitate was formed, which was then filtered, followed by four washes with 120 ml of 100% methanol. The solid product was dried at room temperature under vacuum in an oven for 72 hours.

Samples (100 µL) of each reaction were taken at 0, 2, 4, and 18 hours, respectively. The gtf enzyme was deactivated in each sample by heating at 80° C. for 10 minutes. Each sample was then diluted 10-fold with water and centrifuged at 14,000 rpm for 5 minutes, after which 200 µl of supernatant was used for HPLC analysis to measure sucrose consumption during the reaction. The following HPLC conditions were applied for analyzing each sample: column (AMINEX HPX-87C carbohydrate column, 300×7.8 mm, Bio-Rad, No. 125-0095), eluent (water), flow rate (0.6 mL/min), temperature (85° C.), refractive index detector. HPLC analysis of the samples indicated substantial sucrose consumption during the 0768 gtf reaction (FIG. 1, reaction comprising 100 g/L sucrose) (this sucrose consumption occurred significantly faster than the sucrose consumption observed in a reaction using a dextran sucrase obtained from a commercial source—refer to Example 7).

HPLC was also used to analyze other products of the reaction comprising 100 g/L sucrose. Polymer yield was back-calculated by subtracting the amount of all other saccharides left in the reaction from the amount of the starting sucrose. The back-calculated number was consistent with the viscous product dry weight analysis. Sucrose, leucrose, glucose and fructose were quantified by HPLC with an HPX-87C column (HPLC conditions as described above). DP2-7 disaccharides were quantified by HPLC with the following conditions: column (AMINEX HPX-42A carbohydrate column, 300×7.8 mm, Bio-Rad, No. 125-0097), eluent (water), flow rate (0.6 mL/min), temperature (85° C.), refractive index detector. These HPLC analyses indicated that the glucosyl-containing saccharide products of the 0768 gtf reaction consisted of 91% polymer product, 1% glucose, 6.5% leucrose, and 1.5% DP2-7 oligosaccharides.

The glycosidic linkage profile of the gelling polymer product of the reaction comprising 100 g/L sucrose was determined by $^{13}$C NMR. Dry polymer (25-30 mg) as prepared above was dissolved in 1 mL of deuterated DMSO containing 3 wt % LiCl with stirring at 50° C. Using a glass pipet, 0.8 mL of the preparation was transferred into a 5-mm NMR tube. A quantitative $^{13}$C NMR spectrum was acquired using a Bruker Avance (Billerica, Mass.) 500 MHz NMR spectrometer equipped with a CPDul cryoprobe, at a spectral frequency of 125.76 MHz, using a spectral window of 26041.7 Hz. An inverse-gated decoupling pulse sequence using waltz decoupling was used with an acquisition time of 0.629 second, an inter-pulse delay of 5 seconds, and 6000 pulses. The time domain data were transformed using an exponential multiplication of 2.0 Hz.

The NMR results indicated that the gelling polymer product comprised about 90% alpha-1,6-glucosidic linkages, about 4-5% alpha-1,3-glucosidic linkages, and about 5-6% alpha-1,4 and -1,2 glucosidic linkages. The main chain(s) of the polymer product appeared to mostly comprise alpha-1,6-glucosidic linkages, but also a very small amount of alpha-1,3 and -1,4 glucosidic linkages. Other alpha-1,3 and -1,4 glucosidic linkages, and all of the alpha-1,2-glucosidic linkages, appeared to be in branches off the main chain(s). The gelling product thus appears to be a gelling dextran.

A different protocol (not the above $^{13}$C NMR procedure) is presently recommended herein for determining the linkage profile of dextran produced by gtf 0768. This protocol is disclosed below in Example 9, indicating a linkage profile similar to that disclosed in this Example.

The number-average molecular weight (Mn) and weight-average molecular weight (Mw) of the gelling dextran product of the reaction comprising 100 g/L sucrose was determined by size-exclusion chromatography (SEC). Dry polymer as prepared above was dissolved in DMAc and 5% LiCl (0.5 mg/mL) with shaking overnight at 100° C. The chromatographic system used was an Alliance™ 2695 separation module from Waters Corporation (Milford, Mass.) coupled with three on-line detectors: a differential refractometer 2410 from Waters, a Heleos™ 8+ multiangle light scattering photometer from Wyatt Technologies (Santa Barbara, Calif.), and a ViscoStar™ differential capillary viscometer from Wyatt. Columns used for SEC were four styrene-divinyl benzene columns from Shodex (Japan) and two linear KD-806M, KD-802 and KD-801 columns to improve resolution at the low molecular weight region of a polymer distribution. The mobile phase was DMAc with 0.11% LiCl. The chromatographic conditions used were 50° C. in the column and detector compartments, 40° C. in the sample and injector compartment, a flow rate of 0.5 mL/min, and an injection volume of 100 µL. The software packages used for data reduction were Empower™ version 3 from Waters (calibration with broad glucan polymer standard) and Astra® version 6 from Wyatt (triple detection method with column calibration). It was determined from this procedure that the gelling dextran product had an $M_n$ of 2229400 and an Mw of 5365700.

A different protocol (not the above SEC procedure) is presently recommended herein for determining the molecular weight of dextran produced by gtf 0768. This protocol is disclosed below in Example 9, indicating a molecular weight more than one order of magnitude greater than the molecular weight disclosed in this Example.

Thus, reactions comprising water, sucrose and an enzyme comprising SEQ ID NO:1 synthesized a gelling dextran product, as determined by the product's predominant alpha-1,6 glucosidic linkage profile. Example 8 below discloses comparing the viscosity of this product versus the viscosities of certain commercially available dextrans. Example 9 discloses further production of dextran with a gtf enzyme comprising SEQ ID NO:1, along with yield, molecular weight, and linkage analysis of the dextran.

Example 3

Expression of a Glucosyltransferase (2919) and Use Thereof to Produce a Gelling Dextran Product This Example describes expression of a mature *Weissella cibaria* glucosyltransferase (gtf) enzyme in *B. subtilis*. Also, this Example shows that this enzyme produces a gelling product, likely a dextran, when used is a reaction containing water and sucrose.

A glucosyltransferase gene, WciGtf1, was identified from *Weissella cibaria* KACC 11862. The nucleic acid sequence of this gene (positions 23315 to 27661 of GENBANK Accession No. NZ_AEKT01000035.1) is set forth in SEQ ID NO:3 and encodes the protein sequence of SEQ ID NO:4 (GENBANK Accession No. ZP_08417432). At the N-terminus of the WciGtf1 protein (SEQ ID NO:4) is a signal peptide of 26 amino acids, as predicted by the SIGNALP 4.0 program (Petersen et al., *Nature Methods* 8:785-786). This indicates that WciGtf1 (SEQ ID NO:4) is a secreted protein.

The mature, secreted form of the WciGtf1 protein is herein referred to as 2919 gtf, and is set forth in SEQ ID NO:5.

The nucleotide sequence encoding 2919 gtf was optimized for expression in *B. subtilis*. The optimized sequence (SEQ ID NO:6) was synthesized by Generay (Shanghai, China), and inserted into plasmid p2JM103BBI (Vogtentanz et al., *Protein Expr. Purif.* 55:40-52), resulting in plasmid pZZHB583 (FIG. 2A). Plasmid pZZHB583 contains an aprE promoter operably linked to a sequence encoding (i) an aprE signal sequence used to direct heterologous protein (2919 gtf in this case) secretion in *B. subtilis*, (ii) Ala-Gly-Lys to facilitate the secretion, and (iii) 2919 gtf (SEQ ID NO:5) (i-iii are fused together in the amino-to-carboxy direction).

Plasmid pZZHB583 was transformed into *B. subtilis* cells for 2919 gtf expression and purification (see General Methods).

The activity of 2919 gtf (SEQ ID NO:5) was determined in a 250-mL reaction at room temperature comprising 100 g/L sucrose, 20 mM sodium phosphate buffer (pH 5.5), and 6.25 mL of enzyme stock. The reaction was carried out at room temperature with shaking (150 rpm) for 48 hours.

Samples (100 µL) were taken from the reaction at 0, 1, 3, 5, 24, and 48 hour time points, respectively. Enzyme was deactivated by heating each sample at 80° C. for 10 minutes. Samples were diluted 10-fold with water and centrifuged at 14000 rpm for 5 minutes. Supernatant (200 µL) was used for HPLC analysis.

The concentrations of leucrose, glucose, and fructose in the gtf reaction were determined using HPLC, which was performed with an Agilent 1260 chromatography system equipped with an AMINEX HPX-87C column (300×7.8 mm) placed in a thermostatted column compartment at 85° C., and a refractive index detector. HPLC elution was carried out with Milli-Q® water at 0.6 mL/min. Sucrose, leucrose, glucose, and fructose were identified by comparison with corresponding standards. Their concentrations were calculated based on a peak area standard curves. Sucrose was consumed almost completely by the end of the reaction. Aside from a viscous dextran product, 2919 gtf (SEQ ID NO:5) produced mostly fructose (~50%), and small amounts of leucrose (~5%) and glucose (~1%).

The concentration of oligosaccharides (DP2-DP7) in the gtf reaction was determined by HPLC analysis, which was performed with an Agilent 1260 chromatography system equipped with an AMINEX HPX-42A column (300×7.8 mm) placed in a thermostatted column compartment at 85° C., and a refractive index detector. HPLC elution was carried out with Milli-Q® water at 0.6 mL/min. Formation of oligosaccharides was identified by comparison with corresponding standards. The concentration of the oligosaccharides was calculated based on standard curves from peak area. 2919 gtf (SEQ ID NO:5) produced a small amount of DP2-DP7 oligosaccharides (~3%) by the end of the reaction.

Thus, reactions comprising water, sucrose and an enzyme comprising SEQ ID NO:5 synthesized a gelling product, which is believed to be a dextran polymer. Experimental results demonstrated that gtf 2919 likely has glucosyltransferase activity.

Example 4

Expression of a Glucosyltransferase (2918) and Use Thereof to Produce a Gelling Dextran Product This Example describes expression of a mature *Lactobacillus fermentum* glucosyltransferase (gtf) enzyme in *B. subtilis*. Also, this Example shows that this enzyme produces a gelling product, likely a dextran, when used is a reaction containing water and sucrose.

A glucosyltransferase gene, LfeGtf1, was identified from *Lactobacillus fermentum*. The nucleic acid sequence of this gene (positions 618 to 5009 of GENBANK Accession No. AY697433.1) is set forth in SEQ ID NO:7 and encodes the protein sequence of SEQ ID NO:8 (GENBANK Accession No. AAU08008). At the N-terminus of the LfeGtf1 protein (SEQ ID NO:8) is a signal peptide of 37 amino acids, as predicted by the SIGNALP 4.0 program. This indicates that LfeGtf1 (SEQ ID NO:8) is a secreted protein. The mature, secreted form of the LfeGtf1 protein is herein referred to as 2918 gtf, and is set forth in SEQ ID NO:9.

The nucleotide sequence encoding 2918 gtf was optimized for expression in *B. subtilis*. The optimized sequence (SEQ ID NO:10) was synthesized by Generay (Shanghai, China), and inserted into plasmid p2JM103BBI, resulting in plasmid pZZHB582 (FIG. 2B). Plasmid pZZHB582 contains an aprE promoter operably linked to a sequence encoding (i) an aprE signal sequence used to direct heterologous protein (2918 gtf in this case) secretion in *B. subtilis*, (ii) Ala-Gly-Lys to facilitate the secretion, and (iii) 2918 gtf (SEQ ID NO:9) (i-iii are fused together in the amino-to-carboxy direction).

Plasmid pZZHB582 was transformed into *B. subtilis* cells for 2918 gtf expression and purification (see General Methods).

The activity of 2918 gtf (SEQ ID NO:9) was determined in a 250-mL reaction at room temperature comprising 100 g/L sucrose, 20 mM sodium phosphate buffer (pH 5.5), and 6.25 mL of enzyme stock. The reaction was carried out at room temperature with shaking (150 rpm) for 6 days.

Samples (100 µL) were taken from the reaction at 0, 1, 3, 5, 24, 48 and 144 hour time points, respectively. Enzyme was deactivated by heating each sample at 80° C. for 10 minutes. Samples were diluted 10-fold with water and centrifuged at 14000 rpm for 5 minutes. Supernatant (200 µL) was used for HPLC analysis.

The concentrations of sucrose, leucrose, glucose, fructose and oligosaccharides (DP2-DP7) in the gtf reaction were determined using HPLC procedures as described in Example 3. Sucrose was consumed almost completely by the end of the reaction. Aside from a viscous dextran product, 2918 gtf (SEQ ID NO:9) produced mostly fructose (~50%), and small amounts of leucrose (~5%) and glucose (~1%). 2918 gtf (SEQ ID NO:9) produced a small amount of DP2-DP7 oligosaccharides (~1%).

Thus, reactions comprising water, sucrose and an enzyme comprising SEQ ID NO:9 synthesized a gelling product, which is believed to be a dextran polymer. Experimental results demonstrated that gtf 2920 likely has glucosyltransferase activity.

Example 5

Expression of a Glucosyltransferase (2920) and Use Thereof to Produce a Gelling Dextran Product This Example describes expression of a mature *Streptococcus sobrinus* glucosyltransferase (gtf) enzyme in *B. subtilis*. Also, this Example shows that this enzyme produces a gelling product, likely a dextran, when used is a reaction containing water and sucrose.

A glucosyltransferase gene, SsoGtf4, was identified from *Streptococcus sobrinus* 813N. The nucleic acid sequence of this gene (positions 198 to 4718 of GENBANK Accession No. AY966490) is set forth in SEQ ID NO:11 and encodes the protein sequence of SEQ ID NO:12 (GENBANK Accession No. AAX76986). At the N-terminus of the SsoGtf4 protein (SEQ ID NO:12) is a signal peptide of 41 amino acids, as predicted by the SIGNALP 4.0 program. This indicates that SsoGtf4 (SEQ ID NO:12) is a secreted protein. The mature, secreted form of the SsoGtf4 protein is herein referred to as 2920 gtf, and is set forth in SEQ ID NO:13.

The nucleotide sequence encoding 2920 gtf was optimized for expression in *B. subtilis*. The optimized sequence (SEQ ID NO:14) was synthesized by Generay (Shanghai, China), and inserted into plasmid p2JM103BBI, resulting in plasmid pZZHB584 (FIG. 2C). Plasmid pZZHB584 contains an aprE promoter operably linked to a sequence encoding (i) an aprE signal sequence used to direct heterologous protein (2920 gtf in this case) secretion in *B. subtilis*, (ii) Ala-Gly-Lys to facilitate the secretion, and (iii) 2920 gtf (SEQ ID NO:13) (i-iii are fused together in the amino-to-carboxy direction).

Plasmid pZZHB584 was transformed into *B. subtilis* cells for 2920 gtf expression and purification (see General Methods).

The activity of 2920 gtf (SEQ ID NO:13) was determined in a 250-mL reaction at room temperature comprising 100 g/L sucrose, 20 mM sodium phosphate buffer (pH 5.5), and 6.25 mL of enzyme stock. The reaction was carried out at room temperature with shaking (150 rpm) for 6 days.

Samples (100 µL) were taken from the reaction at 0, 1, 3, 5, 24, 48, 72 and 144 hour time points, respectively. Enzyme was deactivated by heating each sample at 80° C. for 10 minutes. Samples were diluted 10-fold with water and centrifuged at 14000 rpm for 5 minutes. Supernatant (200 µL) was used for HPLC analysis.

The concentrations of sucrose, leucrose, glucose, fructose and oligosaccharides (DP2-DP7) in the gtf reaction were determined using HPLC procedures as described in Example 3. Sucrose was consumed almost completely by the end of the reaction. Aside from a viscous dextran product, 2920 gtf (SEQ ID NO:13) produced mostly fructose (~50%), leucrose (~20%), and a small amount of glucose (~3%). 2920 gtf (SEQ ID NO:13) produced a small amount of DP2-DP7 oligosaccharides (~1%).

Thus, reactions comprising water, sucrose and an enzyme comprising SEQ ID NO:13 synthesized a gelling product, which is believed to be a dextran polymer. Experimental results demonstrated that gtf 2920 likely has glucosyltransferase activity.

Example 6

Expression of a Glucosyltransferase (2921) and Use Thereof to Produce a Gelling Dextran Product This Example describes expression of a mature *Streptococcus downei* glucosyltransferase (gtf) enzyme in *B. subtilis*. Also, this Example shows that this enzyme produces a gelling product, likely a dextran, when used is a reaction containing water and sucrose.

A glucosyltransferase gene, SdoGtf7, was identified from *Streptococcus downei* MFe28. The nucleic acid sequence of this gene (positions 16 to 2375 of GENBANK Accession No. AB476746) is set forth in SEQ ID NO:15 and encodes the protein sequence of SEQ ID NO:16 (GENBANK Accession No. ZP_08549987.1). At the N-terminus of the SdoGtf7 protein (SEQ ID NO:16) is a signal peptide of 44 amino acids, as predicted by the SIGNALP 4.0 program. This indicates that SdoGtf7 protein (SEQ ID NO:16) is a secreted protein. The mature, secreted form of the SdoGtf7 protein is herein referred to as 2921 gtf, and is set forth in SEQ ID NO:17.

The nucleotide sequence encoding 2921 gtf was optimized for expression in *B. subtilis*. The optimized sequence (SEQ ID NO:18) was synthesized by Generay (Shanghai, China), and inserted into plasmid p2JM103BBI, resulting in plasmid pZZHB585 (FIG. 2D). Plasmid pZZHB585 contains an aprE promoter operably linked to a sequence encoding (i) an aprE signal sequence used to direct heterologous protein (2921 gtf in this case) secretion in *B. subtilis*, (ii) Ala-Gly-Lys to facilitate the secretion, and (iii) 2921 gtf (SEQ ID NO:17) (i-iii are fused together in the amino-to-carboxy direction).

Plasmid pZZHB585 was transformed into *B. subtilis* cells for 2921 gtf expression and purification (see General Methods).

The activity of 2921 gtf (SEQ ID NO:17) was determined in a 250-mL reaction at room temperature comprising 100 g/L sucrose, 20 mM sodium phosphate buffer (pH 5.5), and 6.25 mL of enzyme stock. The reaction was carried out at room temperature with shaking (150 rpm) for 8 days.

Samples (100 µL) were taken from the reaction at the reaction start and on 1, 2, 3, 6, 7 and 8 day time points, respectively. Enzyme was deactivated by heating each sample at 80° C. for 10 minutes. Samples were diluted 10-fold with water and centrifuged at 14000 rpm for 5 minutes. Supernatant (200 µL) was used for HPLC analysis.

The concentrations of sucrose, leucrose, glucose, fructose and oligosaccharides (DP2-DP7) in the gtf reaction were determined using HPLC procedures as described in Example 3. About 43% sucrose remained in the reaction on day 8. Aside from a viscous dextran product, 2921 gtf (SEQ ID NO:17) produced mostly fructose (~31%), leucrose (~6%), and glucose (~3%). No obvious production of DP2-DP7 oligosaccharides was observed.

Thus, reactions comprising water, sucrose and an enzyme comprising SEQ ID NO:17 synthesized a gelling product, which is believed to be a dextran polymer. Experimental results demonstrated that gtf 2921 likely has glucosyltransferase activity.

Example 7 (Comparative)

Production of Dextran Using Commercially Available Dextran Sucrase

This Example describes synthesizing dextran using a commercially available dextran sucrase in reactions comprising water and sucrose. The dextran produced in this was analyzed in Example 8 in comparison to the gelling dextran products synthesized in Examples 1-6.

Reagents for preparing dextran sucrase reaction:
Sucrose (Sigma Prod. No. S-9378). 400 g/L stock solution was prepared.
Sodium phosphate buffer stock (200 mM) (pH 5.5): prepare 250 mL in water using sodium phosphate monobasic monohydrate (Sigma Prod. No. S9638) and sodium phosphate dibasic heptahydrate (Sigma Prod. No. S9390), accordingly.
Dextran sucrase, lyophilized powder, ≥100 units/mg protein, from *Leuconostoc mesenteroides* (Sigma Prod. No. D9909).

A 50-mL reaction was prepared containing 20 mM sodium phosphate (pH 5.5), 110 g/L sucrose, and 10 units of dextran sucrase from Sigma-Aldrich. The dextran sucrase was added last when preparing the reaction. The reaction was carried out in a 125-mL capped shake flask at 26° C. with shaking (100 rpm) for 7 days. Samples (100 µL) of the reaction were taken at 0, 3, 6, 24, 48 and 168 hours, respectively. The dextran sucrase was deactivated in each sample by heating at 80° C. for 10 minutes. Each sample was then diluted 10-fold with water and centrifuged at 14,000 rpm for 5 minutes, after which 200 µl of supernatant was used for HPLC analysis to measure sucrose consumption during the reaction.

The following HPLC conditions were applied for analyzing each sample: column (AMINEX HPX-87C carbohydrate column, 300×7.8 mm, Bio-Rad, No. 125-0095), eluent (water), flow rate (0.6 mL/min), temperature (85° C.), refractive index detector. HPLC analysis of the samples indicated sucrose consumption during the dextran sucrase reaction (FIG. 3). It is notable that the sucrose consumption rate by the commercial dextran sucrase was much slower compared to the sucrose consumption rate of gtf 0768 (Example 2). Specifically, while gtf 0768 depleted most sucrose after about 17-18 hours of reaction time (FIG. 1), commercial dextran sucrase depleted only about 20% of sucrose within this same time period, and required about 168 hours to deplete all or most sucrose.

HPLC was also used to analyze other products of the reaction. Dextran yield was back-calculated by subtracting the amount of all other saccharides left in the reaction from the amount of the starting sucrose. The back-calculated number was consistent with dextran dry weight analysis. Sucrose, leucrose, glucose, fructose, and DP2-7 disaccharides were quantified by HPLC as described in Example 2. These HPLC analyses indicated that the saccharide products of the commercial dextran sucrase reaction consisted of 49% dextran, 0.3% sucrose, 44% fructose, 1% glucose, 5% leucrose, and 1% DP2-7 oligosaccharides.

The dextran produced in this Example was analyzed in Example 8 in comparison to the gelling dextran products synthesized in Examples 1-6.

Example 8

Viscosity of Dextran Samples

This Example describes measuring the viscosities of the dextran polymers produced in Examples 1-7, as well as the viscosity of dextran obtained from a commercial source. Viscosity measurements were made at various shear rates.

Dextran polymer samples were prepared as described in Examples 1-7. Specifically, enzymatic reactions were conducted, after which polymer was methanol-precipitated and washed with methanol (100%) four times, and then dried. Solutions (2 wt % and/or 3 wt %) of each sample were prepared by adding the appropriate amount of polymer to de-ionized (DI) water. Each preparation was then mixed using a bench top vortexer until polymer was fully in solution. Each of these samples is referred to in Tables 2 and 3 (below) as "After PPT" (after precipitation). A 2 wt % solution of dextran (Mw=956978) obtained from TCI America (Portland, Oreg.; catalogue No. D0061) was similarly prepared; this dextran is referred to below as "commercial dextran".

To determine the viscosity of each polymer solution at various shear rates, each solution was subjected to various shear rates using a viscometer while the temperature was held constant at 20° C. Also, polymer samples obtained directly, without precipitation, from each of the enzymatic reactions described in Examples 1-7 were subjected to various shear rates (referred to in Tables 2 and 3 as "Before PPT"). The shear rate was increased using a gradient program which increased from 0-10 rpm and the shear rate was increased by 0.17 (1/s) every 30 seconds. The results of this experiment are listed in Table 2.

TABLE 2

Viscosity of Certain Dextran Solutions at Various Shear Rates

| Dextran Sample[a] | Viscosity (cPs) @ 0.17 rpm | Viscosity (cPs) @ 1.03 rpm | Viscosity (cPs) @ 2.62 rpm | Viscosity (cPs) @ 4.22 rpm |
|---|---|---|---|---|
| Gtf 0768 (SEQ ID NO: 1) Before PPT (Example 2, 100 g/L sucrose reaction) | 47976.13 | 11376.70 | 12956.11 | 14390.76 |
| Gtf 0768 (SEQ ID NO: 1) After PPT - 3 wt % (Example 2, 100 g/L sucrose reaction) | | 15778.40 | 6245.31[b] | 4119.58[b] |
| Gtf 0768 (SEQ ID NO: 1) After PPT - 2 wt % (Example 2, 100 g/L sucrose reaction) | | 4091.84 | 3417.10 | 2874.10 |
| Gtf 2918 (SEQ ID NO: 9) Before PPT (Example 4) | | n/a[b] | n/a[b] | n/a[b] |
| Gtf 2919 (SEQ ID NO: 5) Before PPT (Example 3) | | 98864 | 38671 | 25580 |
| Gtf 2920 (SEQ ID NO: 13) Before PPT (Example 5) | | 3874.85 | 4205.66 | 4119.58[b] |
| Gtf 2920 (SEQ ID NO: 13) After PPT - 3 wt % (Example 5) | | 6168.76 | 3294.43 | 2288.24 |
| Gtf 2921 (SEQ ID NO: 17) Before PPT (Example 6) | | 3533.86 | 2143.72 | 1748.95 |
| Gtf 2921 (SEQ ID NO: 17) After PPT - 3 wt % (Example 6) | | 4634.32 | 2780.4 | 1984.89 |
| Commercial dextran sucrase Before PPT (Example 7) | 16759.42 | | | |

[a]Polymer samples are listed according to the respective enzyme used to synthesize the sample.
[b]Measurement was outside the specification limits of the viscometer.

Polymer samples were also subjected to various higher shear rates using a viscometer while the temperature was held constant at 20° C. The shear rate was increased using a gradient program which increased from 10-250 rpm and the shear rate was increased by 7.36 (1/s) every 20 seconds. The results of this experiment are listed in Table 3.

TABLE 3

Viscosity of Certain Dextran Solutions at Various Shear Rates

| Dextran Sample[a] | Viscosity (cPs) @ 14.72 rpm | Viscosity (cPs) @ 102.9 rpm | Viscosity (cPs) @ 250 rpm |
|---|---|---|---|
| Gtf 2918 (SEQ ID NO: 9) After PPT - 3 wt % (Example 4) | 149.95 | 69.68 | 48.97 |
| Gtf 2919 (SEQ ID NO: 5) After PPT - 3 wt % (Example 3) | 80.82 | 41.23 | 29.49 |

TABLE 3-continued

Viscosity of Certain Dextran Solutions at Various Shear Rates

| | | | |
|---|---|---|---|
| 2 wt % Commercial dextran | 241.41 | 105.28 | 68.88 |
| Commercial dextran sucrase After PPT - 2 wt % (Example 7) | 11.09[b] | 10.31[b] | 8.27 |

| | Viscosity (cPs) @ 14.11 rpm | Viscosity (cPs) @ 98.69 rpm | Viscosity (cPs) @ 162.1 rpm |
|---|---|---|---|
| Gtf 0768 (SEQ ID NO: 1) After PPT - 2 wt % (Example 2, 400 g/L sucrose reaction) | 49.89 | 23.61 | 18.32 |
| Gtf 0768 (SEQ ID NO: 1) After PPT - 2 wt % (Example 2, 800 g/L sucrose reaction) | 5.44 | 2.72 | 1.58 |

[a]Polymer samples are listed according to the respective enzyme used to synthesize the sample. Alternatively, dextran obtained from a commercial source was analyzed ("Commercial dextran").
[b]Measurement was outside the specification limits of the viscometer.

These data demonstrate that solutions of the dextran product of a glucosyltransferase comprising SEQ ID NO:1 can in most cases exhibit increased viscosity even after precipitation and resolvation, as compared to the viscosities of commercially obtained dextran and the dextran product of a commercially obtained dextran sucrase. This observation also appears to apply to the respective polymer products of glucosyltransferases comprising SEQ ID NO:5, 9, 13, or 17.

It is also noteworthy that, based on Tables 2-3, as the amount of sucrose in a gtf 0768 reaction is decreased from 800 g/L to 100 g/L, the viscosity of the dextran product appears to increase. Specifically, Table 3 indicates (at 14.11 rpm/2 wt % loading) viscosities of 5.44 cPs and 49.89 cPs for dextran products of reactions comprising 800 and 400 g/L sucrose, respectively, and Table 2 (gtf 0768, 2 wt % loading) may indicate a viscosity of about 957 cPs (exponential extrapolated at a rotation of 14.11 rpm) for dextran product of a reaction comprising 100 g/L sucrose. This result suggests that the viscosity of a dextran product can be controlled by modifying the level of sucrose initially provided to reaction.

Example 9

Further Production and Analysis of Dextran Synthesized by Gtf 0768

This Example is in addition to Example 2, describing another reaction comprising water, sucrose and gtf 0768. Also, this Example provides additional linkage and molecular weight analyses of the gelling product synthesized by gtf 0768, showing that this product is a type of dextran.

Reagents for Preparing Gtf Reaction:
Sucrose (Sigma Prod. No. S-9378).
Sodium phosphate buffer stock (1 M, pH 6.5, Teknova Cat No: S0276).
Gtf 0768 enzyme solution (cell lysate as prepared in Example 1).

Gtf Reaction Conditions:

A 50-mL reaction was prepared containing 20 mM sodium phosphate buffer (buffer was diluted 50-fold with ddH2O from 1 M stock, pH 6.5), 100 g/L sucrose, and 0.1 mL of gtf 0768 enzyme solution. The reaction was shaken at 100 rpm in an incubator shaker (Innova, Model 4000) at 26° C. for 43 hours; the reaction became viscous after about 24 hours.

The gtf enzyme was deactivated by heating the reaction at 80° C. for 10 minutes. The deactivated viscous reaction was then mixed with 75 mL of 100% methanol to precipitate the viscous product. A white precipitate was formed. After carefully decanting the supernatant, the white precipitate was washed twice with 75 mL of 100% methanol. The solid product was dried at 45° C. under vacuum in an oven for 48 hours.

Samples (1 mL) of the reaction were taken at 0, 0.5, 1, 2, and 24 hours, respectively. The gtf enzyme was deactivated in each sample by heating at 80° C. for 10 minutes. Each sample was then diluted 10-fold with sterile water. 500 µL of diluted sample was transferred into a centrifuge tube filter (SPIN-X, 0.45-µm Nylon, 2.0 mL Polypropylene Tube, Costar #8170) and centrifuged at 12,000 rpm in a table centrifuge for 60 minutes, after which 200 µL of flowthrough was used for HPLC analysis to measure sucrose consumption during the reaction. The following HPLC conditions were applied for analyzing each sample: column (AMINEX HPX-87C carbohydrate column, 300×7.8 mm, Bio-Rad, No. 125-0095), eluent (water), flow rate (0.6 mL/min), temperature (85° C.), refractive index detector. HPLC analysis of the samples indicated substantial sucrose consumption during the 0768 gtf reaction.

HPLC was also used to analyze other products of the reaction. Polymer yield was back-calculated by subtracting the amount of all other saccharides left in the reaction from the amount of the starting sucrose. The back-calculated number was consistent with the viscous product dry weight analysis. Sucrose, leucrose, glucose and fructose were quantified by HPLC with an HPX-87C column (HPLC conditions as described above). DP2-7 oligosaccharides were quantified by HPLC with the following conditions: column (AMINEX HPX-42A carbohydrate column, 300×7.8 mm, Bio-Rad, No. 125-0097), eluent (water), flow rate (0.6 mL/min), temperature (85° C.), refractive index detector. These HPLC analyses indicated that the glucosyl-containing saccharide products of the 0768 gtf reaction consisted of 92.3% polymer product, 1.3% glucose, 5.0% leucrose, and 1.4% DP2-7 oligosaccharides.

A sample of dry dextran powder product (~0.2 g) of the above reaction was used for molecular weight analysis. Molecular weight was determined by a flow injection chromatographic method using an Alliance™ 2695 separation module from Waters Corporation (Milford, Mass.) coupled with three online detectors: a differential refractometer 2414 from Waters, a Heleos™-2 18-angle multiangle light scattering (MALS) photometer with quasielastic light scattering (QELS) detector from Wyatt Technologies (Santa Barbara, Calif.), and a ViscoStar™ differential capillary viscometer from Wyatt. The dry dextran powder was dissolved at 0.5 mg/mL in aqueous Tris (Tris[hydroxymethyl]aminomethane) buffer (0.075 M) containing 200 ppm NaN$_3$. The dissolution of dextran was achieved by shaking overnight at 50° C. Two AQUAGEL-OH GUARD columns from Agilent Technologies (Santa Clara, Calif.) were used to separate the dextran polymer peak from the injection peak. The mobile base for this procedure was the same as the dextran solvent, the flow rate was 0.2 mL/min, the injection volume was 0.1 mL, and the column temperature was 30° C. Empower™ version 3 software from Waters was used for data acquisition, and Astra™ version 6 software from Wyatt was used for multidetector data reduction. It was determined from this work that the dextran polymer product had a weight-average molecular weight (Mw) of 1.022 (+/−0.025)×10$^8$ g/mol (i.e., roughly 100 million Daltons) (from MALS analysis), a z-average radius of gyration of 243.33 (+/−0.42) nm (from MALS analysis), and a z-average hydrodynamic radius of 215 nm (from QELS analysis). It was also determined from QELS analysis that the dextran has a standard deviation of particle size distribution (PSD) of about 0.259, indicating that the dextran likely is polydisperse in terms of hydrodynamic size.

For glycosidic linkage analysis purposes, a 50-mL gtf reaction was prepared as described above in this Example, except that the reaction time was 24 hours (reaction had become viscous). The gtf enzyme was deactivated by heating the reaction at 80° C. for 10 minutes. The deactivated viscous reaction was then placed into a regenerated cellulose sturdy dialysis tubing with a molecular weight cut-off (MWCO) of 12-14 kDa (Spectra/Por® 4 Dialysis Tubing, Part No. 132706, Spectrum Laboratories, Inc.) and dialyzed against 4 L of filter water at room temperature over one week. Water was exchanged every day during this dialysis. The dialyzed viscous reaction was then precipitated and dried as described above in this Example. About 0.2 g of dry powder was submitted for GC/MS linkage analysis.

Linkage analysis was performed according to methods described by Pettolino et al. (*Nature Protocols* 7:1590-1607), which is incorporated herein by reference. Briefly, a dry dextran sample was dissolved in dimethyl sulfoxide (DMSO) or 5% lithium chloride in DMSO, then all free hydroxyl groups were methylated by sequential addition of a sodium hydroxide/DMSO slurry followed by iodomethane. The methylated polymer was then extracted into methylene chloride and hydrolyzed to monomeric units using aqueous trifluoroacetic acid (TFA) at 120° C. The TFA was then evaporated from the sample and reductive ring opening was done using sodium borodeuteride, which also labeled the reducing end with a deuterium atom. The hydroxyl groups created by hydrolyzing the glycosidic linkages were then acetylated by treating with acetyl chloride and TFA at a temperature of 50° C. Finally, the derivatizing reagents were evaporated and the resulting methylated/acetylated monomers were reconstituted in acetonitrile and analyzed by gas chromatography with mass spectrometry (GC/MS) using a biscyanopropyl cyanopropylphenyl polysiloxane column. The relative positioning of the methyl and acetyl functionalities, along with the deuterium label, yielded species that have distinctive retention time indices and mass spectra that can be compared to published databases. In this way, the derivatives of the monomeric units indicated how each monomer was originally linked in the dextran polymer and whether the monomer was a branch point. The results of analyzing these samples (dextran initially dissolved in DMSO or DMSO/5% LiCl) are provided in Table 4.

TABLE 4

Linkage Profile of Gtf 0768 Dextran Product

| Sample | Wt %/Mol % of Glucose Monomers in Dextran | | | | |
|---|---|---|---|---|---|
| | 3-glc [a] | 6-glc [b] | 4-glc [c] | 3,6-glc [d] | 2,6- + 4,6-glc [e] |
| DMSO | 0.4 | 90.2 | 0.4 | 8.3 | 0.7 |
| DMSO/5% LiCl | 0.9 | 89.3 | 0.4 | 8.0 | 1.4 |

[a] Glucose monomer linked at carbon positions 1 and 3.
[b] Glucose monomer linked at carbon positions 1 and 6.
[c] Glucose monomer linked at carbon positions 1 and 4.
[d] Glucose monomer linked at carbon positions 1, 3 and 6.
[e] Glucose monomer linked at carbon positions 1, 2 and 6, or 1, 4 and 6.

In general, the results in Table 4 indicate that the dextran product analyzed above comprises:

(i) about 87-93 wt % glucose linked only at positions 1 and 6;

(ii) about 0.1-1.2 wt % glucose linked only at positions 1 and 3;

(iii) about 0.1-0.7 wt % glucose linked only at positions 1 and 4;

(iv) about 7.7-8.6 wt % glucose linked only at positions 1, 3 and 6; and (v) about 0.4-1.7 wt % glucose linked only at (a) positions 1, 2 and 6, or (b) positions 1, 4 and 6.

Based on this information and some other studies (data not shown), it is contemplated that this product is a branched structure in which there are long chains (containing mostly or all alpha-1,6-linkages) of about 20 DP in length (average) that iteratively branch from each other (e.g., a long chain can be a branch from another long chain, which in turn can itself be a branch from another long chain, and so on). The branched structure also appears to comprise short branches from the long chains; these short chains are believed to be 1-3 DP in length and mostly comprise alpha-1,3 and -1,4 linkages, for example. Branch points in the dextran, whether from a long chain branching from another long chain, or a short chain branching from a long chain, appear to comprise alpha-1,3, -1,4, or -1,2 linkages off of a glucose involved in alpha-1,6 linkage. Roughly 25% of all the branch points of the dextran branched into a long chain.

Thus, reactions comprising water, sucrose and an enzyme comprising SEQ ID NO:1 synthesized a very large gelling dextran product, as determined by the product's high Mw and predominant alpha-1,6 glucosidic linkage profile.

Example 10

Formulation Comprising Dextran Synthesized by Gtf 0768

This Example discloses a formulation comprising the dextran product of gtf 0768. This formulation was shown to have better sensory characteristics (or "feel") compared to formulations comprising certain compounds (xanthan gum, Carbopol®) commonly used for providing viscosity to certain consumer products (e.g., personal care compositions such as lotion).

Three different emulsions were prepared and compared against each other in a skinfeel study, as follows.

Dextran-Based Emulsion:

Dextran was produced using gtf 0768 (comprising SEQ ID NO:1) in a reaction similar to the reaction disclosed in Example 9. At room temperature, polysorbate 80, sorbitan monooleate and mineral oil (Phase B, Table 5) were combined in a small vessel, and mixed by hand until homogeneous. Phase B was slowly added to water (Phase A, Table 5) under moderate propeller mixing. The mixture was homogenized at 5000-9000 rpm for approximately 5-10 minutes. Dextran (Phase C, Table 5) was then added under moderate propeller mixing. Germaben® II (Phase D, Table 5) was then added as a preservative under moderate propeller mixing. The dextran could optionally have been pre-hydrated using a portion of the water from phase A.

TABLE 5

Dextran-Based Emulsion

| Ingredients | % Activity | wt % (Desired) | wt % (Neat) | Grams |
|---|---|---|---|---|
| Phase A | | | | |
| Water (deionized) | | | 73.50 | 73.50 |
| Phase B | | | | |
| Polysorbate 80 | 100.00 | 2.43 | 2.43 | 2.43 |
| Sorbitan Monooleate | 100.00 | 2.57 | 2.57 | 2.57 |
| Mineral Oil | 100.00 | 20.00 | 20.00 | 20.00 |
| Phase C | | | | |
| Dextran | 100.00 | 1.00 | 1.00 | 1.00 |
| Phase D | | | | |
| Germaben ® II | 100.00 | 0.50 | 0.50 | 0.50 |
| | | | 100.00 | 100.00 |

Xanthan Gum-Based Emulsion (Control 1):

At room temperature, xanthan gum and water (Phase A, Table 6) were combined under moderate propeller mixing until homogeneous. Polysorbate 80, sorbitan monooleate and mineral oil (Phase B, Table 6) were combined in a small vessel, and mixed by hand until homogeneous. Phase B was slowly added to Phase A under moderate propeller mixing. The mixture was homogenized at 5000-9000 rpm for approximately 5-10 minutes. Germaben® II (Phase C, Table 6) was then added as a preservative under moderate propeller mixing.

TABLE 6

Xanthan Gum-Based Emulsion

| Ingredients | % Activity | wt % (Desired) | wt % (Neat) | Grams |
|---|---|---|---|---|
| Phase A | | | | |
| Water (deionized) | | | 74.00 | 74.00 |
| Xanthan Gum | 100.00 | 0.50 | 0.50 | 0.50 |
| Phase B | | | | |
| Polysorbate 80 | 100.00 | 2.43 | 2.43 | 2.43 |
| Sorbitan Monooleate | 100.00 | 2.57 | 2.57 | 2.57 |
| Mineral Oil | 100.00 | 20.00 | 20.00 | 20.00 |
| Phase C | | | | |
| Germaben ® II | 100.00 | 0.50 | 0.50 | 0.50 |
| | | | 100.00 | 100.00 |

Carbopol® Ultrez 10-Based Emulsion (Control 2):

At room temperature, Carbopol® Ultrez 10 and water (Phase A, Table 7) were combined under moderate propeller mixing until homogeneous. Polysorbate 80, sorbitan monooleate and mineral oil (Phase B, Table 7) were combined in a small vessel, and mixed by hand until homogeneous. Phase B was slowly added to Phase A under moderate propeller mixing. The mixture was homogenized at 5000-9000 rpm for approximately 5-10 minutes. Germaben® II (Phase C, Table 7) was then added as a preservative under moderate propeller mixing. A 20-wt % solution of sodium hydroxide was used to neutralize the emulsion to pH 5.5.

TABLE 7

Carbopol ® Ultrez 10-Based Emulsion

| Ingredients | % Activity | wt % (Desired) | wt % (Neat) | Grams |
|---|---|---|---|---|
| Phase A | | | | |
| Water (deionized) | | | 74.00 | 74.00 |
| Carbopol ® Ultrez 10 | 100.00 | 0.50 | 0.50 | 0.50 |
| Phase B | | | | |
| Polysorbate 80 | 100.00 | 2.43 | 2.43 | 2.43 |
| Sorbitan Monooleate | 100.00 | 2.57 | 2.57 | 2.57 |
| Mineral Oil | 100.00 | 20.00 | 20.00 | 20.00 |
| Phase C | | | | |
| Germaben ® II | 100.00 | 0.50 | 0.50 | 0.50 |
| | | | 100.00 | 100.00 |

Skinfeel Analysis and Results:

A double-blind, skinfeel analysis was performed according to ASTM E1490-3 ("Standard Practice for Descriptive Skinfeel Analysis of Creams and Lotions", ASTM International, West Conshohocken, Pa., 2003, DOI: 10.15201E1490-03, incorporated herein by reference) to compare each of the above emulsions. The primary attributes evaluated in this study were rub-out sliminess, afterfeel stickiness, pick-up stringiness and pick-up stickiness. Panelists assessed attributes on a scale from 1-5, where 1 exhibits the least of the attribute and 5 exhibits the most of the attribute. The results are reported in Table 8 below as an average value of the panelists' ratings for each attribute. The sum average of these values (Σ, Table 8) indicates that the overall sensory experience for emulsions (e.g., lotions) produced with dextran as presently disclosed exceeds the results of similar emulsions produced with either xanthan gum or Carbopol® Ultrez 10.

TABLE 8

Carbopol ® Ultrez 10-Based Emulsion

| | Average Rating | | |
|---|---|---|---|
| Skinfeel Attribute | Dextran | Xanthan Gum | Carbopol ® Ultrez 10 |
| Rub-Out Sliminess | 2 | 3 | 2 |
| Afterfeel Stickiness | 2 | 2 | 3 |
| Pick-Up Stringiness | 1 | 3 | 3 |
| Pick-Up Stickiness | 2 | 3 | 2 |
| Σ | 7 | 11 | 10 |

It is noteworthy that the dextran-containing emulsion scored better than the control emulsions in the skinfeel analysis, especially since there was two-times the amount of dextran (1 wt %) in the emulsion compared to the amount of xanthan gum (0.5 wt %) or Carbopol® Ultrez 10 (0.5 wt %) in the control emulsions.

Thus, dextran produced by gtf 0768 (comprising SEQ ID NO:1) can be suitable for use in compositions where enhanced sensory characteristics are desirable, such as in personal care and food products, for example.

Example 11

Dextran-Comprising Cleanser with Suspended Particles

This Example discloses a cleanser comprising the dextran product of gtf 0768. Jojoba ester beads could be suspended in this composition, indicating that the dextran can function as a dispersant.

Dextran was produced using gtf 0768 (comprising SEQ ID NO:1) in a reaction similar to the reaction disclosed in Example 9. At room temperature water, dextran, glycerin, polysorbate 20, cocamidopropyl betaine, PPG-2 hydroxyethyl cocamide and disodium EDTA were combined according to the formulation in Table 9, and mixed by hand until homogeneous. Jojoba beads were then added and mixing was continued until the beads were homogeneously dispersed. The dextran could optionally have been pre-hydrated using a portion of the water component.

TABLE 9

| Dextran-Based Jojoba Bead Suspension | | | | |
|---|---|---|---|---|
| Ingredient | % Activity | wt % (Desired) | wt % (Neat) | Grams |
| Water (deionized) | | | 22.95 | 22.95 |
| Dextran | 100 | 5 | 5 | 5 |
| Glycerin | 100 | 10 | 10 | 10 |
| Polysorbate 20 | 100 | 5.25 | 5.25 | 5.25 |
| Cocamidopropyl Betaine | 35.97 | 20 | 55.6 | 55.6 |
| PPG-2 Hydroxyethyl Cocamide | 100 | 1 | 1 | 1 |
| Disodium EDTA | 100 | 0.1 | 0.1 | 0.1 |
| Jojoba Ester Beads | 100 | 0.1 | 0.1 | 0.1 |
| | | | 100 | 100 |

Thus, dextran produced by gtf 0768 (comprising SEQ ID NO:1) can be used as a dispersant in aqueous compositions such as certain personal care products.

---

What is claimed is:

1. A composition comprising an isolated dextran, wherein said dextran comprises:
   (i) about 87-93 wt % glucose linked at positions 1 and 6;
   (ii) about 0.1-1.2 wt % glucose linked at positions 1 and 3;
   (iii) about 0.1-0.7 wt % glucose linked at positions 1 and 4;
   (iv) about 7.7-8.6 wt % glucose linked at positions 1, 3 and 6; and
   (v) about 0.4-1.7 wt % glucose linked at:
      (a) positions 1, 2 and 6, or
      (b) positions 1, 4 and 6;
   wherein the weight-average molecular weight (Mw) of said dextran is about 50-200 million Daltons, the z-average radius of gyration of said dextran is about 200-280 nm, and the dextran is a product of an isolated glucosyltransferase enzyme comprising an amino acid sequence that is at least 90% identical to SEQ ID NO:1 or SEQ ID NO:2.

2. The composition of claim 1, wherein the dextran comprises:
   (i) about 89.5-90.5 wt % glucose linked at positions 1 and 6;
   (ii) about 0.4-0.9 wt % glucose linked at positions 1 and 3;
   (iii) about 0.3-0.5 wt % glucose linked at positions 1 and 4;
   (iv) about 8.0-8.3 wt % glucose linked at positions 1, 3 and 6; and
   (v) about 0.7-1.4 wt % glucose linked at:
      (a) positions 1, 2 and 6, or
      (b) positions 1, 4 and 6.

3. The composition of claim 1, wherein the dextran comprises chains iteratively linked together within a branching structure, wherein said chains are similar in length and comprise substantially alpha-1,6-glucosidic linkages.

4. The composition of claim 3, wherein the average length of the chains is about 10-50 monomeric units.

5. The composition of claim 1, wherein the dextran is a product of an isolated glucosyltransferase enzyme comprising an amino acid sequence that is at least 95% identical to SEQ ID NO:1 or SEQ ID NO:2.

6. The composition of claim 1, wherein the composition is an aqueous composition having a viscosity of at least about 25 centipoise.

7. The composition of claim 1, wherein the Mw of the dextran is about 80-120 million Daltons.

8. The composition of claim 1, wherein the z-average radius of gyration of said dextran is about 230-250 nm.

9. The composition of claim 1, wherein the composition is in the form of a food product, personal care product, pharmaceutical product, household product, or industrial product.

10. The composition of claim 9, wherein the composition is in the form of a confectionery.

11. A method for increasing the viscosity of an aqueous composition, the method comprising:

contacting dextran according to claim 1 with the aqueous composition, wherein the viscosity of the aqueous composition is increased by said dextran compared to the viscosity of the aqueous composition before the contacting step.

12. A method of treating a material, said method comprising:

contacting the material with an aqueous composition comprising dextran according to claim 1.

* * * * *